US008629107B2

(12) United States Patent
Schiemann et al.

(10) Patent No.: US 8,629,107 B2
(45) Date of Patent: Jan. 14, 2014

(54) GENES AND PROTEINS ASSOCIATED WITH ANGIOGENESIS AND USES THEREOF

(75) Inventors: William P. Schiemann, Denver, CO (US); Allan R. Albig, Denver, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 13/417,033

(22) Filed: Mar. 9, 2012

(65) Prior Publication Data

US 2012/0283188 A1 Nov. 8, 2012

Related U.S. Application Data

(63) Continuation of application No. 11/542,670, filed on Oct. 2, 2006, now Pat. No. 8,158,107.

(60) Provisional application No. 60/816,969, filed on Jun. 27, 2006, provisional application No. 60/722,694, filed on Sep. 30, 2005.

(51) Int. Cl.
*A61K 38/00* (2006.01)
*A61K 48/00* (2006.01)
*A61P 35/00* (2006.01)

(52) U.S. Cl.
USPC .................................. 514/13.3; 514/44 R

(58) Field of Classification Search
USPC .............................. 514/13.3, 44 R
See application file for complete search history.

(56) References Cited

U.S. PATENT DOCUMENTS 8,158,107 B2 4/2012 Schiemann et al.

FOREIGN PATENT DOCUMENTS

WO WO 2004/048938 6/2004

OTHER PUBLICATIONS

Bodolay, et al., "Angiogenesis and Chemokines in rheumatoid arthritis and other systemic inflammatory rheumatic diseases", J Cell. Mol. Med., 2002, vol. 6, No. 3, pp. 357-376.

Bruyninx, et al., "A Novel Gene Overexpressed in the Prostate of Castrated Rats: Hormonal Regulation, Relationship to Apoptosis and to Acquired Prostatic Cell Androgen Independence", Endocrinology, Oct. 1999, pp. 4789-4799, vol. 140, No. 10, The Endocrine Society.
Cornet, et al., "Prostatic Androgen Repressed Message-I (PARM-I) May Play a Role in Prostatic Cell Immortalisation", The Prostate, Aug. 2003, pp. 220-230, vol. 56, No. 3 Wiley-Liss, Inc.
Creighton, et al., "Profiling of pathway-specific changes in gene expression following growth of human cancer cell lines transplanted into mice", Genome Biology, Jun. 23, 2003, pp. R46.1-R46.12, vol. 4, Issue 7, Article R46.
Davis, et al., "Endothelial Extracellular Matrix: Biosynthesis, Remodeling and Functions During vascular Morphogenesis and Neovessel stabilization", Circulation Research, Nov. 25, 2005, pp. 1093-1106, vol. 97.
Gibson, et al., "Microfibril-associated Glycoprotein-2 (MAGP-2) Is Specifically Associated with Fibrillin-containing Microfibrils but Exhibits More Restricted Patterns of Tissue Localization and Development Expression That Its Structural Relative MAGP-1", The Journal of Histochemistry and Cytochemistry, 1998, pp. 871-885, Vo. 46.
Graham, et al., "Altered Progesterone Receptor Isoform Expression Remodels Progestin Responsiveness of Breast Cancer Cells", Molecular Endocrinology, Jun. 23, 2005, pp. 2713-2735, vol. 19, The Endocrine Society.
Hanahan, et al., "Patterns and Emerging Mechanisms of the Angiogenic Switch during Tumorigenesis", Cell, Aug. 9, 1996, pp. 353-364, vol. 86, Cell Press.
Leong, et al., "Activated Notch4 Inhibits Angiogenesis: Role of β1-Integrin Activation", Molecular and Cellular Biology, Apr. 2002, pp. 2830-2841, vol. 22, No. 8, American Society of Microbiology.
Nehring, et al., "The Extracellular Matrix Protein MAGP-2 Interacts with Jagged1 and Induces Its Shedding from the Cell Surface", The Journal of Biological Chemistry, May 27, 2005, pp. 20349-20355, vol. 280, No. 21, The American Society for Biochemistry and Molecular Biology, Inc.
Stupack, et al., "ECM Remodeling Regulates Angiogenesis: Endothelial Integrins Look for New Ligands", Science's STKE, Feb. 12, 2002, pp. 1-6, vol. 119.
International Search Report for International (PCT) Patent Application No. PCT/US06/38709, mailed Jun. 26, 2008.
Written Opinion for International (PCT) Patent Application No. PCT/US06/38709, mailed Jun. 26, 2008.

*Primary Examiner* — Chih-Min Kam
(74) *Attorney, Agent, or Firm* — Sheridan Ross P.C.

(57) ABSTRACT

Disclosed is a panel of biomarkers associated with angiogenesis, and the use of such biomarkers (genes, proteins, homologues and analogs thereof) to regulate angiogenesis. Methods for identifying compounds useful for regulating angiogenesis and conditions related thereto are disclosed.

5 Claims, 14 Drawing Sheets

GENES AND PROTEINS ASSOCIATED WITH ANGIOGENESIS AND USES THEREOF

CROSS-REFERENCE TO RELATED APPLICATIONS

This application is a continuation of U.S. patent application Ser. No. 11/542,670, filed Oct. 2, 2006, now U.S. Pat. No. 8,158,107, which claims the benefit of priority under 35 U.S.C. §119(e) from U.S. Provisional Patent Application No. 60/722,694, filed Sep. 30, 2005, and from U.S. Provisional Patent Application No. 60/816,969, filed Jun. 27, 2006. The entire disclosures of each of U.S. patent application Ser. No. 11/542,670, U.S. Provisional Patent Application No. 60/722,694, and U.S. Provisional Patent Application No. 60/816,969, are incorporated herein by reference in their entirety.

GOVERNMENT SUPPORT

This invention was made in part with government support under NIH Grant No. CA095519 and NIH Grant No. CA99321, each awarded by the National Institutes of Health. The government has certain rights to this invention.

REFERENCE TO SEQUENCE LISTING

This application contains a Sequence Listing submitted as an electronic text file named "Sequence Listing.txt", having a size in bytes of 266 kb, and created on Oct. 2, 2006. The information contained in this electronic file is hereby incorporated by reference in its entirety pursuant to 37 CFR §1.52 (e)(5).

FIELD OF THE INVENTION

The present invention generally relates to genes and proteins, including homologues and agonist or antagonist analogs thereof, as targets for regulating angiogenesis. The present invention also relates to methods to identify regulators of angiogenesis using such biomarkers, and methods related thereto.

BACKGROUND OF THE INVENTION

Angiogenesis is the process whereby new blood vessels are formed from preexisting vessels; it is a highly regulated event that encompasses a coordinated cascade of gene expression and repression, and one that is influenced by many factors, including a variety of environmental cues provided by the extracellular matrix (ECM) (Sottile, 2004; Stupack and Cheresh, 2002). Cancer cells play a vital role in eliciting many of these environmental cues in part via their ability to produce and secrete numerous angiogenic factors and proteases that create tumor microenvironments conductive to angiogenesis (Bissell et al, 2002; Pupa et al, 2002; Sottile, 2004). Although previously believed to be innocent bystanders during angiogenic reactions, it is becoming increasingly apparent that endothelial cells (ECs) also make important contributions to the activation and resolution of angiogenesis. Indeed, ECs generate a variety of environmental cues that shape and remodel tumor and vascular microenvironments, ultimately leading to altered vessel development (Davis and Senger, 2005; Sottile, 2004). Unfortunately, the molecular mechanisms whereby ECs and the molecules they secrete actively direct angiogenesis activation and resolution remain to be determined definitively. It is known that tumor angiogenesis depends upon the coordinated cooperation between cancer and endothelial cells (ECs), and results in the formation and infiltration of new vessels into tumor microenvironments, thereby providing developing tumors with a source of nutrients and oxygen, as well as a route for cancer cell metastasis (Carmeliet and Jain, 2000; Folkman and Shing, 1992). Failure to establish these cancer:EC connections prevents the development and progression of small, innocuous cancer growths, and as such, tumors remain in a dormant, benign state (Bergers and Benjamin, 2003; Hanahan and Folkman, 1996). Recently, significant inroads in understanding of the role of cancer cells in mediating tumor angiogenesis and EC activation have taken place. Indeed, cancer cells actively induce tumor angiogenesis via their ability to produce and secrete a variety of pro-angiogenic factors (Liotta and Kohn, 2001; Stupack and Cheresh, 2002), a process known as the angiogenic switch (Bergers and Benjamin, 2003; Hanahan and Folkman, 1996). In contrast, comparably little is known concerning the role of ECs during this process, particularly the functional consequences of their ability to remodel vascular and tumor microenvironments during angiogenesis. Although ECs are known to remodel their microenvironment by secreting various extracellular proteases, such as MMPs (matrix metalloproteases), ADAMs (a disintegrin and metalloprotease domain), and ADAMTS (a disintegrin and metalloprotease domain with thrombospondin motifs; Stupack and Cheresh, 2002), a thorough understanding of how these molecules and their stromal targets mediate angiogenesis activation or resolution remains incompletely understood. Thus, identifying and characterizing novel proteins secreted by angiogenic ECs will offer important insights into the role of the endothelium in mediating angiogenesis, as well as its potential to be targeted therapeutically to prevent tumor angiogenesis. Specifically, mapping and defining the EC secretome will significantly enhance understanding of angiogenesis, as well as identify novel therapeutic agents and/or targets that can be exploited to prevent tumor angiogenesis and metastasis in cancer patients.

SUMMARY OF THE INVENTION

One embodiment of the present invention relates to a method to regulate angiogenesis in cells or a tissue of a patient. The method comprises regulating the expression or biological activity in the cells or tissue of any one or more biomarkers selected from a biomarker represented in any one or more of Table I, Table IV, Table V, and/or Table VI.

In one aspect of this embodiment, the biomarkers are any one or more of the biomarkers in Table VI. In another aspect of this embodiment, the biomarkers are any one or more of the biomarkers selected from: ADAMts7, CRELD-2, Decorin, ECM1, Inhibin β-b, Integrin α-3, Integrin α-6, Lipocalin-7, Loxl-3, Lumican, MAGP-2, Matrilin-2, Nephronectin, SerpinE2, and/or SMOC-2.

In another aspect of this embodiment, the biomarkers are any one or more of the biomarkers selected from: 0610007C21Rik, apoptosis related protein APR-3, 1810014L12Rik, Cd14 (encoding CD14 antigen represented herein by SEQ ID NO:5 and SEQ ID NO:6), Cd38 (comprising a nucleic acid sequence represented herein by SEQ ID NO:7 and encoding CD38 antigen); Cd53 (encoding CD53 antigen represented herein by SEQ ID NO:8 and SEQ ID NO:9), Emp2 (encoding epithelial membrane protein represented herein by SEQ ID NO:10 and SEQ ID NO:11), Fcgrt (encoding Fc receptor (IgG, alpha chain transporter) represented herein by SEQ ID NO:12 and SEQ ID NO:13), Islr (encoding immunoglobulin superfamily containing leucine-rich repeat represented herein by SEQ ID NO:14 and SEQ ID NO:15); Lrp2 (comprising a nucleic acid sequence represented herein by SEQ ID NO:16 and SEQ ID NO:17 and encoding low density lipoprotein receptor-related protein 2); Ly6a (encoding lymphocyte antigen 6 complex, locus A represented herein by SEQ ID NO:18); P2rx4 (encoding purinergic receptor P2X, ligand-gated ion channel 4, represented herein by SEQ ID NO:19 and SEQ ID NO:20; Pcdhb9 (encoding protocadherin beta 9 represented herein by SEQ ID NO:21 and SEQ ID NO:22); Ptpre (encoding protein tyrosine phosphatase receptor type E represented herein by SEQ ID NO:23 and SEQ ID NO:24); Slc4a3 (encoding solute carrier family 4 (anion exchanger) member 3, represented herein by SEQ ID NO:25 and SEQ ID NO:26); and/or Tmc6 (encoding transmembrane channel-like gene family 6, represented herein by SEQ ID NO:27).

In another aspect of this embodiment, the biomarkers are any one or more of the biomarkers selected from: 9130213B05Rik (encoding a protein represented herein by SEQ ID NO: 29); C1s (encoding complement component 1, s subcomponent, represented herein by SEQ ID NO: 34 and SEQ ID NO: 35); C3 (encoding complement component 3 represented herein by SEQ ID NO: 30 and SEQ ID NO: 31); Cfh (comprising a nucleic acid sequence represented herein by SEQ ID NO: 32 and SEQ ID NO: 33 and encoding complement component factor h); Col9a3 (comprising a nucleic acid sequence represented herein by SEQ ID NO: 36 and SEQ ID NO: 37 and encoding procollagen, type IX, alpha 3); Grem1 (encoding cysteine knot superfamily 1, BMP antagonist 1, represented herein by SEQ ID NO: 38 and SEQ ID NO: 39); Lox13 (encoding lysyl oxidase-like 3, represented herein by SEQ ID NO: 40 and SEQ ID NO: 41); MAGP-2 (comprising a nucleic acid sequence represented herein by SEQ ID NO: 123 and SEQ ID NO: 124 and encoding microfibrillar associated protein 5, represented herein by SEQ ID NO: 42 and SEQ ID NO: 43); Mglap (encoding matrix gamma-carboxyglutamate (gla) protein represented herein by SEQ ID NO: 44 and SEQ ID NO: 45); Naga (encoding N-acetyl galactosaminidase, alpha, represented herein by SEQ ID NO: 46 and SEQ ID NO: 47); Nbl1 (encoding neuroblastoma, suppression of tumorigenicity 1, represented herein by SEQ ID NO: 48 and SEQ ID NO: 49); Ngfb (encoding nerve growth factor, beta, represented herein by SEQ ID NO: 50 and SEQ ID NO: 51), Npnt (represented herein by SEQ ID NO: 52 and SEQ ID NO: 53 and encoding nephronectin); Olfm1 (encoding olfactomedin 1, represented herein by SEQ ID NO: 54 and SEQ ID NO: 55); and/or U90926 (encoding a protein represented herein by SEQ ID NO: 56).

Any combinations of any of the above-identified biomarkers are included in the invention. In a preferred aspect of this embodiment, the biomarker is MAGP-2.

In one aspect, the step of regulating comprises contacting the cells or tissue of from the patient with an antagonist of the biomarker. In another aspect, the step of regulating comprises contacting the cells or tissue of from the patient with the biomarker or a biologically active homologue or agonist thereof. In another aspect, the step of regulating comprises expressing a recombinant nucleic acid molecule encoding the biomarker or a homologue thereof in the tissue of the patient.

In one aspect of this embodiment, angiogenesis is upregulated. Such an aspect of the invention can be used to treat a patient that has vascular deficiencies, cardiovascular disease, or would benefit from stimulation of endothelial cell activation and stabilization of newly formed microvessels or other vessels, such as in ischemia or stroke.

In another aspect of this embodiment angiogenesis is downregulated. Such an aspect of the invention can be used to treat conditions that are characterized or caused by abnormal or excessive angiogenesis, including, but are not limited to: cancer (e.g., activation of oncogenes, loss of tumor suppressors); infectious diseases (e.g., pathogens express angiogenic genes, enhance angiogenic programs); autoimmune disorders (e.g., activation of mast cells and other leukocytes); vascular malformations (e.g., Tie-2 mutation); DiGeorge syndrome (e.g., low VEGF and neuropilin-1 expression); HHT (e.g., mutations of endoglin or LK-1), cavernous hemangioma (e.g., loss of Cx37 and Cx40); atherosclerosis; transplant ateriopathy; obesity (e.g., angiogenesis induced by fatty diet, weight loss by angiogenesis inhibitors); psoriasis; warts; allergic dermatitis; scar keloids; pyogenic granulomas; blistering disease; Kaposi sarcoma in AIDS patients; persistent hyperplastic vitreous syndrome (e.g., loss of Ang-2 or VEGF164); diabetic retinopathy; retinopathy of prematurity; choroidal neovascularization (e.g., TIMP-3 mutation); primary pulmonary hypertension (e.g., germline BMPR-2 mutation, somatic EC mutation); asthma; nasal polyps; inflammatory bowel disease; periodontal disease; ascites; peritoneal adhesions; endometriosis; uterine bleeding; ovarian cysts; ovarian hyperstimulation; arthritis; synovitis; osteomyelitis; and/or osteophyte formation.

Another embodiment of the present invention relates to a method to reduce tumorigenicity in a patient, comprising regulating the expression or biological activity of any one or more biomarkers selected from a biomarker represented in any one or more of Table I, Table IV, Table V, and/or Table VI. In one aspect of this embodiment, the biomarkers are any one or more of the biomarkers in Table VI.

In another aspect of this embodiment, the biomarkers are any one or more of the biomarkers selected from: ADAMts7, CRELD-2, Decorin, ECM1, Inhibin β-b, Integrin α-3, Integrin α-6, Lipocalin-7, Loxl-3, Lumican, MAGP-2, Matrilin-2, Nephronectin, SerpinE2, and/or SMOC-2.

In another aspect of this embodiment, the biomarkers are any one or more of the biomarkers selected from: 0610007C21Rik, apoptosis related protein APR-3, 1810014L12Rik, Cd14 (encoding CD14 antigen represented herein by SEQ ID NO:5 and SEQ ID NO:6), Cd38 (comprising a nucleic acid sequence represented herein by SEQ ID NO:7 and encoding CD38 antigen); Cd53 (encoding CD53 antigen represented herein by SEQ ID NO:8 and SEQ ID NO:9), Emp2 (encoding epithelial membrane protein represented herein by SEQ ID NO:10 and SEQ ID NO:11), Fcgrt (encoding Fc receptor (IgG, alpha chain transporter) represented herein by SEQ ID NO:12 and SEQ ID NO:13), Islr (encoding immunoglobulin superfamily containing leucine-rich repeat represented herein by SEQ ID NO:14 and SEQ ID NO:15); Lrp2 (comprising a nucleic acid sequence represented herein by SEQ ID NO:16 and SEQ ID NO:17 and encoding low density lipoprotein receptor-related protein 2); Ly6a (encoding lymphocyte antigen 6 complex, locus A represented herein by SEQ ID NO:18); P2rx4 (encoding purinergic receptor P2X, ligand-gated ion channel 4, represented herein by SEQ ID NO:19 and SEQ ID NO:20; Pcdhb9 (encoding protocadherin beta 9 represented herein by SEQ ID NO:21 and SEQ ID NO:22); Ptpre (encoding protein tyrosine phosphatase receptor type E represented herein by SEQ ID NO:23 and SEQ ID NO:24); Slc4a3 (encoding solute carrier family 4 (anion exchanger) member 3, represented herein by SEQ ID NO:25 and SEQ ID NO:26); and/or Tmc6 (encoding transmembrane channel-like gene family 6, represented herein by SEQ ID NO:27).

In yet another aspect of this embodiment, the biomarkers are any one or more of the biomarkers selected from: 9130213B05Rik (encoding a protein represented herein by SEQ ID NO:29); C1s (encoding complement component 1, s subcomponent, represented herein by SEQ ID NO:34 and SEQ ID NO:35); C3 (encoding complement component 3 represented herein by SEQ ID NO:30 and SEQ ID NO:31); Cfh (comprising a nucleic acid sequence represented herein by SEQ ID NO:32 and SEQ ID NO:33 and encoding complement component factor h); Col9a3 (comprising a nucleic acid sequence represented herein by SEQ ID NO:36 and SEQ ID NO:37 and encoding procollagen, type IX, alpha 3); Grem1 (encoding cysteine knot superfamily 1, BMP antagonist 1, represented herein by SEQ ID NO:38 and SEQ ID NO:39); Loxl3 (encoding lysyl oxidase-like 3, represented herein by SEQ ID NO:40 and SEQ ID NO:41); MAGP-2 (comprising a nucleic acid sequence represented herein by SEQ ID NO:124 and SEQ ID NO:125 and encoding microfibrillar associated protein 5, represented herein by SEQ ID NO:42 and SEQ ID NO:43); Mglap (encoding matrix gamma-carboxyglutamate (gla) protein represented herein by SEQ ID NO:44 and SEQ ID NO:45); Naga (encoding N-acetyl galactosaminidase, alpha, represented herein by SEQ ID NO:46 and SEQ ID NO:47); Nbl1 (encoding neuroblastoma, suppression of tumorigenicity 1, represented herein by SEQ ID NO:48 and SEQ ID NO:49); Ngfb (encoding nerve growth factor, beta, represented herein by SEQ ID NO:50 and SEQ ID NO:51), Npnt (represented herein by SEQ ID NO:52 and SEQ ID NO:53 and encoding nephronectin); Olfm1 (encoding olfactomedin 1, represented herein by SEQ ID NO:54 and SEQ ID NO:55); and/or U90926 (encoding a protein represented herein by SEQ ID NO:56).

Any combinations of any of the above-identified biomarkers are included in the invention. In a preferred aspect of this embodiment, the biomarker is MAGP-2.

Another embodiment of the present invention relates to a method to identify a compound that regulates angiogenesis. The method includes the steps of: (a) detecting an initial level of the expression or activity of one or more biomarkers in a cell or soluble product derived therefrom, wherein the biomarker is a biomarker selected from a biomarker represented in any one or more of Table I, Table IV, Table V, and Table VI; (b) contacting the cell with a test compound; (c) detecting a level of the biomarker expression or activity in the cell or soluble product derived therefrom after contact of the cell with the compound; and, (d) selecting a compound that changes the level of biomarker expression or activity in the cell or soluble product therefrom, as compared to in the absence of the compound and/or as compared to the initial level of biomarker expression or activity, as a compound that regulates angiogenesis.

In one aspect of this embodiment, the biomarkers are any one or more of the biomarkers in Table VI.

In another aspect of this embodiment, the biomarkers are any one or more of the biomarkers selected from: ADAMts7, CRELD-2, Decorin, ECM1, Inhibin β-b, Integrin α-3, Integrin α-6, Lipocalin-7, Loxl-3, Lumican, MAGP-2, Matrilin-2, Nephronectin, SerpinE2, and/or SMOC-2.

In another aspect of this embodiment, the biomarkers are any one or more of the biomarkers selected from: 0610007C21Rik, apoptosis related protein APR-3, 1810014L12Rik, Cd14 (encoding CD14 antigen represented herein by SEQ ID NO:5 and SEQ ID NO:6), Cd38 (comprising a nucleic acid sequence represented herein by SEQ ID NO:7 and encoding CD38 antigen); Cd53 (encoding CD53 antigen represented herein by SEQ ID NO:8 and SEQ ID NO:9), Emp2 (encoding epithelial membrane protein represented herein by SEQ ID NO:10 and SEQ ID NO:11), Fcgrt (encoding Fc receptor (IgG, alpha chain transporter) represented herein by SEQ ID NO:12 and SEQ ID NO:13), Islr (encoding immunoglobulin superfamily containing leucine-rich repeat represented herein by SEQ ID NO:14 and SEQ ID NO:15); Lrp2 (comprising a nucleic acid sequence represented herein by SEQ ID NO:16 and SEQ ID NO:17 and encoding low density lipoprotein receptor-related protein 2); Ly6a (encoding lymphocyte antigen 6 complex, locus A represented herein by SEQ ID NO:18); P2rx4 (encoding purinergic receptor P2X, ligand-gated ion channel 4, represented herein by SEQ ID NO:19 and SEQ ID NO:20; Pcdhb9 (encoding protocadherin beta 9 represented herein by SEQ ID NO:21 and SEQ ID NO:22); Ptpre (encoding protein tyrosine phosphatase receptor type E represented herein by SEQ ID NO:23 and SEQ ID NO:24); Slc4a3 (encoding solute carrier family 4 (anion exchanger) member 3, represented herein by SEQ ID NO:25 and SEQ ID NO:26); and/or Tmc6 (encoding transmembrane channel-like gene family 6, represented herein by SEQ ID NO:27).

In yet another aspect of this embodiment, the biomarkers are any one or more of the biomarkers selected from: 9130213B05Rik (encoding a protein represented herein by SEQ ID NO:29); C1s (encoding complement component 1, s subcomponent, represented herein by SEQ ID NO:34 and SEQ ID NO:35); C3 (encoding complement component 3 represented herein by SEQ ID NO:30 and SEQ ID NO:31); Cfh (comprising a nucleic acid sequence represented herein by SEQ ID NO:32 and SEQ ID NO:33 and encoding complement component factor h); Col9a3 (comprising a nucleic acid sequence represented herein by SEQ ID NO:36 and SEQ ID NO:37 and encoding procollagen, type IX, alpha 3); Grem1 (encoding cysteine knot superfamily 1, BMP antagonist 1, represented herein by SEQ ID NO:38 and SEQ ID NO:39); Loxl3 (encoding lysyl oxidase-like 3, represented herein by SEQ ID NO:40 and SEQ ID NO:41); MAGP-2 (comprising a nucleic acid sequence represented herein by SEQ ID NO:124 and SEQ ID NO:125 and encoding microfibrillar associated protein 5, represented herein by SEQ ID NO:42 and SEQ ID NO:43); Mglap (encoding matrix gamma-carboxyglutamate (gla) protein represented herein by SEQ ID NO:44 and SEQ ID NO:45); Naga (encoding N-acetyl galactosaminidase, alpha, represented herein by SEQ ID NO:46 and SEQ ID NO:47); Nbl1 (encoding neuroblastoma, suppression of tumorigenicity 1, represented herein by SEQ ID NO:48 and SEQ ID NO:49); Ngfb (encoding nerve growth factor, beta, represented herein by SEQ ID NO:50 and SEQ ID NO:51), Npnt (represented herein by SEQ ID NO:52 and SEQ ID NO:53 and encoding nephronectin); Olfm1 (encoding olfactomedin 1, represented herein by SEQ ID NO:54 and SEQ ID NO:55); and/or U90926 (encoding a protein represented herein by SEQ ID NO:56).

Any combinations of any of the above-identified biomarkers are included in the invention. In a preferred aspect of this embodiment, the biomarker is MAGP-2.

Another embodiment of the invention relates to a method to identify a compound useful for inhibition of tumor growth or malignancy. The method includes the steps of: (a) detecting an initial level of the expression or activity of one or more biomarkers in a cell or soluble product derived therefrom, wherein the biomarker is a biomarker represented in any one or more of Table I, Table IV, Table V, and Table VI; (b) contacting the tumor cell with a test compound; (c) detecting a level of biomarker expression or activity in the tumor cell or soluble product derived therefrom after contact of the tumor cell with the compound; and, (d) selecting a compound that changes the level of the biomarker expression or activity in the tumor cell or soluble product therefrom, as compared to the initial level of biomarker expression or activity, toward a baseline level of biomarker expression or activity established from a non-tumor cell, wherein the selected compound is predicted to be useful for inhibition of tumor growth or malignancy.

Yet another embodiment of the present invention relates to a method for assessing the presence of tumor cells or potential therefore in a patient. The method includes the steps of: (a) detecting a level of expression or activity of the expression or activity of one or more biomarkers in a test sample from a patient to be diagnosed, wherein the biomarker is a biomarker represented in any one or more of Table I, Table IV, Table V, and Table VI; and (b) comparing the level of expression or activity of the biomarker in the test sample to a baseline level of biomarker expression or activity established from a control sample. Detection of a statistically significant difference in the biomarker expression or activity in the test sample, as compared to the baseline level of biomarker expression or biological activity, is an indicator of the presence of tumor cells or the potential therefore in the test sample as compared to cells in the control sample.

In one aspect of this embodiment, the step of detecting comprises detecting biomarker mRNA transcription by cells in the test sample. For example, such a step of detecting can be performed by a method selected from, but not limited to, polymerase chain reaction (PCR), reverse transcriptase-PCR (RT-PCR), in situ hybridization, Northern blot, sequence analysis, gene microarray analysis, and detection of a reporter gene. In one aspect, the step of detecting comprises detecting biomarker protein in the test sample. For example, such a step of detecting can be performed by a method selected from, but not limited to, immunoblot, enzyme-linked immunosorbant assay (ELISA), radioimmunoassay (RIA), immunoprecipitation, immunohistochemistry and immunofluorescence. In one aspect, the step of detecting comprises detecting biomarker biological activity in the test sample. For example, such a step of detecting can be performed by a method selected from, but not limited to, measuring proliferation of cells expressing the biomarker, measuring angiogenic sprouting of cells expressing the biomarker, and measuring migration and invasion ability of endothelial cells expressing the biomarker.

In one aspect of this embodiment, the test sample is from a source selected from the group consisting of: breast, kidney, ovary, colon, and uterus, in the patient. In another aspect, the test sample is from a patient being diagnosed for cancer and wherein the baseline level is established from a negative control sample that is established as non-tumorigenic.

In one aspect, the baseline level is established by a method selected from the group consisting of: (1) establishing a baseline level of biomarker expression or activity in an autologous control sample from the patient, wherein the autologous sample is from a same cell type, tissue type or bodily fluid type as the test sample of step (a); (2) establishing a baseline level of biomarker expression or activity from at least one previous detection of biomarker expression or activity in a previous test sample from the patient, wherein the previous test sample was of a same cell type, tissue type or bodily fluid type as the test sample of step (a); and, (3) establishing a baseline level of biomarker expression or activity from an average of control samples of a same cell type, tissue type or bodily fluid type as the test sample of step (a), the control samples having been obtained from a population of matched individuals.

Yet another embodiment of the invention relates to an assay kit for assessing angiogenesis or the presence of tumor cells in a patient, comprising: (a) a reagent for detecting the expression or activity of a biomarker in a test sample, wherein the biomarker is a biomarker represented in any one or more of Table I, Table IV, Table V, and Table VI; and (b) a reagent for detecting a control marker characteristic of a cell or tissue type that is in the test sample or that is secreted into the test sample by the cell or tissue. In one aspect, the reagent of (a) is selected from the group consisting of: a hybridization probe of at least about 8 nucleotides that hybridizes under stringent hybridization conditions to a nucleic acid molecule encoding the biomarker or a fragment thereof; an oligonucleotide primer for amplification of mRNA encoding the biomarker or a fragment thereof; and an antibody that selectively binds to the biomarker. In one aspect, the reagent of (b) is selected from the group consisting of: a hybridization probe of at least about 8 nucleotides that hybridizes under stringent hybridization conditions to a nucleic acid molecule encoding the control marker or a fragment thereof; an oligonucleotide primer for amplification of mRNA encoding the control marker or a fragment thereof; and an antibody that selectively binds to the control marker. In one aspect, the reagents of (a) and (b) are suitable for use in a method of detection selected from the group consisting of immunohistochemistry and immunofluorescence.

Yet another embodiment of the invention relates to a method to reduce angiogenesis in cells or a tissue of a patient, comprising decreasing the expression or biological activity of Microfibril-associated glycoprotein-2 (MAGP-2) in the cells or tissue.

Another embodiment of the invention relates to a method to promote angiogenesis in cells or a tissue of a patient, comprising increasing the expression or biological activity of MAGP-2 in the cells or tissue.

Another embodiment of the invention relates to the use of MAGP-2 or a fragment or homologue thereof, or a nucleic acid molecule encoding MAGP-2 or a fragment or homologue thereof, or an agonist or antagonist of MAGP-2, in the preparation of a medicament for the regulation of angiogenesis.

BRIEF DESCRIPTION OF THE FIGURES OF THE INVENTION

FIG. 1A is a bar graph shows DNA synthesis (determined by measuring [$^3$H]thymidine incorporation into cellular DNA) in serum-starved MB114 cells stably expressing either GFP or various putative angiogenic agents, stimulated in the absence or presence of either bFGF (50 ng/ml) or EGF (10 ng/ml) for 24 h at 37° C. (data are the mean (±SEM) of five independent experiments for MAGP-2 and SMOC-2, and of three independent experiments of CRELD-2; *, $p<0.05$; Student's T-Test).

Figure 2A:
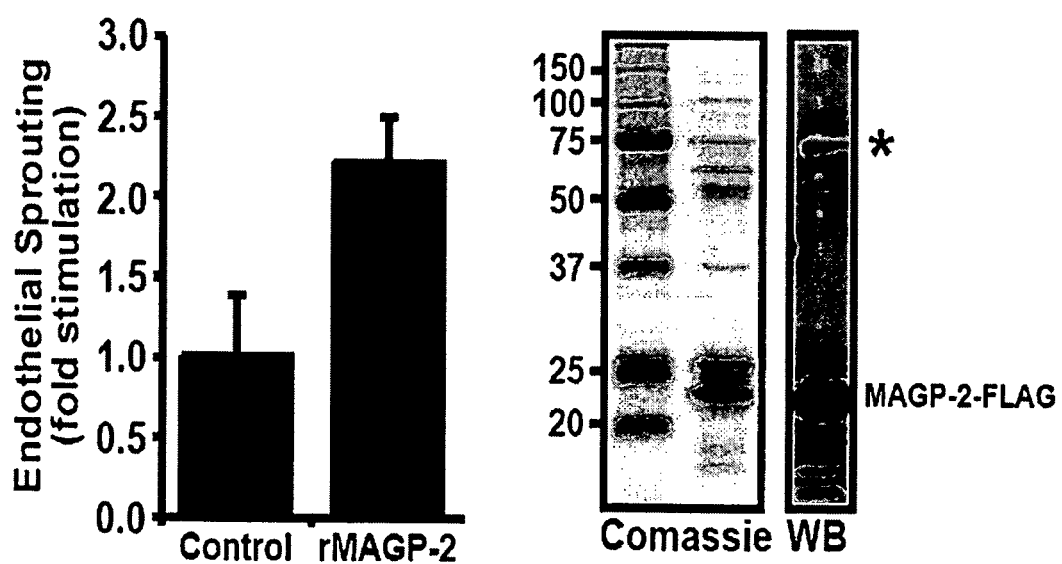
FIG. 2A shows that MAGP-2 (MAGP-2 purity was monitored by coomassie staining, and by immunoblotting with anti-FLAG M2 monoclonal antibodies (right panel)) promotes angiogenesis in vivo, as measured by angiogenic sprouting of quiescent MB114 cell monolayers (left panel) (data are the mean (±SEM) of two independent experiments; *, $p<0.05$; Student's T-Test).
Figure 2B:
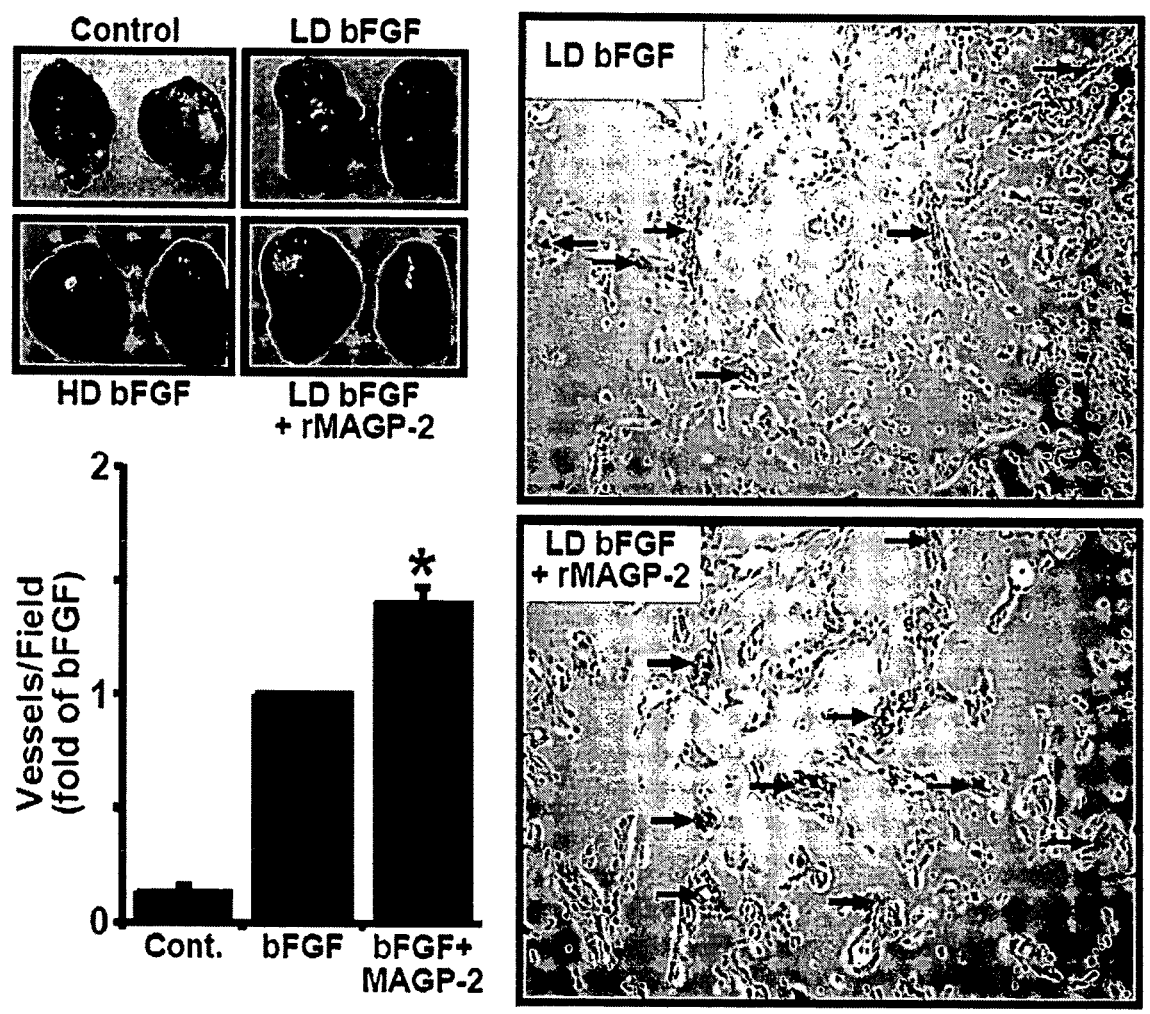

FIG. 2B shows the results of subcutaneous injection of C57BL/6 female mice with Matrigel supplemented either with diluent (D), bFGF (50 ng/ml, LD; or 300 ng/ml, HD), or bFGF (50 ng/ml) in combination with MAGP-2 (1 µg/ml), where plugs were harvested and photographed (left panels), and then fixed, sectioned, and stained with Masson's trichrome to visualize infiltrating blood vessels (right panels; arrows denote blood vessels) (data are the mean (±SEM) of four independent experiments; *, , *, $p<0.05$; Student's Test).

Figure 3A:
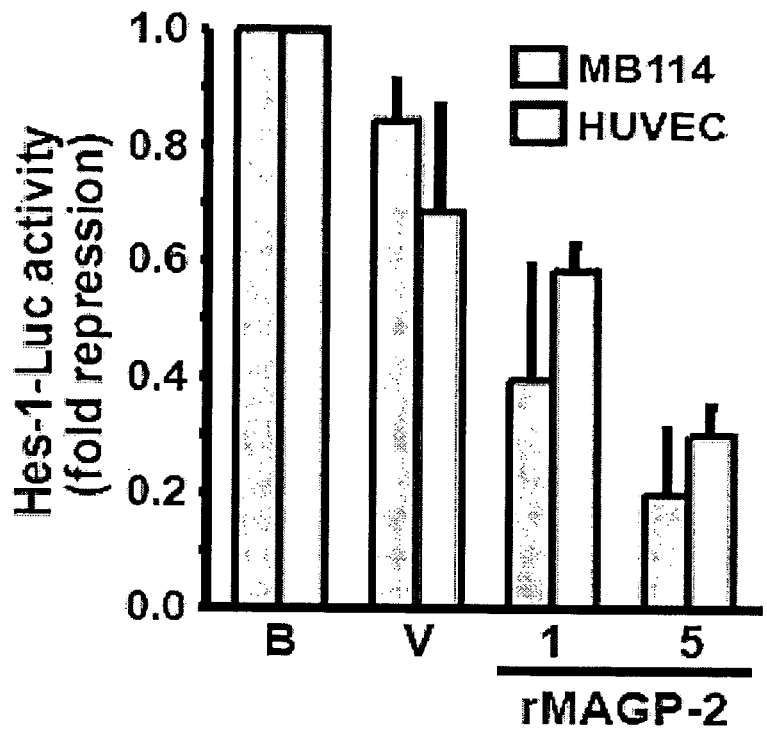

FIG. 3A is a bar graph showing that MAGP-2 inhibits Hes-1 promoter activity in ECs (data are mean (±SEM) of 2 independent experiments).

Figure 3B:
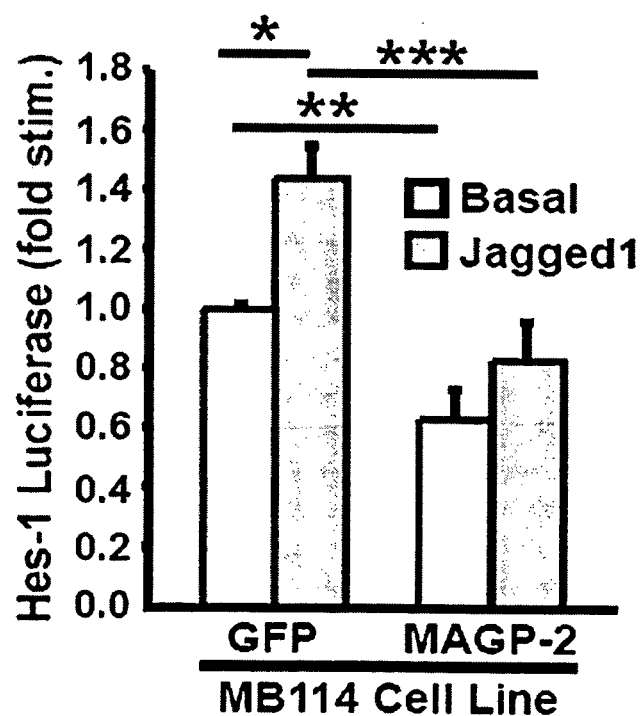

FIG. 3B is a bar graph also showing that MAGP-2 inhibits Hes-1 promoter activity in ECs (data are the mean (±SEM) of four independent experiments; *, , *, $p<0.05$; Student's Test).

Figure 4A:
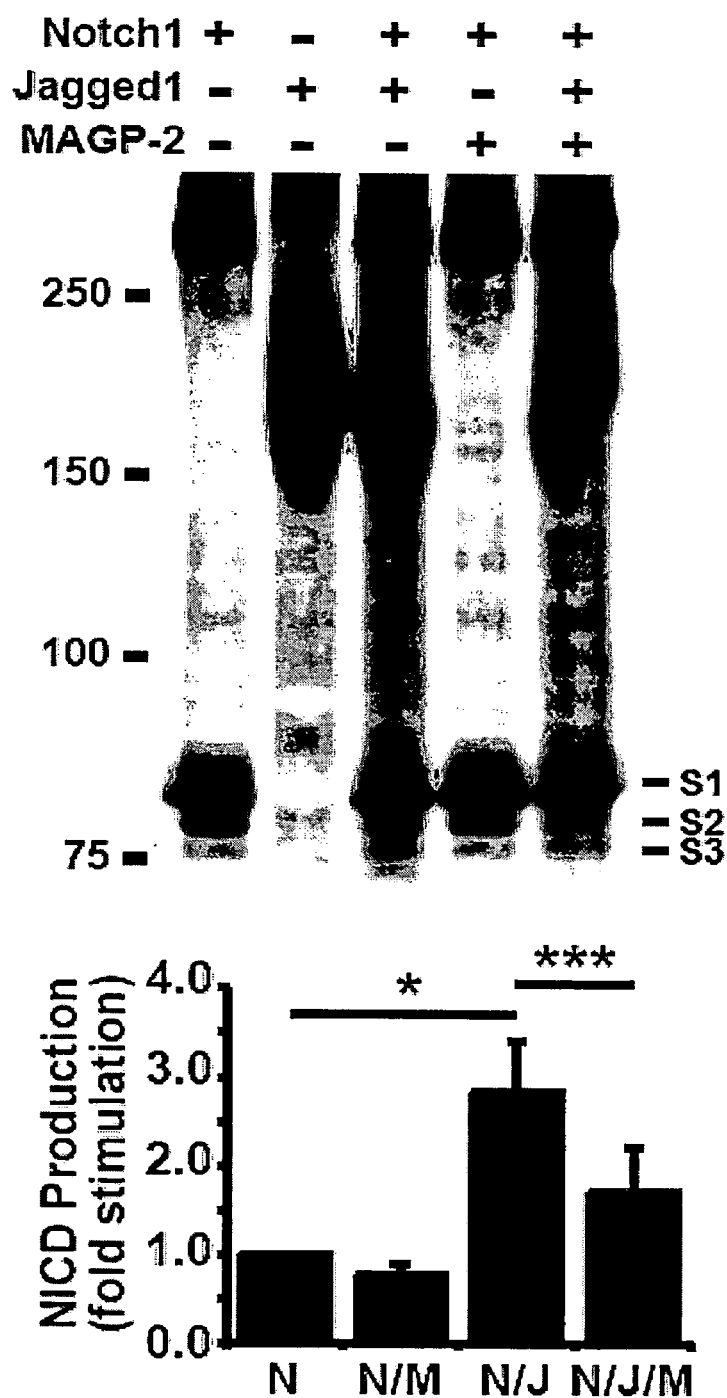

FIG. 4A shows Notch1 cleavage products (upper) and the densitometric analysis of Notch1 NICD production in response to experimental treatments (lower) in human 293T cells transiently transfected with cDNAs encoding Myc-tagged versions of Notch1, Jagged-1, and MAGP-2 in all combinations as indicated (data are the mean (±SEM) of four independent experiments; *, **, $p<0.05$; Student's T-Test; N, Notch1; N/M, Notch1 plus MAGP-2; N/J, Notch1 plus Jagged-1; N/J/M, Notch1, Jagged-1, and MAGP-2).

Figure 4B:
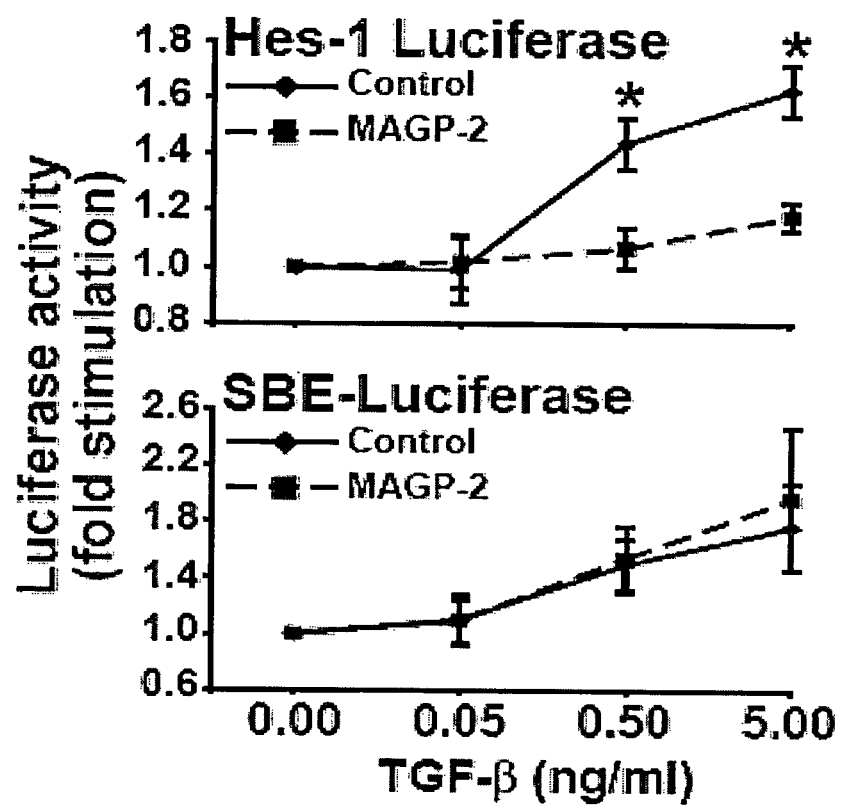

FIG. 4B shows luciferase activity after stimulation with TGF-β1 in GFP- and MAGP-2-expressing MB114 cells transiently transfected with either pHes1- or pSBE-luciferase, both together with pCMV-β-gal as indicated (data are the mean (±SEM) of 3 independent experiments; *, $p<0.05$; Student's T-Test).

Figure 5A:
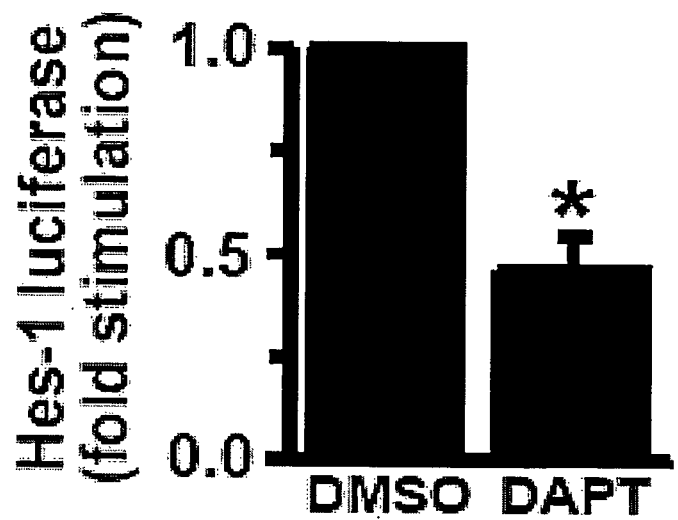

FIG. 5A is a bar graph showing Hes-1 luciferase activity in MB114 cells transiently transfected with pHes1-luciferase and pCMV-β-gal cDNAs, incubated overnight in the absence or presence of DAPT (10 µM) (data are the mean (±SEM) of two independent experiments).

Figure 5B:
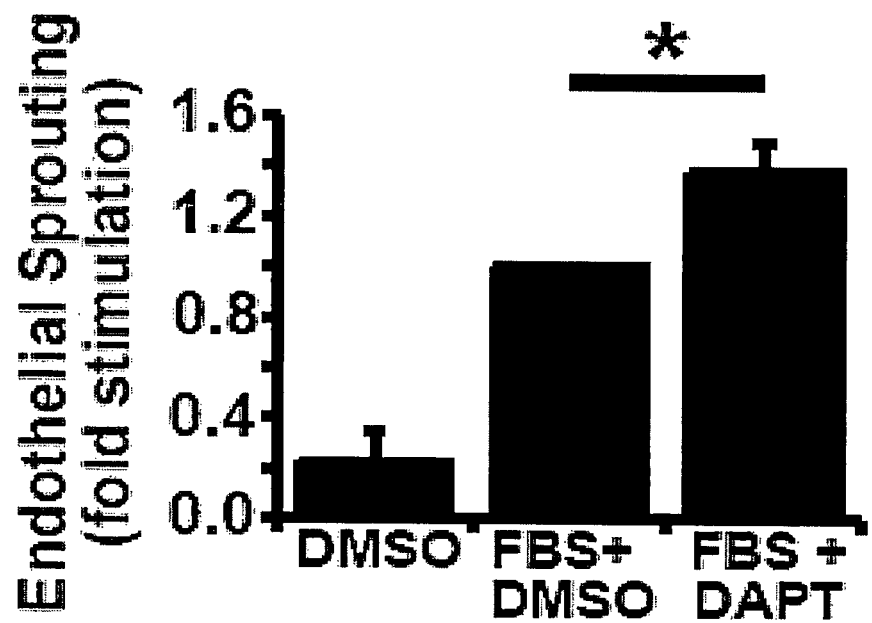

FIG. 5B is a bar graph showing endothelial angiogenic sprouting in quiescent MB114 cell monolayers induced to form angiogenic sprouts by addition of 10% FBS supplemented with or without DAPT (10 µM) (data are the mean (±SEM) of four independent experiment. (*, $p<0.05$; Student's T-Test)).

Figure 5C:
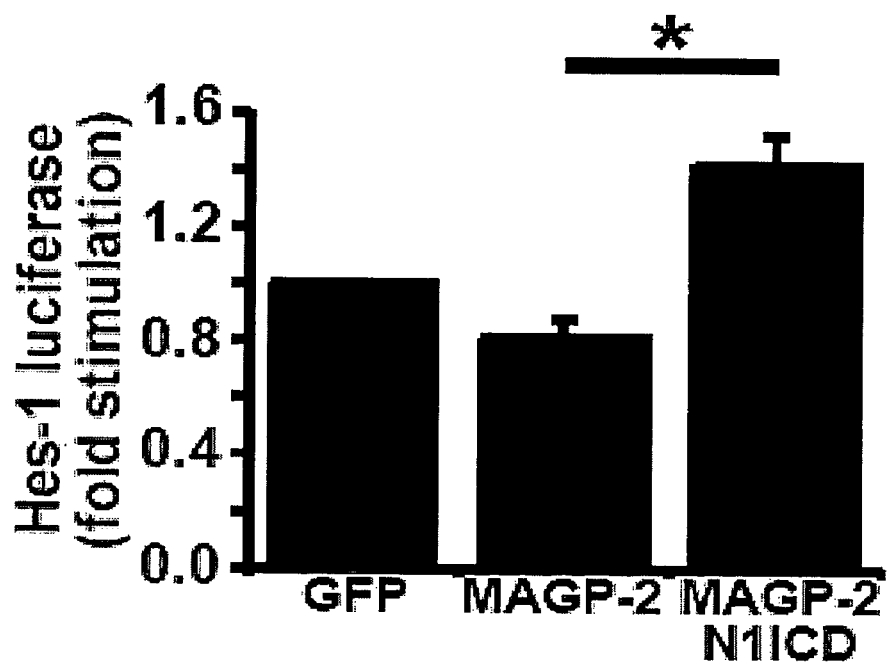

FIG. 5C is a bar graph showing Hes-1 luciferase activity in GFP-, MAGP-2-, and MAGP-2/N1ICD-expressing MB114 cells transiently transfected with pHes1-luciferase and pCMV-β-gal cDNAs (data are the mean (±SEM) of two independent experiments).

Figure 5D:
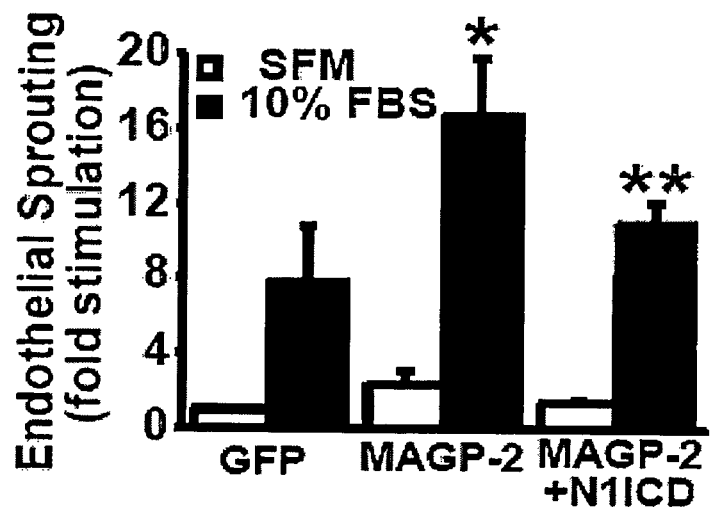
Figure 5D:
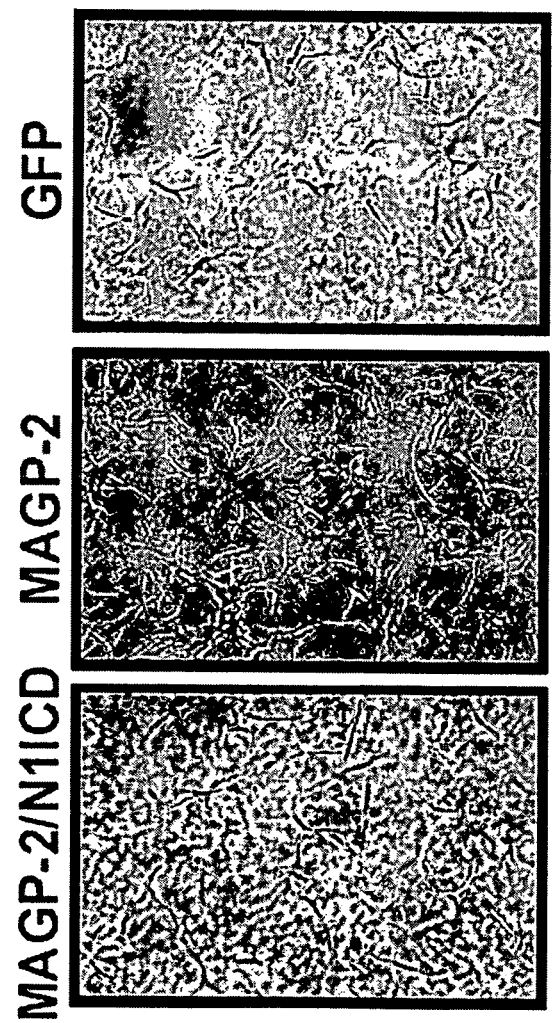

FIG. 5D is a bar graph showing endothelial angiogenic sprouting in quiescent monolayers of GFP-, MAGP-2-, and MAGP-2/N1ICD-expressing MB114 cells (bottom shows representative photomicrographs of angiogenic sprouts produced by GFP-, MAGP-2-, and MAGP-2/N1ICD-expressing MB114 cells; data are the mean (±SEM) of four independent experiments; *, **, $p<0.05$; Student's T-Test).

Figure 6:
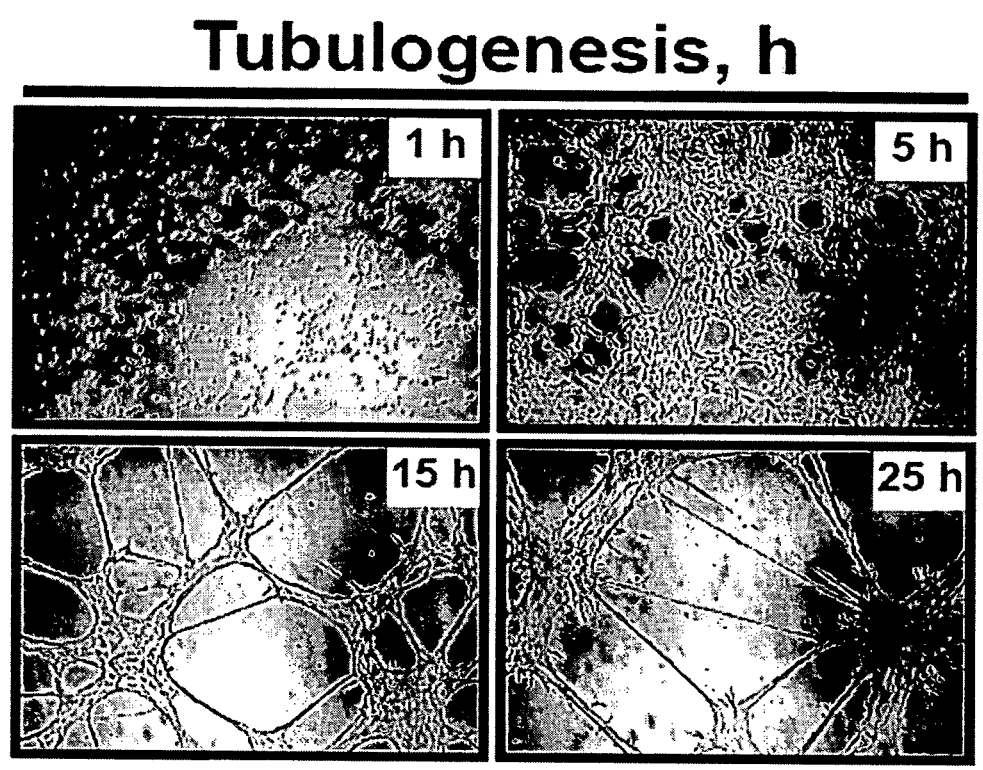

FIG. 6 is a digitized image showing the time course of angiogenesis in vitro.

Figure 7A:
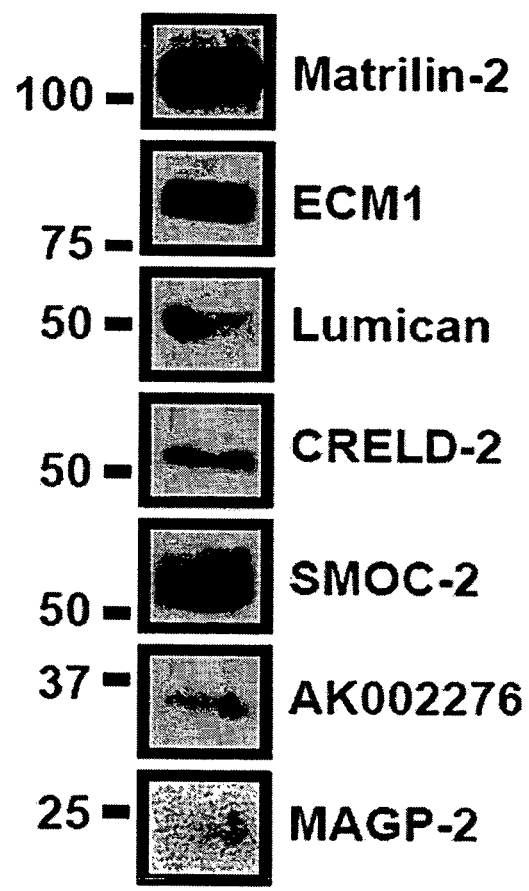
Figure 7B:
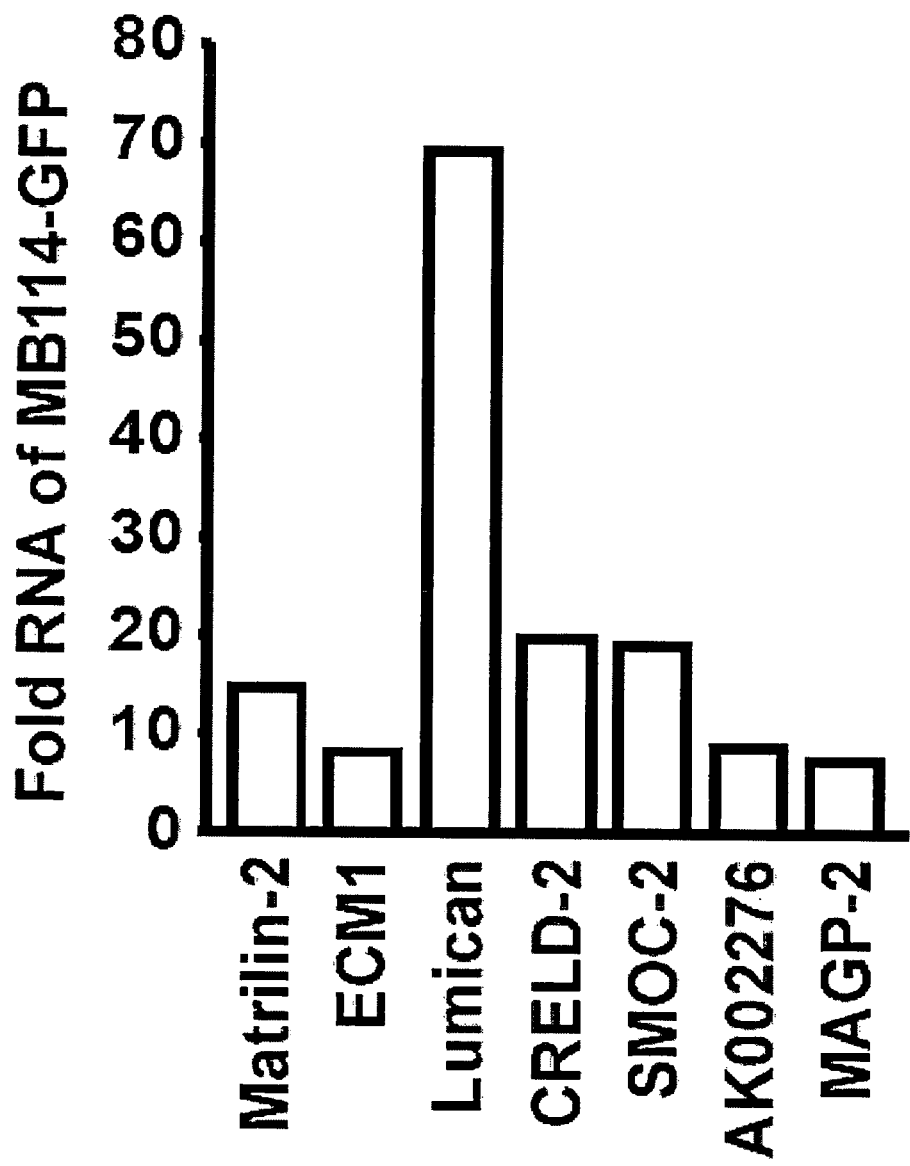

FIGS. 7A and 7B show retroviral expression of selected potential angiogenic proteins in MB114 cells via detergent-solubilized cell extracts (FIG. 7A) and semi-quantitative real-time PCR (FIG. 7B).

Figure 8:
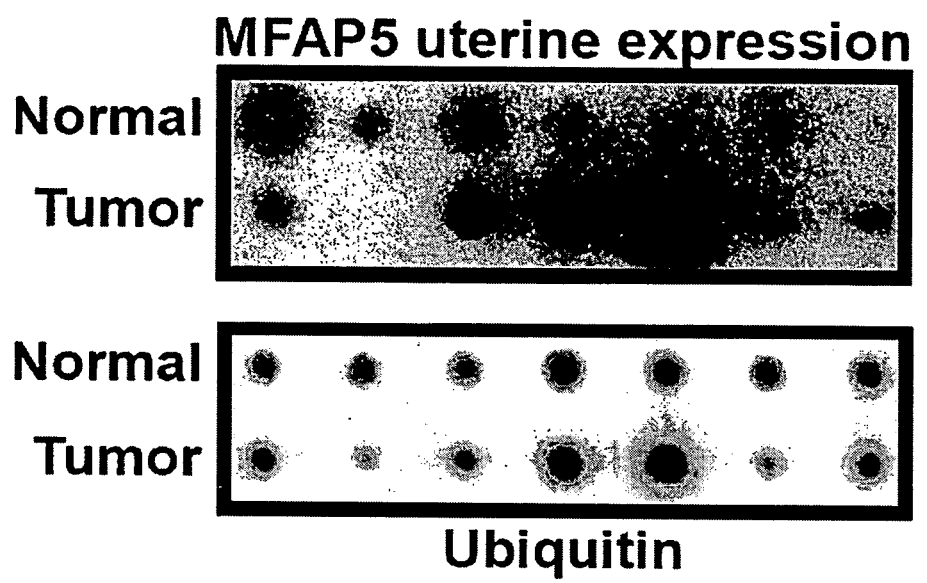

FIG. 8 is a digitized image showing that MAGP-2 is expressed aberrantly in a majority of human uterine tumors.

DETAILED DESCRIPTION OF THE INVENTION

The present invention generally relates to the discovery by the present inventor of several genes, and the proteins encoded thereby, that are associated with angiogenesis. More particularly, the present inventors used microarray analyses to monitor changes in the transcriptome of ECs undergoing angiogenesis when cultured onto tumor-derived basement membranes in vitro. In doing so, the inventors identified 308 genes whose expression was altered at least 3-fold during the angiogenic time course. Of these differentially-expressed genes, 63 encoded for EC secretory proteins and several were shown to mediate pro- or anti-angiogenic activities in vitro (e.g., SMOC-2, secreted MAGP-2 Promotes Angiogenesis modular calcium-binding protein-2; CRELD-2, cysteine-rich with EGF-like domains-1; MAGP-2, microfibril-associated glycoprotein-2; lumican; ECM-1, extracellular matrix protein-1). Expression of one of these genes, MAGP-2 (also known as Microfibrillar associated protein-5 (MFAP-5)), enhanced EC proliferation and p38 MAPK activation stimulated by bFGF, as well as stimulated EC invasion through synthetic basement membranes. The inventors have also demonstrated that MAGP-2 promoted EC sprouting in vitro, and as such, stimulated vessel formation and infiltration into Matrigel plugs implanted into genetically normal mice. Importantly, the inventors show herein that Notch1 activation prevented angiogenesis in vitro, a reaction that was overcome by MAGP-2-mediated antagonism of Notch1 signaling in ECs. Collectively, the inventors' findings have established MAGP-2 as a novel inducer of angiogenesis, doing so in part through its ability to antagonize Notch1 signaling in ECs. In addition, the inventors' findings have identified several additional targets for use in diagnostic, drug discovery and therapeutic applications related to the inhibition or promotion of angiogenesis.

More particularly, in order to increase the understanding of the role of ECs in mediating the remodeling of tumor and vascular microenvironments during pathological angiogenesis, the inventors cultured ECs on tumor-derived basement membranes to induce angiogenesis in vitro, and subsequently performed microarray analyses to identify alterations within the EC transcriptome that accompanied angiogenesis activation. In doing so, they focused specifically on genes that encoded secretory proteins or components of the ECM, which collectively comprised 20% (i.e., 63 out of 308 genes) of the differentially-expressed EC genes identified by the inventors (Table I). The analyses described herein also identified an additional 35 (~11%) membrane-spanning and/or membrane-associated genes, whose expression and activation likely mediate paracrine and/or autocrine signaling in angiogenic ECs. Thus, secreted molecules constituted a significant fraction (~31%) of all differentially regulated EC genes identified herein, thereby highlighting the importance of microenvironment remodeling during angiogenesis. The proportion of differentially-expressed EC genes classified as secretory proteins was similar to those observed in other recent EC transcriptome analyses (Aitkenhead et al, 2002; Bell et al, 2001; Kahn et al, 2000). However, unlike these profiling studies, the present inventors specifically investigated the inductive effect of tumor-derived basement membranes (i.e., Matrigel matrices) in regulating gene expression in tubulating ECs, and as such, numerous secretory proteins not previously associated with angiogenesis were identified (see Table I). Moreover, the inventors' identification of known angiogenic genes (Table I) validated this experimental design and gave credence to the notion that many of these newly identified genes may function as bone fide regulators of angiogenesis. Indeed, the present inventors' findings implicate ECM-1 and lumican as mediators of angiostasis, while CRELD-2 and SMOC-2 are proposed herein to function as novel mediators of angiogenesis (see discussion below). The ability of these EC secretory proteins to affect vessel development in vivo, as well as the molecular mechanisms whereby they mediate their pro- or anti-angiogenic activities in ECs can now be evaluated using the guidance provided herein.

An especially important finding of the present study was the inventors' identification of MAGP-2 as a novel mediator of angiogenesis. Indeed, the present inventors show for the first time that MAGP-2 expression stimulates EC proliferation, invasion, and angiogenic sprouting, as well as enhances EC activation of p38 MAPK in response to bFGF and EGF (FIG. 1). Moreover, MAGP-2 is shown to enhance the ability of bFGF to promote neovascularization and vessel infiltration into Matrigel plugs implanted into genetically normal mice (FIG. 2). Mechanistically, MAGP-2 is shown to induce angiogenesis through its ability to inhibit Notch1 processing and activation (FIGS. 3 and 4), an inhibitory reaction that is rescued by constitutive expression of Notch1 NICD (FIG. 5). Collectively, these findings have established MAGP-2 as a novel activator of angiogenesis, doing so in part via its ability to inhibit the Notch1 signaling pathway.

The precise mechanism whereby MAGP-2 antagonizes Notch1 signaling remains to be determined Recent studies using heterologous cell expression systems have shown MAGP-2 to interact physically with Notch1 and its ligand, Jagged-1, resulting in their shedding from the cell surface (Miyamoto et al, 2006; Nehring et al, 2005). Although the inventors made no attempt to measure Notch1 and/or Jagged-1 extracellular domain shedding in response to MAGP-2, the production of such soluble Notch1 and Jagged-1 extracellular domains readily inhibits Notch signaling (Rebay et al, 1993; Small et al, 2001). In this fashion, MAGP-2 expression was observed to block the ability of Jagged-1 to stimulate Notch1 processing and the production of NICD, thereby preventing transactivation of the Hes1 promoter in ECs. Thus, MAGP-2 may promote angiogenesis in part by inducing Notch1 and/or Jagged-1 ectodomain shedding in ECs. In contrast to the present inventors' findings, Miyamoto et al (Miyamoto et al, 2006) recently found that MAGP-2 not only induces Notch1 ectodomain shedding in Cos-7 and NIH-3T3 cells, but also Notch1 processing and NICD production, leading to transcriptional activation of the Hes5 and CSL promoters. The reasons underlying this discrepancy are currently unknown, but most likely reflect differences in the cell types studied (i.e., ECs versus fibroblasts and kidney epithelial cells), as well as differences in microenvironmental factors that may influence the interactions between MAGP-2 and Notch1. In addition, cell-type specific expression of various Notch receptor and ligand combinations may also impact the ability of MAGP-2 to regulate, either positively or negatively, Notch signaling in responsive cells. Indeed, the present inventors, without being bound by theory, believe that MAGP-2 regulates angiogenesis in a context-specific manner via its ability to target both Notch signaling and elastin microfibril networks.

The present inventors' findings demonstrating the ability of MAGP-2 to stimulate angiogenesis by preventing Notch1 activation is intellectually credible in light of the established function of Notch in mediating angiostasis (Leong et al, 2002; Liu et al, 2006; Noseda et al, 2004; Williams et al, 2006; Zimrin et al, 1996). Moreover, the inventors recently observed MAGP-2 expression to be abnormally elevated in human uterine cancers (Example 6), and to significantly increase the growth and vascularization of MCA102 fibrosarcomas produced in mice (Albig and Schiemann, unpublished observation). It should be noted, however, that Notch activation also has been shown to stimulate angiogenesis (Leong and Karsan, 2005; Shawber and Kitajewski, 2004), and as such, it cannot yet be ascertained whether MAGP-2 promotes tumorigenesis by alleviating Notch1-mediated angiostasis, or by facilitating Notch1-mediated angiogenesis. The mechanisms whereby Notch mediates such disparate activities in ECs remains unclear, but may reflect a complex integration of cellular and environmental cues. Indeed, Notch signaling is subject to regulation by (i) the relative expression levels of various Notch receptors (Delaney et al, 2005; Duarte et al, 2004); (ii) the extent and form of Notch receptor glycosylation (Haines and Irvine, 2003); (iii) the availability of various Notch ligands within vascular microenvironments; and (iv) the activation of various Notch inhibitors, including MINT, Numb, NRARP, and proteolyzed ligands (Kadesch, 2004). The present inventors' findings herein and those by others (Miyamoto et al, 2006; Sakamoto et al, 2002) clearly show Notch signaling to be influenced by environmental cues, such as those produced by MAGP-2 (demonstrated herein).

Numerous additional EC secretory proteins were identified whose expression was also regulated by angiogenesis (Tables I and VI), suggesting that EC expression of these genes was obligatory for vessel development. Moreover, in vitro assays that modeled key steps in the angiogenic process showed that several these newly identified genes did indeed regulate EC activities-coupled to angiogenesis. For instance, lumican expression was found to inhibit MB114 cell proliferation (data not shown) and angiogenic sprouting (FIG. 1), as well as reduce the ability of bFGF and EGF to activate p38 MAPK in MB114 cells (FIG. 1). Lumican belongs the SLRP (small leucine-rich proteoglycan) family of ECM proteins, which also includes fibromodulin, biglycan, and the angiogenesis antagonist, decorin (Davies Cde et al, 2001; Kao et al, 2006; Sulochana et al, 2005). Genetic ablation of lumican in mice indicates that this secreted proteoglycan functions in organizing collagen fibrils in the skin and cornea (Chakravarti et al, 1998). Additionally, lumican interacts physically with FasL (Fas-ligand), leading to enhanced Fas expression in and subsequent apoptosis of corneal fibroblasts (Vij et al, 2004; Vij et al, 2005). Recently, elevated lumican expression has been associated with cancers of the pancreas (Ping Lu et al, 2002), breast (Leygue et al, 1998), cervix (Naito et al, 2002), and colon (Lu et al, 2002), suggesting that lumican may promote tumorigenesis in these organs. In stark contrast, lumican expression also has been shown to inhibit the anchorage-independent growth and invasion of B16F1 melanoma cells in vitro, as well as their ability to form tumors in when implanted into mice (Vuillermoz et al, 2004). Thus, lumican also may function in suppressing cancer development and progression. Along these lines, the inventors have found that lumican antagonizes the development and infiltration of vessels in Matrigel plugs implanted into mice, as well as decreases the growth and blood vessel density of MCA102 fibrosarcomas produced in mice (Albig and Schiemann, unpublished observations).

The inventors further showed that ECM-1 is functionally similar to lumican and antagonized angiogenic sprouting by MB114 cells (FIG. 1). ECM-1 is a broadly distributed glycoprotein that plays important roles in maintaining normal skin structure, function, and homeostasis (Chan, 2004). In humans, loss of function mutations in ECM-1 elicit a rare genetic skin disease called lipoid proteinosis (Chan, 2004; Hamada et al, 2002), whose clinicopathological features are phenocopied in patients with lichen sclerosus, an acquired inflammatory disorder of the skin and mucous membranes associated with the development self-reactive ECM-1 antibodies (Oyama et al, 2003). Interestingly, both skin conditions are characterized by the (i) abnormal development of cutaneous microvessels, and (ii) excessive deposition of basement membrane proteins, leading to thickened mucous and vascular basement membranes (Kowalewski et al, 2005). ECM-1 overexpression is observed in cancers of the breast, esophagus, thyroid, stomach, and colon (Han et al, 2001; Kebebew et al, 2005; Wang et al, 2003), and has been associated with the acquisition of angiogenic (Han et al, 2001) and metastatic phenotypes (Wang et al, 2003). Thus, ECM-1 is an important regulator of basement membrane protein secretion and deposition, and quite possibly, of microenvironment remodeling (Kowalewski et al, 2005; Mirancea et al, 2006). As such, aberrant ECM-1 production likely dysregulates normal microenvironment conditions operant in balancing pro- and anti-angiogenic signals, leading to altered vessel formation and disease development in humans.

In contrast to lumican and ECM-1, the inventors observed CRELD-2 expression to significantly increase MB114 cell invasion, and to promote a trend towards enhanced angiogenic sprouting (FIG. 1), indicating that this secreted EGF-like domain containing protein may serve to enhance angiogenesis. Along these lines, the inventors found SMOC-2 expression to enhance the proliferative response of MB114 cells to bFGF, and more importantly, to increase MB114 cell invasion and angiogenic cell sprouting (FIG. 1). SMOC-2 and its related molecule, SMOC-1, are widely expressed glycoproteins that localize predominantly to basement membranes, and to various ECM structures (Vannahme et al, 2003; Vannahme et al, 2002). Structurally, SMOCs are defined by a unique, centrally located SMOC domain that is flanked N-terminally by follistatin-like and thyroglobulin-like domains, and C-terminally by an extracellular calcium-binding (EC) domain reminiscent of that found in SPARC (Vannahme et al, 2003; Vannahme et al, 2002). Interestingly, proteolytic cleavage of SPARC results in the release of biologically active fragments that can induce angiogenesis (Funk and Sage, 1993; Sage et al, 2003). SPARC, however, also mediates angiostasis by interacting physically with VEGF via its EC domain (Jendraschak and Sage, 1996; Kupprion et al, 1998). Thus, given the functional and structural similarities between SMOC-2 and SPARC, it remains to be determined whether SMOC-2 also mediates pro- and anti-angiogenic activities, and if so, whether these disparate EC activities occur via direct or indirect mechanisms.

Collectively, the inventors' findings indicate that lumican and EMC-1 function as novel angiogenesis antagonists, while CRELD-2 and SMOC-2 function as novel angiogenesis agonists. The molecular mechanisms underlying their ability to impact the activation or resolution of angiogenesis can now be determined.

The present invention more particularly relates to genes, nucleic acid molecules derived therefrom, and proteins or fragments thereof encoded by such genes and nucleic acid molecules, as well as homologues of such genes and proteins and related agents (e.g., antibodies, agonists, antagonists), and the use or targeting of such genes, nucleic acids, proteins, homologues and/or related agents, and/or compositions or formulations comprising the same, in methods related to the inhibition or promotion of angiogenesis, including the inhibition of angiogenesis for the inhibition or treatment of cancer. As discussed above, the present inventors identified 308 genes whose expression in angiogenic ECs was altered≥3-fold. Of these differentially-expressed genes, 63 genes (~20%) encoded EC secretory proteins (Table I), 35 genes (~11%) encoded transmembrane or membrane-associated proteins (Table V), and 210 genes encoded non-secretory proteins (Table IV). This approach identified several secretory proteins that were previously known to be associated with angiogenesis and/or microenvironment remodeling, including ADAMTS1 (Iruela-Arispe et al, 2003), CTGF (Brigstock, 2002), HGF (Gao and Vande Woude, 2005), MMPs 3 and 9 (Heissig et al, 2003), thrombospondins 1 and 2 (Armstrong and Bornstein, 2003), and TIMP3 (Qi et al, 2003) (Table I, bold type face). In addition, the inventors identified numerous secretory proteins not previously associated with angiogenesis (e.g., Table I, regular text face), all of which are encompassed by the present invention. The inventors verified the differential expression of 19 individual genes by semi-quantitative real-time PCR (see Materials and Methods). These analyses showed significant concordance in the expression profiles measured either by real-time PCR or microarray analyses (Table VI), indicating that these (and other) genes are indeed bona fide targets of angiogenic signaling systems in tubulating ECs.

Accordingly genes that are encompassed by the present invention (as well as nucleic acid molecules derived from or comprising at least a portion of the coding region and/or regulatory region of such genes and any proteins or fragments thereof encoded by such genes) include any of the genes or portions of genes (including ESTs) represented in Table I, Table IV, Table V, and/or Table VI. Preferred genes for use in the present invention include any of the genes presented in regular (non-bold)-type face in Table I or Table V and/or any of the genes in Table VI. The invention also includes the use of nucleic acid molecules derived from or comprising at least a portion of the coding region and/or regulatory region of such genes and any proteins or fragments thereof encoded by such genes. Particularly preferred genes for use in the present invention include any of the genes in Table VI. The invention also includes the use of nucleic acid molecules derived from or comprising at least a portion of the coding region and/or regulatory region of such genes and any proteins or fragments thereof encoded by such genes.

In one embodiment, the invention includes the use of genes encoding any one or more of the following proteins, the genes or nucleic acid sequences therein, or primers used to amplify and identify such genes being identified in Table I and/or Table III and/or Table VI:

murine ADAMts7 (encoded by a gene comprising the nucleic acid sequence found in GenBank Accession No. AL359939), human ADAMts7 (encoded by a gene comprising the nucleic acid sequence found in GenBank Accession No. AF140675), murine CRELD-2 or the human equivalent thereof (murine CRELD-2 encoded by a gene comprising the nucleic acid sequence found in GenBank Accession No. AK017880), murine Decorin (encoded by a gene comprising the nucleic acid sequence found in GenBank Accession No. NM_007833), human Decorin (encoded by a gene comprising the nucleic acid sequence found in GenBank Accession No. AH002681), murine ECM1 (encoded by a gene comprising the nucleic acid sequence found in GenBank Accession No. NM_007899), human ECM1 (encoded by a gene comprising the nucleic acid sequence found in GenBank Accession No. NP_001415), murine Inhibin β-b (encoded by a gene comprising the nucleic acid sequence represented herein by SEQ ID NO:97 or SEQ ID NO:98)

human Inhibin β-b (encoded by a gene comprising the nucleic acid sequence found in GenBank Accession No. NM_002193), murine Integrin α-3 (encoded by a gene comprising the nucleic acid sequence represented herein by SEQ ID NO:99 or SEQ ID NO:100), human Integrin α-3 (encoded by a gene comprising the nucleic acid sequence found in GenBank Accession No. E16082), murine Integrin α-6 (encoded by a gene comprising the nucleic acid sequence represented herein by SEQ ID NO:101 or SEQ ID NO:102), human Integrin α-6 (encoded by a gene comprising the nucleic acid sequence found in, for example, GenBank Accession No. AH008066), murine Lipocalin-7 (encoded by a gene comprising the nucleic acid sequence found in GenBank Accession No. BC005738 and represented herein by SEQ ID NO:103 or SEQ ID NO:104), human Lipocalin-7 (encoded by a gene comprising the nucleic acid sequence found in GenBank Accession No. NM_022164), murine Loxl-3 (encoded by a gene comprising the nucleic acid sequence found in GenBank Accession No. NM_013586, the amino acid sequence encoded by which is represented herein by SEQ ID NO:40), human Loxl-3 (encoded by a gene comprising the nucleic acid sequence found in GenBank Accession No. AAH71865, the amino acid sequence encoded by which is represented herein by SEQ ID NO:41), murine Lumican (encoded by a gene comprising the nucleic acid sequence found in GenBank Accession No. AK014312), human Lumican (encoded by a gene comprising the nucleic acid sequence found in GenBank Accession No. AF239660), murine MAGP-2 (encoded by a gene comprising the nucleic acid sequence found in GenBank Accession No. NM_015776 and represented herein by SEQ ID NO:123, the amino acid sequence encoded by which is represented herein by SEQ ID NO:42), human MAGP-2 (encoded by a gene comprising the nucleic acid sequence found in GenBank Accession No. AAC83942 and represented herein by SEQ ID NO:124, the amino acid sequence encoded by which is represented herein by SEQ ID NO:43), murine Matrilin-2 (encoded by a gene comprising the nucleic acid sequence found in GenBank Accession No. BC005429), human Matrilin-2 (encoded by a gene comprising the nucleic acid sequence found in GenBank Accession No. BC010444), murine Nephronectin (encoded by a gene comprising the nucleic acid sequence found in GenBank Accession No. AA223007 the amino acid sequence encoded by which is represented herein by SEQ ID NO:52), human Nephronectin (encoded by a gene comprising the nucleic acid sequence found in GenBank Accession No. NM_001033047, the amino acid sequence encoded by which is represented herein by SEQ ID NO:53), murine SerpinE2 (encoded by a gene comprising the nucleic acid sequence found in GenBank Accession No. NM_009255), human SerpinE2 (encoded by a gene comprising the nucleic acid sequence found in GenBank Accession No. BC042628), murine SMOC-2 (encoded by a gene comprising the nucleic acid sequence found in GenBank Accession No. NM_022315), and human SMOC-2 (encoded by a gene comprising the nucleic acid sequence found in GenBank Accession No. NM_022138).

The invention also includes the use of nucleic acid molecules derived from or comprising at least a portion of the coding region and/or regulatory region of such genes and any proteins or fragments thereof encoded by such genes, as well as agonists and antagonists of any of such proteins or genes.

In another embodiment, the invention includes the use of genes from Table V encoding any one or more of the following proteins:

murine 0610007C21Rik (GenBank Accession No. AK002276; encoding a protein represented herein by SEQ ID NO:1);

human apoptosis related protein APR-3 (GenBank Accession No. AF144055; encoding a protein represented herein by SEQ ID NO:2);

murine 1810014L12Rik (GenBank Accession No. NM_133706; encoding a protein represented herein by SEQ ID NO:3);

human 1810014L12Rik (GenBank Accession No. NP_055388; encoding a protein represented herein by SEQ ID NO:4);

murine Cd14 (GenBank Accession No. NM_009841; encoding CD14 antigen represented herein by SEQ ID NO:5);

human Cd14 (GenBank Accession No. NP_000638; encoding CD14 antigen represented herein by SEQ ID NO:6);

murine Cd38 (GenBank Accession No. BB256012; comprising a nucleic acid sequence represented herein by SEQ ID NO:7 and encoding CD38 antigen);

murine Cd53 (GenBank Accession No. NM_007651; encoding CD53 antigen represented herein by SEQ ID NO:8);

human Cd53 (GenBank Accession No. NP_000551; encoding CD53 antigen represented herein by SEQ ID NO:9);

murine Emp2 (GenBank Accession No. AF083076; encoding epithelial membrane protein represented herein by SEQ ID NO:10);

human Emp2 (GenBank Accession No. NP_001415; encoding epithelial membrane protein represented herein by SEQ ID NO:11);

murine Fcgrt (GenBank Accession No. NM_010189; encoding Fc receptor (IgG, alpha chain transporter) represented herein by SEQ ID NO:12);

human Fcgrt (GenBank Accession No. NP_004098; encoding Fc receptor (IgG, alpha chain transporter) represented herein by SEQ ID NO:13);

murine Islr (GenBank Accession No. NM_012043; encoding immunoglobulin superfamily containing leucine-rich repeat represented herein by SEQ ID NO:14);

human Islr (GenBank Accession No. NP_005536; encoding immunoglobulin superfamily containing leucine-rich repeat represented herein by SEQ ID NO:15);

murine Lrp2 (GenBank Accession No. C80829; comprising a nucleic acid sequence represented herein by SEQ ID NO:16 and encoding low density lipoprotein receptor-related protein 2);

human Lrp2 (GenBank Accession No. NP_004516; comprising a nucleic acid sequence represented herein by SEQ ID NO:17 and encoding low density lipoprotein receptor-related protein 2);

murine Ly6a (GenBank Accession No. BC002070; encoding lymphocyte antigen 6 complex, locus A represented herein by SEQ ID NO:18);

murine P2rx4 (GenBank Accession No. AJ251462; encoding purinergic receptor P2X, ligand-gated ion channel 4, represented herein by SEQ ID NO:19);

human P2rx4 (GenBank Accession No. Q99571; encoding purinergic receptor P2X, ligand-gated ion channel 4, represented herein by SEQ ID NO:20);

murine Pcdhb9 (GenBank Accession No. NM_053134; encoding protocadherin beta 9 represented herein by SEQ ID NO:21);

human Pcdhb9 (GenBank Accession No. AAI03495; encoding protocadherin beta 9 represented herein by SEQ ID NO:22);

murine Ptpre (GenBank Accession No. U35368; encoding protein tyrosine phosphatase receptor type E represented herein by SEQ ID NO:23);

human Ptpre (GenBank Accession No. NM_569119; encoding protein tyrosine phosphatase receptor type E represented by SEQ ID NO:24);

murine Slc4a3 (GenBank Accession No. NM_009208; encoding solute carrier family 4 (anion exchanger) member 3, represented herein by SEQ ID NO:25);

human Slc4a3 (GenBank Accession No. NP_005061; encoding solute carrier family 4 (anion exchanger) member 3, represented herein by SEQ ID NO:26);

murine Tmc6 (GenBank Accession No. BC004840; encoding transmembrane channel-like gene family 6 represented by SEQ ID NO:27).

and/or human Tmc6 (GenBank Accession No. AAH35648; encoding transmembrane channel-like gene family 6 represented herein by SEQ ID NO:28).

The invention also includes the use of nucleic acid molecules derived from or comprising at least a portion of the coding region and/or regulatory region of such genes and any proteins or fragments thereof encoded by such genes, as well as agonists and antagonists of any of such proteins or genes.

In another embodiment, the invention includes the use of genes from Table I encoding any one or more of the following proteins:

murine 9130213B05Rik (GenBank Accession No. BC006604; encoding a protein represented herein by SEQ ID NO:29);

murine C1s (GenBank Accession No. BC022123; encoding complement component 1, s subcomponent, represented herein by SEQ ID NO:34);

human C1s (GenBank Accession No. NM_001734; encoding complement component 1, s subcomponent, represented herein by SEQ ID NO:35);

murine C3 (GenBank Accession No. K02782; encoding complement component 3 represented herein by SEQ ID NO:30);

human C3 (GenBank Accession No. NP_000055; encoding complement component 3 represented herein by SEQ ID NO:31);

murine Cfh (GenBank Accession No. AI987976; comprising a nucleic acid sequence represented herein by SEQ ID NO: 32 and encoding complement component factor h);

human Cfh (GenBank Accession No. CAA30403; comprising a nucleic acid sequence represented herein by SEQ ID NO: 33 and encoding complement component factor h);

murine Col9a3 (GenBank Accession No. BG074456; comprising a nucleic acid sequence represented herein by SEQ ID NO:36 and encoding procollagen, type IX, alpha 3);

human Col9a3 (GenBank Accession No. Q14050; comprising a nucleic acid sequence represented herein by SEQ ID NO:37 and encoding procollagen, type IX, alpha 3);

murine Grem1 (GenBank Accession No. BC015293; encoding cysteine knot superfamily 1, BMP antagonist 1, represented herein by SEQ ID NO:38);

human Grem1 (GenBank Accession No. NP_037504; encoding cysteine knot superfamily 1, BMP antagonist 1, represented herein by SEQ ID NO:39);

murine Loxl3 (GenBank Accession No. NM_013586; encoding lysyl oxidase-like 3, represented herein by SEQ ID NO:40);

human Loxl3 (GenBank Accession No. AAH71865; encoding lysyl oxidase-like 3, represented herein by SEQ ID NO:41);

murine MAGP-2 (GenBank Accession No. NM_015776; comprising a nucleic acid sequence represented herein by SEQ ID NO:123 and encoding microfibril-associated glycoprotein-2 (also known as microfibrillar associated protein 5), represented herein by SEQ ID NO:42);

human MAGP-2 (GenBank Accession No. AAC83942; comprising a nucleic acid sequence represented herein by SEQ ID NO:124 and encoding microfibrillar associated protein 5, represented herein by SEQ ID NO:43);

murine Mglap (GenBank Accession No. NM_008597; encoding matrix gamma-carboxyglutamate (gla) protein represented herein by SEQ ID NO:44);

human Mglap (GenBank Accession No. AAP36640; encoding matrix gamma-carboxyglutamate (gla) protein represented herein by SEQ ID NO:45);

murine Naga (GenBank Accession No. BC021631; encoding N-acetyl galactosaminidase, alpha, represented herein by SEQ ID NO:46);

human Naga (GenBank Accession No. NP_000253; encoding N-acetyl galactosaminidase, alpha, represented herein by SEQ ID NO:47);

murine Nbl1 (GenBank Accession No. NM_008675; encoding neuroblastoma, suppression of tumorigenicity 1, represented herein by SEQ ID NO:48);

human Nbl1 (GenBank Accession No. AAL15440; encoding neuroblastoma, suppression of tumorigenicity 1, represented herein by SEQ ID NO:49);

murine Ngfb (GenBank Accession No. NM_013609; encoding nerve growth factor, beta, represented herein by SEQ ID NO:50);

human Ngfb (GenBank Accession No. AAH32517; encoding nerve growth factor, beta, represented herein by SEQ ID NO:51);

murine Npnt (GenBank Accession No. AA223007; encoding nephronectin and represented herein by SEQ ID NO:52);

human Npnt (GenBank Accession No. NM_001033047; encoding nephronectin and represented herein by SEQ ID NO:53);

murine Olfm1 (GenBank Accession No. C78264; encoding olfactomedin 1, represented herein by SEQ ID NO:54);

human Olfm1 (GenBank Accession No. Q99784; encoding olfactomedin 1, represented herein by SEQ ID NO:55);

and/or murine U90926 (GenBank Accession No. NM_020562; encoding a protein represented herein by SEQ ID NO:56).

The invention also includes the use of nucleic acid molecules derived from or comprising at least a portion of the coding region and/or regulatory region of such genes and any proteins or fragments thereof encoded by such genes.

The genes identified in the Tables herein are identified by name, by GenBank Accession numbers, and by description of the protein, when available. The amino acid sequence for several of the proteins encoded by the genes in the Tables herein are also provided herein. All information associated with the publicly available identifiers and accession numbers in any of the tables described herein, including the nucleic acid sequences of the genes and probes and the amino acid sequences of the proteins encoded thereby, is incorporated herein by reference in its entirety.

Genes and proteins identified in the present invention can also be referred to as "biomarkers". The term "biomarker" as used herein can refer to gene described herein or to the protein encoded by that gene, wherein the gene has been identified as being differentially regulated during angiogenesis. In addition, the term "biomarker" can be generally used to refer to any portion of such a gene or protein that can identify or correlate with the full-length gene or protein, for example, in an assay or other method of the invention.

Microfibril-associated glycoprotein-2 (MAGP-2) is a secreted glycoprotein (25 kDa) that incorporates into and organizes elastin fibril networks by interacting with tropoelastin, and with fibrillins 1 and 2; it also mediates cell adhesion by ligating integrins via its RGD integrin-binding motif (Gibson et al, 1998; Gibson et al, 1999). Abnormally elevated MAGP-2 expression is observed in the skin of systemic sclerosis patients, as well as in mouse models of systemic sclerosis that have associated MAGP-2 expression with excessive matrix deposition of type I collagen (Lemaire et al, 2004; Lemaire et al, 2005). Moreover, skin lesions in systemic sclerosis patients contain aberrant vessel morphologies characteristic of abnormal angiogenesis (Bodolay et al, 2002). In addition, MAGP-2 expression is induced in human T-47DE3 breast cancer cells when treated with progestin (Graham et al, 2005), and in human A549 lung adenocarcinoma cells when implanted into nude mice (Creighton et al, 2003). Most recently, MAGP-2 has been shown to interact physically with Notch1 (Miyamoto et al, 2006) and its ligand, Jagged-1 (Nehring et al, 2005), leading to the ectodomain shedding of both molecules from the cell surface.

Human MAGP-2 cDNA has been cloned and described, for example, in Faraco et al. (*Genomics*. 1995 Feb. 10; 25(3):630-7) and in Gibson et al. (J Biol Chem. 1996 Jan. 12; 271(2): 1096-103). The organization of the human MAGP-2 gene is described in Hatzinikolas and Gibson (*J Biol Chem.* 1998 Nov. 6; 273(45):29309-14). The organization of the mouse MAGP-2 gene has been described by Frankfater et al. (*Mamm Genome.* 2000 March; 11(3):191-5). The nucleotide sequence encoding human MAGP-2 is described in the National Center for Biotechnology Information (NCBI) database Accession No. AH007047 (gi:3983462) and is represented herein by SEQ ID NO:124. The amino acid sequence for human MAGP-2 is represented herein as SEQ ID NO:43 and is also found in the NCBI database Accession No. AAC83942 (gi:3983463). The nucleotide sequences encoding bovine and murine MAGP-2 are also known. The nucleotide sequence encoding murine MAGP-2 is described in NCBI database Accession No. BC025131 (gi:19264044) and is represented herein by SEQ ID NO:123 and encodes the murine MAGP-2 protein, described in NCBI database Accession No. AAH25131 (gi:19264045), also represented herein by SEQ ID NO:42. The nucleotide sequence encoding bovine MAGP-2 is described in NCBI database Accession No. NM_174386 (gi:31342148) and encodes the bovine MAGP-2 protein, described in NCBI database Accession No. NP_776811 (gi:27805993). All of the information contained in the database accession numbers and in the publications referenced herein is incorporated herein by reference.

In accordance with the present invention, an isolated polynucleotide (also referred to as an isolated nucleic acid molecule) is a nucleic acid molecule that has been removed from its natural milieu (e.g., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. The polynucleotides useful in the present invention are typically a portion of a gene (sense or non-sense strand) of the present invention that is suitable for use as a hybridization probe or PCR primer for the identification of a full-length gene (or portion thereof) in a given sample, to encode a protein or fragment thereof, or as a therapeutic reagent (e.g., antisense). An isolated nucleic acid molecule can include a gene or a portion of a gene (e.g., the regulatory region or promoter), for example, to produce a reporter construct according to the present invention. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

The minimum size of a nucleic acid molecule or polynucleotide of the present invention is a size sufficient to encode a protein having a desired biological activity, sufficient to form a probe or oligonucleotide primer that is capable of forming a stable hybrid with the complementary sequence of a nucleic acid molecule encoding the natural protein (e.g., under moderate, high or very high stringency conditions), or to otherwise be used as a target or agent in an assay or in any therapeutic method discussed herein. If the polynucleotide is an oligonucleotide probe or primer, the size of the polynucleotide can be dependent on nucleic acid composition and percent homology or identity between the nucleic acid molecule and a complementary sequence as well as upon hybridization conditions per se (e.g., temperature, salt concentration, and formamide concentration). The minimum size of a polynucleotide that is used as an oligonucleotide probe or primer is at least about 5 nucleotides in length, and preferably ranges from about 5 to about 50 or about 500 nucleotides or greater (1000, 2000, etc.), including any length in between, in whole number increments (i.e., 5, 6, 7, 8, 9, 10, . . . 33, 34, . . . 256, 257, . . . 500 . . . 1000 . . . ), and more preferably from about 10 to about 40 nucleotides, and most preferably from about 15 to about 40 nucleotides in length. In one aspect, the oligonucleotide primer or probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein-encoding sequence or a nucleic acid sequence encoding a full-length protein.

According to the present invention, an oligonucleotide probe (or simply, probe) is a nucleic acid molecule which most typically ranges in size from about 8 nucleotides to several hundred nucleotides in length. Such a molecule is typically used to identify a target nucleic acid sequence in a sample by hybridizing to such target nucleic acid sequence under stringent hybridization conditions. As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

PCR primers are also nucleic acid sequences, although PCR primers are typically oligonucleotides of fairly short length that are used in polymerase chain reactions. PCR primers and hybridization probes can readily be developed and produced by those of skill in the art, using sequence information from the target sequence. (See, for example, Sambrook et al., supra or Glick et al., supra).

Knowing the nucleic acid sequences of certain nucleic acid molecules of the present invention allows one skilled in the art to, for example, (a) make copies of those nucleic acid molecules and/or (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including traditional cloning techniques using oligonucleotide probes to screen appropriate libraries or DNA and PCR amplification of appropriate libraries or DNA using oligonucleotide primers. Preferred libraries to screen or from which to amplify nucleic acid molecule include mammali7an genomic DNA libraries. Techniques to clone and amplify genes are disclosed, for example, in Sambrook et al., ibid.

As used herein, reference to an isolated protein or polypeptide in the present invention, including any of the proteins described particularly herein (e.g., any protein encoded by a gene or nucleic acid sequence referenced in Table I, Table IV, Table V, and/or Table VI), includes full-length proteins, fusion proteins, or any fragment or homologue of such a protein. Such a protein can include, but is not limited to, purified proteins, recombinantly produced proteins, membrane bound proteins, proteins complexed with lipids, soluble proteins and isolated proteins associated with other proteins. More specifically, an isolated protein, such as a MAGP-2 (MFAP-5) protein, by way of example, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. In addition, and again by way of example, a "human MAGP-2 protein" or a protein "derived from" a human MAGP-2 protein refers to a MAGP-2 protein (generally including a homologue of a naturally occurring MAGP-2 protein) from a human (*Homo sapiens*) or to a MAGP-2 protein that has been otherwise produced from the knowledge of the structure (e.g., sequence) and perhaps the function of a naturally occurring MAGP-2 protein from *Homo sapiens*. In other words, a human MAGP-2 protein includes any MAGP-2 protein that has substantially similar structure and function of a naturally occurring MAGP-2 protein from *Homo sapiens* or that is a biologically active (i.e., has biological activity) homologue of a naturally occurring MAGP-2 protein from *Homo sapiens* as described in detail herein. As such, a human MAGP-2 protein can include purified, partially purified, recombinant, mutated/modified and synthetic proteins. According to the present invention, the terms "modification" and "mutation" can be used interchangeably, particularly with regard to the modifications/mutations to the amino acid sequence of protein (or nucleic acid sequences) described herein. An isolated protein useful as an antagonist or agonist according to the present invention can be isolated from its natural source, produced recombinantly or produced synthetically.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

According to the present invention, an isolated protein, including a biologically active homologue or fragment thereof, has at least one characteristic of biological activity of activity the wild-type, or naturally occurring reference protein (which can vary depending on whether the homologue or fragment is an agonist or antagonist of the protein, or whether an agonist or antagonist mimetic of the protein is described). In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications, activities or interactions which result in a decrease in protein expression or a decrease in the activity of the protein, can be referred to as inactivation (complete or partial), down-regulation, reduced action, or decreased action or activity of a protein. Similarly, modifications, activities or interactions which result in an increase in protein expression or an increase in the activity of the protein, can be referred to as amplification, overproduction, activation, enhancement, up-regulation or increased action of a protein. The biological activity of a protein according to the invention can be measured or evaluated using any assay for the biological activity of the protein as known in the art. Such assays can include, but are not limited to, binding assays, assays to determine internalization of the protein and/or associated proteins, enzyme assays, cell signal transduction assays (e.g., phosphorylation assays), and/or assays for determining downstream cellular events that result from activation or binding of the cell surface protein (e.g., expression of downstream genes, production of various biological mediators, etc.).

As used herein, reference to an "agonist" of a given protein refers to any compound that is characterized by the ability to agonize (e.g., stimulate, induce, increase, enhance, or mimic) the biological activity of the naturally occurring protein, and includes any homologue, binding protein (e.g., an antibody), agent that interacts with a protein or receptor bound by the protein, or any suitable product of drug/compound/peptide design or selection which is characterized by its ability to agonize (e.g., stimulate, induce, increase, enhance) the biological activity of the naturally occurring protein in a manner similar to the natural agonist, which is the reference protein.

Similarly, reference to an "antagonist" refers to any compound which inhibits (e.g., antagonizes, reduces, decreases, blocks, reverses, or alters) the effect of a given agonist of a protein (including the protein itself) as described above. More particularly, an antagonist is capable of acting in a manner relative to the activity of the protein, such that the biological activity of the natural agonist or reference protein, is decreased in a manner that is antagonistic (e.g., against, a reversal of, contrary to) to the natural action of the protein. Such antagonists can include, but are not limited to, a protein, peptide, or nucleic acid (including ribozymes, RNAi, aptamers, and antisense), antibodies and antigen binding fragments thereof, or product of drug/compound/peptide design or selection that provides the antagonistic effect.

As used herein, an anti-sense nucleic acid molecule is defined as an isolated nucleic acid molecule that reduces expression of a protein by hybridizing under high stringency conditions to a gene encoding the protein. Such a nucleic acid molecule is sufficiently similar to the gene encoding the protein that the molecule is capable of hybridizing under high stringency conditions to the coding or complementary strand of the gene or RNA encoding the natural protein. RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. A ribozyme is an RNA segment that functions by binding to the target RNA moiety and inactivate it by cleaving the phosphodiester backbone at a specific cutting site. A ribozyme can serve as a targeting delivery vehicle for a nucleic acid molecule, or alternatively, the ribozyme can target and bind to RNA encoding the biomarker, for example, and thereby effectively inhibit the translation of the biomarker. Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers assume a defined three-dimensional structure and are capable of discriminating between compounds with very small differences in structure.

Homologues of a given protein, including peptide and non-peptide agonists and antagonists (analogs), can be products of drug design or selection and can be produced using various methods known in the art. Such homologues can be referred to as mimetics.

Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

As used herein, a mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In one embodiment, a homologue of a given protein comprises, consists essentially of, or consists of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

Also included in the present invention are antibodies and antigen binding fragments thereof that selectively bind to any of the proteins associated with angiogenesis described herein, as well as the use of such antibodies and antigen binding fragments thereof in any of the methods described herein. Antibodies that selectively bind to a protein can be produced using the structural information available for the protein (e.g., the amino acid sequence of at least a portion of the protein). More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured by a variety of methods standard in the art including enzyme immunoassays (e.g., ELISA), immunoblot assays, etc.). Antibodies useful in the assay kit and methods of the present invention can include polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

The invention also extends to non-antibody polypeptides, sometimes referred to as antigen binding partners or antigen binding peptides, that have been designed to bind selectively to the protein of interest. Examples of the design of such polypeptides, which possess a prescribed ligand specificity are given in Beste et al. (*Proc. Natl. Acad. Sci.* 96:1898-1903, 1999), incorporated herein by reference in its entirety.

One embodiment of the present invention relates to a method to identify a compound useful for the inhibition (reduction, decrease) of angiogenesis, which may also be applied to identifying agents useful for inhibition of tumor cell growth, presence, or malignancy. A similar method of the present invention can also be used to identify a compound useful for the promotion (increase, initiation, enhancement) of angiogenesis, which may also be applied to identifying agents useful for conditions in which angiogenesis may be desired (e.g., stroke, ischemia).

Either of such methods generally includes the steps of: (a) detecting an initial level of the expression or activity of one or more genes or proteins encoded thereby (biomarkers) that are associated with angiogenesis as described herein (e.g., any one or more of the genes or the proteins encoded by a gene or nucleic acid sequence referenced in Table I, Table IV, Table V, and/or Table VI, and/or any one or more of the genes or proteins specifically described herein by reference to a particular nucleic acid or amino acid sequence) in a cell or soluble sample or product derived from the cell (e.g., cell supernate); (b) contacting the cell with a test compound; (c)

detecting a level of gene or protein expression or activity in the cell (or sample derived therefrom) after contact of the cell with the compound; and, (d) selecting a compound that regulates the level of gene or protein expression or activity in the cell, as compared to prior to contact with the test compound. In one embodiment, the biomarker is a protein, or the gene encoding such protein, selected from: ADAMts7, CRELD-2, Decorin, ECM1, Inhibin β-b, Integrin α-3, Integrin α-6, Lipocalin-7, Loxl-3, Lumican, MAGP-2, Matrilin-2, Nephronectin, SerpinE2, and/or SMOC-2. These genes and proteins have been described in detail above.

In another embodiment, the biomarker is a gene, or the protein encoded by the gene, selected from: 0610007C21Rik, apoptosis related protein APR-3, 1810014L12Rik, Cd14 (encoding CD14 antigen represented herein by SEQ ID NO:5 and SEQ ID NO:6), Cd38 (comprising a nucleic acid sequence represented herein by SEQ ID NO:7 and encoding CD38 antigen); Cd53 (encoding CD53 antigen represented herein by SEQ ID NO:8 and SEQ ID NO:9), Emp2 (encoding epithelial membrane protein represented herein by SEQ ID NO:10 and SEQ ID NO:11), Fcgrt (encoding Fc receptor (IgG, alpha chain transporter) represented herein by SEQ ID NO:12 and SEQ ID NO:13), Islr (encoding immunoglobulin superfamily containing leucine-rich repeat represented herein by SEQ ID NO:14 and SEQ ID NO:15); Lrp2 (comprising a nucleic acid sequence represented herein by SEQ ID NO:16 and SEQ ID NO:17 and encoding low density lipoprotein receptor-related protein 2); Ly6a (encoding lymphocyte antigen 6 complex, locus A represented herein by SEQ ID NO:18); P2rx4 (encoding purinergic receptor P2X, ligand-gated ion channel 4, represented herein by SEQ ID NO:19 and SEQ ID NO:20; Pcdhb9 (encoding protocadherin beta 9 represented herein by SEQ ID NO:21 and SEQ ID NO:22); Ptpre (encoding protein tyrosine phosphatase receptor type E represented herein by SEQ ID NO:23 and SEQ ID NO:24); Slc4a3 (encoding solute carrier family 4 (anion exchanger) member 3, represented herein by SEQ ID NO:25 and SEQ ID NO:26); and/or Tmc6 (encoding transmembrane channel-like gene family 6, represented herein by SEQ ID NO:27).

In yet another embodiment, the biomarker is a gene, or the protein encoded by the gene, selected from: 9130213B05Rik (encoding a protein represented herein by SEQ ID NO:29); C1s (encoding complement component 1, s subcomponent, represented herein by SEQ ID NO:34 and SEQ ID NO:35); C3 (encoding complement component 3 represented herein by SEQ ID NO:30 and SEQ ID NO:31); Cfh (comprising a nucleic acid sequence represented herein by SEQ ID NO:32 and SEQ ID NO:33 and encoding complement component factor h); Col9a3 (comprising a nucleic acid sequence represented herein by SEQ ID NO:36 and SEQ ID NO:37 and encoding procollagen, type IX, alpha 3); Grem1 (encoding cysteine knot superfamily 1, BMP antagonist 1, represented herein by SEQ ID NO:38 and SEQ ID NO:39); Loxl3 (encoding lysyl oxidase-like 3, represented herein by SEQ ID NO:40 and SEQ ID NO:41); MAGP-2 (comprising a nucleic acid sequence represented herein by SEQ ID NO:123 and SEQ ID NO:124 and encoding microfibril-associated glycoprotein-2, represented herein by SEQ ID NO:42 and SEQ ID NO:43); Mglap (encoding matrix gamma-carboxyglutamate (gla) protein represented herein by SEQ ID NO:44 and SEQ ID NO:45); Naga (encoding N-acetyl galactosaminidase, alpha, represented herein by SEQ ID NO:46 and SEQ ID NO:47); Nbl1 (encoding neuroblastoma, suppression of tumorigenicity 1, represented herein by SEQ ID NO:48 and SEQ ID NO:49); Ngfb (encoding nerve growth factor, beta, represented herein by SEQ ID NO:50 and SEQ ID NO:51), Npnt (represented herein by SEQ ID NO:52 and SEQ ID NO:53 and encoding nephronectin); Olfm1 (encoding olfactomedin 1, represented herein by SEQ ID NO:54 and SEQ ID NO:55); and/or U90926 (encoding a protein represented herein by SEQ ID NO:56).

In yet another embodiment, the biomarker is a gene, or the protein encoded by the gene, selected from any of the genes or proteins specifically identified by a sequence described herein.

Typically, compounds that regulate the expression or activity of the gene or protein in the presence of the compound in the manner that has been associated by the present inventors with angiogenesis can be selected as pro-angiogenic agents or anti-angiogenesis targets (agents that are targets for inhibition in order to inhibit angiogenesis), and compounds that regulate the expression or activity of the gene or protein in the presence of the compound in a manner that is opposite or contrary to the manner that has been associated by the present inventors with angiogenesis, can be selected as anti-angiogenic agents. The method can include a further step of detecting whether a compound selected in (d) has or regulates pro-angiogenic activity or anti-angiogenic activity, such as in a bioassay for angiogenesis described herein.

Detection of the regulation of the expression of a gene (or the protein encoded thereby) in the "manner" associated with the established level of expression for that gene during angiogenesis, at a minimum, refers to the detection of the regulation of a gene that has now been shown by the present inventors to be selectively regulated in during angiogenesis, in the same direction (i.e., upregulation or downregulation) and at a similar or comparable level, as compared to a normal control (the level of expression of the gene that has been or is established under normal, or non-angiogenic conditions). In other words, if "gene X" is upregulated during angiogenesis as compared to a normal control level of expression, then one determines whether the expression of gene X is upregulated in as compared to a normal control, or whether the expression of gene X is more similar to the level of expression of the normal control. In one aspect of the invention, a gene identified as being upregulated or downregulated as compared to a baseline control according to the invention is regulated in the same direction and to at least about 10%, and more preferably at least 20%, and more preferably at least 25%, and more preferably at least 30%, and more preferably at least 35%, and more preferably at least 40%, and more preferably at least 45%, and more preferably at least 50%, and preferably at least 55%, and more preferably at least 60%, and more preferably at least 65%, and more preferably at least 70%, and more preferably at least 75%, and more preferably at least 80%, and more preferably at least 85%, and more preferably at least 90%, and more preferably at least 95%, or even higher (e.g., above 100%) of the level of expression of the gene that has been established during angiogenesis. Statistical significance should be at least $p<0.05$, and more preferably, at least $p<0.01$, and more preferably, $p<0.005$, and even more preferably, $p<0.001$.

Steps (a) and (c) of the method of the present invention require detection of the biomarker (gene or protein encoded thereby) expression and/or biological activity in a cell or in a sample derived from the cell, such as a cellular extract or supernate. Detection of biomarker expression and/or biological activity can include, but is not limited to: detecting biomarker mRNA transcription (e.g., by polymerase chain reaction (PCR), reverse transcriptase-PCR (RT-PCR), in situ hybridization, Northern blot, sequence analysis or detection of a reporter gene); detecting biomarker translation (e.g., by immunoblot, enzyme-linked immunosorbant assay (ELISA), radioimmunoassay (RIA), immunoprecipitation, immunohistochemistry and immunofluorescence); and/or detecting biomarker biological activity (e.g., by detecting any of the activities of the particular biomarker, such as enzyme activity, receptor binding, induction of a growth factor, a cell signal transduction event, etc.). The step of detection in step (a) is the control level of biomarker expression or biological activity for a cell to which the detection in step (c) is to be compared and evaluated. The step of detection in step (c) is the experimental level of biomarker expression or biological activity which indicates whether the test compound can change the level of biomarker expression or biological activity in the cell, as compared to the level determined in step (a). In other words, the assay determines whether a given compound is capable of regulating the expression or activity of the biomarker (up or down), and therefore can predicted to regulate angiogenesis.

One can use a tumor cell or a normal, non-tumor cell, such as an endothelial cell, or a sample derived therefrom, in this assay, in order to identify compounds that regulate biomarker-associated angiogenesis, including angiogenesis that is associated with tumor cells, or to identify compounds in order to screen for putative carcinogens.

A cell suitable for use in the present method is any cell which expresses or can be induced to express, a detectable level of the biomarker of interest. A detectable level of biomarker is a level which can be detected using any of the methods for biomarker detection described herein. Since the biomarkers identified herein are expressed by many mammalian cell types, a variety of cell types could be selected. However, it will be appreciated by those of skill in the art that some cell types are more suitable for use in an in vitro assay (e.g., easy to maintain in culture, easy to obtain), and that certain biomarkers may be more readily detectable in some cell types, and therefore, such cell types are preferable for use in the present invention. A preferred cell type to use in the method of the present invention is any cell type that has a high expression or low expression of the biomarker in a tumor cell as compared to a non-tumor cell of the same cell type, or has a high expression or low expression of the biomarker under angiogenic conditions as compared to non-angiogenic conditions, so that a change in biomarker expression or activity is readily detectable. As discussed above, one can also use a sample derived from such a cell, such as a cell extract or cell supernate. Some preferred cells to use in the method of the present invention include, but are not limited to: fibroblasts (and fibrosarcomas), epithelial cells, endothelial cells, and breast, colon, kidney, ovarian or uterine tumor cells and non-tumor cells that endogenously or recombinantly express the biomarker. In one embodiment, a cell suitable for use in any aspect the general assay method is a cell which has been transfected with a recombinant nucleic acid molecule encoding the biomarker and operatively linked to a transcription control sequence so that the biomarker is expressed by the cell. Methods and reagents for preparing recombinant cells are known in the art.

As used herein, the term "putative regulatory compound" refers to compounds having an unknown or previously unappreciated regulatory activity in a particular process. The above-described method for identifying a compound of the present invention includes a step of contacting a test cell with a compound being tested for its ability to regulate the expression or biological activity of the biomarker. For example, test cells can be grown in liquid culture medium or grown on solid medium in which the liquid medium or the solid medium contains the compound to be tested. In addition, as described above, the liquid or solid medium contains components necessary for cell growth, such as assimilable carbon, nitrogen and micronutrients.

The above-described methods, in one aspect, involve contacting cells with the compound being tested for a sufficient time to allow for interaction of the putative regulatory compound with an element that affects biomarker expression and/or biological activity in a cell. Such elements can include, but are not limited to: a nucleic acid molecule encoding the biomarker (including regulatory regions of such a molecule), the biomarker protein, biomarker inhibitors, biomarker stimulators, and biomarker substrates. The period of contact with the compound being tested can be varied depending on the result being measured, and can be determined by one of skill in the art. For example, for binding assays, a shorter time of contact with the compound being tested is typically suitable, than when activity or expression is assessed. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring. The incubation time for growth of cells can vary but is sufficient to allow for the upregulation or downregulation of biomarker expression or biological activity in a cell. It will be recognized that shorter incubation times are preferable because compounds can be more rapidly screened. A preferred incubation time is between about 1 hour to about 48 hours.

The conditions under which the cell or cell lysate of the present invention is contacted with a putative regulatory compound, such as by mixing, are any suitable culture or assay conditions and includes an effective medium in which the cell can be cultured or in which the cell lysate can be evaluated in the presence and absence of a putative regulatory compound. Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. Cells are contacted with a putative regulatory compound under conditions which take into account the number of cells per container contacted, the concentration of putative regulatory compound(s) administered to a cell, the incubation time of the putative regulatory compound with the cell, and the concentration of compound administered to a cell. Determination of effective protocols can be accomplished by those skilled in the art based on variables such as the size of the container, the volume of liquid in the container, conditions known to be suitable for the culture of the particular cell type used in the assay, and the chemical composition of the putative regulatory compound (i.e., size, charge etc.) being tested. A preferred amount of putative regulatory compound(s) comprises between about 1 nM to about 10 mM of putative regulatory compound(s) per well of a 96-well plate.

In one aspect, the present method also makes use of non-cell based assay systems to identify compounds that can regulate biomarker expression or biological activity and thereby are predicted to be useful for regulating cell growth. For example, biomarker proteins and nucleic acid molecules encoding the biomarker may be recombinantly expressed and utilized in non-cell based assays to identify compounds that bind to the protein or nucleic acid molecule, respectively. In non-cell based assays the recombinantly expressed biomarker or nucleic acid encoding the biomarker is attached to a solid substrate such as a test tube, microtiter well or a column, by means well known to those in the art.

In one embodiment, DNA encoding a reporter molecule can be linked to a regulatory element of the biomarker gene (or a gene encoding a protein that directly regulates the biomarker) and used in appropriate intact cells, cell extracts or lysates to identify compounds that modulate biomarker gene expression, respectively. Appropriate cells or cell extracts are prepared from any cell type that normally expresses the biomarker, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

Following steps (a), (b) and (c) of the method to identify a compound that regulates the biomarker is a step (d) of selecting a compound that regulates (up or down) the level of the biomarker expression or activity in the cell, as compared to in the absence of the compound. Compounds which cause a regulation (increase or decrease) in the level of biomarker expression or biological activity are selected by the present method as being compounds that are predicted to be useful as pro-angiogenesis agents or anti-angiogenesis agents (or targets for regulation of angiogenesis), depending on how the biomarker has been correlated with angiogenesis according to the description provided herein.

Preferably, compounds which are selected in step (d) are compounds for which, after the test cell was contacted with the compound in step (b), the level of biomarker expression or biological activity detected in step (c) was statistically significantly changed (i.e., with at least a 95% confidence level, or p<0.05) as compared to the initial level of biomarker expression or biological activity detected in step (a). Preferably, detection of at least about a 30% change in biomarker expression or biological activity in the cell as compared to initial level results in selection of the compound according to step (d). More preferably, detection of at least about a 50% change and more preferably at least about a 70% change, and more preferably at least about a 90% change, or any percentage change between 5% and higher in 1% increments (i.e., 5%, 6%, 7%, 8% . . . ) in biomarker expression or biological activity in the cell as compared to the initial level results in selection of the compound according to step (d). In one embodiment, a 1.5 fold change in biomarker expression or biological activity in the cell as compared to the initial level results in selection of the compound according to step (d). More preferably, detection of at least about a 3 fold change, and more preferably at least about a 6 fold change, and even more preferably, at least about a 12 fold change, and even more preferably, at least about a 24 fold change, or any fold change from 1.5 up in increments of 0.5 fold (i.e., 1.5, 2.0, 2.5, 3.0 . . . ) in biomarker expression or biological activity as compared to the initial level, results in selection of the compound according to step (d).

It is to be understood that either of steps (a) and (c) of detection in any of the methods to identify a compound described above can result in no detection, or no change in detection, of biomarker expression or biological activity. In addition, since the level of biomarker expression or biological activity in step (a) (i.e., the initial level) is one of the control levels of biomarker for the assay (i.e., in the absence of the test compound), if step (a) reveals no detectable biomarker expression or biological activity, then any detectable level of biomarker expression or biological activity in step (c) is considered to be a positive result and indicative of increased biomarker activity in the cell and the appropriate assessment associated with this result. If the initial level of biomarker expression or biological activity in step (a) is a detectable level, then the level of biomarker expression or biological activity detected in step (c) is evaluated to determine whether it is statistically significantly greater than or less than that of step (a). It is possible that the level of biomarker expression or biological activity in step (c) could be no detectable change, which would indicate that the compound did not increase or decrease biomarker activity. In this scenario, however, it should be determined that the test cell can display an increase or decrease in the particular biomarker expression or biological activity under some conditions (i.e., by contact with a compound known to increase the biomarker activity in the test cell), so that false negatives are not identified.

In one embodiment of this method to identify regulators of biomarkers of the present invention, the method further includes the step of detecting whether the compound selected in step (d) can inhibit tumor cell formation or a characteristic thereof. In this embodiment, the test cell is contacted with the compound as in step (b), and the growth characteristics of the cell before and after contact with the cell are evaluated. Evaluation of cell growth can be by any suitable method in the art, including, but not limited to, proliferation assays (e.g., by measuring uptake of [$^3$H]-thymidine, viewing cells morphologically) and/or evaluating markers of cell growth (e.g., measurement of changes in cell surface markers, measurement of intracellular indicators of cell growth). Such methods are known in the art and are exemplified in the attached examples.

Compounds suitable for testing and use in the methods of the present invention include any known or available proteins, nucleic acid molecules, as well as products of drug design, including peptides, oligonucleotides, carbohydrates and/or synthetic organic molecules. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, supra. Candidate compounds initially identified by drug design methods can be screened for the ability to modulate the expression and/or biological activity of the biomarker using the methods described herein.

Compounds identified by the method described above can be used in a method to regulate angiogenesis, treat a condition or reduce a symptom of a condition in which inhibition of angiogenesis is desirable (e.g., cancer), or treat a condition or reduce a symptom of a condition in which promotion of angiogenesis is desirable (e.g., ischemia, stroke), as described herein and any such compounds are encompassed for use in the method described below.

More particularly, according to one embodiment of the present invention, administration of a compound or composition of the invention or targeting of a biomarker of the invention is useful to inhibit the tumorigenicity of a target cell or to inhibit angiogenesis in a tissue of a patient. Typically, it is desirable to inhibit the growth of a target cell (e.g., a tumor) to obtain a therapeutic benefit in the patient. In one embodiment, patients whom are suitable candidates for methods of the present invention include, but are not limited to, patients that have, or are at risk of developing (e.g., are predisposed to), cancer or a lymphoproliferative disease, or any condition in which regulation of angiogenesis might be beneficial. Particular conditions that are characterized or caused by abnormal or excessive angiogenesis, and therefore may be treated using the methods and compositions of the invention include, but are not limited to: cancer (e.g., activation of oncogenes, loss of tumor suppressors); infectious diseases (e.g., pathogens express angiogenic genes, enhance angiogenic programs); autoimmune disorders (e.g., activation of mast cells and other leukocytes); vascular malformations (e.g., Tie-2 mutation); DiGeorge syndrome (e.g., low VEGF and neuropilin-1 expression); HHT (e.g., mutations of endoglin or LK-1), cavernous hemangioma (e.g., loss of Cx37 and Cx40); atherosclerosis; transplant ateriopathy; obesity (e.g., angiogenesis induced by fatty diet, weight loss by angiogenesis inhibitors); psoriasis; warts; allergic dermatitis; scar keloids; pyogenic granulomas; blistering disease; Kaposi sarcoma in AIDS patients; persistent hyperplastic vitreous syndrome (e.g., loss of Ang-2 or VEGF164); diabetic retinopathy; retinopathy of prematurity; choroidal neovascularization (e.g., TIMP-3 mutation); primary pulmonary hypertension (e.g., germline BMPR-2 mutation, somatic EC mutation); asthma; nasal polyps; inflammatory bowel disease; periodontal disease; ascites; peritoneal adhesions; endometriosis; uterine bleeding; ovarian cysts; ovarian hyperstimulation; arthritis; synovitis; osteomyelitis; and osteophyte formation.

In another embodiment of the invention, administration of a compound or composition of the invention or targeting of a biomarker of the invention is useful to promote angiogenesis. Patients whom are suitable candidates for such a method of the invention include, but are not limited to: patients with vascular deficiencies, cardiovascular disease, or patients in whom stimulation of endothelial cell activation and stabilization of newly formed microvessels or other vessels would be beneficial. For example, such conditions include, but are not limited to, stroke, ischemia and related conditions.

Therefore, yet another embodiment of the invention relates to methods to increase or decrease the expression or biological activity of any one or more of the biomarkers described herein (e.g., Table I, Table IV, Table V, and/or Table VI) in cells (e.g., isolated cells, cells of a tissue, cells in a patient) in order to achieve a goal. This goal can include, but is not limited to, reduction of angiogenesis in a tissue, decreased tumorigenicity of tumor cells, or reduction in the potential for development of tumor cells, enhancement or promotion of angiogenesis in a tissue, or treatment of a disease or condition in which enhanced angiogenesis would be desirable. Such methods generally include the step of increasing or decreasing the expression and/or biological activity of one or more biomarkers described herein, as required for a given cell type, in order to achieve the desired result (e.g., inhibition or promotion of angiogenesis, cancer inhibition, etc.). In one embodiment, the biomarker is a protein, or the gene encoding such protein, selected from: ADAMts7, CRELD-2, Decorin, ECM1, Inhibin β-b, Integrin α-3, Integrin α-6, Lipocalin-7, Loxl-3, Lumican, MAGP-2, Matrilin-2, Nephronectin, SerpinE2, and/or SMOC-2.

In another embodiment, the biomarker is a gene, or the protein encoded by the gene, selected from: 0610007C21Rik, apoptosis related protein APR-3, 1810014L12Rik, Cd14 (encoding CD14 antigen represented herein by SEQ ID NO:5 and SEQ ID NO:6), Cd38 (comprising a nucleic acid sequence represented herein by SEQ ID NO:7 and encoding CD38 antigen); Cd53 (encoding CD53 antigen represented herein by SEQ ID NO:8 and SEQ ID NO:9), Emp2 (encoding epithelial membrane protein represented herein by SEQ ID NO:10 and SEQ ID NO:11), Fcgrt (encoding Fc receptor (IgG, alpha chain transporter) represented herein by SEQ ID NO:12 and SEQ ID NO:13), Islr (encoding immunoglobulin superfamily containing leucine-rich repeat represented herein by SEQ ID NO:14 and SEQ ID NO:15); Lrp2 (comprising a nucleic acid sequence represented herein by SEQ ID NO:16 and SEQ ID NO:17 and encoding low density lipoprotein receptor-related protein 2); Ly6a (encoding lymphocyte antigen 6 complex, locus A represented herein by SEQ ID NO:18); P2rx4 (encoding purinergic receptor P2X, ligand-gated ion channel 4, represented herein by SEQ ID NO:19 and SEQ ID NO:20; Pcdhb9 (encoding protocadherin beta 9 represented herein by SEQ ID NO:21 and SEQ ID NO:22); Ptpre (encoding protein tyrosine phosphatase receptor type E represented herein by SEQ ID NO:23 and SEQ ID NO:24); Slc4a3 (encoding solute carrier family 4 (anion exchanger) member 3, represented herein by SEQ ID NO:25 and SEQ ID NO:26); and/or Tmc6 (encoding transmembrane channel-like gene family 6, represented herein by SEQ ID NO:27).

In yet another embodiment, the biomarker is a gene, or the protein encoded by the gene, selected from: 9130213B05Rik (encoding a protein represented herein by SEQ ID NO:29); Cls (encoding complement component 1, s subcomponent, represented herein by SEQ ID NO:34 and SEQ ID NO:35); C3 (encoding complement component 3 represented herein by SEQ ID NO:30 and SEQ ID NO:31); Cfh (comprising a nucleic acid sequence represented herein by SEQ ID NO:32 and SEQ ID NO:33 and encoding complement component factor h); Col9a3 (comprising a nucleic acid sequence represented herein by SEQ ID NO:36 and SEQ ID NO:37 and encoding procollagen, type IX, alpha 3); Grem1 (encoding cysteine knot superfamily 1, BMP antagonist 1, represented herein by SEQ ID NO:38 and SEQ ID NO:39); Loxl3 (encoding lysyl oxidase-like 3, represented herein by SEQ ID NO:40 and SEQ ID NO:41); MAGP-2 (comprising a nucleic acid sequence represented herein by SEQ ID NO:123 and SEQ ID NO:124 and encoding microfibrillar associated protein 5, represented herein by SEQ ID NO:42 and SEQ ID NO:43); Mglap (encoding matrix gamma-carboxyglutamate (gla) protein represented herein by SEQ ID NO:44 and SEQ ID NO:45); Naga (encoding N-acetyl galactosaminidase, alpha, represented herein by SEQ ID NO:46 and SEQ ID NO:47); Nbl1 (encoding neuroblastoma, suppression of tumorigenicity 1, represented herein by SEQ ID NO:48 and SEQ ID NO:49); Ngfb (encoding nerve growth factor, beta, represented herein by SEQ ID NO:50 and SEQ ID NO:51), Npnt (represented herein by SEQ ID NO:52 and SEQ ID NO:53 and encoding nephronectin); Olfm1 (encoding olfactomedin 1, represented herein by SEQ ID NO:54 and SEQ ID NO:55); and/or U90926 (encoding a protein represented herein by SEQ ID NO:56).

In yet another embodiment, the biomarker is a gene, or the protein encoded by the gene, selected from any of the genes or proteins specifically identified by a sequence described herein.

In the method of the present invention wherein the goals are to reduce angiogenesis in a tissue, decrease tumorigenicity of tumor cells, decrease tumor burden, increase survival, or reduce the potential for the development of tumor cells, preferably, cells that are targeted by the method are cells which, prior to the application of the present method, are exhibiting inappropriate (malignant) cell growth or a potential therefore, or cells in a tissue where it is desirable to inhibit angiogenesis. Preferred cells to regulate according to this aspect of the present invention include tumor cells. Cells in which it is desirable to inhibit tumorigenicity or tissues in which inhibition of angiogenesis is desired can be identified, for example, using the method for assessing the presence of cancer cells or biomarker expression and activity of the present invention as described in detail above. Such methods are particularly useful in patients where increased tumorigenicity (or simply tumor growth) or angiogenesis is, or is predicted to become, problematic. Therefore, such a method is particularly useful to treat patients that have, or are at a risk of developing, tumor cells (i.e., a cancer), or to treat any other patients having a condition characterized by undesirable cell growth (e.g., lymphoproliferative disorders). Other diseases and conditions in which inhibition of tumorigenicity or angiogenesis would be desirable will be apparent to those of skill in the art (many are discussed below) and are intended to be encompassed by the present invention.

Similarly, in the method of the present invention wherein the goals are to enhance or promote angiogenesis in a tissue, preferably, cells that are targeted by the method are cells in a tissue where it is desirable to promote angiogenesis. Preferred cells to regulate according to this aspect of the present invention include vascular endothelial cells. Such methods are particularly useful in patients where increased angiogenesis may be useful, such as in patients that have a vascular insufficiency or where the promotion of vascular stabilization and development is desired. Therefore, such a method is particularly useful to treat patients with vascular deficiencies, cardiovascular disease, or to stimulate endothelial cell activation and stabilization of newly formed microvessels or other vessels. Conditions in which promotion of angiogenesis would be desirable will be apparent to those of skill in the art and are intended to be encompassed by the present invention.

Accordingly, the method of the present invention includes a step of modulating (i.e., upregulating or downregulating) biomarker expression and/or biological activity in a patient that has, or is at risk of developing, inappropriate or unregulated cell growth (e.g., tumors) or angiogenesis, or a patient or subject that is in need of promotion of angiogenesis, depending on the goal of the therapy, as discussed above. Modulating biomarker expression or biological activity according to the present invention can be accomplished by directly affecting biomarker expression (transcription or translation) or biological activity, or by directly affecting the ability of a regulator (inhibitor or stimulator) of the biomarker to bind to the biomarker or to activate the biomarker. Preferably, the method of the present invention is targeted to a particular type of cell or tissue or region of the body in which inhibition of cell growth or regulation of angiogenesis is desired. A targeted cell, for example, could include a tumor cell, wherein the method does not substantially affect biomarker expression or biological activity in non-tumor cells, or in cells of a different type that the tumor cell type. Therefore, the method of the present invention, in one embodiment, is intended to be specifically targeted to biomarker expression and/or biological activity for the purpose of inhibiting or promoting cell growth, or inhibiting or promoting angiogenesis by modulating biomarker expression and/or biological activity.

An increase in biomarker expression and/or biological activity is defined herein as any measurable (detectable) increase (i.e., upregulation, stimulation, enhancement) of the expression or activity of the biomarker. As used herein, to increase biomarker expression and/or biological activity refers to any measurable increase in biomarker expression and/or biological activity by any suitable method of measurement. A decrease in biomarker expression and/or biological activity is defined herein as any measurable (detectable) decrease (i.e., downregulation, inhibition, reduction) of the expression or activity of biomarker. As used herein, to decrease biomarker expression and/or biological activity refers to any measurable decrease in the biomarker expression and/or biological activity by any suitable method of measurement.

Accordingly, one embodiment of the present invention includes the use of a variety of agents (i.e., regulatory compounds) which, by acting directly on the biomarker (or by being the biomarker gene encoding a protein or the biomarker protein itself) or by acting on inhibitors or stimulators of the biomarker or being an inhibitor or stimulator of the biomarker, modulate (regulate up or down) the expression and/or biological activity of the biomarker in a cell to produce a desired effect (e.g., inhibition of tumorigenesis or reduction of tumor burden or tumor stasis/increase of survival, inhibition or promotion of angiogenesis). Agents useful in the present invention include, for example, proteins, nucleic acid molecules, antibodies, and compounds that are products of rational drug design (i.e., drugs). Such compounds can be identified using the method of identifying compounds for regulating tumor cell growth and malignancy or for regulating angiogenesis as described above. Moreover, the expression or biological activity of the biomarker in a cell can be determined using the methods described above.

Therefore, in one embodiment, the method of the present invention increases the transcription and/or the translation of the biomarker by a cell that naturally expresses the biomarker and that is the target for growth regulation, or increases (stimulates, enhances) the biological activity of the biomarker. Methods for increasing the expression of a given biomarker include, but are not limited to, administering an agent that increases the expression or biological activity of the endogenous biomarker, administering biomarker protein or a homologue or analog (agonist) thereof to a subject, and/or overexpressing biomarker in target cells. In one aspect of this embodiment, the biomarker can be effectively overexpressed in a cell by increasing the activity of a promoter for the biomarker gene in the cell such that expression of endogenous biomarker in the cell is increased. For example, the activity of the biomarker gene promoter can be increased by methods which include, contacting the promoter with a transcriptional activator, inhibiting a biomarker promoter inhibitor, and increasing the activity of a biomarker promoter stimulator. Methods by which such compounds (e.g., transcriptional activators) can be administered to a cell are described below. In another embodiment, biomarker activity is increased by administering the biomarker or a homologue or analog (synthetic homologue or mimetic or compound) to the target cells or to the patient in an appropriate carrier or delivery vehicle.

In another embodiment, the method of the present invention decreases the transcription and/or the translation of the biomarker by a cell that naturally expresses the biomarker and that is the target for growth regulation, or inhibits the biological activity of biomarker. In this embodiment, it is desired to modify a target cell in order to decrease in biomarker gene expression, decrease the function of the gene, or decrease the function of the gene product (i.e., the protein encoded by the gene). Such methods can be referred to as inactivation (complete or partial), deletion, interruption, blockage or downregulation of a gene encoding the biomarker. In one embodiment, reduction in biomarker activity or expression is achieved by use of a biomarker antagonist, antagonists having been described above.

In one aspect of this embodiment of the present invention, the expression and/or biological activity of the biomarker is increased by overexpressing the biomarker in the cell in which angiogenesis is to be regulated. Overexpression of a biomarker refers to an increase in expression of the biomarker over a normal, endogenous level of biomarker expression. For some cell types, which do not express detectable levels of the biomarker under normal conditions, such expression can be any detectable level. For cell types which do express detectable levels of the biomarker under normal conditions, an overexpression is any statistically significant increase in expression of the biomarker ($p<0.05$) (or constitutive expression where expression is normally not constitutive) over endogenous levels of expression. One method by which biomarker overexpression can be achieved is by transfecting the cell with a recombinant nucleic acid molecule encoding the biomarker operatively linked to a transcription control sequence, wherein the recombinant biomarker is expressed by the cell. As discussed previously herein, the nucleic acid sequence encoding biomarker, vectors suitable for expressing such a molecule, and methods of transfection of a cell with such a molecule, including in vivo methods, are known and are described in detail below.

A recombinant nucleic acid molecule expressing the biomarker is a molecule that can include at least one of any nucleic acid sequence encoding a protein having the biomarker biological activity operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

Preferably, a recombinant nucleic acid molecule is produced using recombinant DNA technology (e.g., polymerase chain reaction (PCR) amplification, cloning). Suitable nucleic acid sequences encoding the biomarker for use in a recombinant nucleic acid molecule of the present invention include any nucleic acid sequence that encodes the biomarker protein having biological activity and suitable for use in the target host cell. For example, when the target host cell is a human cell, human biomarker-encoding nucleic acid sequences are preferably used, although the present invention is not limited to strict use of naturally occurring sequences or same-species sequences.

A recombinant nucleic acid molecule includes a recombinant vector, which is any nucleic acid sequence, typically a heterologous sequence, which is operatively linked to the isolated nucleic acid molecule encoding a biomarker protein, which is capable of enabling recombinant production of the biomarker protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules. Recombinant vectors are preferably used in the expression of nucleic acid molecules, and can also be referred to as expression vectors. Preferred recombinant vectors are capable of being expressed in a transfected host cell, and particularly, in a transfected mammalian host cell in vivo.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more transcription control sequences. The phrase "operatively linked" refers to linking a nucleic acid molecule to a transcription control sequence in a manner such that the molecule is expressed when transfected (i.e., transformed, transduced or transfected) into a host cell.

Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in a host cell according to the present invention. A variety of suitable transcription control sequences are known to those skilled in the art. Preferred transcription control sequences include those which function in mammalian cells, with cell- or tissue-specific transcription control sequences being particularly preferred. Examples of preferred transcription control sequences include, but are not limited to, transcription control sequences useful for expression of a protein in epithelial cells and tumor cells and the naturally occurring biomarker promoter. Particularly preferred transcription control sequences include inducible promoters, cell-specific promoters, tissue-specific promoters (e.g., insulin promoters) and enhancers. Suitable promoters for these and other cell types will be easily determined by those of skill in the art. Transcription control sequences of the present invention can also include naturally occurring transcription control sequences naturally associated with the protein to be expressed prior to isolation. In one embodiment, a transcription control sequence includes an inducible promoter.

One type of recombinant vector useful in a recombinant nucleic acid molecule of the present invention is a recombinant viral vector. Such a vector includes a recombinant nucleic acid sequence encoding a biomarker protein of the present invention that is packaged in a viral coat that can be expressed in a host cell in an animal or ex vivo after administration. A number of recombinant viral vectors can be used, including, but not limited to, those based on alphaviruses, poxviruses, adenoviruses, herpesviruses, lentiviruses, adeno-associated viruses and retroviruses. Particularly preferred viral vectors are those based on adenoviruses and adeno-associated viruses. Viral vectors suitable for gene delivery are well known in the art and can be selected by the skilled artisan for use in the present invention. A detailed discussion of current viral vectors is provided in "Molecular Biotechnology," Second Edition, by Glick and Pasternak, ASM Press, Washington D.C., 1998, pp. 555-590, the entirety of which is incorporated herein by reference.

For example, a retroviral vector, which is useful when it is desired to have a nucleic acid sequence inserted into the host genome for long term expression, can be packaged in the envelope protein of another virus so that it has the binding specificity and infection spectrum that are determined by the envelope protein (e.g., a pseudotyped virus). In addition, the envelope gene can be genetically engineered to include a DNA element that encodes and amino acid sequence that binds to a cell receptor to create a recombinant retrovirus that infects a specific cell type. Expression of the biomarker gene can be further controlled by the use of a cell or tissue-specific promoter. Retroviral vectors have been successfully used to transfect cells with a gene which is expressed and maintained in a variety of ex vivo systems An adenoviral vector is a preferred vector for use in the present method. An adenoviral vector infects a wide range of human cells and has been used extensively in live vaccines. Adenoviral vectors used in gene therapy do not integrate into the host genome, and therefore, gene therapy using this system requires periodic administration, although methods have been described which extend the expression time of adenoviral transferred genes, such as administration of antibodies directed against T cell receptors at the site of expression (Sawchuk et al., 1996, *Hum. Gene. Ther.* 7:499-506). The efficiency of adenovirus-mediated gene delivery can be enhanced by developing a virus that preferentially infects a particular target cell. For example, a gene for the attachment fibers of adenovirus can be engineered to include a DNA element that encodes a protein domain that binds to a cell-specific receptor. Examples of successful in vivo delivery of genes has been demonstrated and is discussed in more detail below.

Yet another type of viral vector is based on adeno-associated viruses, which are small, nonpathogenic, single-stranded human viruses. This virus can integrate into a specific site on chromosome 19. This virus can carry a cloned insert of about 4.5 kb, and has typically been successfully used to express proteins in vivo from 70 days to at least 5 months. Demonstrating that the art is quickly advancing in the area of gene therapy, however, a publication by Bennett et al. reported efficient and stable transgene expression by adeno-associated viral vector transfer in vivo for greater than 1 year (Bennett et al., 1999, *Proc. Natl. Acad. Sci. USA* 96:9920-9925).

Another type of viral vector that is suitable for use in the present invention is a herpes simplex virus vector. Herpes simplex virus type 1 infects and persists within nondividing neuronal cells, and is therefore a suitable vector for targeting and transfecting cells of the central and peripheral nervous system with a biomarker protein of the present invention. Preclinical trials in experimental animal models with such a vector has demonstrated that the vector can deliver genes to cells of both the brain and peripheral nervous system that are expressed and maintained for long periods of time.

Suitable host cells to transfect with a recombinant nucleic acid molecule according to the present invention include any mammalian cell that can be transfected. Host cells can be either untransfected cells or cells that are already transfected with at least one nucleic acid molecule. Host cells according to the present invention can be any cell capable of producing a biomarker protein as described herein or in which it is desired to produce the biomarker.

According to the present invention, a host cell can also be referred to as a target cell or a targeted cell in vivo, in which a recombinant nucleic acid molecule encoding a biomarker protein having the biological activity of the biomarker is to be expressed. As used herein, the term "target cell" or "targeted cell" refers to a cell to which a recombinant nucleic acid molecule of the present invention is selectively designed to be delivered. The term target cell does not necessarily restrict the delivery of a recombinant nucleic acid molecule only to the target cell and no other cell, but indicates that the delivery of the recombinant molecule, the expression of the recombinant molecule, or both, are specifically directed to a preselected host cell. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., 1986, *Biochemistry* 25: 5500-6; Ho et al., 1987a, *J Biol Chem* 262: 13979-84; Ho et al., 1987b, *J Biol Chem* 262: 13973-8; and U.S. Pat. No. 4,957,735 to Huang et al., each of which is incorporated herein by reference in its entirety). Ways in which viral vectors can be modified to deliver a nucleic acid molecule to a target cell have been discussed above. Alternatively, the route of administration, as discussed below, can be used to target a specific cell or tissue. For example, intracoronary administration of an adenoviral vector has been shown to be effective for the delivery of a gene cardiac myocytes (Maurice et al., 1999, *J. Clin. Invest.* 104:21-29). Intravenous delivery of cholesterol-containing cationic liposomes has been shown to preferentially target pulmonary tissues (Liu et al., *Nature Biotechnology* 15:167, 1997), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

According to the method of the present invention, a host cell is preferably transfected in vivo (i.e., in a mammal) as a result of administration to a mammal of a recombinant nucleic acid molecule, or ex vivo, by removing cells from a mammal and transfecting the cells with a recombinant nucleic acid molecule ex vivo. Transfection of a nucleic acid molecule into a host cell according to the present invention can be accomplished by any method by which a nucleic acid molecule administered into the cell in vivo, and includes, but is not limited to, transfection, electroporation, microinjection, lipofection, adsorption, viral infection, naked DNA injection and protoplast fusion. Methods of administration are discussed in detail below.

In one embodiment of the present invention, a recombinant nucleic acid molecule of the present invention is administered to a patient in a liposome delivery vehicle, whereby the nucleic acid sequence encoding the biomarker protein enters the host cell (i.e., the target cell) by lipofection. A liposome delivery vehicle contains the recombinant nucleic acid molecule and delivers the molecules to a suitable site in a host recipient. According to the present invention, a liposome delivery vehicle comprises a lipid composition that is capable of delivering a recombinant nucleic acid molecule of the present invention, including both plasmids and viral vectors, to a suitable cell and/or tissue in a patient. A liposome delivery vehicle of the present invention comprises a lipid composition that is capable of fusing with the plasma membrane of the target cell to deliver the recombinant nucleic acid molecule into a cell. A liposome delivery vehicle can also be used to deliver a protein, drug, or other regulatory compound to a patient.

A liposome delivery vehicle of the present invention can be modified to target a particular site in a mammal (i.e., a targeting liposome), thereby targeting and making use of a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. Other targeting mechanisms include targeting a site by addition of exogenous targeting molecules (i.e., targeting agents) to a liposome (e.g., antibodies, soluble receptors or ligands).

A liposome delivery vehicle is preferably capable of remaining stable in a patient for a sufficient amount of time to deliver a nucleic acid molecule of the present invention to a preferred site in the patient (i.e., a target cell). A liposome delivery vehicle of the present invention is preferably stable in the patient into which it has been administered for at least about 30 minutes, more preferably for at least about 1 hour and even more preferably for at least about 24 hours. A preferred liposome delivery vehicle of the present invention is from about 0.01 microns to about 1 microns in size.

Suitable liposomes for use with the present invention include any liposome. Preferred liposomes of the present invention include those liposomes commonly used in, for example, gene delivery methods known to those of skill in the art. Preferred liposome delivery vehicles comprise multilamellar vesicle (MLV) lipids and extruded lipids. Methods for preparation of MLV's are well known in the art. According to the present invention, "extruded lipids" are lipids which are prepared similarly to MLV lipids, but which are subsequently extruded through filters of decreasing size, as described in Templeton et al., 1997, *Nature Biotech.*, 15:647-652, which is incorporated herein by reference in its entirety. Small unilamellar vesicle (SUV) lipids can also be used in the composition and method of the present invention. In one embodiment, liposome delivery vehicles comprise liposomes having a polycationic lipid composition (i.e., cationic liposomes) and/or liposomes having a cholesterol backbone conjugated to polyethylene glycol. In a preferred embodiment, liposome delivery vehicles useful in the present invention comprise one or more lipids selected from the group of DOTMA, DOTAP, DOTIM, DDAB, and cholesterol.

Preferably, the transfection efficiency of a nucleic acid:liposome complex of the present invention is at least about 1 picogram (pg) of protein expressed per milligram (mg) of total tissue protein per microgram (μg) of nucleic acid delivered. More preferably, the transfection efficiency of a nucleic acid:liposome complex of the present invention is at least about 10 pg of protein expressed per mg of total tissue protein per μg of nucleic acid delivered; and even more preferably, at least about 50 pg of protein expressed per mg of total tissue protein per μg of nucleic acid delivered; and most preferably, at least about 100 pg of protein expressed per mg of total tissue protein per μg of nucleic acid delivered.

Complexing a liposome with a nucleic acid molecule of the present invention can be achieved using methods standard in the art. A suitable concentration of a nucleic acid molecule of the present invention to add to a liposome includes a concentration effective for delivering a sufficient amount of recombinant nucleic acid molecule into a target cell of a patient such that the biomarker protein encoded by the nucleic acid molecule can be expressed in a an amount effective to inhibit the growth of the target cell or to inhibit or promote angiogenesis at a tissue site. Preferably, from about 0.1 μg to about 10 μg of nucleic acid molecule of the present invention is combined with about 8 nmol liposomes. In one embodiment, the ratio of nucleic acids to lipids (μg nucleic acid:nmol lipids) in a composition of the present invention is preferably at least from about 1:10 to about 6:1 nucleic acid:lipid by weight (i.e., 1:10=1 μg nucleic acid:10 nmol lipid).

According to the present invention, a regulatory compound for regulating the expression or biological activity of a biomarker, including a recombinant nucleic acid molecule encoding the biomarker, is typically administered to a patient in a composition. In addition to the recombinant nucleic acid molecule or other biomarker regulatory compound (i.e., a protein, antibody, carbohydrate, small molecule product of drug design), the composition can include, for example, a pharmaceutically acceptable carrier, which includes pharmaceutically acceptable excipients and/or delivery vehicles, for delivering the recombinant nucleic acid molecule or other regulatory compound to a patient (e.g., a liposome delivery vehicle). As used herein, a pharmaceutically acceptable carrier refers to any substance suitable for delivering a therapeutic composition useful in the method of the present invention to a suitable in vivo or ex vivo site. Preferred pharmaceutically acceptable carriers are capable of maintaining a recombinant nucleic acid molecule of the present invention in a form that, upon arrival of the nucleic acid molecule to a target cell, the nucleic acid molecule is capable of entering the cell and being expressed by the cell. Suitable excipients of the present invention include excipients or formularies that transport or help transport, but do not specifically target a nucleic acid molecule to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into an animal. As used herein, a controlled release formulation comprises recombinant nucleic acid molecule or other biomarker regulatory compound of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Suitable delivery vehicles have been previously described herein, and include, but are not limited to liposomes, viral vectors or other delivery vehicles, including ribozymes. Natural lipid-containing delivery vehicles include cells and cellular membranes. Artificial lipid-containing delivery vehicles include liposomes and micelles. As discussed above, a delivery vehicle of the present invention can be modified to target to a particular site in a patient, thereby targeting and making use of a nucleic acid molecule at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

As discussed above, a composition of the present invention is administered to a patient in a manner effective to deliver the recombinant nucleic acid molecule comprising a nucleic acid sequence encoding a biomarker protein to a target cell, whereby the target cell is transfected by the recombinant molecule and whereby the biomarker protein is expressed in the target cell. When a biomarker regulatory compound is to be delivered to a target cell in a patient, the composition is administered in a manner effective to deliver the biomarker regulatory compound to the target cell, whereby the compound can act on the cell (e.g., enter the cell and act on the biomarker or an inhibitor or stimulator thereof) so that the expression or biological activity of the biomarker is increased or decreased, depending on the isoform and the goal of the therapy. Suitable administration protocols include any in vivo or ex vivo administration protocol.

According to the present invention, an effective administration protocol (i.e., administering a composition of the present invention in an effective manner) comprises suitable dose parameters and modes of administration that result in transfection and expression of a recombinant nucleic acid molecule encoding a biomarker protein or another biomarker regulatory compound, in a target cell of a patient, and subsequent inhibition of the growth of the target cell or inhibition or promotion of angiogenesis, preferably so that the patient obtains some measurable, observable or perceived benefit from such administration. In some situations, where the target cell population is accessible for sampling, effective dose parameters can be determined using methods as described herein for assessment of tumor growth or using methods known in the art for the assessment of angiogenesis. Such methods include removing a sample of the target cell population from the patient prior to and after the recombinant nucleic acid molecule is administered, and measuring changes in biomarker expression or biological activity, as well as measuring inhibition of the cell or impact on angiogenesis of a suitable cell line. Alternatively, effective dose parameters can be determined by experimentation using in vitro cell cultures, in vivo animal models, and eventually, clinical trials if the patient is human. Effective dose parameters can be determined using methods standard in the art for a particular disease or condition that the patient has or is at risk of developing. Such methods include, for example, determination of survival rates, side effects (i.e., toxicity) and progression or regression of disease.

According to the present invention, suitable methods of administering a composition comprising a recombinant nucleic acid molecule of the present invention to a patient include any route of in vivo administration that is suitable for delivering a recombinant nucleic acid molecule into a patient. The preferred routes of administration will be apparent to those of skill in the art, depending on the type of delivery vehicle used, the target cell population, whether the compound is a protein, nucleic acid, or other compound (e.g., a drug) and the disease or condition experienced by the patient. Preferred methods of in vivo administration include, but are not limited to, intravenous administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, pulmonary administration, impregnation of a catheter, and direct injection into a tissue. In an embodiment where the target cells are in or near a tumor, a preferred route of administration is by direct injection into the tumor or tissue surrounding the tumor. For example, when the tumor is a breast tumor, the preferred methods of administration include impregnation of a catheter, and direct injection into the tumor.

Intravenous, intraperitoneal, and intramuscular administrations can be performed using methods standard in the art. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a recombinant nucleic acid molecule to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention. All of the publications discussed below and elsewhere herein with regard to gene delivery and delivery vehicles are incorporated herein by reference in their entirety. For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. Dow et al. also demonstrated successful in vivo delivery of a nucleic acid molecule by direct injection into a site of a tumor. As discussed above, Liu et al., 1997, ibid. demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811:299-308; and von der Leyen et al., 1995, *Proc Natl Acad Sci USA* 92:1137-1141).

As discussed above, delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475-480; Bordignon et al., 1995, *Science* 270:470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al., 1999, ibid. demonstrated that an adenoviral vector encoding a β2-adrenergic receptor, administered by intracoronary delivery, resulted in diffuse multichamber myocardial expression of the gene in vivo, and subsequent significant increases in hemodynamic function and other improved physiological parameters. Levine et al. describe in vitro, ex vivo and in vivo delivery and expression of a gene to human adipocytes and rabbit adipocytes using an adenoviral vector and direct injection of the constructs into adipose tissue (Levine et al., 1998, *J. Nutr. Sci. Vitaminol.* 44:569-572).

In the area of neuronal gene delivery, multiple successful in vivo gene transfers have been reported. Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, *Nat. Biotechnol.* 17:865-869). As discussed above, Bennett et al. reported the use of adeno-associated viral vector to deliver and express a gene by subretinal injection in the neural retina in vivo for greater than 1 year (Bennett, 1999, ibid.).

Gene delivery to synovial lining cells and articular joints has had similar successes. Oligino and colleagues report the use of a herpes simplex viral vector that is deficient for the immediate early genes, ICP4, 22 and 27, to deliver and express two different receptors in synovial lining cells in vivo (Oligino et al., 1999, *Gene Ther.* 6:1713-1720). The herpes vectors were administered by intraarticular injection. Kuboki et al. used adenoviral vector-mediated gene transfer and intraarticular injection to successfully and specifically express a gene in the temporomandibular joints of guinea pigs in vivo (Kuboki et al., 1999, *Arch. Oral. Biol.* 44:701-709). Apparailly and colleagues systemically administered adenoviral vectors encoding IL-10 to mice and demonstrated successful expression of the gene product and profound therapeutic effects in the treatment of experimentally induced arthritis (Apparailly et al., 1998, *J. Immunol.* 160:5213-5220). In another study, murine leukemia virus-based retroviral vector was used to deliver (by intraarticular injection) and express a human growth hormone gene both ex vivo and in vivo (Ghivizzani et al., 1997, *Gene Ther.* 4:977-982). This study showed that expression by in vivo gene transfer was at least equivalent to that of the ex vivo gene transfer. As discussed above, Sawchuk et al. has reported successful in vivo adenoviral vector delivery of a gene by intraarticular injection, and prolonged expression of the gene in the synovium by pretreatment of the joint with anti-T cell receptor monoclonal antibody (Sawchuk et al., 1996, ibid. Finally, it is noted that ex vivo gene transfer of human interleukin-1 receptor antagonist using a retrovirus has produced high level intraarticular expression and therapeutic efficacy in treatment of arthritis, and is now entering FDA approved human gene therapy trials (Evans and Robbins, 1996, *Curr. Opin. Rheumatol.* 8:230-234). Therefore, the state of the art in gene therapy has led the FDA to consider human gene therapy an appropriate strategy for the treatment of at least arthritis. Taken together, all of the above studies in gene therapy indicate that delivery and expression of an biomarker-encoding recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465-1468). Such recombinant nucleic acid molecules are typically injected by direct or intramuscular administration. Recombinant nucleic acid molecules to be administered by naked DNA administration include a nucleic acid molecule of the present invention, and preferably includes a recombinant molecule of the present invention that preferably is replication, or otherwise amplification, competent. A naked nucleic acid reagent of the present invention can comprise one or more nucleic acid molecule of the present invention in the form of, for example, a dicistronic recombinant molecule. Naked nucleic acid delivery can include intramuscular, subcutaneous, intradermal, transdermal, intranasal and oral routes of administration, with direct injection into the target tissue being most preferred. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 µm in diameter) and are propelled into skin cells or muscle with a "gene gun."

In accordance with the present invention, a suitable single dose of a recombinant nucleic acid molecule encoding a biomarker protein as described herein is a dose that is capable of transfecting a host cell and being expressed in the host cell at a level sufficient, in the absence of the addition of any other factors or other manipulation of the host cell, to regulate angiogenesis and/or the tumorigenicity of the host cell when administered one or more times over a suitable time period. Doses can vary depending upon the cell type being targeted, the route of administration, the delivery vehicle used, and the disease or condition being treated.

In one embodiment, an appropriate single dose of a nucleic acid:liposome complex of the present invention is from about 0.1 µg to about 100 µg per kg body weight of the patient to which the complex is being administered. In another embodiment, an appropriate single dose is from about 1 µg to about 10 µg per kg body weight. In another embodiment, an appropriate single dose of nucleic acid:lipid complex is at least about 0.1 µg of nucleic acid, more preferably at least about 1 µg of nucleic acid, even more preferably at least about 10 µg of nucleic acid, even more preferably at least about 50 µg of nucleic acid, and even more preferably at least about 100 µg of nucleic acid.

Preferably, an appropriate single dose of a recombinant nucleic acid molecule encoding a biomarker protein of the present invention results in at least about 1 pg of protein expressed per mg of total tissue protein per µg of nucleic acid delivered. More preferably, an appropriate single dose is a dose which results in at least about 10 pg of protein expressed per mg of total tissue protein per µg of nucleic acid delivered; and even more preferably, at least about 50 pg of protein expressed per mg of total tissue protein per µg of nucleic acid delivered; and most preferably, at least about 100 pg of protein expressed per mg of total tissue protein per µg of nucleic acid delivered.

When the biomarker regulatory agent is a protein, small molecule (i.e., the products of drug design) or antibody, a preferred single dose of such a compound typically comprises between about 0.01 microgram×kilogram$^{-1}$ and about 10 milligram×kilogram$^{-1}$ body weight of an animal. A more preferred single dose of an agent comprises between about 1 microgram×kilogram$^{-1}$ and about 10 milligram×kilogram$^{-1}$ body weight of an animal. An even more preferred single dose of an agent comprises between about 5 microgram×kilogram$^{-1}$ and about 7 milligram×kilogram$^{-1}$ body weight of an animal. An even more preferred single dose of an agent comprises between about 10 microgram×kilogram$^{-1}$ and about 5 milligram×kilogram$^{-1}$ body weight of an animal. Another particularly preferred single dose of an agent comprises between about 0.1 microgram×kilogram$^{-1}$ and about 10 microgram×kilogram$^{-1}$ body weight of an animal, if the agent is delivered parenterally.

In another embodiment, a targeting vector can be used to deliver a particular nucleic acid molecule into a recombinant host cell, wherein the nucleic acid molecule is used to delete or inactivate an endogenous gene (e.g., biomarker-encoding gene) within the host cell or microorganism (i.e., used for targeted gene disruption or knock-out technology). Such a vector may also be known in the art as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to bind to the target gene such that the target gene and the insert undergo homologous recombination, whereby the endogenous target gene is deleted, inactivated or attenuated (i.e., by at least a portion of the endogenous target gene being mutated or deleted).

Compositions of the present invention can be administered to any mammalian patient, and preferably to humans. According to the present invention, administration of a composition is useful to inhibit the tumorigenicity of a target cell or to treat cancer, or to inhibit angiogenesis in a tissue of a patient. Typically, it is desirable to inhibit the growth of a target cell, or to reduce tumor burden in the patient (tumor numbers and/or volume), or to prevent further growth of the tumor in the patient (tumor stasis), or to obtain any therapeutic benefit in the patient (e.g., increased survival). In one embodiment, patients whom are suitable candidates for the method of the present invention include, but are not limited to, patients that have, or are at risk of developing (e.g., are predisposed to), cancer or a lymphoproliferative disease, or any condition in which regulation of angiogenesis might be beneficial. In another embodiment, patients whom are suitable candidates for a method of the invention include, but are not limited to: patients with vascular deficiencies, cardiovascular disease, or patients in whom stimulation of endothelial cell activation and stabilization of newly formed microvessels or other vessels would be beneficial. Increasing or decreasing the expression or biological activity of various biomarkers to inhibit or promote angiogenesis in the absence of obtaining some therapeutic benefit is useful for the purposes of determining factors involved (or not involved) in a disease and preparing a patient to more beneficially receive another therapeutic composition. In a preferred embodiment, however, the methods of the present invention are directed to the inhibition of cancer or inhibition or promotion of angiogenesis in a tissue, which is useful in providing some therapeutic benefit to a patient.

As such, a therapeutic benefit is not necessarily a cure for a particular disease or condition, but rather, preferably encompasses a result which most typically includes alleviation of the disease or condition or increased survival, elimination of the disease or condition, reduction of a symptom associated with the disease or condition (e.g., reduced tumor burden), prevention or alleviation of a secondary disease or condition resulting from the occurrence of a primary disease or condition (e.g., metastatic tumor growth resulting from a primary cancer), and/or prevention of the disease or condition. As used herein, the phrase "protected from a disease" refers to reducing the symptoms of the disease; reducing the occurrence of the disease, and/or reducing the severity of the disease. Protecting a patient can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment). In particular, protecting a patient from a disease is accomplished by inhibiting the tumorigenicity of a target cell in the patient or inhibiting or promoting angiogenesis in the cells or tissues of a patient by regulating biomarker expression or biological activity such that a beneficial effect is obtained. A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

One embodiment of the present invention relates to a method (i.e., an assay) for diagnosing or assessing tumor cells (cancer) or the potential therefore in a patient. In one aspect of this embodiment, the method includes the steps of: (a) detecting a level of expression or activity of one or more biomarkers of the present invention in a test sample from a patient to be diagnosed; and (b) comparing the level of expression or activity of the biomarker(s) in the test sample to a normal level of biomarker expression or activity established from a control sample. For example, it is noted that the present inventor has determined that expression of MAGP-2 is upregulated in uterine tumor cells. According to the present invention, detection of the biomarker can be achieved by any method that detects the expression of the biomarker. Detection of a statistically significant difference in biomarker expression or activity in the test sample, as compared to the control level of biomarker expression or biological activity, is an indicator of a difference in the tumorigenicity or potential therefore of cells in the test sample as compared to cells in the control sample. The expression of the biomarker may be cell- and context-specific. Therefore, biomarker expression or activity could be either upregulated or downregulated in a cell as compared to the control. Typically, the biomarker is upregulated or down-regulated in the manner associated with the expression of the biomarker during angiogenesis as represented in any one or more of the Tables or experiments described herein. The method of the present invention can be used for any type of tumor wherein the biomarker expression or activity is found to be statistically significantly changed in tumor cells as compared to the corresponding normal cells.

According to the present invention, the phrase "tumorigenicity" refers primarily to the tumor status of a cell or cells (e.g., the extent of neoplastic transformation of a cell, the malignancy of a cell, the propensity for a cell to form a tumor and/or have characteristics of a tumor, or simply the presence or absence of tumor cells in a patient or tissue/organ), which is reflective of a change of a cell or population of cells from a normal to malignant state. Tumorigenicity indicates that tumor cells are present in a sample, and/or that the transformation of cells from normal to tumor cells is in progress, as may be confirmed by any standard of measurement of tumor development. The change typically involves cellular proliferation at a rate which is more rapid than the growth observed for normal cells under the same conditions, and which is typically characterized by one or more of the following traits: continued growth even after the instigating factor (e.g., carcinogen, virus) is no longer present; a lack of structural organization and/or coordination with normal tissue, and typically, a formation of a mass of tissue, or tumor. A tumor, therefore, is most generally described as a proliferation of cells (e.g., a neoplasia, a growth, a polyp) resulting from neoplastic growth and is most typically a malignant tumor. In the case of a neoplastic transformation, a neoplasia is malignant or is predisposed to become malignant. Malignant tumors are typically characterized as being anaplastic (primitive cellular growth characterized by a lack of differentiation), invasive (moves into and destroys surrounding tissues) and/or metastatic (spreads to other parts of the body). As used herein, reference to a "potential for neoplastic transformation", "potential for tumorigenicity" or a "potential for tumor cell growth" refers to an expectation or likelihood that, at some point in the future, a cell or population of cells will display characteristics of neoplastic transformation, including rapid cellular proliferation characterized by anaplastic, invasive and/or metastatic growth.

This method of the present invention has several different uses. First, the method can be used to diagnose tumorigenicity, or the potential for tumorigenicity, or simply the presence or absence of tumor cells, in a subject. The subject can be an individual who is suspected of having a tumor, or an individual who is presumed to be healthy, but who is undergoing a routine or diagnostic screening for the presence of a tumor (cancer). The subject can also be an individual who has previously been diagnosed with cancer and treated, and who is now under surveillance for recurring tumor growth. The terms "diagnose", "diagnosis", "diagnosing" and variants thereof refer to the identification of a disease or condition on the basis of its signs and symptoms. As used herein, a "positive diagnosis" indicates that the disease or condition, or a potential for developing the disease or condition, has been identified. In contrast, a "negative diagnosis" indicates that the disease or condition, or a potential for developing the disease or condition, has not been identified. Therefore, in the present invention, a positive diagnosis (i.e., a positive assessment) of tumor growth or tumorigenicity (i.e., malignant or inappropriate cell growth or neoplastic transformation), or the potential therefore, means that the indicators (e.g., signs, symptoms) of tumor presence and/or growth according to the present invention (i.e., a change in biomarker expression or biological activity as compared to a baseline control) have been identified in the sample obtained from the subject. Such a subject can then be prescribed treatment to reduce or eliminate the tumor growth. Similarly, a negative diagnosis (i.e., a negative assessment) for tumor growth or a potential therefore or the absence of tumor cells means that the indicators of tumor growth or tumor presence or a likelihood of developing tumors as described herein (i.e., a change in biomarker expression or biological activity as compared to a baseline control) have not been identified in the sample obtained from the subject. In this instance, the subject is typically not prescribed any treatment, but may be reevaluated at one or more timepoints in the future to again assess tumor growth. Baseline levels for this particular embodiment of the method of assessment of tumorigenicity of the present invention are typically based on a "normal" or "healthy" sample from the same bodily source as the test sample (i.e., the same tissue, cells or bodily fluid), as discussed in detail below.

In a second embodiment, the method of the present invention can be used more specifically to "stage" a tumor in a patient. Therefore, the patient can be diagnosed as having a tumor or potential therefore by the method as discussed above, or by any other suitable method (e.g., physical exam, X-ray, CT scan, blood test for a tumor antigen, surgery), and then (or at the same time, when the present method is also used as a diagnostic), the method of the present invention can be used to determine the stage of progression of tumor growth in an individual. For most cancer types, standard staging criteria exist and are known in the art. For example, in breast tumors, there are five different general stages of tumor development which are known and acknowledged in the art as stages 0, I, II, III and IV (although these stages can be grouped into more complex subgroups based on more specific indicators). In this embodiment of the method of the present invention, the biomarker expression and/or biological activity in the patient sample is compared to a panel of several different "baseline" levels of biomarker expression or biological activity, wherein each baseline level represents a previously established level for a given stage of the cancer being diagnosed. The ability to "stage" a tumor in the method of the present invention allows the physician to more appropriately prescribe treatment for the patient.

In a third embodiment of this method of the present invention, the method is used to monitor the success, or lack thereof, of a treatment for cancer in a patient that has been diagnosed as having cancer. In this embodiment, the baseline or control level of biomarker expression or biological activity typically includes the previous level of biomarker expression or biological activity in a sample of the patient's tumor, so that a new level of biomarker expression or biological activity can be compared to determine whether tumor cell growth is decreasing, increasing, or substantially unchanged as compared to the previous, or first sample (i.e., the initial sample which presented a positive diagnosis). In addition, or alternatively, a baseline established as a "normal" or "healthy" level of biomarker expression or biological activity can be used in this embodiment, particularly to determine in what manner the biomarker expression is regulated in tumors for the given cell type. This embodiment allows the physician to monitor the success, or lack of success, of a treatment that the patient is receiving for cancer, and can help the physician to determine whether the treatment should be modified. In one embodiment of the present invention, the method includes additional steps of modifying cancer treatment for the patient based on whether an increase or decrease in tumor cell growth is indicated by evaluation of biomarker expression and/or biological activity in the patient.

The first step of the method of the present invention includes detecting biomarker expression or biological activity in a test sample from a patient. According to the present invention, the term "test sample" can be used generally to refer to a sample of any type which contains cells or products that have been secreted from cells (e.g., some biomarkers of the invention are secreted proteins and so one can evaluate a cell supernate, bodily fluid or other media into which such biomarkers may have been secreted by a cell) to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells that are preferably evaluated. Cells can be obtained, for example, by scraping of a tissue, processing of a tissue sample to release individual cells, or isolation from a bodily fluid. A tissue sample, although similar to a sample of isolated cells, is defined herein as a section of an organ or tissue of the body which typically includes several cell types and/or cytoskeletal structure which holds the cells together. One of skill in the art will appreciate that the term "tissue sample" may be used, in some instances, interchangeably with a "cell sample", although it is preferably used to designate a more complex structure than a cell sample. A tissue sample can be obtained by a biopsy, for example, including by cutting, slicing, or a punch. A bodily fluid sample, like the tissue sample, contains the cells to be evaluated for biomarker expression or biological activity and/or contains the soluble biomarker secreted by cells, and is a fluid obtained by any method suitable for the particular bodily fluid to be sampled. Bodily fluids suitable for sampling include, but are not limited to, blood, mucous, seminal fluid, saliva, breast milk, bile and urine.

In general, the sample type (i.e., cell, tissue or bodily fluid) is selected based on the accessibility and structure of the organ or tissue to be evaluated for tumor cell growth and/or on what type of cancer is to be evaluated. For example, if the organ/tissue to be evaluated is the breast, the sample can be a sample of epithelial cells from a biopsy (i.e., a cell sample) or a breast tissue sample from a biopsy (a tissue sample). The sample that is most useful in the present invention will be cells, tissues or bodily fluids isolated from a patient by a biopsy or surgery or routine laboratory fluid collection.

Once a sample is obtained from the patient, the sample is evaluated for detection of biomarker expression or biological activity in the cells of the sample. The phrase "biomarker expression" can generally refer to biomarker mRNA transcription or biomarker protein translation. Preferably, the method of detecting biomarker expression or biological activity in the patient is the same or qualitatively equivalent to the method used for detection of biomarker expression or biological activity in the sample used to establish the baseline level.

Methods suitable for detecting biomarker transcription include any suitable method for detecting and/or measuring mRNA levels from a cell or cell extract. Such methods include, but are not limited to: polymerase chain reaction (PCR), reverse transcriptase PCR (RT-PCR), in situ hybridization, Northern blot, sequence analysis, gene microarray analysis (gene chip analysis) and detection of a reporter gene. Such methods for detection of transcription levels are well known in the art, and many of such methods are described in detail in the attached examples, in Sambrook et al., *Molecular Cloning: A Laboratory Manual*, Cold Spring Harbor Labs Press, 1989 and/or in Glick et al., *Molecular Biotechnology: Principles and Applications of Recombinant DNA*, ASM Press, 1998; Sambrook et al., ibid., and Glick et al., ibid. are incorporated by reference herein in their entireties.

Measurement of biomarker transcription is suitable when the sample is a cell or tissue sample; therefore, when the sample is a bodily fluid sample containing cells or cellular extracts, the cells are typically isolated from the bodily fluid to perform the expression assay, or the fluid is evaluated for the presence of secreted biomarker protein.

Biomarker expression can also be identified by detection of biomarker translation (i.e., detection of biomarker protein in a sample). Methods suitable for the detection of biomarker protein include any suitable method for detecting and/or measuring proteins from a cell or cell extract. Such methods include, but are not limited to, immunoblot (e.g., Western blot), enzyme-linked immunosorbant assay (ELISA), radio-immunoassay (RIA), immunoprecipitation, immunohistochemistry and immunofluorescence. Particularly preferred methods for detection of proteins include any single-cell assay, including immunohistochemistry and immunofluorescence assays. Such methods are well known in the art. Furthermore, antibodies against certain of the biomarkers described herein are known in the art and are described in the public literature, and methods for production of antibodies that can be developed against biomarkers are well known in the art.

The method of the present invention includes a step of comparing the level of biomarker expression or biological activity detected in step (a) to a baseline level (also known as a control level) of biomarker expression or biological activity established from a control sample. According to the present invention, a "baseline level" is a control level, and in some embodiments (but not all embodiments, depending on the method), a normal level, of biomarker expression or activity against which a test level of biomarker expression or biological activity (i.e., in the test sample) can be compared. Therefore, it can be determined, based on the control or baseline level of biomarker expression or biological activity, whether a sample to be evaluated for tumor cell growth has a measurable increase, decrease, or substantially no change in biomarker expression or biological activity, as compared to the baseline level. As discussed above, the baseline level can be indicative of different states of cell tumorigenicity or lack thereof, depending on the primary use of the assay. For example, the baseline level can be indicative of the cell growth expected in a normal (i.e., healthy, negative control, non-tumor) cell sample. Therefore, the term "negative control" or "normal control" used in reference to a baseline level of biomarker expression or biological activity typically refers to a baseline level established in a sample from the patient or from a population of individuals which is believed to be normal (i.e., non-tumorous, not undergoing neoplastic transformation, not exhibiting inappropriate cell growth). For some biomarkers, the negative control may have a higher level of biomarker expression or activity than the tumor type. In another embodiment, a baseline can be indicative of a positive diagnosis of tumor cell growth. Such a baseline level, also referred to herein as a "positive control" baseline, refers to a level of biomarker expression or biological activity established in a cell sample from the patient, another patient, or a population of individuals, wherein the sample was believed, based on data for that cell sample, to be neoplastically transformed (i.e., tumorous, exhibiting inappropriate cell growth, cancerous). In one aspect, the baseline can be indicative of a particular stage of tumor cell growth, which will allow a patient's sample to be "staged" (i.e., the stage of the cancer in the patient can be identified). In yet another embodiment, the baseline level can be established from a previous sample from the patient being tested, so that the tumor growth of a patient can be monitored over time and/or so that the efficacy of a given therapeutic protocol can be evaluated over time. Methods for detecting biomarker expression or biological activity are described in detail above.

The method for establishing a baseline level of biomarker expression or activity is selected based on the sample type, the tissue or organ from which the sample is obtained, the status of the patient to be evaluated, and, as discussed above, the focus or goal of the assay (e.g., diagnosis, staging, monitoring). Preferably, the method is the same method that will be used to evaluate the sample in the patient. In a most preferred embodiment, the baseline level is established using the same cell type as the cell to be evaluated. Baseline levels can be established from an autologous control sample obtained from the patient. According to the present invention, and as used in the art, the term "autologous" means that the sample is obtained from the same patient from which the sample to be evaluated is obtained. The control sample should be of or from the same cell type and preferably, the control sample is obtained from the same organ, tissue or bodily fluid as the sample to be evaluated, such that the control sample serves as the best possible baseline for the sample to be evaluated. In one embodiment, when the goal of the assay is diagnosis of abnormal cell growth, it is desirable to take the control sample from a population of cells, a tissue or a bodily fluid which is believed to represent a "normal" cell, tissue, or bodily fluid, or at a minimum, a cell or tissue which is least likely to be undergoing or potentially be predisposed to develop tumor cell growth. For example, if the sample to be evaluated is an area of apparently abnormal cell growth, such as a tumorous mass, the control sample is preferably obtained from a section of apparently normal tissue (i.e., an area other than and preferably a reasonable distance from the tumorous mass) in the tissue or organ where the tumorous mass is growing.

In another embodiment, when the goal is to monitor tumor cell growth in the patient, the autologous baseline sample is typically a previous sample from the patient which was taken from an apparent or confirmed tumorous mass, and/or from apparently normal (i.e., non-tumor) tissue in the patient (or a different type of baseline for normal can be used, as discussed below). Therefore, a second method for establishing a baseline level of biomarker expression or biological activity is to establish a baseline level of biomarker expression or biological activity from at least one measurement of biomarker expression or biological activity in a previous sample from the same patient. Such a sample is also an autologous sample, but is taken from the patient at a different time point than the sample to be tested. Preferably, the previous sample(s) were of a same cell type, tissue type or bodily fluid type as the sample to be presently evaluated. In one embodiment, the previous sample resulted in a negative diagnosis (i.e., no tumor cell growth, or potential therefore, was identified). In this embodiment, a new sample is evaluated periodically (e.g., at annual physicals), and as long as the patient is determined to be negative for tumor development, an average or other suitable statistically appropriate baseline of the previous samples can be used as a "negative control" for subsequent evaluations. For the first evaluation, an alternate control can be used, as described below, or additional testing may be performed to confirm an initial negative diagnosis, if desired, and the value for biomarker expression or biological activity can be used thereafter. This type of baseline control is frequently used in other clinical diagnosis procedures where a "normal" level may differ from patient to patient and/or where obtaining an autologous control sample at the time of diagnosis is not possible, not practical or not beneficial.

In another embodiment, the previous sample from the patient resulted in a positive diagnosis (i.e., tumor growth was positively identified). In this embodiment, the baseline provided by the previous sample is effectively a positive control for tumor growth, and the subsequent samplings of the patient are compared to this baseline to monitor the progress of the tumor growth and/or to evaluate the efficacy of a treatment that is being prescribed for the cancer. In this embodiment, it may also be beneficial to have a negative baseline level of biomarker expression or biological activity (i.e., a normal cell baseline control), so that a baseline for remission or regression of the tumor can be set. Monitoring of a patient's tumor growth can be used by the clinician to modify cancer treatment for the patient based on whether an increase or decrease in cell growth is indicated.

It will be clear to those of skill in the art that some samples to be evaluated will not readily provide an obvious autologous control sample, or it may be determined that collection of autologous control samples is too invasive and/or causes undue discomfort to the patient. In these instances, an alternate method of establishing a baseline level of biomarker expression or biological activity can be used.

Another method for establishing a baseline level of biomarker expression or biological activity is to establish a baseline level of biomarker expression or biological activity from control samples, and preferably control samples that were obtained from a population of matched individuals. It is preferred that the control samples are of the same sample type as the sample type to be evaluated for biomarker expression or biological activity (e.g., the same cell type, and preferably from the same tissue or organ). According to the present invention, the phrase "matched individuals" refers to a matching of the control individuals on the basis of one or more characteristics which are suitable for the type of cell or tumor growth to be evaluated. For example, control individuals can be matched with the patient to be evaluated on the basis of gender, age, race, or any relevant biological or sociological factor that may affect the baseline of the control individuals and the patient (e.g., preexisting conditions, consumption of particular substances, levels of other biological or physiological factors). For example, levels of biomarker expression in the uterine tissue of a normal individual (i.e., having uterine tissue that is not neoplastically transformed or predisposed to such transformation) may be lower or higher in individuals of a given classification (e.g., elderly vs. teenagers, smokers vs. non-smokers) (although such variation in groups is not currently known). To establish a control or baseline level of biomarker expression or biological activity, samples from a number of matched individuals are obtained and evaluated for biomarker expression or biological activity. The sample type is preferably of the same sample type and obtained from the same organ, tissue or bodily fluid as the sample type to be evaluated in the test patient. The number of matched individuals from whom control samples must be obtained to establish a suitable control level (e.g., a population) can be determined by those of skill in the art, but should be statistically appropriate to establish a suitable baseline for comparison with the patient to be evaluated (i.e., the test patient). The values obtained from the control samples are statistically processed using any suitable method of statistical analysis to establish a suitable baseline level using methods standard in the art for establishing such values.

It will be appreciated by those of skill in the art that a baseline need not be established for each assay as the assay is performed but rather, a baseline can be established by referring to a form of stored information regarding a previously determined baseline level of biomarker expression for a given control sample, such as a baseline level established by any of the above-described methods. Such a form of stored information can include, for example, but is not limited to, a reference chart, listing or electronic file of population or individual data regarding "normal" (negative control) or tumor positive (including staged tumors) biomarker expression; a medical chart for the patient recording data from previous evaluations; or any other source of data regarding baseline biomarker expression that is useful for the patient to be diagnosed.

After the level of biomarker expression or biological activity is detected in the sample to be evaluated for tumor cell growth, such level is compared to the established baseline level of biomarker expression or biological activity, determined as described above. Also, as mentioned above, preferably, the method of detecting used for the sample to be evaluated is the same or qualitatively and/or quantitatively equivalent to the method of detecting used to establish the baseline level, such that the levels of the test sample and the baseline can be directly compared. In comparing the test sample to the baseline control, it is determined whether the test sample has a measurable decrease or increase in biomarker expression or biological activity over the baseline level, or whether there is no statistically significant difference between the test and baseline levels. After comparing the levels of biomarker expression or biological activity in the samples, the final step of making a diagnosis, monitoring, or staging of the patient can be performed as discussed above.

As discussed above, a positive diagnosis indicates that increased cell growth, and possibly tumor cell growth (neoplastic transformation), has occurred, is occurring, or is statistically likely to occur in the cells or tissue from which the sample was obtained. In order to establish a positive diagnosis, the level of biomarker activity is modulated as compared to the established baseline by an amount that is statistically significant (i.e., with at least a 95% confidence level, or $p<0.05$). Preferably, detection of at least about a 10% change in biomarker expression or biological activity in the sample as compared to the baseline level results in a positive diagnosis of cancer for said sample, as compared to the baseline. More preferably, detection of at least about a 30% change in biomarker expression or biological activity in the sample as compared to the baseline level results in a positive diagnosis of cancer for said sample, as compared to the baseline. More preferably, detection of at least about a 50% change, and more preferably at least about a 70% change, and more preferably at least about a 90% change, or any percentage change between 5% and higher in 1% increments (i.e., 5%, 6%, 7%, 8% . . . ) in biomarker expression or biological activity in the sample as compared to the baseline level results in a positive diagnosis of cancer for said sample. In one embodiment, a 1.5 fold change in biomarker expression or biological activity in the sample as compared to the baseline level results in a positive diagnosis of cancer for said sample. More preferably, detection of at least about a 3 fold change, and more preferably at least about a 6 fold change, and even more preferably, at least about a 12 fold change, and even more preferably, at least about a 24 fold change, or any fold change from 1.5 up in increments of 0.5 fold (i.e., 1.5, 2.0, 2.5, 3.0 . . . ) in biomarker expression or biological activity as compared to the baseline level, results in a positive diagnosis of cancer for said sample.

Once a positive diagnosis is made using the present method, the diagnosis can be substantiated, if desired, using any suitable alternate method of detection of tumor cells, including pathology screening, blood screening for tumor antigens, and surgery.

Included in the present invention are kits for assessing angiogenesis in cells or for diagnosing tumor cells (cancer) in a patient. The assay kit includes: (a) reagents for detecting biomarker expression or activity in a test sample (e.g., a probe that hybridizes under stringent hybridization conditions to a nucleic acid molecule encoding the biomarker or a fragment thereof; RT-PCR primers for amplification of mRNA encoding the biomarker or a fragment thereof; and/or an antibody, antigen-binding fragment thereof or other antigen-binding peptide that selectively binds to the biomarker); and (b) reagents for detecting a control marker characteristic of a cell type in the test sample (e.g., a probe that hybridizes under stringent hybridization conditions to a nucleic acid molecule encoding a protein marker; PCR primers which amplify such a nucleic acid molecule; and/or an antibody, antigen binding fragment thereof, or antigen binding peptide that selectively binds to the control marker in the sample).

The reagents for detecting of part (a) and or part (b) of the assay kit of the present invention can be conjugated to a detectable tag or detectable label. Such a tag can be any suitable tag which allows for detection of the reagents of part (a) or (b) and includes, but is not limited to, any composition or label detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

In addition, the reagents for detecting of part (a) and or part (b) of the assay kit of the present invention can be immobilized on a substrate. Such a substrate can include any suitable substrate for immobilization of a detection reagent such as would be used in any of the previously described methods of detection. Briefly, a substrate suitable for immobilization of a means for detecting includes any solid support, such as any solid organic, biopolymer or inorganic support that can form a bond with the means for detecting without significantly effecting the activity and/or ability of the detection means to detect the desired target molecule. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand.

According to the present invention, the method and assay for assessing tumor cells in a patient, as well as other methods disclosed herein, are suitable for use in a patient that is a member of the Vertebrate class, Mammalia, including, without limitation, primates, livestock and domestic pets (e.g., a companion animal). Most typically, a patient will be a human patient.

The following examples are provided for the purpose of illustration and are not intended to limit the scope of the present invention. Each publication or other reference disclosed below and elsewhere herein is incorporated herein by reference in its entirety.

EXAMPLES

The following Materials and Methods were used in Examples 1-5 below.

Plasmids

All retroviral expression vectors encoding various putative angiogenic factors were generated by first PCR amplifying their full-length cDNAs from expressed sequence tags using oligonucleotides that facilitated their subsequent subcloning into the pcDNA3.1/Myc-His B vector (Invitrogen). The resulting full-length Myc-His$_6$-tagged cDNAs were PCR amplified using oligonucleotides that permitted their ligation into the bicistronic retroviral vector, pMSCV-IRES-YFP (Albig and Schiemann, 2005). Table II identifies all of the IMAGE clones and oligonucleotides used to synthesize these retroviral vectors. All putative angiogenic factor inserts were sequenced in their entirety on an Applied Biosystems 377A DNA sequencing machine.

TABLE II

Cloning oligonucleotides

| Gene name | Image clone | Oligos for subcloning to pcDNA3.1/Myc-His | Oligos for subcloning to pMSCV-YFP |
|---|---|---|---|
| Matrilin-2 | 5063535 | 5'(NotI)<br>GGCGGCGCGGCCGCATGGAGAAGATGTTGGTG<br>SEQ ID NO: 57<br>3'(SacII)<br>GGCGGCCCGCGGTCTGTATTTTAGGCGATT<br>SEQ ID NO: 58 | 5'(XhoI)<br>GGCGGCCTCGAGATGGAGAAGATGTTGGTG<br>SEQ ID NO: 59<br>3'(EcoRI)<br>CCGGCCGAATTCTCAATGGTGATGGTGATGATGACC<br>SEQ ID NO: 60 |
| Lumican | 5707371 | 5'(BamHI)<br>GGCGCCGGATCCATGAATGTATGTGCGTTC<br>SEQ ID NO: 61<br>3'(NotI)<br>GGCGCCGGATCCATGAATGTATGTGCGTTC<br>SEQ ID NO: 62 | 5'(BglII)<br>GGCGCCAGATCTATGAATGTATGTGCGTTC<br>SEQ ID NO: 63<br>3'(EcoRI)<br>CCGGCCGAATTCTCAATGGTGATGGTGATGATGACC<br>SEQ ID NO: 64 |
| ECM1 | 5347298 | 5'(BamHI)<br>GGCGGCGGATCCATGGGGACCGTATCCAGA<br>SEQ ID NO: 65<br>3'(SacII)<br>GGCGGCCCGCGGTTCTTCCTTGGACCCAGG<br>SEQ ID NO: 66 | 5'(ECM1)<br>GGCGCCAGATCTATGAATGTATGTGCGTTC<br>SEQ ID NO: 67<br>3'(HpaI)<br>GGCCGGGTTAACTCAATGGTGATGGTGATGATG<br>SEQ ID NO: 68 |
| SMOC-2 | 3988177 | 5'(HindIII)<br>GGCGGCAAGCTTATGCTGCCGCCACAGCTG<br>SEQ ID NO: 69<br>3'(SacII)<br>GGCGGCCCGCGGTCCTTGTTTCCTGGGCTG<br>SEQ ID NO: 70 | 5'(BglII)<br>GGCGGCCTCGAGATGTGGCCCCAACCACCC<br>SEQ ID NO: 71<br>3'(EcoRI)<br>CCGGCCGAATTCTCAATGGTGATGGTGATGATGACC<br>SEQ ID NO: 72 |
| MAGP-2 | 3469761 | 5'(HindIII)<br>GGCGGCAAGCTTATGCTGTTCTTGGGGCAG<br>SEQ ID NO: 73<br>3'(SacII)<br>GGCGGCCCGCGGCAGACCATCGGGTCTCTG<br>SEQ ID NO: 74 | 5'(XhoI)<br>GGCGGCCTCGAGATGTGGCCCCAACCACCC<br>SEQ ID NO: 75<br>3'(EcoRI)<br>CCGGCCGAATTCTCAATGGTGATGGTGATGATGACC<br>SEQ ID NO: 76 |
| AK002276 | 1481807 | 5'(HindIII)<br>GGCGGCAAGCTTATGGCGTCTCGGGAGTCA<br>SEQ ID NO: 77<br>3'(SacIII)<br>GGCGGCCCGCGGTGAAGCCTTGGCTTTCCG<br>SEQ ID NO: 78 | 5'(EcoRI)<br>GGCGGCGAATTCATGGCGTCTCGGGAGTCA<br>SEQ ID NO: 79<br>3'(EcoRI)<br>CCGGCCGAATTCTCAATGGTGATGGTGATGATGACC<br>SEQ ID NO: 80 |
| CRELD-2 | 6336331 | 5'(HindIII)<br>GGCGGCCCGCGGTGAAGCCTTGGCTTTCCG<br>SEQ ID NO: 81<br>3'(SacII)<br>GGCGGCCCGCGGCAAATCCTCACGGGAGGG<br>SEQ ID NO: 82 | 5'(BglII)<br>GGCGGCAGATCTATGCACCTGCTGCTTGCA<br>SEQ ID NO: 83<br>3'(XhoI)<br>CCGGCCCTCGAGTCAATGGTGATGGTGATGATGACC<br>SEQ ID NO: 84 |

The Myc-tagged mammalian expression vectors encoding murine Notch1 [pCS2+mN1FL6MT; (Mumm et al, 2000)] and Jagged-1 [pCS2+Jag1-6MT; (Mumm et al, 2000)] were kindly provided by Dr. Raphael Kopan (Washington University, St. Louis, Mo.). A retroviral Notch1 ICD vector was constructed by PCR amplifying the murine Notch1 ICD domain (amino acids 1744-2531 and contained in pCS2-mN1FL6MT) using a 5' oligonucleotide that contained a unique Xho I restriction site, a Kozak consensus sequence, and a start codon:

SEQ ID NO: 121)
(5'GGCGGCCTCGAGGCCACCATGGTGCTGCTGTCCCGC;

and a 3' oligonucleotide that contained a unique Hpa I restriction site, a stop codon, and the C-terminal Myc-tag:

SEQ ID NO: 122)
(5'GGCGGCGTTAACTCATGAATTCAAGTCCTCTTCAGA;

The resulting PCR product was ligated into identical restriction sites in the bicistronic retroviral vector, pMSCV-IRES-GFP (Albig and Schiemann, 2005). The pHes1-luciferase, pCMV-Hes1, and pCMV-NICD plasmids were kindly provided by Dr. Jan Jensen (University of Colorado Health Science Center, Denver, Colo.).

Cell Culture and Retroviral Infections

Retroviral supernatants were produced by EcoPack2 retroviral packaging cells (Clontech, Mountain View, Calif.) and used to infect MB114 cells as described previously (Albig et al, 2006; Albig and Schiemann, 2004). Infected cells were analyzed 48 h post-infection and the highest 10% of GFP-expressing cells were collected on a MoFlo cell sorter (Cytomation, Fort Collins, Colo.). Afterward, isolated cells were expanded to yield stable polyclonal populations that were ≥95% positive for transgene expression. Human kidney 293T cells were cultured in DMEM media supplemented with 10% fetal bovine serum (FBS), while human umbilical vein ECs (HUVEC; passages 3-6) were maintained in EGM-2 media (Cambrex Corp., East Rutherford, N.J.) supplemented with EC growth factors (Bullet Kit, Cambrex).

Recombinant MAGP-2 Protein Production

A bacterial MAGP-2 expression vector was synthesized by PCR amplifying the full-length MAGP-2 cDNA (less its signal sequence) using oligonucleotides that incorporated unique Nde I (N-terminus) and Bam HI (C-terminus). The resulting PCR fragment was ligated into identical sites in pSBET (Schenk et al, 1995), which appended a FLAG-tag to the C-terminus of MAGP-2. FLAG-tagged recombinant MAGP-2 protein was purified by passing TBS/0.1% Triton X-100-solubilized bacterial cell extracts over a column containing immobilized FLAG-M2 monoclonal antibodies (Sigma, St. Louis, Mo.). Bound proteins were washed initially with 10 column volumes of TBS/0.1% Triton X-100, followed by an additional 20 column volumes of TBS. Afterward, recombinant MAGP-2 was eluted by addition of 2.5 column volumes of FLAG M2 peptide (100 g/ml), and subsequently was concentrated by centrifugation against PBS (5 kDa cutoff; Sartorius, Goettingen, Germany).

EC Activity Assays

The effect putative angiogenic agents had on MB114 cell activities were determined as follows: (i) cell proliferation using a [$^3$H]thymidine incorporation assay as described (Albig et al, 2006; Albig and Schiemann, 2004; Albig and Schiemann, 2005); (ii) cell invasion through Matrigel matrices using a modified Boyden-chamber assay as described (Albig et al, 2006; Albig and Schiemann, 2004; Albig and Schiemann, 2005); (iii) p38 MAPK phosphorylation using immunoblot analyses as described (Albig et al, 2006; Albig and Schiemann, 2004; Albig and Schiemann, 2005); (iv) angiogenic sprouting in rat tail collagen matrices as described (Albig et al, 2006; Albig and Schiemann, 2004); and (v) Hes1- and SBE-driven luciferase reporter gene assays as described (Albig et al, 2006; Albig and Schiemann, 2004; Albig and Schiemann, 2005).

Notch1 Processing Assay

To monitor the effects of MAGP-2 on the processing and S3 cleavage of Notch1, human kidney 293T cells were transiently transfected in 6-well plates with LT-1 liposomes containing 0.5 μg/well of Notch1 (pCS2+mN1FL6MT), 0.5 μg/well Jagged-1 (pCS2+Jag1-6MT), or 1.5 μg/well of MAGP-2 (pcDNA3.1-MAGP-2/Myc-His) in all combinations. Forty-eight h post-transfection, the cells were washed with ice-cold PBS, lysed immediately in Buffer H/1% Triton X-100 [500 μl/well; (Schiemann et al, 2002)], and incubated on ice for 30 min. Afterward, insoluble material was removed by microcentrifugation and 100 μl of the resulting clarified extract was fractionated through 6% SDS-PAGE gels. The fractionated proteins were transferred electrophoretically to nitrocellulose and probed with anti-Myc 9E10 monoclonal antibodies (Covance, Princeton, N.J.) to visual Notch1 cleavage species.

Matrigel Plug Implantation Assay

The effect of MAGP-2 on vessel formation and infiltration into Matrigel plugs implanted into genetically normal mice was determined as described (Albig et al, 2006). Briefly, phenol red-free Matrigel (BD biosciences, Bedford, Mass.) was mixed with PBS (diluent), bFGF (50 or 300 ng/ml; R&D Systems, Minneapolis, Minn.), or recombinant MAGP-2 (1 μg/ml) together with bFGF (50 ng/ml), and the resulting mixtures were injected twice subcutaneously in the ventral groin area (400 μl/injection) of C57BL/6 mice. The mice were sacrificed 10 days post-implantation and the Matrigel plugs were dissected, fixed overnight in 10% formalin, and sectioned in the National Jewish Histology Laboratory. Afterward, Masson's trichrome staining was performed to visualize infiltrating vessels, which were quantified under a light microscope by determining the average number of vessels present in 5 random fields (200× magnification). Only those fields that contained at least one vessel in the area underlying the skin were tallied. Two mice were used per experimental condition and this experiment was performed three times in its entirety. All animal studies were performed according to protocol procedures approved by the Animal Care and Use Committee at National Jewish Medical and Research Center.

Semi-Quantitative Real-Time PCR

Semi-quantitative real-time PCR was performed as previously described (Albig et al, 2006; Albig and Schiemann, 2005). Briefly, MB114 cells were induced to tubulate on Matrigel matrices for 1-25 h, whereupon total RNA was isolated using the RNAqueous kit, followed by an additional round of phenol/chloroform extraction and ethanol precipitation as described above. Total RNA (1 μg) was reverse transcribed with random hexamers and iScript reverse transcriptase according to the manufacturer's recommendations (BioRad, Hercules, Calif.). The resulting cDNA reaction mixtures were diluted 40-fold in H$_2$O and employed in semi-quantitative real-time PCR reactions (25 μl) that used the SYBR Green PCR system (Applied Biosystems, Foster City, Calif.) supplemented with 10 μl of diluted cDNA and 0.1 μM of the oligonucleotide pairs listed in Table III. PCR reactions were performed and analyzed on an ABI 7000 sequence detection system (Applied Biosystems). Differences in RNA concentrations were controlled by normalizing individual gene signals to their corresponding GAPDH RNA signals.

TABLE III

Real-Time PCR oligonucleotides

| Gene name | Real Time PCR Forward Oligonucleotide | Real-Time PCR Reverse Oligonucleotide |
|---|---|---|
| ADAMts1 | 5' AATGTTTGATGGACAAGCCCC SEQ ID NO: 85 | 5' TGCTTGGATTCCTCTCCGAA SEQ ID NO: 86 |
| ADAMts7 | 5' ACCAGGAACGCCTACCTTTTC SEQ ID NO: 87 | 5' TCCAGTTTCCTACTTGCCAGC SEQ ID NO: 88 |
| CTGF | 5' CTGCCAGTGGAGTTCAAATGC SEQ ID NO: 89 | 5' TCATTGTCCCCAGGACAGTTG SEQ ID NO: 90 |

TABLE III-continued

Real-Time PCR oligonucleotides

| Gene name | Real Time PCR Forward Oligonucleotide | Real-Time PCR Reverse Oligonucleotide |
|---|---|---|
| Decorin | 5' GGCATTCAAACCTCTCGTGAA SEQ ID NO: 91 | 5' TCATGGACACGAAGTTCCTGG SEQ ID NO: 92 |
| ECM1 | 5' CGGAGGAATTCGTGGAAAGA SEQ ID NO: 93 | 5' CCACTAAAGCCACGTTCCTCA SEQ ID NO: 94 |
| Inhibin β-a | 5' TCCCCAAGGCTAACAGAACCA SEQ ID NO: 95 | 5' CCCCTTTAAGCCCATTTCCTC SEQ ID NO: 96 |
| Inhibin β-b | 5' CAGACATCGCATCCGCAAA SEQ ID NO: 97 | 5' AATGATCCAGTCGTTCCAGCC SEQ ID NO: 98 |
| Integrin α-3 | 5' AACCCCTTCAAACGGAACCA SEQ ID NO: 99 | 5' TCGACGTGGACAGCTGAAGAA SEQ ID NO: 100 |
| Integrin α-6 | 5' CTCGTTCTTCGTTCCAGGTTG SEQ ID NO: 101 | 5' AGCAGCAGCGGTGACATCTAT SEQ ID NO: 102 |
| Lipocalin-7 | 5' GGACAACTGCAATCGATGCA SEQ ID NO: 103 | 5' GCCTCGGTTGATGGCTTTAAT SEQ ID NO: 104 |
| Loxl-3 | 5' AAGTGTGACAGAATGCGCCTC SEQ ID NO: 105 | 5' ACTTGCAACTGATGCTCCACC SEQ ID NO: 106 |
| Lumican | 5' AGTGTGCCAATGGTTCCTCCT SEQ ID NO: 107 | 5' TGCAGGTCTGTGACGTTCTCA SEQ ID NO: 108 |
| Matrilin-2 | 5' CACAGGCATCCTGATCTTTGC SEQ ID NO: 109 | 5' TGAAATTGGCCACCAGGAAG SEQ ID NO: 110 |
| Nephronectin | 5' GGTGATGGAGGACATGCGAAT SEQ ID NO: 111 | 5' TTGTTGGCTTGGAAGTAGGCC SEQ ID NO: 112 |
| SerpinE-2 | 5' AATCTGATCGATGGTGCCCTT SEQ ID NO: 113 | 5' CGAATGTCCGTTTCTTTGTGC SEQ ID NO: 114 |
| SMOC-2 | 5' CACCAAATGGAAGACCCATCA SEQ ID NO: 115 | 5' ATCATCTGCTTTCCCTGCTCC SEQ ID NO: 116 |
| CRELD-2 | 5' GCAGAGGAACGAGACCCACAGCATC SEQ ID NO: 117 | 5' GTGCCCAGCCCACTTCACACTG SEQ ID NO: 118 |
| MAGP-2 | 5' GCTTGTCTTGGCAGTCAGCATCCC SEQ ID NO: 119 | 5' GGTCGTCTGTGAATGTCTCAGGCAC SEQ ID NO: 120 |

Oligonucleotide Microarray Analysis

Murine brain microvascular MB114 ECs were cultured as previously described (Albig et al, 2006; Albig and Schiemann, 2004). To identify genes differentially expressed during angiogenesis, log phase-growing MB114 cells ($2 \times 10^6$ cells/plate) were plated onto 10-cm plates that contained 4 ml of solidified Matrigel matrices [diluted 5:3 in serum-free media (SFM)]. Tubulogenesis was allowed to proceed for 1, 5, 15, or 25 h, at which point the cells were gently washed twice with ice-cold PBS, and subsequently were scraped, together with their Matrigel cushions, into 16 ml of lysis/binding buffer to isolate total RNA using the RNAqueous kit (Ambion, Austin, Tex.). Isolated total RNA samples were subjected to phenol:choloroform extraction and ethanol precipitation, followed by additional purification using the RNeasy kit (Qiagen, Valencia, Calif.). Afterward, the quality and integrity of purified total RNA (1.5 µg/lane) was analyzed on an Agilent 2100 Bioanalyzer (Agilent Technologies, Palo Alto, Calif.). Biotin-labeled cRNA probes were synthesized using 8 µg of total RNA that was primed with olido-dT and reverse transcribed with Superscript II (Invitrogen, Carlsbad, Calif.), and subsequently were fragmented and hybridized overnight to Affymetrix MOE430A GeneChips according to the manufacturer's recommendations (Affymetrix, Santa Clara, Calif.) in the University of Colorado Health Sciences Center Microarray Core Facility. The microarrays were scanned (2.5-3µ resolution) on a Affymetrix GeneChip Scanner 3000, and differentially expressed mRNAs were identified using GeneSpring 6.0 software (Agilent Technologies). In doing so, individual time points were first compiled into a single experiment that was filtered on flags (i.e., 6 out of 12 flags needed to pass filter). The remaining genes then were filtered by expression levels such that only those genes that were differentially regulated ≥3-fold ≤ in at least one time point were considered significant.

EXAMPLE 1

The following example describes the identification of secretory proteins differentially expressed in tubulating ECs.

To characterize the secretome of ECs undergoing tumor-induced angiogenesis, murine brain microvascular MB114 cells were cultured on tumor-derived basement membranes (i.e., Matrigel matrices) to stimulate angiogenesis activation and the formation of capillary-like structures in vitro. MB114 cells cultured onto Matrigel matrices for 0-25 hours as indicated in FIG. 6 spontaneously reorganized into elongated, capillary-like structures, a response that was readily detected by 5 h, and one that continued to develop over the next 20 h (FIG. 6). Total RNA was isolated at various times after the initiation of tubulogenesis in MB114 cells, and subsequently was used to synthesize biotinylated cRNA probes that were hybridized to Affymetrix MOE430 GeneChips (see Materials and Methods). In doing so, 308 genes were identified whose expression in angiogenic ECs was altered≥3-fold≤. Of these differentially-expressed genes, 63 genes (~20%) encoded EC secretory proteins (Table I), 35 genes (~11%) encoded transmembrane or membrane-associated proteins (Table V), and 210 genes encoded non-secretory proteins (Table IV). This approach identified several secretory proteins known to be associated with angiogenesis and/or microenvironment remodeling, including ADAMTS1 (Iruela-Arispe et al, 2003), CTGF (Brigstock, 2002), HGF (Gao and Vande Woude, 2005), MMPs 3 and 9 (Heissig et al, 2003), thrombospondins 1 and 2 (Armstrong and Bornstein, 2003), and TIMP3 (Qi et al, 2003) (Table I, bold type face). In addition, numerous secretory proteins not previously associated with angiogenesis were identified (Table I, regular text face). The differential expression of 19 individual genes was verified by semi-quantitative real-time PCR (see Materials and Methods). These analyses showed significant concordance in the expression profiles measured either by real-time PCR or microarray analyses (Table VI), indicating that these (and other) genes are indeed bona fide targets of angiogenic signaling systems in tubulating ECs.

TABLE I

Secreted proteins differentially regulated during MB114 tubulogenesis.

| Name | GenBank # | Hours of tubulogenesis | | | | Description |
| --- | --- | --- | --- | --- | --- | --- |
| | | 1 | 5 | 15 | 25 | |
| 9130213B05Rik | BC006604 | 1.0 | 0.3 | 0.3 | 0.6 | RIKEN cDNA 9130213B05 gene (has signal peptide) |
| Adamts1 | D67076 | 1.0 | 0.3 | 0.6 | 0.8 | Adamts1 |
| Adamts7 | AL359935 | 1.0 | 2.4 | 4.8 | 4.2 | Adamts7 |
| C1r | NM_023143 | 1.0 | 1.0 | 2.3 | 5.6 | complement component 1, r subcomponent |
| C1s | BC022123 | 1.0 | 1.0 | 3.8 | 10.7 | complement component 1, s subcomponent |
| C3 | K02782 | 1.0 | 0.7 | 7.9 | 23.0 | complement component 3 |
| Ccl2 | AF065933 | 1.0 | 0.7 | 0.2 | 0.1 | chemokine (C-C motif) ligand 2 |
| Ccl5 | NM_013653 | 1.0 | 2.7 | 3.4 | 3.2 | chemokine (C-C motif) ligand 5 |
| Ccl7 | AF128193 | 1.0 | 0.5 | 0.3 | 0.3 | chemokine (C-C motif) ligand 7 |
| Ccl8 | NM_021443 | 1.0 | 1.1 | 2.8 | 4.9 | chemokine (C-C motif) ligand 8 |
| Cfh | AI987976 | 1 | 1.5 | 3.4 | 12.5 | complement component factor h |
| Clu | NM_013492 | 1.0 | 0.9 | 1.7 | 6.6 | clusterin |
| Col3a1 | AW550625 | 1.0 | 1.3 | 3.0 | 3.9 | procollagen, type III, alpha 1 |
| Col9a3 | BG074456 | 1.0 | 0.8 | 6.7 | 3.2 | procollagen, type IX, alpha 3 |
| Creld2 | AK017880 | 1.0 | 3.1 | 1.0 | 1.1 | cysteine-rich with EGF-like domains 2 |
| Csf3 | NM_009971 | 1.0 | 1.7 | 0.3 | 0.3 | colony stimulating factor 3 (granulocyte) |
| Ctgf | NM_010217 | 1.0 | 0.2 | 0.3 | 0.3 | connective tissue growth factor |
| Cxcl16 | BC019961 | 1 | 3.9 | 3.4 | 3.0 | chemokine (C-X-C motif) ligand 16 |
| Cxcl2 | NM_009140 | 1.0 | 1.2 | 0.2 | 0.1 | chemokine (C-X-C motif) ligand 2 |
| Cyr61 | NM_010516 | 1.0 | 0.5 | 0.3 | 0.2 | cysteine rich protein 61 |
| Dcn | NM_007833 | 1.0 | 2.1 | 6.9 | 11.0 | decorin |
| Ecm1 | NM_007899 | 1.0 | 1.7 | 2.9 | 3.6 | extracellular matrix protein 1 |
| F3 | BC024886 | 1.0 | 0.2 | 0.2 | 0.4 | coagulation factor III |
| Grem1 | BC015293 | 1.0 | 3.8 | 2.5 | 3.9 | cysteine knot superfamily 1, BMP antagonist 1 |
| Hgf | AF042856 | 1.0 | 1.2 | 4.4 | 5.0 | hepatocyte growth factor |
| Igfbp4 | BC019836 | 1.0 | 1.7 | 3.5 | 4.3 | insulin-like growth factor binding protein 4 |
| Igfbp5 | NM_010518 | 1.0 | 0.9 | 3.8 | 5.2 | insulin like growth factor binding protein 5 |
| Il6 | NM_031168 | 1.0 | 3.1 | 3.2 | 2.7 | interleukin 6 |
| Inhba | NM_008380 | 1.0 | 1.9 | 0.4 | 0.3 | inhibin beta-A |
| Lbp | NM_008489 | 1.0 | 0.7 | 2.3 | 5.2 | lipopolysaccharide binding protein |
| Lcn2 | X14607 | 1.0 | 1.3 | 24.7 | 97.3 | lipocalin 2 |
| Lcn7 | BC005738 | 1.0 | 0.6 | 0.3 | 0.3 | lipocalin 7 |
| Lif | AF065917 | 1.0 | 0.6 | 0.2 | 0.1 | leukemia inhibitory factor |
| Loxl3 | NM_013586 | 1.0 | 1.2 | 4.0 | 4.7 | lysyl oxidase-like 3 |
| Lum | AK014312 | 1.0 | 1.1 | 1.8 | 3.2 | lumican |
| MFAP5 (MAGP-2) | NM_015776 | 1.0 | 3.2 | 1.0 | 1.2 | microfibrillar associated protein 5 |
| Matn2 | BC005429 | 1.0 | 1.4 | 6.4 | 9.9 | Matrilin-2 |
| Mglap | NM_008597 | 1.0 | 1.9 | 7.4 | 17.8 | matrix gamma-carboxyglutamate (gla) protein |

TABLE I-continued

Secreted proteins differentially regulated during MB114 tubulogenesis.

| Name | GenBank # | Hours of tubulogenesis | | | | Description |
|---|---|---|---|---|---|---|
| | | 1 | 5 | 15 | 25 | |
| Mmp10 | NM_019471 | 1.0 | 5.4 | 11.8 | 12.1 | matrix metalloproteinase 10 |
| Mmp11 | NM_008606 | 1.0 | 1.4 | 4.9 | 9.4 | matrix metalloproteinase 11 |
| Mmp19 | AF153199 | 1.0 | 1.9 | 5.7 | 9.4 | matrix metalloproteinase 19 |
| Mmp3 | NM_010809 | 1.0 | 1.6 | 3.5 | 10.3 | matrix metalloproteinase 3 |
| Mmp9 | NM_013599 | 1.0 | 4.4 | 5.7 | 3.6 | matrix metalloproteinase 9 |
| Naga | BC021631 | 1.0 | 1.6 | 4.4 | 8.2 | N-acetyl galactosaminidase, alpha |
| Nbl1 | NM_008675 | 1.0 | 1.2 | 2.8 | 5.8 | neuroblastoma, suppression of tumorigenicity 1 |
| Ngfb | NM_013609 | 1.0 | 0.3 | 0.1 | 0.1 | nerve growth factor, beta |
| Npnt | AA223007 | 1 | 0.6 | 0.2 | 0.2 | Nephronectin |
| Npr3 | NM_008728 | 1.0 | 0.6 | 0.2 | 0.2 | natriuretic peptide receptor 3 |
| Olfm1 | D78264 | 1.0 | 1.5 | 3.6 | 3.2 | olfactomedin 1 |
| Plau | NM_008873 | 1.0 | 0.9 | 0.2 | 0.3 | plasminogen activator, urokinase |
| Ptx3 | NM_008987 | 1.0 | 0.1 | 0.3 | 0.3 | pentaxin related gene |
| Serpinb2 | NM_011111 | 1.0 | 1.8 | 1.4 | 1.9 | serine (or cysteine) proteinase inhibitor, clade B, member 2 |
| Serpine1 | NM_008871 | 1.0 | 0.6 | 0.2 | 0.1 | serine (or cysteine) proteinase inhibitor, clade E, member 1 |
| Serpine2 | NM_009255 | 1.0 | 3.6 | 16.3 | 29.5 | serine (or cysteine) proteinase inhibitor, clade E, member 2 |
| Sfrp2 | NM_009144 | 1.0 | 0.8 | 4.1 | 5.5 | secreted frizzled related sequence protein 2 |
| Slpi | NM_011414 | 1.0 | 1.2 | 3.7 | 6.9 | secretory leukocyte protease inhibitor |
| Smoc2 | NM_022315 | 1.0 | 7.2 | 10.6 | 5.5 | Secreted modular calcium binding protein-2 |
| Tgfb3 | BC014690 | 1.0 | 5.4 | 2.2 | 2.8 | transforming growth factor, beta 3 |
| Thbs1 | AI385532 | 1.0 | 0.2 | 0.4 | 0.5 | thrombospondin 1 |
| Thbs2 | NM_011581 | 1.0 | 0.9 | 3.6 | 6.6 | thrombospondin 2 |
| Timp3 | BI111620 | 1.0 | 0.6 | 0.2 | 0.1 | tissue inhibitor of metalloproteinase 3 |
| U90926 | NM_020562 | 1.0 | 1.0 | 0.3 | 0.3 | cDNA sequence U90926 (predicted signal peptide) |
| Wisp1 | NM_018865 | 1.0 | 0.9 | 0.4 | 0.2 | WNT1 inducible signaling pathway protein 1 |

Shown in Table I are differentially-expressed genes that encode for secretory proteins whose expression was altered at least 3-fold in at least one time point during the angiogenic timecourse. in tubulating ECs. Identified genes encoding known angiogenic regulators are shown in bold type face. Identified genes encoding putative angiogenic regulators are shown in regular text face.

TABLE IV

Non-secretory proteins differentially regulated during MB114 tubulogenesis

| Name | GenBank # | Hours of Tubulogenesis | | | | Description |
|---|---|---|---|---|---|---|
| | | 1 | 5 | 15 | 25 | |
| Abca1 | BB144704 | 1.0 | 1.6 | 4.8 | 5.4 | ATP-binding cassette, sub-family A (ABC1), member 1 |
| Abca7 | NM_013850 | 1.0 | 1.2 | 3.4 | 4.1 | ATP-binding cassette, sub-family A (ABC1), member 7 |
| Abcb1a | M30697 | 1.0 | 3.6 | 4.1 | 2.7 | ATP-binding cassette, sub-family B (MDR/TAP), member 1A |
| Abhd4 | NM_134076 | 1.0 | 1.1 | 3.4 | 3.8 | abhydrolase domain containing 4 |
| Abtb1 | NM_030251 | 1.0 | 1.9 | 5.0 | 5.4 | ankyrin repeat and BTB (POZ) domain containing 1 |
| Acta2 | NM_007392 | 1.0 | 0.7 | 0.2 | 0.2 | actin, alpha 2, smooth muscle, aorta |
| Actg2 | NM_009610 | 1.0 | 0.7 | 0.3 | 0.3 | actin, gamma 2, smooth muscle, enteric |
| Ahi1 | BQ175532 | 1.0 | 3.2 | 3.4 | 2.5 | Abelson helper integration site |
| Akr1c18 | NM_134066 | 1.0 | 1.9 | 6.1 | 9.1 | aldo-keto reductase family 1, member C18 |
| Ampd3 | D85596 | 1.0 | 1.0 | 3.7 | 3.7 | AMP deaminase 3 |
| Ankrd1 | AK009959 | 1.0 | 0.3 | 0.3 | 0.2 | ankyrin repeat domain 1 (cardiac muscle) |

TABLE IV-continued

Non-secretory proteins differentially regulated during MB114 tubulogenesis

| Name | GenBank # | Hours of Tubulogenesis | | | | Description |
| | | 1 | 5 | 15 | 25 | |
|---|---|---|---|---|---|---|
| Aox1 | NM_009676 | 1.0 | 1.0 | 6.7 | 11.8 | aldehyde oxidase 1 |
| Apbb3 | BC024809 | 1.0 | 2.0 | 4.2 | 6.1 | amyloid beta (A4) precursor protein-binding, family B, member 3 |
| Aps | NM_018825 | 1.0 | 2.5 | 4.1 | 3.5 | adaptor protein with pleckstrin homology and src |
| Arc | NM_018790 | 1.0 | 0.3 | 0.2 | 0.1 | activity regulated cytoskeletal-associated protein |
| Arg2 | NM_009705 | 1.0 | 1.4 | 4.1 | 5.2 | arginase type II |
| Ass1 | NM_007494 | 1.0 | 1.7 | 3.0 | 3.7 | argininosuccinate synthetase 1 |
| Bckdha | NM_007533 | 1.0 | 1.6 | 3.3 | 3.3 | branched chain ketoacid dehydrogenase E1, alpha polypeptide |
| Atoh8 | AK016909 | 1.0 | 8.5 | 9.3 | 6.8 | atonal homolog 8 (Drosophila) |
| Bbs2 | AF342737 | 1.0 | 1.8 | 3.6 | 4.2 | Bardet-Biedl syndrome 2 homolog (human) |
| Bhlhb2 | NM_011498 | 1.0 | 0.3 | 0.2 | 0.3 | basic helix-loop-helix domain containing, class B2 |
| Bst1 | AI647987 | 1.0 | 1.4 | 3.9 | 5.9 | bone marrow stromal cell antigen 1 |
| Cbfa2t1h | X79989 | 1.0 | 0.4 | 4.7 | 8.4 | CBFA2T1 identified gene homolog (human) |
| Cbr2 | BC010758 | 1.0 | 1.1 | 5.3 | 18.0 | carbonyl reductase 2 |
| Ccnb1 | AU015121 | 1.0 | 0.9 | 0.3 | 0.2 | cyclin B1 |
| Ccng2 | U95826 | 1.0 | 1.7 | 3.4 | 3.1 | cyclin G2 |
| Cdc6 | NM_011799 | 1.0 | 0.7 | 0.2 | 0.1 | cell division cycle 6 homolog (S. cerevisiae) |
| Cdk5r | BB177836 | 1.0 | 0.5 | 0.2 | 0.2 | cyclin-dependent kinase 5, regulatory subunit (p35) |
| Cdkn1a | AK007630 | 1.0 | 1.9 | 0.2 | 0.1 | cyclin-dependent kinase inhibitor 1A (P21) |
| Cebpd | BB831146 | 1.0 | 3.6 | 6.5 | 8.8 | CCAAT/enhancer binding protein (C/EBP), delta |
| Chc1 | NM_133878 | 1.0 | 1.0 | 0.3 | 0.2 | chromosome condensation 1 |
| Cit | AF086823 | 1.0 | 4.0 | 3.5 | 0.5 | citron |
| Cte1 | NM_012006 | 1.0 | 1.0 | 5.0 | 7.1 | mitochondrial acyl-CoA thioesterase 1 |
| Cyp51 | NM_020010 | 1.0 | 0.5 | 0.2 | 0.3 | cytochrome P450, 51 |
| Cyp7b1 | NM_007825 | 1.0 | 3.5 | 3.9 | 6.6 | cytochrome P450, family 7, subfamily b, polypeptide 1 |
| Dbp | BB550183 | 1.0 | 0.6 | 5.1 | 7.7 | D site albumin promoter binding protein |
| Dck | BB030204 | 1.0 | 1.0 | 0.3 | 0.1 | deoxycytidine kinase |
| Dcxr | BC012247 | 1.0 | 2.3 | 8.4 | 20.7 | dicarbonyl L-xylulose reductase |
| Dhrs7 | AK009385 | 1.0 | 1.8 | 3.5 | 5.6 | dehydrogenase/reductase (SDR family) member 7 |
| Dhrs8 | NM_053262 | 1.0 | 0.9 | 4.8 | 5.4 | dehydrogenase/reductase (SDR family) member 8 |
| Diap3 | NM_019670 | 1.0 | 0.5 | 0.2 | 0.1 | diaphanous homolog 3 (Drosophila) |
| Dio2 | AF177196 | 1.0 | 0.5 | 5.5 | 25.1 | deiodinase, iodothyronine, type II |
| Dscr1 | AF282255 | 1.0 | 0.5 | 0.2 | 0.2 | Down syndrome critical region homolog 1 (human) |
| Dusp2 | L11330 | 1.0 | 0.3 | 0.2 | 0.1 | dual specificity phosphatase 2 |
| Dusp9 | AV295798 | 1.0 | 1.0 | 0.2 | 0.1 | dual specificity phosphatase 9 |
| Ech1 | NM_016772 | 1.0 | 1.5 | 3.1 | 4.9 | enoyl coenzyme A hydratase 1, peroxisomal |
| Egr1 | NM_007913 | 1.0 | 0.2 | 0.3 | 0.3 | early growth response 1 |
| Egr2 | X06746 | 1.0 | 0.2 | 0.2 | 0.2 | early growth response 2 |
| Erdr1 | AJ007909 | 1.0 | 0.6 | 0.3 | 0.3 | DNA segment, Chr 14, Wayne State University 89, expressed |
| Fabp5 | BC002008 | 1.0 | 1.0 | 0.3 | 0.2 | fatty acid binding protein 5, epidermal |
| Fbxo32 | AF441120 | 1.0 | 1.4 | 9.3 | 16.4 | F-box only protein 32 |
| Fos | AV026617 | 1.0 | 0.2 | 0.2 | 0.3 | FBJ osteosarcoma oncogene |
| Fosl1 | U34245 | 1.0 | 0.8 | 0.2 | 0.2 | fos-like antigen 1 |
| Foxm1 | NM_008021 | 1.0 | 0.6 | 0.3 | 0.0 | forkhead box M1 |
| Gabpb1 | NM_010249 | 1.0 | 0.9 | 0.2 | 0.2 | GA repeat binding protein, beta 1 |
| Ggtl3 | BC005772 | 1.0 | 2.4 | 3.3 | 4.1 | gamma-glutamyltransferase-like 3 |
| Gjb3 | NM_008126 | 1.0 | 0.9 | 0.2 | 0.2 | gap junction membrane channel protein beta 3 |
| Gstt3 | BC003903 | 1.0 | 1.3 | 3.7 | 3.6 | glutathione S-transferase, theta 3 |
| Hbp1 | BC026853 | 1.0 | 1.1 | 3.0 | 3.5 | high mobility group box transcription factor 1 |
| Hdac11 | BC016208 | 1.0 | 0.7 | 4.2 | 5.9 | histone deacetylase 11 |
| Hmgcr | BB123978 | 1.0 | 0.5 | 0.3 | 0.3 | 3-hydroxy-3-methylglutaryl-Coenzyme A reductase |
| Hmgcs1 | BB705380 | 1.0 | 0.3 | 0.3 | 0.4 | 3-hydroxy-3-methylglutaryl-Coenzyme A synthase 1 |
| Hnrpab | NM_010448 | 1.0 | 0.8 | 0.3 | 0.3 | heterogeneous nuclear ribonucleoprotein A/B |
| Hs6st2 | AW536432 | 1.0 | 0.5 | 0.3 | 0.3 | heparan sulfate 6-O-sulfotransferase 2 |
| Hsd17b7 | NM_010476 | 1.0 | 0.4 | 0.2 | 0.3 | hydroxysteroid (17-beta) dehydrogenase 7 |
| Idi1 | BC004801 | 1.0 | 0.5 | 0.2 | 0.3 | isopentenyl-diphosphate delta isomerase |
| Ier2 | NM_010499 | 1.0 | 0.5 | 0.3 | 0.3 | immediate early response 2 |
| Ier5 | BF147705 | 1.0 | 0.5 | 0.3 | 0.3 | immediate early response 5 |
| Ifi203 | M74124 | 1.0 | 8.5 | 8.4 | 7.2 | interferon activated gene 205 |
| Ifrd1 | NM_013562 | 1.0 | 0.4 | 0.2 | 0.2 | interferon-related developmental regulator 1 |
| Junb | NM_008416 | 1.0 | 0.4 | 0.3 | 0.3 | Jun-B oncogene |
| Kcnip1 | NM_027398 | 1.0 | 0.8 | 0.2 | 0.1 | Kv channel-interacting protein 1 |
| Klf4 | BG069413 | 1.0 | 0.5 | 0.2 | 0.2 | Kruppel-like factor 4 (gut) |
| Kpnb1 | NM_008379 | 1.0 | 0.6 | 0.3 | 0.3 | karyopherin (importin) beta 1 |
| Lhx1 | AV335209 | 1.0 | 0.4 | 0.2 | 0.2 | LIM homeobox protein 1 |
| Lyar | NM_025281 | 1.0 | 1.0 | 0.3 | 0.2 | Ly1 antibody reactive clone |
| Mafk | NM_010757 | 1.0 | 0.3 | 0.3 | 0.3 | v-maf musculoaponeurotic fibrosarcoma oncogene family, protein K (avian) |
| Map3k5 | NM_008580 | 1.0 | 3.4 | 4.2 | 4.2 | mitogen activated protein kinase kinase kinase 5 |
| Mark1 | BM213279 | 1.0 | 1.7 | 8.6 | 18.7 | MAP/microtubule affinity-regulating kinase 1 |
| Mcm3 | BI658327 | 1.0 | 0.8 | 0.3 | 0.1 | minichromosome maintenance deficient 3 (S. cerevisiae) |
| Mgst2 | AV066880 | 1.0 | 2.3 | 11.2 | 17.9 | microsomal glutathione S-transferase 2 |

TABLE IV-continued

Non-secretory proteins differentially regulated during MB114 tubulogenesis

| | | Hours of Tubulogenesis | | | | |
|---|---|---|---|---|---|---|
| Name | GenBank # | 1 | 5 | 15 | 25 | Description |
| Mthfd2 | BG076333 | 1.0 | 1.4 | 0.2 | 0.2 | methylenetetrahydrofolate dehydrogenase (NAD+ dependent), methenyltetrahydrofolate cyclohydrolase |
| Mybl2 | NM_008652 | 1.0 | 0.9 | 0.3 | 0.2 | myeloblastosis oncogene-like 2 |
| Myd116 | NM_008654 | 1.0 | 0.4 | 0.3 | 0.3 | myeloid differentiation primary response gene 116 |
| Myl9 | AK007972 | 1.0 | 0.6 | 0.1 | 0.3 | myosin, light polypeptide 9, regulatory |
| Narg2 | BE952805 | 1.0 | 4.1 | 3.7 | 2.8 | NMDA receptor-regulated gene 2 |
| Ndrg2 | NM_013864 | 1.0 | 1.5 | 5.0 | 5.1 | N-myc downstream regulated 2 |
| Ndrg4 | AV006122 | 1.0 | 1.5 | 3.8 | 3.4 | N-myc downstream regulated 4 |
| Nfatc4 | BF227641 | 1.0 | 0.9 | 4.4 | 5.1 | nuclear factor of activated T-cells, cytoplasmic, calcineurin-dependent 4 |
| Nfkbia | NM_010907 | 1.0 | 0.5 | 0.3 | 0.3 | nuclear factor of kappa light chain gene enhancer in B-cells inhibitor, alpha |
| Nolc1 | BM213850 | 1.0 | 0.8 | 0.3 | 0.2 | nucleolar and coiled-body phosphoprotein 1 |
| Nr4a2 | NM_013613 | 1.0 | 1.7 | 4.3 | 4.1 | nuclear receptor subfamily 4, group A, member 2 |
| Nudt7 | AK011172 | 1.0 | 2.2 | 3.1 | 4.1 | nudix (nucleoside diphosphate linked moiety X)-type motif 7 |
| Pa2g4 | AA672939 | 1.0 | 0.8 | 0.3 | 0.2 | proliferation-associated 2G4 |
| Parc | BC026469 | 1.0 | 1.4 | 3.4 | 3.6 | p53-associated parkin-like cytoplasmic protein |
| Paxip1 | AW742928 | 1.0 | 0.8 | 0.3 | 0.3 | PAX interacting (with transcription-activation domain) protein 1 |
| Pdk2 | NM_133667 | 1.0 | 0.9 | 3.7 | 4.6 | pyruvate dehydrogenase kinase, isoenzyme 2 |
| Pdzrn3 | NM_018884 | 1.0 | 0.7 | 3.1 | 5.1 | semaF cytoplasmic domain associated protein 3 |
| Phyh | NM_010726 | 1.0 | 1.3 | 3.5 | 5.6 | phytanoyl-CoA hydroxylase |
| Plk4 | AI385771 | 1.0 | 0.7 | 0.3 | 0.1 | polo-like kinase 4 (*Drosophila*) |
| Pprc1 | BM199989 | 1.0 | 0.6 | 0.3 | 0.2 | cDNA sequence BC013720 |
| Ptp4a1 | BC003761 | 1.0 | 0.4 | 0.3 | 0.3 | protein tyrosine phosphatase 4a1 |
| Ptpre | U35368 | 1.0 | 1.0 | 0.3 | 0.3 | protein tyrosine phosphatase, receptor type, E |
| Ran | AV090150 | 1.0 | 0.9 | 0.3 | 0.2 | RAN, member RAS oncogene family |
| Rgs16 | U94828 | 1.0 | 1.3 | 0.2 | 0.2 | regulator of G-protein signaling 16 |
| Rgs2 | AF215668 | 1.0 | 2.4 | 7.9 | 12.4 | regulator of G-protein signaling 2 |
| Rgs5 | NM_133736 | 1.0 | 2.0 | 4.8 | 6.5 | regulator of G-protein signaling 5 |
| Rin2 | AK014548 | 1.0 | 2.1 | 3.4 | 4.5 | Ras and Rab interactor 2 |
| Rnase4 | BC005569 | 1.0 | 1.0 | 5.0 | 9.2 | RIKEN cDNA C730049F20 gene |
| Rps10 | AV283093 | 1.0 | 0.7 | 0.3 | 0.3 | RIKEN cDNA 2210402A09 gene |
| Sc4mol | AK005441 | 1.0 | 0.6 | 0.2 | 0.2 | sterol-C4-methyl oxidase-like |
| Sdpr | BE197945 | 1.0 | 0.2 | 0.2 | 0.2 | serum deprivation response |
| Sesn1 | AV016566 | 1.0 | 1.2 | 3.3 | 3.4 | sestrin 1 |
| Shmt1 | AF237702 | 1.0 | 1.0 | 0.3 | 0.1 | serine hydroxymethyl transferase 1 (soluble) |
| Sil | BC004585 | 1.0 | 0.7 | 0.3 | 0.2 | Tal1 interrupting locus |
| Snrpa1 | BC013777 | 1.0 | 0.9 | 0.3 | 0.2 | small nuclear ribonucleoprotein polypeptide A' |
| Socs3 | BB241535 | 1.0 | 2.1 | 4.3 | 6.3 | suppressor of cytokine signaling 3 |
| Sox9 | BC024958 | 1.0 | 0.4 | 0.3 | 0.3 | SRY-box containing gene 9 |
| Srm | NM_009272 | 1.0 | 0.9 | 0.3 | 0.3 | spermidine synthase |
| T2bp | BB277065 | 1.0 | 1.2 | 4.9 | 7.1 | Traf2 binding protein |
| Tagln | BB114067 | 1.0 | 0.9 | 0.2 | 0.1 | transgelin |
| Tcof1 | AW209012 | 1.0 | 0.8 | 0.3 | 0.2 | Treacher Collins Franceschetti syndrome 1, homolog |
| Timm8a | W82151 | 1.0 | 1.1 | 0.2 | 0.2 | translocase of inner mitochondrial membrane 8 homolog a (yeast) |
| Tiparp | BB707122 | 1.0 | 0.3 | 0.2 | 0.2 | TCDD-inducible poly(ADP-ribose) polymerase |
| Tle2 | AU067681 | 1.0 | 0.9 | 4.2 | 8.0 | transducin-like enhancer of split 2, homolog of *Drosophila* E(spl) |
| Tle6 | NM_053254 | 1.0 | 1.1 | 3.2 | 3.5 | transducin-like enhancer of split 6, homolog of *Drosophila* E(spl) |
| Tnfaip3 | NM_009397 | 1.0 | 0.4 | 0.1 | 0.1 | tumor necrosis factor, alpha-induced protein 3 |
| Tnnt2 | NM_011619 | 1.0 | 10.6 | 9.1 | 1.4 | troponin T2, cardiac |
| Tprt | AK011869 | 1.0 | 0.8 | 0.3 | 0.2 | trans-prenyltransferase |
| Trib1 | AV237242 | 1.0 | 0.5 | 0.2 | 0.3 | tribbles homolog 1 (*Drosophila*) |
| Trip13 | AK010336 | 1.0 | 1.0 | 0.3 | 0.1 | thyroid hormone receptor interactor 13 |
| Txnip | AF173681 | 1.0 | 2.8 | 4.3 | 4.9 | thioredoxin interacting protein |
| Ugt1a2 | BC019434 | 1.0 | 2.4 | 4.2 | 6.5 | UDP glycosyltransferase 1 family, polypeptide A6 |
| Uhrf1 | BB702754 | 1.0 | 0.7 | 0.3 | 0.1 | ubiquitin-like, containing PHD and RING finger domains, 1 |
| Ung | BC004037 | 1.0 | 0.5 | 0.2 | 0.2 | uracil-DNA glycosylase |
| Xdh | AV286265 | 1.0 | 1.1 | 9.2 | 27.5 | xanthine dehydrogenase |
| Zfp36 | X14678 | 1.0 | 0.3 | 0.3 | 0.3 | TIS11 (AA 1-183); Mouse TPA-induced TIS11 mRNA. |
| Zfp36l2 | BG094962 | 1.0 | 0.3 | 0.4 | 0.3 | zinc finger protein 36, C3H type-like 2 |
| Zfp60 | NM_009560 | 1.0 | 4.5 | 6.2 | 4.2 | zinc finger protein 60 |
| | | | | | | ESTs |
| | AA223007 | 1.0 | 0.6 | 0.2 | 0.2 | |
| | AA414485 | 1.0 | 0.7 | 0.3 | 0.3 | |
| | AA672926 | 1.0 | 0.5 | 0.3 | 0.2 | |
| | AI324124 | 1.0 | 0.3 | 0.2 | 0.2 | |
| | AK009010 | 1.0 | 0.6 | 0.2 | 0.2 | |
| | AK011311 | 1.0 | 1.2 | 0.3 | 0.2 | |

TABLE IV-continued

Non-secretory proteins differentially regulated during MB114 tubulogenesis

| Name | GenBank # | Hours of Tubulogenesis | | | | Description |
|------|-----------|---|---|---|---|---|
|  |  | 1 | 5 | 15 | 25 |  |
|  | AK012043 | 1.0 | 0.6 | 0.3 | 0.3 |  |
|  | AK014587 | 1.0 | 0.4 | 0.3 | 0.2 |  |
|  | AK015966 | 1.0 | 0.7 | 0.3 | 0.3 |  |
|  | AK017688 | 1.0 | 2.5 | 5.9 | 3.8 |  |
|  | AK018202 | 1.0 | 1.7 | 3.4 | 3.6 |  |
|  | AU017197 | 1.0 | 0.7 | 0.3 | 0.1 |  |
|  | AU018569 | 1.0 | 1.0 | 0.3 | 0.2 |  |
|  | AV167760 | 1.0 | 0.5 | 0.3 | 0.3 |  |
|  | AV171622 | 1.0 | 1.6 | 3.5 | 5.3 |  |
|  | AV171622 | 1.0 | 1.6 | 4.6 | 6.1 |  |
|  | AV171622 | 1.0 | 1.5 | 4.6 | 7.7 |  |
|  | AV209892 | 1.0 | 1.9 | 3.6 | 4.3 |  |
|  | AV221013 | 1.0 | 0.7 | 0.3 | 0.3 |  |
|  | AV232798 | 1.0 | 0.5 | 0.2 | 0.3 |  |
|  | AV371987 | 1.0 | 1.9 | 3.8 | 6.3 |  |
|  | AV374246 | 1.0 | 0.5 | 0.3 | 0.3 |  |
|  | AW488471 | 1.0 | 0.8 | 0.2 | 0.2 |  |
|  | AW554921 | 1.0 | 1.1 | 0.2 | 0.0 |  |
|  | AW744519 | 1.0 | 5.6 | 14.8 | 18.5 |  |
|  | AW744519 | 1.0 | 2.1 | 5.5 | 6.0 |  |
|  | AY029778 | 1.0 | 1.1 | 16.1 | 24.5 |  |
|  | BB010153 | 1.0 | 1.9 | 3.1 | 4.2 |  |
|  | BB042892 | 1.0 | 0.3 | 0.3 | 0.1 |  |
|  | BB230053 | 1.0 | 1.0 | 0.2 | 0.2 |  |
|  | BB332449 | 1.0 | 1.1 | 5.8 | 9.7 |  |
|  | BB371300 | 1.0 | 3.9 | 4.5 | 5.1 |  |
|  | BB377340 | 1.0 | 1.2 | 3.3 | 4.8 |  |
|  | BB407228 | 1.0 | 0.7 | 0.3 | 0.3 |  |
|  | BB530223 | 1.0 | 1.3 | 5.0 | 4.7 |  |
|  | BB550907 | 1.0 | 0.5 | 9.1 | 32.0 |  |
|  | BB628049 | 1.0 | 1.3 | 3.2 | 3.5 |  |
|  | BC006604 | 1.0 | 0.3 | 0.3 | 0.6 |  |
|  | BC006717 | 1.0 | 1.8 | 4.8 | 5.6 |  |
|  | BC011479 | 1.0 | 1.3 | 3.9 | 3.8 |  |
|  | BC021353 | 1.0 | 0.2 | 0.2 | 0.2 |  |
|  | BC021353 | 1.0 | 0.3 | 0.2 | 0.2 |  |
|  | BC021353 | 1.0 | 0.3 | 0.3 | 0.3 |  |
|  | BC021407 | 1.0 | 1.2 | 4.4 | 3.7 |  |
|  | BC021429 | 1.0 | 0.9 | 0.3 | 0.3 |  |
|  | BC021522 | 1.0 | 2.3 | 4.0 | 4.1 |  |
|  | BC021842 | 1.0 | 1.8 | 4.5 | 6.6 |  |
|  | BC022135 | 1.0 | 0.6 | 0.3 | 0.3 |  |
|  | BC025169 | 1.0 | 0.7 | 0.2 | 0.1 |  |
|  | BC026867 | 1.0 | 0.8 | 0.3 | 0.2 |  |
|  | BF118393 | 1.0 | 0.7 | 0.3 | 0.2 |  |
|  | BF578669 | 1.0 | 0.5 | 0.3 | 0.2 |  |
|  | BG064632 | 1.0 | 10.2 | 14.7 | 16.6 |  |
|  | BG066982 | 1.0 | 0.8 | 0.3 | 0.2 |  |
|  | BG075321 | 1.0 | 0.7 | 3.7 | 5.0 |  |
|  | BG080055 | 1.0 | 0.7 | 0.3 | 0.2 |  |
|  | BG143461 | 1.0 | 0.5 | 0.3 | 0.2 |  |
|  | BG868949 | 1.0 | 1.3 | 3.6 | 3.5 |  |
|  | BG868949 | 1.0 | 1.3 | 4.4 | 4.3 |  |
|  | BI251603 | 1.0 | 1.9 | 4.0 | 3.8 |  |
|  | BI454991 | 1.0 | 2.0 | 3.7 | 4.2 |  |
|  | BI466783 | 1.0 | 0.5 | 0.2 | 0.2 |  |
|  | BI558298 | 1.0 | 1.1 | 0.3 | 0.2 |  |
|  | BI660196 | 1.0 | 1.2 | 3.6 | 4.4 |  |
|  | BM117243 | 1.0 | 1.4 | 3.3 | 4.1 |  |
|  | BM117243 | 1.0 | 1.6 | 3.6 | 3.9 |  |
|  | BM200151 | 1.0 | 1.0 | 0.3 | 0.3 |  |
|  | BM213835 | 1.0 | 0.8 | 0.3 | 0.2 |  |
|  | BM247465 | 1.0 | 0.5 | 0.2 | 0.1 |  |
|  | C78203 | 1.0 | 2.5 | 3.7 | 3.4 |  |
|  | NM_020562 | 1.0 | 1.0 | 0.3 | 0.3 |  |
|  | NM_026235 | 1.0 | 1.3 | 3.1 | 7.2 |  |
|  | NM_026839 | 1.0 | 0.7 | 0.3 | 0.2 |  |
|  | NM_030697 | 1.0 | 0.5 | 3.4 | 5.0 |  |
|  | NM_054098 | 1.0 | 2.1 | 15.0 | 24.3 |  |
|  | NM_133706 | 1.0 | 1.0 | 0.3 | 0.2 |  |
|  | NM_133775 | 1.0 | 1.8 | 3.2 | 4.3 |  |

Genes encoding non-secretory proteins that demonstrated at least 3-fold differential expression in at least one time-point over a 25 h angiogenesis timecourse.

TABLE V

Transmembrane proteins differentially regulated during MB114 tubulogenesis

| Name | GenBank | Hours of tubulogenesis | | | | Description |
|---|---|---|---|---|---|---|
| | | 1 | 5 | 15 | 25 | |
| 0610007C21Rik | AK002276 | 1.0 | 1.5 | 2.1 | 3.3 | Clone IMAGE: 1513950, mRNA (predicted transmembrane) |
| 1810014L12Rik | NM_133706 | 1.0 | 1.0 | 0.3 | 0.2 | RIKEN cDNA 1810014L12 gene (predicted transmembrane) |
| Alcam | U95030 | 1 | 3.4 | 4.2 | 2.6 | activated leukocyte cell adhesion molecule |
| Anpep | NM_008486 | 1 | 3.5 | 7.0 | 9.3 | alanyl (membrane) aminopeptidase |
| Areg | NM_009704 | 1 | 0.7 | 0.2 | 0.1 | amphiregulin |
| Cacna2d1 | NM_009784 | 1.0 | 2.3 | 3.9 | 4.3 | calcium channel, voltage-dependent, alpha2/delta subunit 1 |
| Cd14 | NM_009841 | 1.0 | 2.0 | 4.0 | 6.4 | CD14 antigen |
| Cd38 | BB256012 | 1.0 | 4.5 | 4.8 | 5.1 | CD38 antigen |
| Cd44 | X66083 | 1.0 | 1.2 | 0.3 | 0.2 | CD44 antigen |
| Cd53 | NM_007651 | 1.0 | 2.0 | 9.6 | 10.4 | CD53 antigen |
| Dtr | L07264 | 1.0 | 0.4 | 0.1 | 0.1 | diphtheria toxin receptor |
| Emp2 | AF083876 | 1 | 2.6 | 3.1 | 3.2 | epithelial membrane protein 2 |
| Epha2 | NM_010139 | 1.0 | 0.4 | 0.2 | 0.2 | Eph receptor A2 |
| Fcgrt | NM_010189 | 1.0 | 1.1 | 2.5 | 6.1 | Fc receptor, IgG, alpha chain transporter |
| Islr | NM_012043 | 1.0 | 1.2 | 2.4 | 4.2 | immunoglobulin superfamily containing leucine-rich repeat |
| Itga3 | NM_013565 | 1.0 | 0.9 | 0.3 | 0.2 | integrin alpha 3 |
| Itga6 | BM935811 | 1.0 | 1.3 | 0.1 | 0.1 | integrin alpha 6 |
| Ldlr | AF425607 | 1.0 | 0.2 | 0.2 | 0.2 | low density lipoprotein receptor |
| Lrp1 | NM_008512 | 1.0 | 1.3 | 3.2 | 5.5 | low density lipoprotein receptor-related protein 1 |
| Lrp2 | C80829 | 1.0 | 0.5 | 0.3 | 0.2 | low density lipoprotein receptor-related protein 2 |
| Ly6a | BC002070 | 1.0 | 0.7 | 2.3 | 4.8 | lymphocyte antigen 6 complex, locus A |
| Npr3 | NM_008728 | 1 | 0.5 | 0.2 | 0.2 | natriuretic peptide receptor 3 |
| P2rx4 | AJ251462 | 1 | 1.1 | 3.2 | 5.2 | purinergic receptor P2X, ligand-gated ion channel 4 |
| Pcdh18 | AK014140 | 1.0 | 0.2 | 0.3 | 0.3 | protocadherin 18 |
| Pcdhb9 | NM_053134 | 1.0 | 1.1 | 3.2 | 4.7 | protocadherin beta 9 |
| Ptpre | U35368 | 1.0 | 1.0 | 0.3 | 0.3 | protein tyrosine phosphatase, receptor type, E |
| Ramp1 | NM_016894 | 1.0 | 1.3 | 4.0 | 5.9 | receptor (calcitonin) activity modifying protein 1 |
| Sele | NM_011345 | 1.0 | 1.3 | 0.3 | 0.3 | selectin, endothelial cell |
| Slc4a3 | NM_009208 | 1 | 1.7 | 3.1 | 4.5 | solute carrier family 4 (anion exchanger), member 3 |
| Slc7a5 | BC026131 | 1 | 1.4 | 0.3 | 0.1 | solute carrier family 7 (cationic amino acid transporter, y+ system), member 5 |
| Tfrc | AK011596 | 1.0 | 1.1 | 0.3 | 0.3 | transferrin receptor |
| Tm4sf12 | BB072896 | 1.0 | 2.3 | 3.3 | 3.5 | transmembrane 4 superfamily member 12 |
| Tmc6 | BC004840 | 1.0 | 2.1 | 3.4 | 3.3 | transmembrane channel-like gene family 6 |

Genes encoding transmembrane or membrane-associated proteins that demonstrated at least 3-fold differential expression in at least one time-point over the 25 h angiogenesis timecourse. Identified genes encoding known angiogenic regulators are shown in bold type face. Identified genes encoding putative angiogenic regulators are shown in regular text face.

TABLE VI

Real-Time PCR analysis of select proteins

| Name | Hrs. of Tubulogenesis | | | |
|---|---|---|---|---|
| | 1 | 5 | 15 | 25 |
| ADAMts1 | 1.0 | 0.4 | 1.6 | 2.4 |
| ADAMts7 | 1.0 | 2.0 | 4.9 | 5.1 |
| CRELD-2 | 1.0 | 11.4 | 5.8 | 10.0 |
| CTGF | 1.0 | 0.3 | 0.4 | 0.3 |
| Decorin | 1.0 | 3.6 | 8.4 | 16.6 |
| ECM1 | 1.0 | 4.3 | 6.3 | 9.0 |
| Inhibin β-a (Inhβ-a) | 1.0 | 4.9 | 1.4 | 1.1 |
| Inhibin β-b (Inhβ-b) | 1.0 | 0.1 | 0.5 | 0.7 |
| Integrin α-3 | 1.0 | 1.4 | 0.8 | 0.3 |
| Integrin α-6 | 1.0 | 1.2 | 0.6 | 0.4 |
| Lipocalin-7 | 1.0 | 0.9 | 0.6 | 0.6 |
| Loxl-3 | 1.0 | 2.8 | 18.0 | 17.9 |
| Lumican | 1.0 | 0.4 | 0.9 | 1.7 |
| MAGP-2 | 1.0 | 8.4 | 2.3 | 4.2 |
| Matrilin-2 | 1.0 | 1.6 | 6.7 | 8.0 |
| Nephronectin | 1.0 | 0.9 | 0.5 | 0.5 |
| SerpinE2 | 1.0 | 0.8 | 5.1 | 10.1 |
| SMOC-2 | 1.0 | 21.5 | 58.3 | 13.1 |
| TIMP-3 | 1.0 | 2.5 | 0.5 | 0.5 |

Real-time PCR analysis was conducted to confirm differential expression of selected genes from microarray analysis.

EXAMPLE 2

The following example describes the effects of putative angiogenic gene expression on EC activities-coupled to angiogenesis.

The microarray analyses described in Example 1 identified numerous genes whose expression is regulated by angiogenesis, indicating that the expression of these genes is required during vessel formation. To test this hypothesis and to identify novel regulators of EC activities-coupled to angiogenesis, a series of in vitro assays was performed that modeled angiogenesis activation in ECs (Albig et al, 2006; Albig and Schiemann, 2004; Albig and Schiemann, 2005). In doing so, bicistronic retroviral transduction of MB114 cells was used to stably express six identified secretory proteins, namely matrilin-2, CRELD-2 (cysteine-rich with EGF-Like domains-2), MAGP-2, lumican, SMOC-2 (secreted modular calcium-binding protein-2), and ECM-1, (extracellular protein-1), and one putative transmembrane protein, AK002276 Immunoblotting and semi-quantitative real-time PCR analyses both showed that the expression of all individual transgenes were readily detected in MB114 cells (FIGS. 7A and 7B). In these experiments, MB114 cells were infected with retrovirus encoding either GFP (i.e., control) or various potential angiogenic agents as indicated. Afterward, infected cells were FACS-sorted by GFP expression (highest 10%) to establish stable polyclonal populations of transgenic MB114 cells. Transgene expression was detected by immunoblotting nickel-captured secretory proteins with anti-Myc antibodies, except AK002276 which was captured from detergent-solubilized cell extracts (FIG. 7A) and by performing semi-quantitative real-time PCR (FIG. 7B).

Figure 1A:
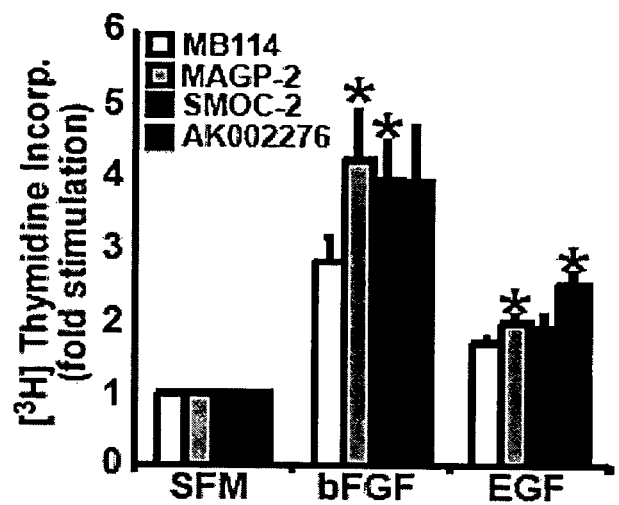
FIG. 1B is a bar graph showing the invasion of MB114 cells expressing either GFP or various putative angiogenic agents through synthetic basement membranes over 48 h using a modified Boyden-chamber assay (data are the mean (±SEM) of three independent experiments; *, $p<0.05$; Student's T-Test).
FIGS. 1C and 1D are bar graphs showing p38 MAPK phosphorylation in serum-starved MB114 cells expressing MAGP-2 (FIG. 1C) or lumican (FIG. 1D), stimulated with either bFGF (50 ng/ml) or EGF (10 ng/ml) 0-15 min (data are the mean (±SEM) of 5 independent experiments; *, $p<0.05$; Student's T-Test).
FIG. 1E is a bar graph showing endothelial cell sprouting in MB114 cells expressing either GFP or various putative angiogenic agents (data are the mean (±SEM) of 5 independent experiments for lumican, SMOC-2, CRELD-2, MAGP-2, and Matrilin-2, and of three independent experiments for AK76 and ECM-1; *, $p<0.05$; Student's T-Test).
Figure 1B:
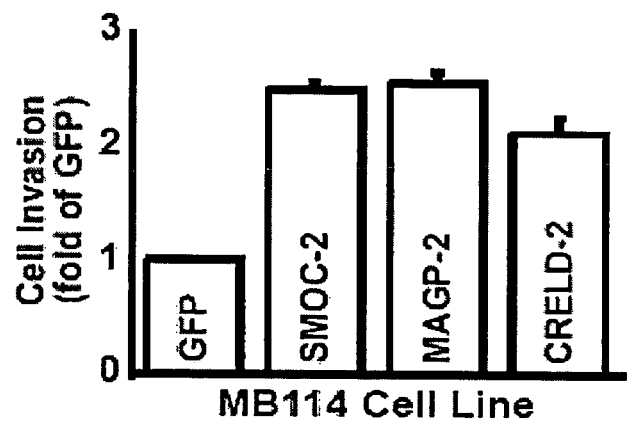

FIG. 1A show results from an experiment in which serum-starved MB114 cells, stably expressing either GFP or various putative angiogenic agents, were stimulated in the absence or presence of either bFGF (50 ng/ml) or EGF (10 ng/ml) for 24 h at 37° C. Differences in MB114 cell DNA synthesis was determined by measuring [$^3$H]thymidine incorporation into cellular DNA. Functionally, MAGP-2 and SMOC-2 expression significantly enhanced the proliferative response of MB114 cells to bFGF, while MAGP-2 and AK002276 expression significantly enhanced that to EGF (FIG. 1A). In contrast, expression of all other transgenes failed to effect the proliferative response of MB114 cells to either bFGF or EGF (data not shown). FIG. 1B shows that SMOC-2, MAGP-2, and CRELD-2 expression all significantly induced MB114 cell invasion through synthetic basement membranes, a response that was not mimicked by expression of additional transgenes (data not shown). In this experiment, invasion of MB114 cells expressing either GFP or various putative angiogenic agents through synthetic basement membranes was determined over 48 h using a modified Boyden-chamber assay.

Figure 1C:
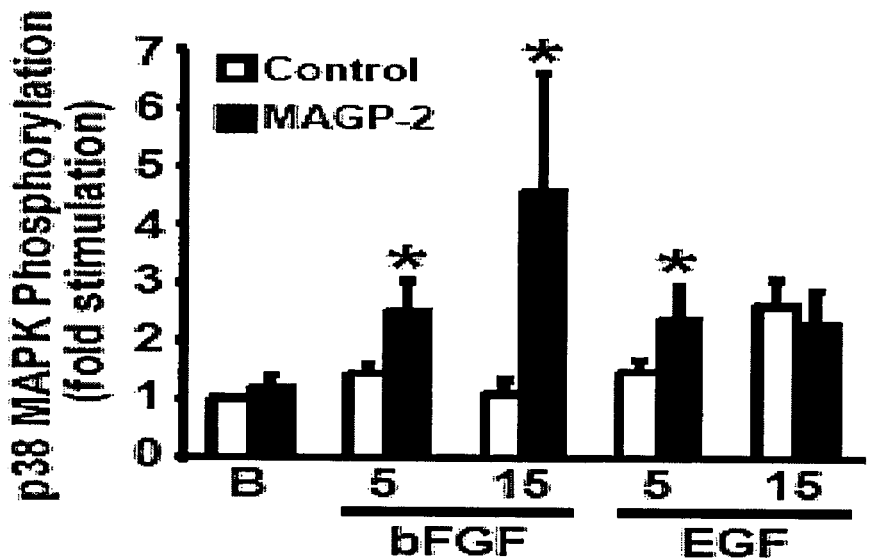
Figure 1D:
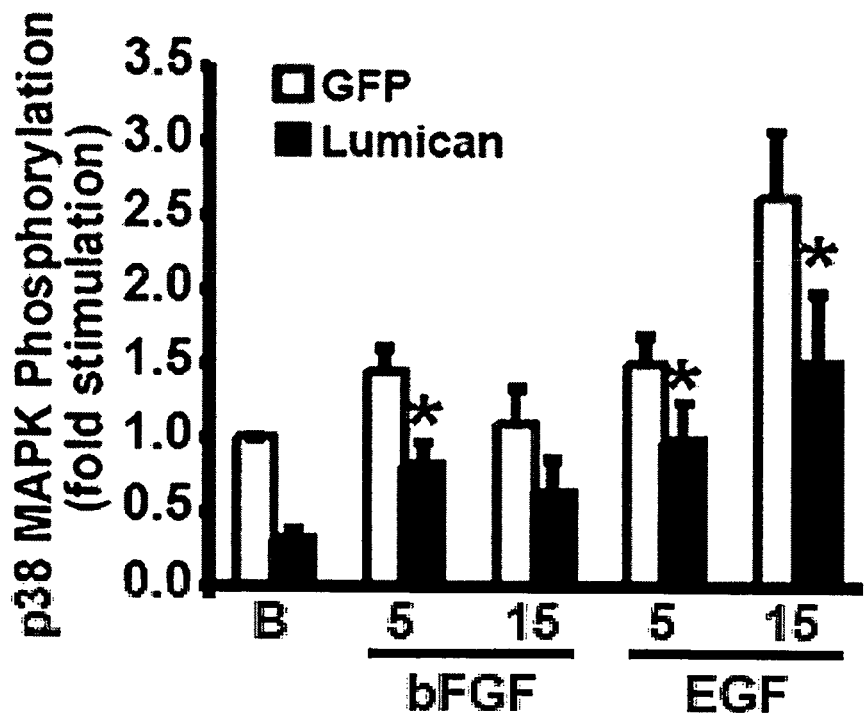

The inventors' previous studies have associated stimulation of p38 MAPK activity with angiogenesis of MB114 cells and, conversely, inhibition of p38 MAPK activity with angiostasis of MB114 cells (Albig et al, 2006; Albig and Schiemann, 2004; Albig and Schiemann, 2005). Serum-starved MB114 cells expressing MAGP-2 (FIG. 1C) or lumican (FIG. 1D) were stimulated with either bFGF (50 ng/ml) or EGF (10 ng/ml) 0-15 min as indicated in the figures. The phosphorylation status of p38 MAPK was determined by immunoblotting whole cell lysates with phospho-specific p38 MAPK antibodies (p38-P). Differences in protein loading were monitored by reprobing stripped membranes with anti-p38 MAPK polyclonal antibodies (p38). FIG. 1C shows that MAGP-2 expression significantly enhanced p38 MAPK phosphorylation in MB114 cells stimulated with either bFGF or EGF stimulation. In contrast, lumican expression significantly inhibited p38 MAPK activation in MB114 cells treated with either growth factor (FIG. 1D).

Figure 1E:
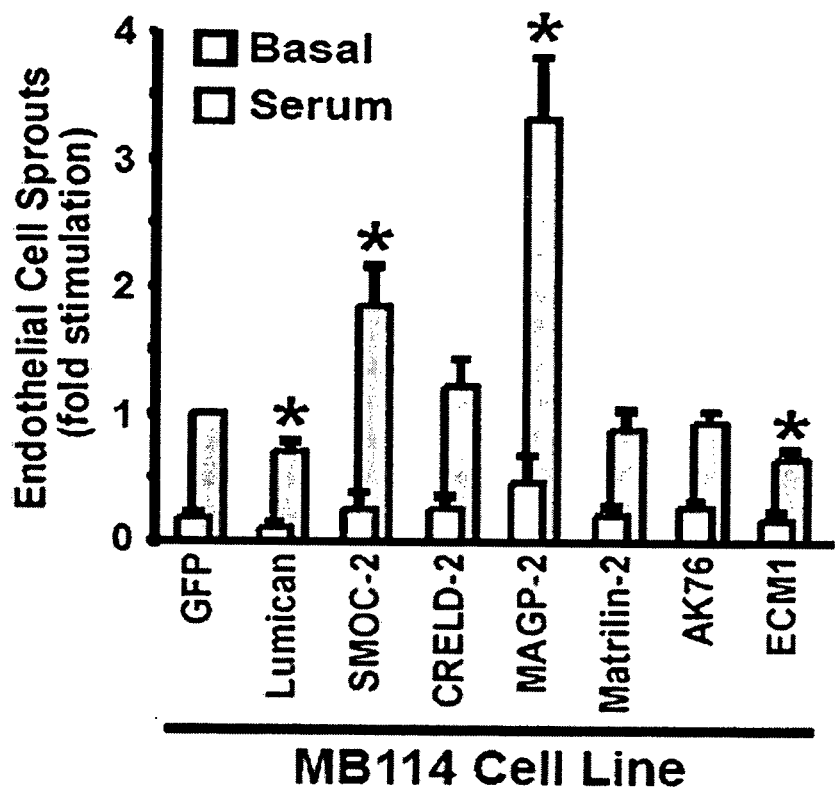

Finally, it was determined whether expression of these putative angiogenic factors could effect the angiogenic sprouting of quiescent MB114 cells monolayers. MB114 cells expressing either GFP or various putative angiogenic agents were grown to confluency, and subsequently were overlaid with rat tail collagen matrices. Angiogenic sprouting by quiescent EC monolayers was stimulated by inclusion of 10% FBS and allowed to proceed for 5 days. The quantity of invading angiogenic sprouts was determined by manual counting under a light microscope. FIG. 1E shows that expression of CRELD-2, matrillin-2, or AK002276 failed to significantly affect MB114 cell angiogenic sprouting in response to serum. In stark contrast, expression of MAGP-2 or SMOC-2 both significantly increased the sprouting of MB114 cells cell sprouting, while that of lumican and ECM-1 significantly decreased the ability of MB114 cells to form angiogenic sprouts in collagen matrices (FIG. 1E).

Collectively, these findings demonstrate that tubulating ECs upregulate expression of lumican and ECM-1 during the latter stages of angiogenesis, consistent with their involvement in mediating angiogenesis resolution. Accordingly, both proteins antagonized angiogenic sprouting in MB114 cells, and as such, the inventors propose lumican and ECM-1 as novel mediators of angiostasis. Conversely, tubulating ECs were observed to upregulate expression of MAGP-2 and SMOC-2 during the early stages of angiogenesis, implicating their involvement in mediating angiogenesis activation. Indeed, both proteins stimulated various angiogenic activities, including angiogenic sprouting in MB114 cells. Thus, it is proposed herein that MAGP-2 and SMOC-2 are novel mediators of angiogenesis. Because MAGP-2 was the only protein to exhibit angiogenic activity in all measured indices in vitro, the inventors chose to further characterize the molecular mechanisms whereby MAGP-2 induces angiogenesis in quiescent ECs.

EXAMPLE 3

The following example demonstrates that MAGP-2 promotes angiogenesis in vivo.

The ability of MAGP-2 to stimulate EC activities coupled to angiogenesis in vitro indicated that MAGP-2 may function to induce vessel formation in vivo. The inventors tested this hypothesis by utilizing the Matrigel plug implantation assay, which monitors the ability of various angiogenic agents to alter vessel formation and infiltration into Matrigel plugs implanted subcutaneously into normal mice. In doing so, first, recombinant FLAG-tagged MAGP-2 (rMAGP-2) was expressed and purified from bacterial cells (FIG. 2A). More particularly, recombinant FLAG-tagged MAGP-2 (rMAGP-2) was purified from detergent-solubilized bacterial cell extracts by anti-FLAG chromatography. MAGP-2 purity was monitored by coomassie staining, and by immunoblotting with anti-FLAG M2 monoclonal antibodies (FIG. 2A; right panel). rMAGP-2 (1 µg/ml) stimulated angiogenic sprouting of quiescent MB114 cell monolayers (FIG. 2A; left panel). Similar to its constitutive expression in MB114 cells, purified rMAGP-2 protein (1 µg/ml) also was found to stimulate angiogenic sprouting of quiescent MB114 cells, thereby demonstrating that these rMAGP-2 preparations were biologically active (FIG. 2A). To further demonstrate that MAGP-2 promotes angiogenesis in vivo, C57BL/6 female mice were injected subcutaneously with Matrigel supplemented either with diluent (D), bFGF (50 ng/ml, LD; or 300 ng/ml, HD), or bFGF (50 ng/ml) in combination with MAGP-2 (1 µg/ml). Mice were sacrificed on day 10 and the plugs harvested and photographed (FIG. 2B; left panels). Afterward, the Matrigel plugs were fixed, sectioned, and stained with Masson's trichrome to visualize infiltrating blood vessels (FIG. 2B; right panels; arrows denote blood vessels), which were quantified by manual counting under a light microscope. FIG. 2B shows that bFGF dose-dependently stimulated significant vascularization of implanted Matrigel plugs. Importantly, rMAGP-2 administration (1 µg/ml) significantly increased the development and infiltration of vessels into Matrigel plugs supplemented with bFGF as compared to those solely containing bFGF (FIG. 2B). Collectively, these findings, together with the in vitro analyses, provide strong evidence implicating MAGP-2 as a bona fide promoter of angiogenesis.

EXAMPLE 4

The following example demonstrates that MAGP-2 inhibits Notch1 signaling.

MAGP-2 can interact physically with Notch1 and its ligand, Jagged-1 (Miyamoto et al, 2006; Nehring et al, 2005), resulting in the ectodomain shedding of both molecules from the cell surface. Notch signaling also plays an essential role in regulating normal vessel development and angiogenesis in mammals (Leong and Karsan, 2005; Shawber and Kitajewski, 2004). Given these two facts, the inventors hypothesized that MAGP-2 promotes angiogenesis by modulating Notch1 signaling. To test this hypothesis, first measured were changes in luciferase expression driven by a Hes1-luciferase reporter gene whose expression is induced by Notch1 activation (Iso et al, 2003). MB114 and HUVEC cells were transiently transfected either with pHes1-luciferase, pCMV-β-gal, and MAGP-2 cDNAs, or with pHes1-luciferase and pCMV-β-gal cDNAs and subsequently stimulated with rMAGP-2 (1 or 5 mg/ml). Afterward, luciferase and β-gal activities contained in detergent-solubilized cell extracts were measured. In addition, GFP- and MAGP-2-expressing MB114 cells were transiently transfected with pHes1-luciferase and pCMV-β-gal cDNAs, together with or without Jagged-1 cDNA as indicated. Afterward, luciferase and β-gal activities were measured as above. FIG. 3A shows that MAGP-2 expression in or rMAGP-2 treatment of either MB114 or HUVEC cells repressed Hes1-driven luciferase activity. More importantly, MAGP-2 expression abrogated the ability of Jagged-1 to induce Hes1-luciferase activity in MB114 cells (FIG. 3B), suggesting that MAGP-2 functions to antagonize Jagged-1 and, consequently, Notch1 signaling in ECs.

Activation of Notch1 signaling involves three proteolytic processing events, termed S1, S2, and S3, that produce three distinct Notch1 fragments, termed TMIC, NEXT, and NICD, respectively (Mumm et al, 2000). NICD production is mediated by a gamma-secretase cleavage reaction that cuts Notch1 at a membrane proximal cytoplasmic site (Mumm et al, 2000), resulting in the release and subsequent translocation of NICD to the nucleus where it regulates the expression of Notch1-responsive genes, including Hes1 (Iso et al, 2003). The findings described above indicate that MAGP-2 antagonizes Notch1 signaling, and as such, indicate that MAGP-2 may do so by inhibiting Notch1 proteolytic processing. The inventors tested this possibility by transiently transfecting human 293T cells with cDNAs encoding Myc-tagged versions of Notch1, Jagged-1, and MAGP-2 in all combinations, and subsequently monitored changes in NICD production and accumulation by immunoblot analyses using anti-Myc monoclonal antibodies. As expected, Jagged-1 expression significantly enhanced Notch1 processing and the production of NICD as compared to cells solely expressing Notch1 (FIG. 4A). Importantly, the ability of Jagged-1 to induce Notch1 cleavage and NICD production in 293T cells was reduced significantly by co-expression of MAGP-2 (FIG. 4A). Thus, these findings indicate that MAGP-2 inhibits Notch1 signaling and Hes1 expression in part by preventing Notch1 processing and NICD production.

To further investigate the impact of MAGP-2 on Notch1 processing and NICD accumulation, the inventors took advantage of recent findings showing that the ability of TGF-β to induce Hes1 promoter activity requires Smad3 to interact physically with NICD (Blokzijl et al, 2003), a reaction that is dispensable for canonical Smad3-mediated signaling stimulated by TGF-β (Blokzijl et al, 2003). It was therefore reasoned that the ability of MAGP-2 to inhibit NICD production in ECs would reduce the capacity of TGF-β to induce luciferase expression driven by the Hes1 promoter, but not that driven by the synthetic Smad2/3-binding element (SBE). GFP- and MAGP-2-expressing MB114 cells were transiently transfected with either pHes1- or pSBE-luciferase, both together with pCMV-β-gal as indicated in FIG. 4B. Afterward, the resulting transfectants were stimulated overnight with increasing concentrations of TGF-β1 (0-5 ng/ml). MAGP-2 expression in MB114 cells significantly decreased the ability of TGF-β to stimulate Hes1-luciferase activity, but had no effect on its stimulation of SBE-luciferase activity (FIG. 4B). Similar effects of MAGP-2 on TGF-β-stimulated Hes1- and SBE-luciferase activities also were observed in HUVEC cells, indicating that MAGP-2-mediated inhibition of Notch1 processing and NICD production was not restricted solely to MB114 cells (data not shown). Collectively, these findings demonstrate that MAGP-2 antagonizes Notch1 signaling by preventing its cleavage and ultimate release of the Notch1 signaling fragment, NICD.

EXAMPLE 5

The following examples shows that MAGP-2 promotes angiogenesis by antagonizing Notch signaling.

Based on the findings described in the Examples above, the inventors hypothesized that MAGP-2 promotes angiogenesis by antagonizing Notch1 signaling. To test this hypothesis, it was first determined whether inhibiting Notch signaling in MB114 cells would enhance their angiogenic sprouting. In doing so, MB114 cells were transiently transfected with the Hes1-luciferase reporter gene (and pCMV-β-gal cDNA as control), and subsequently were treated overnight with or without the highly specific gamma-secretase inhibitor, DAPT (Sastre et al, 2001), which inhibits S3-mediated cleavage of Notch1 and, consequently, NICD-mediated induction of Hes1 expression. Afterward, luciferase and β-gal activities were determined. As expected, DAPT administration (10 µM) significantly inhibited Hes1 promoter activity in MB114 cells (FIG. 5A). More importantly, MB114 cells treated with DAPT formed significantly more angiogenic sprouts than did their untreated counterparts (FIG. 5B). In this experiment, quiescent MB114 cell monolayers were overlaid with rat tail collagen matrices, and were induced to form angiogenic sprouts by addition of 10% FBS supplemented with or without DAPT (10 µM). Five days later the number of invading angiogenic spouts were quantified by manual counting on a light microscope. Based on these findings, the inventors conclude that Notch activation functions in mediating angiostasis in MB114 cells. This conclusion is bolstered further by the inventors' observation that the Notch ligands Jagged-1 and Delta-like-4, and the Hes1 transcription factor were all strongly downregulated in tubulating MB114 cells (Table VII). Collectively, these findings indicate that Notch1 signaling antagonizes angiogenic sprouting in MB114 cells, and that downregulation of Notch1 signaling components is necessary for angiogenesis activation in MB114 cells.

TABLE VII

Expression of Notch signaling components During Tubulogenesis

| Name | Genbank | Hours of Tubulogenesis | | | |
|------|---------|---|---|---|---|
| | | 1 | 5 | 15 | 25 |
| Dll1 | NM_007865 | 1.0 | 0.9 | 1.3 | 1.1 |
| Dll3 | AB013440 | 1.0 | 0.8 | 0.6 | 0.9 |
| Dll4 | AK004739 | 1.0 | 1.2 | 0.3 | 0.4 |
| Jag1 | AA880220 | 1.0 | 0.7 | 0.2 | 0.2 |
| Jag2 | AV264681 | 1.0 | 0.4 | 0.7 | 1.3 |
| Notch1 | NM_008714 | 1.0 | 1.4 | 0.6 | 0.7 |
| Notch2 | D32210 | 1.0 | 1.1 | 1.1 | 1.2 |
| Notch3 | NM_008716 | 1.0 | 0.9 | 1.3 | 1.5 |
| Notch4 | NM_010929 | 1.0 | 1.1 | 1.1 | 1.1 |
| Hes1 | BC018375 | 1.0 | 0.5 | 0.2 | 0.1 |

Expression of various components of the Notch signaling pathway during MB114 cell tubulogenesis on Matrigel matrices.

Having shown that Notch1 signaling mediates angiostasis in MB114 cells, the inventors next asked whether MAGP-2 promotes angiogenesis in MB114 cells via its ability to antagonize Notch signaling. To do so, MAGP-2-expressing MB114 cells were engineered to constitutively express active Notch1 NICD fragment in an attempt to overcome the block of Notch processing mediated by MAGP-2. More particularly, GFP-, MAGP-2-, and MAGP-2/N1ICD-expressing MB114 cells were transiently transfected with pHes1-luciferase and pCMV-β-gal cDNAs. Luciferase and β-gal activities were determined 48 h post-transfection. As the inventors observed previously, MAGP-2 expression reduced Hes1-luciferase activity in MB114 cells (FIG. 5C), a reaction that was bypassed by co-expression of NICD in these cells (FIG. 5C). More importantly, the ability of MAGP-2 to promote angiogenic sprouting was prevented completely by constitutive N1ICD expression in MB114 cells (FIG. 5D). In this experiment, quiescent monolayers of GFP-, MAGP-2-, and MAGP-2/N1ICD-expressing MB114 cells were overlaid with rat tail collagen matrices and incubated in the absence or presence of 10% FBS for 5 days. Afterward, the number of invading angiogenic sprouts were determined by manual counting under a light microscope. Taken together, these results demonstrate that Notch1 activation antagonizes angiogenesis in MB114 cells, and most notably, that MAGP-2 promotes angiogenesis in part via its ability to antagonize Notch1 processing and signaling in ECs.

EXAMPLE 6

The following example shows that MAGP-2 is expressed aberrantly in the majority of human uterine tumors.

Radiolabeled cDNA probes corresponding to either murine MAGP-2 (FIG. 8A; upper panel) or human ubiquitin (FIG. 8A; lower panel) were hybridized to matched human normal:tumor cDNA array. The resulting phosphor-images depict MAGP-2 and ubiquitin expression in paired normal (upper spot) and malignant (bottom spot) uterine tissue. MAGP-2 expression was normalized to that of ubiquitin, followed by a determination of tumor:normal tissue MAGP-2 expression ratios. Ratios ≥2 or ≤0.5 were considered significant. The results showed that MAGP-2 is expressed aberrantly in the majority of human uterine tumors tested.

Each publication or other reference disclosed below and elsewhere herein is incorporated herein by reference in its entirety.

References

Aitkenhead et al., (2002) Microvasc Res 63: 159-171
Albig et al., (2006) in vivo. Cancer Res 66: 2621-2629
Albig et al., (2006) Cancer Res 66: 2621-2629
Albig and Schiemann (2004) DNA Cell Biol 23: 367-379
Albig and Schiemann (2005) Mol Biol Cell 16: 609-625
Alva and Iruela-Arispe (2004) Curr Opin Hematol 11: 278-283
Armstrong and Bornstein (2003) Matrix Biol 22: 63-71
Bell et al., (2001) J Cell Sci 114: 2755-2773
Bergers and Benjamin (2003) Nat Rev Cancer 3: 401-410
Bissell et al., (2002) Differentiation 70: 537-546
Blokzijl et al., (2003) J Cell Biol 163: 723-728
Bodolay et al., (2002) J Cell Mol Med 6: 357-376
Brigstock (2002) Angiogenesis 5: 153-165
Carmeliet and Jain (2000) Nature 407: 249-257
Chakravarti et al., (1998) J Cell Biol 141: 1277-1286
Chan (2004) Clin Exp Dermatol 29: 52-56
Creighton et al., (2003) Genome Biol 4: R46
Davies et al., (2001) Microvasc Res 62: 26-42
Davis and Senger (2005) Circ Res 97: 1093-1107
Delaney et al., (2005) Blood 106: 2693-2699
Duarte et al., (2004) Genes Dev 18: 2474-2478
Folkman and Shing (1992) J Biol Chem 267: 10931-10934
Funk and Sage (1993) J Cell Physiol 154: 53-63

Gao and Vande Woude (2005) *Cell Res* 15: 49-51
Gibson et al., (1998) *J Histochem Cytochem* 46: 871-886
Gibson et al., (1999) *J Biol Chem* 274: 13060-13065
Graham et al., (2005) *Mol Endocrinol* 19: 2713-2735
Haines and Irvine (2003) *Nat Rev Mol Cell Biol* 4: 786-797
Hamada et al., (2002) *Hum Mol Genet.* 11: 833-840
Han et al., (2001) *FASEB J* 15: 988-994
Hanahan and Folkman (1996) *Cell* 86: 353-364
Heissig et al., (2003) *Curr Opin Hematol,* 10: 136-141
Iruela-Arispe et al., (2003) *Ann N Y Acad Sci* 995: 183-190
Iso et al., (2003) *J Cell Physiol* 194: 237-255
Jendraschak and Sage (1996) *Semin Cancer Biol* 7: 139-146
Kadesch (2004) *Curr Opin Genet Dev* 14: 506-512
Kahn et al., (2000) *Am J Pathol* 156: 1887-1900
Kao et al., (2006) *Exp Eye Res* 82: 3-4
Kebebew et al., (2005) *Ann Surg* 242: 353-361
Kowalewski et al., (2005) *J Dermatol Sci* 38: 215-224
Kupprion et al., (1998) *J Biol Chem* 273: 29635-29640
Lemaire et al., (2004) *Arthritis Rheum* 50: 915-926
Lemaire et al., (2005) *Arthritis Rheum* 52: 1812-1823
Leong et al., (2002) *Mol Cell Biol* 22: 2830-2841
Leong and Karsan (2006) *Blood* 107: 2223-2233
Leygue et al., (1998) *Cancer Res* 58: 1348-1352
Liotta and Kohn (2001) *Nature* 411: 375-379
Liu et al., (2006) *FASEB J*20: 1009-1011
Lu et al., (2002) *Pathol Int* 52: 519-526
Mirancea et al., (2006) *J Dermatol Sci PMID* 16497486
Miyamoto et al., (2006) *J Biol Chem* 281: 10089-10097
Mumm et al., (2000) *Mol Cell* 5: 197-206
Naito et al., (2002) *Int J Oncol* 20: 943-948
Nehring et al., (2005) *J Biol Chem* 280: 20349-20355
Noseda et al., (2004) *Mol Cell Biol* 24: 8813-8822
Pupa et al., (2002) *J Cell Physiol* 192: 259-267
Qi et al., (2003) *Nat Med* 9: 407-415
Oyama et al., (2003) *Lancet* 362: 118-123
Ping et al., (2002) *J Pathol* 196: 324-330
Rebay et al., (1993) *Cell* 74: 319-329
Sage et al., (2003) *J Biol Chem* 278: 37849-37857
Sakamoto et al., (2002) *J Biol Chem* 277: 29399-29405
Sastre et al., (2001) *EMBO Rep* 2: 835-841
Schenk et al., (1995) *Biotechniques* 19: 196-198
Schiemann et al., (2002) *J Biol Chem* 277: 27367-27377
Shawber and Kitajewski (2004) *Bioessays* 26: 225-234
Small et al., (2001) *J Biol Chem* 276: 32022-32030
Sottile (2004) *Biochim Biophys Acta* 1654: 13-22
Stupack and Cheresh (2002) *Sci STKE* 2002: PE7
Sulochana et al., (2005) *J Biol Chem* 280: 27935-27948
Vannahme et al., (2003) *Biochem J* 373: 805-814
Vannahme et al., (2002) *J Biol Chem* 277: 37977-37986
Vij et al., (2004) *Exp Eye Res* 78: 957-971
Vij et al., (2005) *Invest Ophthalmol Vis Sci* 46: 88-95
Vuillermoz et al., (2004) *Exp Cell Res* 296: 294-306
Wang et al., (2003) *Cancer Lett* 200: 57-67
Williams et al., (2006) *Blood* 107: 931-939
Zimrin et al., (1996) *J Biol Chem* 271: 32499-32502
U.S. Provisional Application No. 60/722,694
U.S. Provisional Application No. 60/816,969

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method for determining the presence of uterine tumor cells in a patient being diagnosed for uterine cancer, comprising:
   a) obtaining a test sample from the patient;
   b) performing an assay to detect a level of nucleic acid expression of Microfibril-associated glycoprotein-2 (MAGP-2) in the test sample from the patient; and
   c) comparing the level of nucleic acid expression of MAGP-2 in the test sample to MAGP-2 nucleic acid expression of a control sample determined by performing an assay to detect MAGP-2 level of nucleic acid expression in the control sample, wherein detection of a statistically significant increase in the MAGP-2 nucleic acid expression in the test sample, as compared to the MAGP-2 nucleic acid expression in the control sample, is an indicator of the presence of tumor cells in the test sample as compared to cells in the control sample, and wherein the control sample level is established from a negative control sample that is established as non-tumorigenic.

2. The method of claim 1, wherein the step of detecting comprises detecting MAGP-2 mRNA transcription by cells in the test sample.

3. The method of claim 1, wherein the step of detecting is by a method selected from the group consisting of polymerase chain reaction (PCR), reverse transcriptase-PCR (RT-PCR), in situ hybridization, Northern blot, sequence analysis, gene microarray analysis, and detection of a reporter gene.

4. The method of claim 1, wherein the test sample is from the uterus of the patient.

5. The method of claim 1, wherein the control sample level has a baseline MAGP-2 nucleic acid expression level established by a method selected from the group consisting of:
   (1) establishing a baseline level of MAGP-2 nucleic acid expression in an autologous control sample from the patient, wherein the autologous sample is from a same cell type, tissue type or bodily fluid type as the test sample of step (a);
   (2) establishing a baseline level of MAGP-2 nucleic acid expression from at least one previous detection of MAGP-2 nucleic acid expression in a previous test sample from the patient, wherein the previous test sample was of a same cell type, tissue type or bodily fluid type as the test sample of step (a); and,
   (3) establishing a baseline level of MAGP-2 nucleic acid expression from an average of control samples of a same cell type, tissue type or bodily fluid type as the test sample of step (a), the control samples having been obtained from a population of matched individuals.

* * * * *

SEQUENCE LISTING

```
<160> NUMBER OF SEQ ID NOS: 124

<210> SEQ ID NO 1
<211> LENGTH: 223
<212> TYPE: PRT
<213> ORGANISM: Mus musculus

<400> SEQUENCE: 1

Met Ala Ser Arg Glu Ser Gly Gly Ser Arg Ala Ala Ala Leu Leu Leu
1               5                   10                  15

Val Leu Gly Val Glu Arg Ser Leu Ala Leu Pro Lys Ile Cys Thr Leu
            20                  25                  30

Cys Pro Gly Gly Met His Asn Leu Ser Arg Val Ala Ala Tyr Cys Glu
        35                  40                  45

Asp Thr Ser Lys Leu Met Gln Ala Arg Cys Cys Leu Asn Gln Lys Gly
    50                  55                  60

Pro Ile Leu Gly Leu Asn Leu Gln Asn Cys Ser Leu Lys Asp Pro Gly
65                  70                  75                  80

Pro Asn Phe Leu Gln Ala Tyr Thr Ala Ile Ile Ile Asp Leu Gln Ala
                85                  90                  95

Asn Pro Leu Lys Asp Asp Leu Ala Asn Thr Phe Arg Gly Phe Thr Gln
            100                 105                 110

Leu Gln Thr Leu Ile Leu Pro Gln Asp Val Pro Cys Pro Gly Gly Ser
        115                 120                 125

Asn Ala Trp Asp Asn Val Thr Ser Phe Lys Asp Lys Gln Ile Cys Gln
    130                 135                 140
```

```
Gly Gln Arg Asp Leu Cys Asn Ser Thr Gly Ser Pro Glu Met Cys Pro
145                 150                 155                 160

Glu Asn Gly Ser Cys Ala Ser Asp Gly Pro Gly Leu Leu Gln Cys Val
            165                 170                 175

Cys Ala Asp Gly Phe His Gly Tyr Lys Cys Met Arg Gln Gly Ser Phe
            180                 185                 190

Ser Leu Leu Met Phe Phe Gly Ile Gly Ser Thr Thr Leu Ala Ile
            195                 200                 205

Ser Ile Leu Leu Trp Gly Thr Gln Arg Arg Lys Ala Lys Ala Ser
            210                 215                 220

<210> SEQ ID NO 2
<211> LENGTH: 229
<212> TYPE: PRT
<213> ORGANISM: Homo sapiens

<400> SEQUENCE: 2

Met Ala Pro His Gly Pro Gly Ser Leu Thr Thr Leu Val Pro Trp Ala
1               5                   10                  15

Ala Ala Leu Leu Leu Ala Leu Gly Val Glu Arg Ala Leu Ala Leu Pro
            20                  25                  30

Glu Ile Cys Thr Gln Cys Pro Gly Ser Val Gln Asn Leu Ser Lys Val
        35                  40                  45

Ala Phe Tyr Cys Lys Thr Thr Arg Glu Leu Met His Ala Arg Cys
    50                  55                  60

Cys Leu Asn Gln Lys Gly Thr Ile Leu Gly Leu Asp Leu Gln Asn Cys
65                  70                  75                  80

Ser Leu Glu Asp Pro Gly Pro Asn Phe His Gln Ala His Thr Thr Val
                85                  90                  95

Ile Ile Asp Leu Gln Ala Asn Pro Leu Lys Gly Asp Leu Ala Asn Thr
            100                 105                 110

Phe Arg Gly Phe Thr Gln Leu Gln Thr Leu Ile Leu Pro Gln His Val
        115                 120                 125

Asn Cys Pro Gly Gly Ile Asn Ala Trp Asn Thr Ile Thr Ser Tyr Ile
130                 135                 140

Asp Asn Gln Ile Cys Gln Gly Gln Lys Asn Leu Cys Asn Asn Thr Gly
145                 150                 155                 160

Asp Pro Glu Met Cys Pro Glu Asn Gly Ser Cys Val Pro Asp Gly Pro
                165                 170                 175

Gly Leu Leu Gln Cys Val Cys Ala Asp Gly Phe His Gly Tyr Lys Cys
            180                 185                 190

Met Arg Gln Gly Ser Phe Ser Leu Leu Met Phe Phe Gly Ile Leu Gly
        195                 200                 205

Ala Thr Thr Leu Ser Val Ser Ile Leu Leu Trp Ala Thr Gln Arg Arg
    210                 215                 220

Lys Ala Lys Thr Ser
225

<210> SEQ ID NO 3
<211> LENGTH: 176
<212> TYPE: PRT
<213> ORGANISM: Mus musculus

<400> SEQUENCE: 3

Met Gly Ala Leu Ala Ala Arg Arg Cys Val Glu Trp Leu Leu Gly Leu
1               5                   10                  15

Tyr Phe Val Ser His Ile Pro Ile Thr Leu Phe Ile Asp Leu Gln Ala
```

```
                    20                  25                  30
Val Leu Pro Pro Glu Leu Tyr Pro Gln Glu Phe Ser Asn Leu Leu Arg
                35                  40                  45

Trp Tyr Ser Lys Glu Phe Lys Asp Pro Leu Met Gln Glu Pro Pro Val
 50                  55                  60

Trp Phe Lys Ser Phe Leu Leu Cys Glu Leu Val Phe Gln Leu Pro Phe
 65                  70                  75                  80

Phe Pro Ile Ala Ala Tyr Ala Phe Phe Lys Gly Ser Cys Arg Trp Ile
                85                  90                  95

Arg Ile Pro Ala Ile Ile Tyr Ala Ala His Thr Ile Thr Thr Leu Ile
                100                 105                 110

Pro Ile Leu Tyr Thr Leu Leu Phe Glu Asp Phe Ser Lys Ala Val Ala
                115                 120                 125

Phe Lys Gly Gln Arg Pro Glu Ser Phe Arg Glu Leu Thr Leu Val
                130                 135                 140

Gly Val Tyr Ala Pro Tyr Leu Ile Ile Pro Leu Ile Leu Leu Phe
145                 150                 155                 160

Met Leu Arg Asn Pro Tyr Tyr Lys Tyr Glu Glu Lys Arg Lys Lys Lys
                165                 170                 175

<210> SEQ ID NO 4
<211> LENGTH: 176
<212> TYPE: PRT
<213> ORGANISM: Homo sapiens

<400> SEQUENCE: 4

Met Gly Ala Pro Ala Thr Arg Arg Cys Val Glu Trp Leu Leu Gly Leu
 1                   5                  10                  15

Tyr Phe Leu Ser His Ile Pro Ile Thr Leu Phe Met Asp Leu Gln Ala
                20                  25                  30

Val Leu Pro Arg Glu Leu Tyr Pro Val Glu Phe Arg Asn Leu Leu Lys
                35                  40                  45

Trp Tyr Ala Lys Glu Phe Lys Asp Pro Leu Leu Gln Glu Pro Pro Ala
 50                  55                  60

Trp Phe Lys Ser Phe Leu Phe Cys Glu Leu Val Phe Gln Leu Pro Phe
 65                  70                  75                  80

Phe Pro Ile Ala Thr Tyr Ala Phe Leu Lys Gly Ser Cys Lys Trp Ile
                85                  90                  95

Arg Thr Pro Ala Ile Ile Tyr Ser Val His Thr Met Thr Thr Leu Ile
                100                 105                 110

Pro Ile Leu Ser Thr Phe Leu Phe Glu Asp Phe Ser Lys Ala Ser Gly
                115                 120                 125

Phe Lys Gly Gln Arg Pro Glu Thr Leu His Glu Arg Leu Thr Leu Val
                130                 135                 140

Ser Val Tyr Ala Pro Tyr Leu Leu Ile Pro Phe Ile Leu Ile Phe
145                 150                 155                 160

Met Leu Arg Ser Pro Tyr Tyr Lys Tyr Glu Glu Lys Arg Lys Lys Lys
                165                 170                 175

<210> SEQ ID NO 5
<211> LENGTH: 366
<212> TYPE: PRT
<213> ORGANISM: Mus musculus

<400> SEQUENCE: 5

Met Glu Arg Val Leu Gly Leu Leu Leu Leu Leu Val His Ala Ser
 1                   5                  10                  15
```

```
Pro Ala Pro Pro Glu Pro Cys Glu Leu Asp Glu Glu Ser Cys Ser Cys
             20                  25                  30

Asn Phe Ser Asp Pro Lys Pro Asp Trp Ser Ser Ala Phe Asn Cys Leu
             35                  40                  45

Gly Ala Ala Asp Val Glu Leu Tyr Gly Gly Arg Ser Leu Glu Tyr
 50                  55                  60

Leu Leu Lys Arg Val Asp Thr Glu Ala Asp Leu Gly Gln Phe Thr Asp
 65                  70                  75                  80

Ile Ile Lys Ser Leu Ser Leu Lys Arg Leu Thr Val Arg Ala Ala Arg
                 85                  90                  95

Ile Pro Ser Arg Ile Leu Phe Gly Ala Leu Arg Val Leu Gly Ile Ser
             100                 105                 110

Gly Leu Gln Glu Leu Thr Leu Glu Asn Leu Glu Val Thr Gly Thr Ala
             115                 120                 125

Pro Pro Pro Leu Leu Glu Ala Thr Gly Pro Asp Leu Asn Ile Leu Asn
 130                 135                 140

Leu Arg Asn Val Ser Trp Ala Thr Arg Asp Ala Trp Leu Ala Glu Leu
145                 150                 155                 160

Gln Gln Trp Leu Lys Pro Gly Leu Lys Val Leu Ser Ile Ala Gln Ala
                 165                 170                 175

His Ser Leu Asn Phe Ser Cys Glu Gln Val Arg Val Phe Pro Ala Leu
             180                 185                 190

Ser Thr Leu Asp Leu Ser Asp Asn Pro Glu Leu Gly Glu Arg Gly Leu
             195                 200                 205

Ile Ser Ala Leu Cys Pro Leu Lys Phe Pro Thr Leu Gln Val Leu Ala
 210                 215                 220

Leu Arg Asn Ala Gly Met Glu Thr Pro Ser Gly Val Cys Ser Ala Leu
225                 230                 235                 240

Ala Ala Ala Arg Val Gln Leu Gln Gly Leu Asp Leu Ser His Asn Ser
                 245                 250                 255

Leu Arg Asp Ala Ala Gly Ala Pro Ser Cys Asp Trp Pro Ser Gln Leu
             260                 265                 270

Asn Ser Leu Asn Leu Ser Phe Thr Gly Leu Lys Gln Val Pro Lys Gly
             275                 280                 285

Leu Pro Ala Lys Leu Ser Val Leu Asp Leu Ser Tyr Asn Arg Leu Asp
 290                 295                 300

Arg Asn Pro Ser Pro Asp Glu Leu Pro Gln Val Gly Asn Leu Ser Leu
305                 310                 315                 320

Lys Gly Asn Pro Phe Leu Asp Ser Glu Ser His Ser Glu Lys Phe Asn
                 325                 330                 335

Ser Gly Val Val Thr Ala Gly Ala Pro Ser Ser Gln Ala Val Ala Leu
             340                 345                 350

Ser Gly Thr Leu Ala Leu Leu Leu Gly Asp Arg Leu Phe Val
             355                 360                 365

<210> SEQ ID NO 6
<211> LENGTH: 374
<212> TYPE: PRT
<213> ORGANISM: Homo sapiens

<400> SEQUENCE: 6

Met Leu Ser Thr Ser Arg Ser Arg Phe Ile Arg Asn Thr Asn Glu Ser
 1               5                  10                  15

Gly Glu Glu Val Thr Thr Phe Phe Asp Tyr Asp Tyr Gly Ala Pro Cys
             20                  25                  30
```

His Lys Phe Asp Val Lys Gln Ile Gly Ala Gln Leu Leu Pro Leu
        35                  40                  45
Tyr Ser Leu Val Phe Ile Phe Gly Phe Val Gly Asn Met Leu Val
 50                  55                  60
Leu Ile Leu Ile Asn Cys Lys Lys Leu Lys Cys Leu Thr Asp Ile Tyr
 65                  70                  75                  80
Leu Leu Asn Leu Ala Ile Ser Asp Leu Leu Phe Leu Ile Thr Leu Pro
                     85                  90                  95
Leu Trp Ala His Ser Ala Ala Asn Glu Trp Val Phe Gly Asn Ala Met
                    100                 105                 110
Cys Lys Leu Phe Thr Gly Leu Tyr His Ile Gly Tyr Phe Gly Gly Ile
                    115                 120                 125
Phe Phe Ile Ile Leu Leu Thr Ile Asp Arg Tyr Leu Ala Ile Val His
                    130                 135                 140
Ala Val Phe Ala Leu Lys Ala Arg Thr Val Thr Phe Gly Val Val Thr
145                 150                 155                 160
Ser Val Ile Thr Trp Leu Val Ala Val Phe Ala Ser Val Pro Gly Ile
                    165                 170                 175
Ile Phe Thr Lys Cys Gln Lys Glu Asp Ser Val Tyr Val Cys Gly Pro
                    180                 185                 190
Tyr Phe Pro Arg Gly Trp Asn Asn Phe His Thr Ile Met Arg Asn Ile
                    195                 200                 205
Leu Gly Leu Val Leu Pro Leu Leu Ile Met Val Ile Cys Tyr Ser Gly
                    210                 215                 220
Ile Leu Lys Thr Leu Leu Arg Cys Arg Asn Glu Lys Lys Arg His Arg
225                 230                 235                 240
Ala Val Arg Val Ile Phe Thr Ile Met Ile Val Tyr Phe Leu Phe Trp
                    245                 250                 255
Thr Pro Tyr Asn Ile Val Ile Leu Leu Asn Thr Phe Gln Glu Phe Phe
                    260                 265                 270
Gly Leu Ser Asn Cys Glu Ser Thr Ser Gln Leu Asp Gln Ala Thr Gln
                    275                 280                 285
Val Thr Glu Thr Leu Gly Met Thr His Cys Cys Ile Asn Pro Ile Ile
                    290                 295                 300
Tyr Ala Phe Val Gly Glu Lys Phe Arg Ser Leu Phe His Ile Ala Leu
305                 310                 315                 320
Gly Cys Arg Ile Ala Pro Leu Gln Lys Pro Val Cys Gly Gly Pro Gly
                    325                 330                 335
Val Arg Pro Gly Lys Asn Val Lys Val Thr Thr Gln Gly Leu Leu Asp
                    340                 345                 350
Gly Arg Gly Lys Gly Lys Ser Ile Gly Arg Ala Pro Glu Ala Ser Leu
                    355                 360                 365
Gln Asp Lys Glu Gly Ala
        370

<210> SEQ ID NO 7
<211> LENGTH: 678
<212> TYPE: DNA
<213> ORGANISM: Mus musculus
<220> FEATURE:
<221> NAME/KEY: misc_feature
<222> LOCATION: (18)..(18)
<223> OTHER INFORMATION: n is a, c, g, or t

<400> SEQUENCE: 7
ttccctcatt gatttatnta atgagccctt agtctttatt ttagaaaata tagaaatttt      60

-continued

```
ttctagcatt ctggaatatc ttcagttttt tgaggcaaat gcttagacca ttgatatttc    120
agtctgtttt ctacacatgt actttaggat tctaggtttc tccctgagcc ctgctttcga    180
tgtaaccctg aatttctgta tgtcttact ggttagttac tttgatagtt tgtatatgct     240
tgacccagtg agtggcagga ttagaaggta tggccttgct ggaataggtg tgccactgtg    300
ggtgtagtct taagacccctt accctagctg cctggaggcc actattccac taacagcctt   360
caaatgaaaa tataaaactc tcagctctgc ctgtgccatg cctgcctgga tgctgccatg    420
ctcccacctt gatgataatg gactgaacct ctgaacctgt aagccagccc caatttgttg    480
tccttataaa agacttgctt tggtcatggt atctgttcac agcagaaaga acctaactaa    540
gacagttacc attcagttca aaataattct tgattttatt gttatttaga catgtgatat    600 ttactttca acatctggag aattgtttag gttttttttt gtgtgtgtgt ctttagtagg     660
tattaataaa ctaaattg                                                  678
```

<210> SEQ ID NO 8
<211> LENGTH: 219
<212> TYPE: PRT
<213> ORGANISM: Mus musculus

<400> SEQUENCE: 8

```
Met Gly Met Ser Ser Leu Lys Leu Leu Lys Tyr Val Leu Phe Ile Phe
1               5                   10                  15

Asn Leu Leu Phe Trp Val Cys Gly Cys Cys Ile Leu Gly Phe Gly Ile
            20                  25                  30

Tyr Phe Leu Val Gln Asn Thr Tyr Gly Val Leu Phe Arg Asn Leu Pro
        35                  40                  45

Phe Leu Thr Leu Gly Asn Ile Leu Val Ile Val Gly Ser Ile Ile Met
    50                  55                  60

Val Val Ala Phe Leu Gly Cys Met Gly Ser Ile Lys Glu Asn Lys Cys
65                  70                  75                  80

Leu Leu Met Ser Phe Phe Val Leu Leu Ile Ile Leu Leu Ala Glu
                85                  90                  95

Val Thr Ile Ala Ile Leu Leu Phe Val Tyr Glu Gln Lys Leu Asn Thr
            100                 105                 110

Leu Val Ala Glu Gly Leu Asn Asp Ser Ile Gln His Tyr His Ser Asp
        115                 120                 125

Asn Ser Thr Met Lys Ala Trp Asp Phe Ile Gln Thr Gln Leu Gln Cys
    130                 135                 140

Cys Gly Val Asn Gly Ser Ser Asp Trp Thr Ser Gly Pro Pro Ser Ser
145                 150                 155                 160

Cys Pro Ser Gly Ala Asp Val Gln Gly Cys Tyr Asn Lys Ala Lys Ser
                165                 170                 175

Trp Phe His Ser Asn Phe Leu Tyr Ile Gly Ile Ile Thr Ile Cys Val
            180                 185                 190

Cys Val Ile Gln Val Leu Gly Met Ser Phe Ala Leu Thr Leu Asn Cys
        195                 200                 205

Gln Ile Asp Lys Thr Ser Gln Ala Leu Gly Leu
    210                 215
```

<210> SEQ ID NO 9
<211> LENGTH: 219
<212> TYPE: PRT
<213> ORGANISM: Homo sapiens

<400> SEQUENCE: 9

```
Met Gly Met Ser Ser Leu Lys Leu Leu Lys Tyr Val Leu Phe Phe Phe
1               5                   10                  15

Asn Leu Leu Phe Trp Ile Cys Gly Cys Cys Ile Leu Gly Phe Gly Ile
            20                  25                  30

Tyr Leu Leu Ile His Asn Asn Phe Gly Val Leu Phe His Asn Leu Pro
            35                  40                  45

Ser Leu Thr Leu Gly Asn Val Phe Val Ile Val Gly Ser Ile Ile Met
    50                  55                  60

Val Val Ala Phe Leu Gly Cys Met Gly Ser Ile Lys Glu Asn Lys Cys
65                  70                  75                  80

Leu Leu Met Ser Phe Phe Ile Leu Leu Ile Ile Leu Leu Ala Glu
                85                  90                  95

Val Thr Leu Ala Ile Leu Leu Phe Val Tyr Glu Gln Lys Leu Asn Glu
                100                 105                 110

Tyr Val Ala Lys Gly Leu Thr Asp Ser Ile His Arg Tyr His Ser Asp
            115                 120                 125

Asn Ser Thr Lys Ala Ala Trp Asp Ser Ile Gln Ser Phe Leu Gln Cys
    130                 135                 140

Cys Gly Ile Asn Gly Thr Ser Asp Trp Thr Ser Gly Pro Pro Ala Ser
145                 150                 155                 160

Cys Pro Ser Asp Arg Lys Val Glu Gly Cys Tyr Ala Lys Ala Arg Leu
                165                 170                 175

Trp Phe His Ser Asn Phe Leu Tyr Ile Gly Ile Ile Thr Ile Cys Val
            180                 185                 190

Cys Val Ile Glu Val Leu Gly Met Ser Phe Ala Leu Thr Leu Asn Cys
            195                 200                 205

Gln Ile Asp Lys Thr Ser Gln Thr Ile Gly Leu
    210                 215

<210> SEQ ID NO 10
<211> LENGTH: 172
<212> TYPE: PRT
<213> ORGANISM: Mus musculus

<400> SEQUENCE: 10

Met Leu Val Ile Leu Ala Phe Ile Ile Val Phe His Ile Val Ser Thr
1               5                   10                  15

Ala Leu Leu Phe Ile Ser Thr Ile Asp Asn Ala Trp Trp Val Gly Asp
            20                  25                  30

Ser Phe Ser Ala Asp Leu Trp Arg Val Cys Thr Asn Ser Thr Asn Cys
            35                  40                  45

Thr Glu Ile Asn Glu Leu Thr Gly Pro Glu Ala Phe Glu Gly Tyr Ser
    50                  55                  60

Val Met Gln Ala Val Gln Ala Thr Met Ile Leu Ser Thr Ile Leu Ser
65                  70                  75                  80

Cys Ile Ser Phe Leu Ile Phe Leu Leu Gln Leu Phe Arg Leu Lys Gln
                85                  90                  95

Gly Glu Arg Phe Val Leu Thr Ser Ile Ile Gln Leu Met Ser Cys Leu
            100                 105                 110

Cys Val Met Ile Gly Ala Ser Ile Tyr Thr Asp Arg Arg Gln Asp Leu
            115                 120                 125

His Gln Gln Asn Arg Lys Leu Tyr Tyr Leu Leu Gln Glu Gly Ser Tyr
    130                 135                 140

Gly Tyr Ser Phe Ile Leu Ala Trp Val Ala Phe Ala Phe Thr Phe Ile
145                 150                 155                 160
```

Ser Gly Leu Met Tyr Met Ile Leu Arg Lys Arg Lys
                165                 170

<210> SEQ ID NO 11
<211> LENGTH: 167
<212> TYPE: PRT
<213> ORGANISM: Homo sapiens

<400> SEQUENCE: 11

Met Leu Val Leu Leu Ala Phe Ile Ile Ala Phe His Ile Thr Ser Ala
1               5                   10                  15

Ala Leu Leu Phe Ile Ala Thr Val Asp Asn Ala Trp Trp Val Gly Asp
                20                  25                  30

Glu Phe Phe Ala Asp Val Trp Arg Ile Cys Thr Asn Asn Thr Asn Cys
            35                  40                  45

Thr Val Ile Asn Asp Ser Phe Gln Glu Tyr Ser Thr Leu Gln Ala Val
        50                  55                  60

Gln Ala Thr Met Ile Leu Ser Thr Ile Leu Cys Cys Ile Ala Phe Phe
65                  70                  75                  80

Ile Phe Val Leu Gln Leu Phe Arg Leu Lys Gln Gly Glu Arg Phe Val
                85                  90                  95

Leu Thr Ser Ile Ile Gln Leu Met Ser Cys Leu Cys Val Met Ile Ala
                100                 105                 110

Ala Ser Ile Tyr Thr Asp Arg Arg Glu Asp Ile His Asp Lys Asn Ala
            115                 120                 125

Lys Phe Tyr Pro Val Thr Arg Glu Gly Ser Tyr Gly Tyr Ser Tyr Ile
        130                 135                 140

Leu Ala Trp Val Ala Phe Ala Cys Thr Phe Ile Ser Gly Met Met Tyr
145                 150                 155                 160

Leu Ile Leu Arg Lys Arg Lys
                165

<210> SEQ ID NO 12
<211> LENGTH: 365
<212> TYPE: PRT
<213> ORGANISM: Mus musculus

<400> SEQUENCE: 12

Met Gly Met Pro Leu Pro Trp Ala Leu Ser Leu Leu Val Leu Leu
1               5                   10                  15

Pro Gln Thr Trp Gly Ser Glu Thr Arg Pro Pro Leu Met Tyr His Leu
                20                  25                  30

Thr Ala Val Ser Asn Pro Ser Thr Gly Leu Pro Ser Phe Trp Ala Thr
            35                  40                  45

Gly Trp Leu Gly Pro Gln Gln Tyr Leu Thr Tyr Asn Ser Leu Arg Gln
        50                  55                  60

Glu Ala Asp Pro Cys Gly Ala Trp Val Trp Asn Gln Val Ser Trp
65                  70                  75                  80

Tyr Trp Glu Lys Glu Thr Thr Asp Leu Lys Ser Lys Glu Gln Leu Phe
                85                  90                  95

Leu Glu Ala Leu Lys Thr Leu Glu Lys Ile Leu Asn Gly Thr Tyr Thr
                100                 105                 110

Leu Gln Gly Leu Leu Gly Cys Glu Leu Ala Ser Asp Asn Ser Ser Val
            115                 120                 125

Pro Thr Ala Val Phe Ala Leu Asn Gly Glu Glu Phe Met Lys Phe Asn
        130                 135                 140

```
Pro Arg Ile Gly Asn Trp Thr Gly Glu Trp Pro Thr Glu Ile Val
145                 150                 155                 160

Ala Asn Leu Trp Met Lys Gln Pro Asp Ala Arg Lys Glu Ser Glu
            165                 170                 175

Phe Leu Leu Asn Ser Cys Pro Glu Arg Leu Leu Gly His Leu Glu Arg
        180                 185                 190

Gly Arg Arg Asn Leu Glu Trp Lys Glu Pro Pro Ser Met Arg Leu Lys
    195                 200                 205

Ala Arg Pro Gly Asn Ser Gly Ser Ser Val Leu Thr Cys Ala Ala Phe
210                 215                 220

Ser Phe Tyr Pro Pro Glu Leu Lys Phe Arg Phe Leu Arg Asn Gly Leu
225                 230                 235                 240

Ala Ser Gly Ser Gly Asn Cys Ser Thr Gly Pro Asn Gly Asp Gly Ser
                245                 250                 255

Phe His Ala Trp Ser Leu Leu Glu Val Lys Arg Gly Asp Glu His His
            260                 265                 270

Tyr Gln Cys Gln Val Glu His Glu Gly Leu Ala Gln Pro Leu Thr Val
        275                 280                 285

Asp Leu Asp Ser Ser Ala Arg Ser Ser Val Pro Val Val Gly Ile Val
290                 295                 300

Leu Gly Leu Leu Leu Val Val Val Ala Ile Ala Gly Gly Val Leu Leu
305                 310                 315                 320

Trp Gly Arg Met Arg Ser Gly Leu Pro Ala Pro Trp Leu Ser Leu Ser
                325                 330                 335

Gly Asp Asp Ser Gly Asp Leu Leu Pro Gly Gly Asn Leu Pro Pro Glu
                340                 345                 350

Ala Glu Pro Gln Gly Ala Asn Ala Phe Pro Ala Thr Ser
            355                 360                 365

<210> SEQ ID NO 13
<211> LENGTH: 365
<212> TYPE: PRT
<213> ORGANISM: Homo sapiens

<400> SEQUENCE: 13

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160
```

```
Ser Gln Arg Trp Gln Gln Gln Asp Lys Ala Ala Asn Lys Glu Leu Thr
            165                 170                 175

Phe Leu Leu Phe Ser Cys Pro His Arg Leu Arg Glu His Leu Glu Arg
        180                 185                 190

Gly Arg Gly Asn Leu Glu Trp Lys Glu Pro Pro Ser Met Arg Leu Lys
            195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
            245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
        290                 295                 300

Ile Gly Val Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
            355                 360                 365

<210> SEQ ID NO 14
<211> LENGTH: 428
<212> TYPE: PRT
<213> ORGANISM: Mus musculus

<400> SEQUENCE: 14

Met Arg Ala Leu Cys Leu Leu Cys Trp Ala Val Leu Asn Leu Val
1               5                   10                  15

Arg Ala Cys Pro Glu Pro Cys Asp Cys Gly Glu Lys Tyr Gly Phe Gln
            20                  25                  30

Ile Ala Asp Cys Ala Tyr Arg Asp Leu Glu Gly Val Pro Pro Gly Phe
        35                  40                  45

Pro Ala Asn Val Thr Thr Leu Ser Leu Ser Ala Asn Arg Leu Pro Gly
    50                  55                  60

Leu Pro Glu Gly Ala Phe Arg Glu Val Pro Leu Leu Gln Ser Leu Trp
65                  70                  75                  80

Leu Ala His Asn Glu Ile Arg Ser Val Ala Ile Gly Ala Leu Ala Pro
                85                  90                  95

Leu Ser His Leu Lys Ser Leu Asp Leu Ser His Asn Leu Leu Ser Glu
            100                 105                 110

Phe Ala Trp Ser Asp Leu His Asn Leu Ser Ala Leu Gln Leu Leu Lys
        115                 120                 125

Met Asp Ser Asn Glu Leu Ala Phe Ile Pro Arg Asp Ala Phe Ser Ser
    130                 135                 140

Leu Ser Ala Leu Arg Ser Leu Gln Leu Asn His Asn Arg Leu His Ala
145                 150                 155                 160

Leu Ala Glu Gly Thr Phe Ala Pro Leu Thr Ala Leu Ser His Leu Gln
                165                 170                 175
```

```
Ile Asn Asp Asn Pro Phe Asp Cys Thr Cys Gly Ile Val Trp Phe Lys
            180                 185                 190

Thr Trp Ala Leu Ala Ser Ala Val Ser Ile Pro Glu Gln Asp Asn Ile
        195                 200                 205

Ala Cys Thr Thr Pro His Val Leu Lys Gly Ile Pro Leu Gly Arg Leu
    210                 215                 220

Pro Pro Leu Pro Cys Ser Ala Pro Ser Val Gln Leu Ser Tyr Gln Pro
225                 230                 235                 240

Ser Gln Asp Gly Ala Glu Leu Arg Pro Gly Phe Val Leu Ala Leu His
                245                 250                 255

Cys Asp Val Asp Gly Gln Pro Val Pro Gln Leu His Trp His Ile His
                260                 265                 270

Thr Pro Gly Gly Thr Val Glu Ile Ala Ser Pro Asn Val Gly Thr Asp
        275                 280                 285

Gly Arg Ala Leu Pro Gly Ala Leu Ala Thr Ser Gly Gln Pro Arg Phe
        290                 295                 300

Gln Ala Phe Ala Asn Gly Ser Leu Leu Ile Pro Asp Phe Gly Lys Leu
305                 310                 315                 320

Glu Glu Gly Thr Tyr Ser Cys Leu Ala Thr Asn Glu Leu Gly Ser Ala
                325                 330                 335

Glu Ser Ser Val Asn Val Ala Leu Ala Thr Pro Gly Glu Gly Gly Glu
                340                 345                 350

Asp Ala Val Gly His Lys Phe His Gly Lys Ala Val Glu Gly Lys Gly
                355                 360                 365

Cys Tyr Thr Val Asp Asn Glu Val Gln Pro Ser Pro Glu Asp Asn
        370                 375                 380

Val Val Ile Ile Tyr Leu Ser Arg Ala Gly Pro Pro Glu Ala Ala Ile
385                 390                 395                 400

Ala Ala Asp Gly Arg Pro Ala Gln Gln Phe Ser Gly Ile Leu Leu Leu
                405                 410                 415

Gly Gln Ser Leu Leu Val Leu Ser Phe Phe Tyr Phe
                420                 425

<210> SEQ ID NO 15
<211> LENGTH: 428
<212> TYPE: PRT
<213> ORGANISM: Homo sapiens

<400> SEQUENCE: 15

Met Gln Glu Leu His Leu Leu Trp Trp Ala Leu Leu Leu Gly Leu Ala
1               5                   10                  15

Gln Ala Cys Pro Glu Pro Cys Asp Cys Gly Glu Lys Tyr Gly Phe Gln
                20                  25                  30

Ile Ala Asp Cys Ala Tyr Arg Asp Leu Glu Ser Val Pro Pro Gly Phe
            35                  40                  45

Pro Ala Asn Val Thr Thr Leu Ser Leu Ser Ala Asn Arg Leu Pro Gly
        50                  55                  60

Leu Pro Glu Gly Ala Phe Arg Glu Val Pro Leu Leu Gln Ser Leu Trp
65                  70                  75                  80

Leu Ala His Asn Glu Ile Arg Thr Val Ala Ala Gly Ala Leu Ala Ser
                85                  90                  95

Leu Ser His Leu Lys Ser Leu Asp Leu Ser His Asn Leu Ile Ser Asp
                100                 105                 110

Phe Ala Trp Ser Asp Leu His Asn Leu Ser Ala Leu Gln Leu Leu Lys
            115                 120                 125
```

-continued

```
Met Asp Ser Asn Glu Leu Thr Phe Ile Pro Arg Asp Ala Phe Arg Ser
    130                 135                 140

Leu Arg Ala Leu Arg Ser Leu Gln Leu Asn His Asn Arg Leu His Thr
145                 150                 155                 160

Leu Ala Glu Gly Thr Phe Thr Pro Leu Thr Ala Leu Ser His Leu Gln
                165                 170                 175

Ile Asn Glu Asn Pro Phe Asp Cys Thr Cys Gly Ile Val Trp Leu Lys
                180                 185                 190

Thr Trp Ala Leu Thr Thr Ala Val Ser Ile Pro Glu Gln Asp Asn Ile
                195                 200                 205

Ala Cys Thr Ser Pro His Val Leu Lys Gly Thr Pro Leu Ser Arg Leu
210                 215                 220

Pro Pro Leu Pro Cys Ser Ala Pro Ser Val Gln Leu Ser Tyr Gln Pro
225                 230                 235                 240

Ser Gln Asp Gly Ala Glu Leu Arg Pro Gly Phe Val Leu Ala Leu His
                245                 250                 255

Cys Asp Val Asp Gly Gln Pro Ala Pro Gln Leu His Trp His Ile Gln
                260                 265                 270

Ile Pro Ser Gly Ile Val Glu Ile Thr Ser Pro Asn Val Gly Thr Asp
                275                 280                 285

Gly Arg Ala Leu Pro Gly Thr Pro Val Ala Ser Ser Gln Pro Arg Phe
290                 295                 300

Gln Ala Phe Ala Asn Gly Ser Leu Leu Ile Pro Asp Phe Gly Lys Leu
305                 310                 315                 320

Glu Glu Gly Thr Tyr Ser Cys Leu Ala Thr Asn Glu Leu Gly Ser Ala
                325                 330                 335

Glu Ser Ser Val Asp Val Ala Leu Ala Thr Pro Gly Glu Gly Gly Glu
                340                 345                 350

Asp Thr Leu Gly Arg Arg Phe His Gly Lys Ala Val Glu Gly Lys Gly
                355                 360                 365

Cys Tyr Thr Val Asp Asn Glu Val Gln Pro Ser Gly Pro Glu Asp Asn
370                 375                 380

Val Val Ile Ile Tyr Leu Ser Arg Ala Gly Asn Pro Glu Ala Ala Val
385                 390                 395                 400

Ala Glu Gly Val Pro Gly Gln Leu Pro Pro Gly Leu Leu Leu Leu Gly
                405                 410                 415

Gln Ser Leu Leu Leu Phe Phe Phe Leu Thr Ser Phe
                420                 425

<210> SEQ ID NO 16
<211> LENGTH: 580
<212> TYPE: DNA
<213> ORGANISM: Mus musculus
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
```

<222> LOCATION: (364)..(364)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t

<400> SEQUENCE: 16

```
aggcaaacag agaaaaatat attttttat aaagtattga atgttaactt cttttcatt      60
tgtctgtaaa aaatatatgt gcaaaagtga gtgtctaaat gttccctaga gagttggcaa   120
ggctatacat cagagtcttc cttcacaagg tttgcggtgt ctttaaaggt gtcttctgtg   180
gcagtgtagc ctggagtcga acttcttttt gaagctttag caggaagaga aggagatgga   240
gggggagcca cagccacagc ttccttttgc tcagtgtcca tctctgcata gattggattt   300
tcgaagtcgt gtctgctggg gttttcngtt tgaagnaatt ccatttgggn ccngagtttc   360
catnagctcc aggggaggct ggctttggct ctggaactat ctcagaaggt ctatggacct   420
tcctagttct ggttttccac attttctggt acagtcacct gtgagcttac tgacggtccc   480
tgcatgncag gcccactttg gnaatactgt cttggctgca tacattgggt ttcaaatatt   540
cacaggctgc ttgcctacct ccatgacgaa tgttcattca                         580
```

<210> SEQ ID NO 17
<211> LENGTH: 4655
<212> TYPE: PRT
<213> ORGANISM: Homo sapiens

<400> SEQUENCE: 17

```
Met Asp Arg Gly Pro Ala Ala Val Ala Cys Thr Leu Leu Ala Leu
1               5                   10                  15

Val Ala Cys Leu Ala Pro Ala Ser Gly Gln Glu Cys Asp Ser Ala His
                20                  25                  30

Phe Arg Cys Gly Ser Gly His Cys Ile Pro Ala Asp Trp Arg Cys Asp
        35                  40                  45

Gly Thr Lys Asp Cys Ser Asp Ala Asp Glu Ile Gly Cys Ala Val
    50                  55                  60

Val Thr Cys Gln Gln Gly Tyr Phe Lys Cys Gln Ser Glu Gly Gln Cys
65                  70                  75                  80

Ile Pro Ser Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp
        115                 120                 125

His Val Arg Asp Cys Pro Asp Gly Ala Asp Glu Asn Asp Cys Gln Tyr
    130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
                180                 185                 190

Gly Glu Cys Ile Pro Arg Ala Tyr Val Cys Asp His Asp Asn Asp Cys
        195                 200                 205
```

```
Gln Asp Gly Ser Asp Glu His Ala Cys Asn Tyr Pro Thr Cys Gly Gly
    210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
                260                 265                 270

Cys Pro Glu Ser Gly Arg Cys Ile Ser Ile Tyr Lys Val Cys Asp Gly
        275                 280                 285

Ile Leu Asp Cys Pro Gly Arg Glu Asp Glu Asn Asn Thr Ser Thr Gly
        290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
                340                 345                 350

Gln Ile Trp Gly Ile Cys Asp Gln Lys Cys Glu Ser Arg Pro Gly Arg
        355                 360                 365

His Leu Cys His Cys Glu Glu Gly Tyr Ile Leu Glu Arg Gly Gln Tyr
        370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
                420                 425                 430

Tyr His Leu Gln Arg Val Phe Trp Thr Asp Thr Val Gln Asn Lys Val
        435                 440                 445

Phe Ser Val Asp Ile Asn Gly Leu Asn Ile Gln Glu Val Leu Asn Val
        450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
                500                 505                 510

Arg Gly Ile Ala Val Asp Pro Thr Val Gly Tyr Leu Phe Phe Ser Asp
        515                 520                 525

Trp Glu Ser Leu Ser Gly Glu Pro Lys Leu Glu Arg Ala Phe Met Asp
        530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
                580                 585                 590

Thr Val Val His Gly Gly Ser Leu Ile Pro His Pro Phe Gly Val Ser
        595                 600                 605

Leu Phe Glu Gly Gln Val Phe Phe Thr Asp Trp Thr Lys Met Ala Val
        610                 615                 620

Leu Lys Ala Asn Lys Phe Thr Glu Thr Asn Pro Gln Val Tyr Tyr Gln
625                 630                 635                 640
```

```
Ala Ser Leu Arg Pro Tyr Gly Val Thr Val Tyr His Ser Leu Arg Gln
            645                 650                 655

Pro Tyr Ala Thr Asn Pro Cys Lys Asp Asn Gly Gly Cys Glu Gln
            660                 665                 670

Val Cys Val Leu Ser His Arg Thr Asp Asn Asp Gly Leu Gly Phe Arg
            675                 680                 685

Cys Lys Cys Thr Phe Gly Phe Gln Leu Asp Thr Asp Glu Arg His Cys
690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
            740                 745                 750

Ser Thr Ile Phe Phe Ser Asp Met Ser Lys His Met Ile Phe Lys Gln
            755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
            820                 825                 830

Val His Pro Phe Ala Gly Tyr Leu Phe Phe Thr Asp Trp Phe Arg Pro
            835                 840                 845

Ala Lys Ile Met Arg Ala Trp Ser Asp Gly Ser His Leu Leu Pro Val
850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Arg Leu Gly His Ile Glu Gln
            900                 905                 910

Met Thr His Pro Phe Gly Leu Ala Ile Phe Gly Glu His Leu Phe Phe
            915                 920                 925

Thr Asp Trp Arg Leu Gly Ala Ile Ile Arg Val Arg Lys Ala Asp Gly
930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
            995                 1000                1005

Asn His Leu Thr Cys Glu Gly Asp Pro Thr Asn Glu Pro Pro Thr
         1010                1015                1020

Glu Gln Cys Gly Leu Phe Ser Phe Pro Cys Lys Asn Gly Arg Cys
         1025                1030                1035

Val Pro Asn Tyr Tyr Leu Cys Asp Gly Val Asp Asp Cys His Asp
         1040                1045                1050

Asn Ser Asp Glu Gln Leu Cys Gly Thr Leu Asn Asn Thr Cys Ser
```

-continued

```
            1055                1060                1065

Ser  Ser  Ala  Phe  Thr  Cys  Gly  His  Gly  Glu  Cys  Ile  Pro  Ala  His
     1070                1075                1080

Trp  Arg  Cys  Asp  Lys  Arg  Asn  Asp  Cys  Val  Asp  Gly  Ser  Asp  Glu
     1085                1090                1095

His  Asn  Cys  Pro  Thr  His  Ala  Pro  Ala  Ser  Cys  Leu  Asp  Thr  Gln
     1100                1105                1110

Tyr  Thr  Cys  Asp  Asn  His  Gln  Cys  Ile  Ser  Lys  Asn  Trp  Val  Cys
     1115                1120                1125

Asp  Thr  Asp  Asn  Asp  Cys  Gly  Asp  Gly  Ser  Asp  Glu  Lys  Asn  Cys
     1130                1135                1140

Asn  Ser  Thr  Glu  Thr  Cys  Gln  Pro  Ser  Gln  Phe  Asn  Cys  Pro  Asn
     1145                1150                1155

His  Arg  Cys  Ile  Asp  Leu  Ser  Phe  Val  Cys  Asp  Gly  Asp  Lys  Asp
     1160                1165                1170

Cys  Val  Asp  Gly  Ser  Asp  Glu  Val  Gly  Cys  Val  Leu  Asn  Cys  Thr
     1175                1180                1185

Ala  Ser  Gln  Phe  Lys  Cys  Ala  Ser  Gly  Asp  Lys  Cys  Ile  Gly  Val
     1190                1195                1200

Thr  Asn  Arg  Cys  Asp  Gly  Val  Phe  Asp  Cys  Ser  Asp  Asn  Ser  Asp
     1205                1210                1215

Glu  Ala  Gly  Cys  Pro  Thr  Arg  Pro  Pro  Gly  Met  Cys  His  Ser  Asp
     1220                1225                1230

Glu  Phe  Gln  Cys  Gln  Glu  Asp  Gly  Ile  Cys  Ile  Pro  Asn  Phe  Trp
     1235                1240                1245

Glu  Cys  Asp  Gly  His  Pro  Asp  Cys  Leu  Tyr  Gly  Ser  Asp  Glu  His
     1250                1255                1260

Asn  Ala  Cys  Val  Pro  Lys  Thr  Cys  Pro  Ser  Ser  Tyr  Phe  His  Cys
     1265                1270                1275

Asp  Asn  Gly  Asn  Cys  Ile  His  Arg  Ala  Trp  Leu  Cys  Asp  Arg  Asp
     1280                1285                1290

Asn  Asp  Cys  Gly  Asp  Met  Ser  Asp  Glu  Lys  Asp  Cys  Pro  Thr  Gln
     1295                1300                1305

Pro  Phe  Arg  Cys  Pro  Ser  Trp  Gln  Trp  Gln  Cys  Leu  Gly  His  Asn
     1310                1315                1320

Ile  Cys  Val  Asn  Leu  Ser  Val  Val  Cys  Asp  Gly  Ile  Phe  Asp  Cys
     1325                1330                1335

Pro  Asn  Gly  Thr  Asp  Glu  Ser  Pro  Leu  Cys  Asn  Gly  Asn  Ser  Cys
     1340                1345                1350

Ser  Asp  Phe  Asn  Gly  Gly  Cys  Thr  His  Glu  Cys  Val  Gln  Glu  Pro
     1355                1360                1365

Phe  Gly  Ala  Lys  Cys  Leu  Cys  Pro  Leu  Gly  Phe  Leu  Leu  Ala  Asn
     1370                1375                1380

Asp  Ser  Lys  Thr  Cys  Glu  Asp  Ile  Asp  Glu  Cys  Asp  Ile  Leu  Gly
     1385                1390                1395

Ser  Cys  Ser  Gln  His  Cys  Tyr  Asn  Met  Arg  Gly  Ser  Phe  Arg  Cys
     1400                1405                1410

Ser  Cys  Asp  Thr  Gly  Tyr  Met  Leu  Glu  Ser  Asp  Gly  Arg  Thr  Cys
     1415                1420                1425

Lys  Val  Thr  Ala  Ser  Glu  Ser  Leu  Leu  Leu  Leu  Val  Ala  Ser  Gln
     1430                1435                1440

Asn  Lys  Ile  Ile  Ala  Asp  Ser  Val  Thr  Ser  Gln  Val  His  Asn  Ile
     1445                1450                1455
```

```
Tyr Ser Leu Val Glu Asn Gly Ser Tyr Ile Val Ala Val Asp Phe
    1460            1465            1470

Asp Ser Ile Ser Gly Arg Ile Phe Trp Ser Asp Ala Thr Gln Gly
    1475            1480            1485

Lys Thr Trp Ser Ala Phe Gln Asn Gly Thr Asp Arg Arg Val Val
    1490            1495            1500

Phe Asp Ser Ser Ile Ile Leu Thr Glu Thr Ile Ala Ile Asp Trp
    1505            1510            1515

Val Gly Arg Asn Leu Tyr Trp Thr Asp Tyr Ala Leu Glu Thr Ile
    1520            1525            1530

Glu Val Ser Lys Ile Asp Gly Ser His Arg Thr Val Leu Ile Ser
    1535            1540            1545

Lys Asn Leu Thr Asn Pro Arg Gly Leu Ala Leu Asp Pro Arg Met
    1550            1555            1560

Asn Glu His Leu Leu Phe Trp Ser Asp Trp Gly His His Pro Arg
    1565            1570            1575

Ile Glu Arg Ala Ser Met Asp Gly Ser Met Arg Thr Val Ile Val
    1580            1585            1590

Gln Asp Lys Ile Phe Trp Pro Cys Gly Leu Thr Ile Asp Tyr Pro
    1595            1600            1605

Asn Arg Leu Leu Tyr Phe Met Asp Ser Tyr Leu Asp Tyr Met Asp
    1610            1615            1620

Phe Cys Asp Tyr Asn Gly His His Arg Arg Gln Val Ile Ala Ser
    1625            1630            1635

Asp Leu Ile Ile Arg His Pro Tyr Ala Leu Thr Leu Phe Glu Asp
    1640            1645            1650

Ser Val Tyr Trp Thr Asp Arg Ala Thr Arg Arg Val Met Arg Ala
    1655            1660            1665

Asn Lys Trp His Gly Gly Asn Gln Ser Val Val Met Tyr Asn Ile
    1670            1675            1680

Gln Trp Pro Leu Gly Ile Val Ala Val His Pro Ser Lys Gln Pro
    1685            1690            1695

Asn Ser Val Asn Pro Cys Ala Phe Ser Arg Cys Ser His Leu Cys
    1700            1705            1710

Leu Leu Ser Ser Gln Gly Pro His Phe Tyr Ser Cys Val Cys Pro
    1715            1720            1725

Ser Gly Trp Ser Leu Ser Pro Asp Leu Leu Asn Cys Leu Arg Asp
    1730            1735            1740

Asp Gln Pro Phe Leu Ile Thr Val Arg Gln His Ile Ile Phe Gly
    1745            1750            1755

Ile Ser Leu Asn Pro Glu Val Lys Ser Asn Asp Ala Met Val Pro
    1760            1765            1770

Ile Ala Gly Ile Gln Asn Gly Leu Asp Val Glu Phe Asp Asp Ala
    1775            1780            1785

Glu Gln Tyr Ile Tyr Trp Val Glu Asn Pro Gly Glu Ile His Arg
    1790            1795            1800

Val Lys Thr Asp Gly Thr Asn Arg Thr Val Phe Ala Ser Ile Ser
    1805            1810            1815

Met Val Gly Pro Ser Met Asn Leu Ala Leu Asp Trp Ile Ser Arg
    1820            1825            1830

Asn Leu Tyr Ser Thr Asn Pro Arg Thr Gln Ser Ile Glu Val Leu
    1835            1840            1845

Thr Leu His Gly Asp Ile Arg Tyr Arg Lys Thr Leu Ile Ala Asn
    1850            1855            1860
```

```
Asp Gly Thr Ala Leu Gly Val Gly Phe Pro Ile Gly Ile Thr Val
    1865                1870                1875

Asp Pro Ala Arg Gly Lys Leu Tyr Trp Ser Asp Gln Gly Thr Asp
    1880                1885                1890

Ser Gly Val Pro Ala Lys Ile Ala Ser Ala Asn Met Asp Gly Thr
    1895                1900                1905

Ser Val Lys Thr Leu Phe Thr Gly Asn Leu Glu His Leu Glu Cys
    1910                1915                1920

Val Thr Leu Asp Ile Glu Glu Gln Lys Leu Tyr Trp Ala Val Thr
    1925                1930                1935

Gly Arg Gly Val Ile Glu Arg Gly Asn Val Asp Gly Thr Asp Arg
    1940                1945                1950

Met Ile Leu Val His Gln Leu Ser His Pro Trp Gly Ile Ala Val
    1955                1960                1965

His Asp Ser Phe Leu Tyr Tyr Thr Asp Glu Gln Tyr Glu Val Ile
    1970                1975                1980

Glu Arg Val Asp Lys Ala Thr Gly Ala Asn Lys Ile Val Leu Arg
    1985                1990                1995

Asp Asn Val Pro Asn Leu Arg Gly Leu Gln Val Tyr His Arg Arg
    2000                2005                2010

Asn Ala Ala Glu Ser Ser Asn Gly Cys Ser Asn Met Asn Ala
    2015                2020                2025

Cys Gln Gln Ile Cys Leu Pro Val Pro Gly Gly Leu Phe Ser Cys
    2030                2035                2040

Ala Cys Ala Thr Gly Phe Lys Leu Asn Pro Asp Asn Arg Ser Cys
    2045                2050                2055

Ser Pro Tyr Asn Ser Phe Ile Val Val Ser Met Leu Ser Ala Ile
    2060                2065                2070

Arg Gly Phe Ser Leu Glu Leu Ser Asp His Ser Glu Thr Met Val
    2075                2080                2085

Pro Val Ala Gly Gln Gly Arg Asn Ala Leu His Val Asp Val Asp
    2090                2095                2100

Val Ser Ser Gly Phe Ile Tyr Trp Cys Asp Phe Ser Ser Ser Val
    2105                2110                2115

Ala Ser Asp Asn Ala Ile Arg Arg Ile Lys Pro Asp Gly Ser Ser
    2120                2125                2130

Leu Met Asn Ile Val Thr His Gly Ile Gly Glu Asn Gly Val Arg
    2135                2140                2145

Gly Ile Ala Val Asp Trp Val Ala Gly Asn Leu Tyr Phe Thr Asn
    2150                2155                2160

Ala Phe Val Ser Glu Thr Leu Ile Glu Val Leu Arg Ile Asn Thr
    2165                2170                2175

Thr Tyr Arg Arg Val Leu Leu Lys Val Thr Val Asp Met Pro Arg
    2180                2185                2190

His Ile Val Val Asp Pro Lys Asn Arg Tyr Leu Phe Trp Ala Asp
    2195                2200                2205

Tyr Gly Gln Arg Pro Lys Ile Glu Arg Ser Phe Leu Asp Cys Thr
    2210                2215                2220

Asn Arg Thr Val Leu Val Ser Glu Gly Ile Val Thr Pro Arg Gly
    2225                2230                2235

Leu Ala Val Asp Arg Ser Asp Gly Tyr Val Tyr Trp Val Asp Asp
    2240                2245                2250

Ser Leu Asp Ile Ile Ala Arg Ile Arg Ile Asn Gly Glu Asn Ser
```

```
            2255                2260                2265

Glu Val Ile Arg Tyr Gly Ser Arg Tyr Pro Thr Pro Tyr Gly Ile
2270                2275                2280

Thr Val Phe Glu Asn Ser Ile Ile Trp Val Asp Arg Asn Leu Lys
2285                2290                2295

Lys Ile Phe Gln Ala Ser Lys Glu Pro Glu Asn Thr Glu Pro Pro
2300                2305                2310

Thr Val Ile Arg Asp Asn Ile Asn Trp Leu Arg Asp Val Thr Ile
2315                2320                2325

Phe Asp Lys Gln Val Gln Pro Arg Ser Pro Ala Glu Val Asn Asn
2330                2335                2340

Asn Pro Cys Leu Glu Asn Asn Gly Gly Cys Ser His Leu Cys Phe
2345                2350                2355

Ala Leu Pro Gly Leu His Thr Pro Lys Cys Asp Cys Ala Phe Gly
2360                2365                2370

Thr Leu Gln Ser Asp Gly Lys Asn Cys Ala Ile Ser Thr Glu Asn
2375                2380                2385

Phe Leu Ile Phe Ala Leu Ser Asn Ser Leu Arg Ser Leu His Leu
2390                2395                2400

Asp Pro Glu Asn His Ser Pro Pro Phe Gln Thr Ile Asn Val Glu
2405                2410                2415

Arg Thr Val Met Ser Leu Asp Tyr Asp Ser Val Ser Asp Arg Ile
2420                2425                2430

Tyr Phe Thr Gln Asn Leu Ala Ser Gly Val Gly Gln Ile Ser Tyr
2435                2440                2445

Ala Thr Leu Ser Ser Gly Ile His Thr Pro Thr Val Ile Ala Ser
2450                2455                2460

Gly Ile Gly Thr Ala Asp Gly Ile Ala Phe Asp Trp Ile Thr Arg
2465                2470                2475

Arg Ile Tyr Tyr Ser Asp Tyr Leu Asn Gln Met Ile Asn Ser Met
2480                2485                2490

Ala Glu Asp Gly Ser Asn Arg Thr Val Ile Ala Arg Val Pro Lys
2495                2500                2505

Pro Arg Ala Ile Val Leu Asp Pro Cys Gln Gly Tyr Leu Tyr Trp
2510                2515                2520

Ala Asp Trp Asp Thr His Ala Lys Ile Glu Arg Ala Thr Leu Gly
2525                2530                2535

Gly Asn Phe Arg Val Pro Ile Val Asn Ser Ser Leu Val Met Pro
2540                2545                2550

Ser Gly Leu Thr Leu Asp Tyr Glu Glu Asp Leu Leu Tyr Trp Val
2555                2560                2565

Asp Ala Ser Leu Gln Arg Ile Glu Arg Ser Thr Leu Thr Gly Val
2570                2575                2580

Asp Arg Glu Val Ile Val Asn Ala Ala Val His Ala Phe Gly Leu
2585                2590                2595

Thr Leu Tyr Gly Gln Tyr Ile Tyr Trp Thr Asp Leu Tyr Thr Gln
2600                2605                2610

Arg Ile Tyr Arg Ala Asn Lys Tyr Asp Gly Ser Gly Gln Ile Ala
2615                2620                2625

Met Thr Thr Asn Leu Leu Ser Gln Pro Arg Gly Ile Asn Thr Val
2630                2635                2640

Val Lys Asn Gln Lys Gln Cys Asn Asn Pro Cys Glu Gln Phe
2645                2650                2655
```

-continued

| | | | | | | | | | |
|---|---|---|---|---|---|---|---|---|---|
|Asn|Gly|Gly|Cys|Ser|His|Ile|Cys|Ala|Pro|Gly|Pro|Asn|Gly|Ala|

Asn Gly Gly Cys Ser His Ile Cys Ala Pro Gly Pro Asn Gly Ala
            2660                 2665                 2670

Glu Cys Gln Cys Pro His Glu Gly Asn Trp Tyr Leu Ala Asn Asn
    2675                 2680                 2685

Arg Lys His Cys Ile Val Asp Asn Gly Glu Arg Cys Gly Ala Ser
    2690                 2695                 2700

Ser Phe Thr Cys Ser Asn Gly Arg Cys Ile Ser Glu Glu Trp Lys
    2705                 2710                 2715

Cys Asp Asn Asp Asn Asp Cys Gly Asp Gly Ser Asp Glu Met Glu
    2720                 2725                 2730

Ser Val Cys Ala Leu His Thr Cys Ser Pro Thr Ala Phe Thr Cys
    2735                 2740                 2745

Ala Asn Gly Arg Cys Val Gln Tyr Ser Tyr Arg Cys Asp Tyr Tyr
    2750                 2755                 2760

Asn Asp Cys Gly Asp Gly Ser Asp Glu Ala Gly Cys Leu Phe Arg
    2765                 2770                 2775

Asp Cys Asn Ala Thr Thr Glu Phe Met Cys Asn Asn Arg Arg Cys
    2780                 2785                 2790

Ile Pro Arg Glu Phe Ile Cys Asn Gly Val Asp Asn Cys His Asp
    2795                 2800                 2805

Asn Asn Thr Ser Asp Glu Lys Asn Cys Pro Asp Arg Thr Cys Gln
    2810                 2815                 2820

Ser Gly Tyr Thr Lys Cys His Asn Ser Asn Ile Cys Ile Pro Arg
    2825                 2830                 2835

Val Tyr Leu Cys Asp Gly Asp Asn Asp Cys Gly Asp Asn Ser Asp
    2840                 2845                 2850

Glu Asn Pro Thr Tyr Cys Thr His Thr Cys Ser Ser Ser Glu
    2855                 2860                 2865

Phe Gln Cys Ala Ser Gly Arg Cys Ile Pro Gln His Trp Tyr Cys
    2870                 2875                 2880

Asp Gln Glu Thr Asp Cys Phe Asp Ala Ser Asp Glu Pro Ala Ser
    2885                 2890                 2895

Cys Gly His Ser Glu Arg Thr Cys Leu Ala Asp Glu Phe Lys Cys
    2900                 2905                 2910

Asp Gly Gly Arg Cys Ile Pro Ser Glu Trp Ile Cys Asp Gly Asp
    2915                 2920                 2925

Asn Asp Cys Gly Asp Met Ser Asp Glu Asp Lys Arg His Gln Cys
    2930                 2935                 2940

Gln Asn Gln Asn Cys Ser Asp Ser Glu Phe Leu Cys Val Asn Asp
    2945                 2950                 2955

Arg Pro Pro Asp Arg Arg Cys Ile Pro Gln Ser Trp Val Cys Asp
    2960                 2965                 2970

Gly Asp Val Asp Cys Thr Asp Gly Tyr Asp Glu Asn Gln Asn Cys
    2975                 2980                 2985

Thr Arg Arg Thr Cys Ser Glu Asn Glu Phe Thr Cys Gly Tyr Gly
    2990                 2995                 3000

Leu Cys Ile Pro Lys Ile Phe Arg Cys Asp Arg His Asn Asp Cys
    3005                 3010                 3015

Gly Asp Tyr Ser Asp Glu Arg Gly Cys Leu Tyr Gln Thr Cys Gln
    3020                 3025                 3030

Gln Asn Gln Phe Thr Cys Gln Asn Gly Arg Cys Ile Ser Lys Thr
    3035                 3040                 3045

Phe Val Cys Asp Glu Asp Asn Asp Cys Gly Asp Gly Ser Asp Glu
    3050                 3055                 3060

```
Leu Met His Leu Cys His Thr Pro Glu Pro Thr Cys Pro Pro His
    3065                3070                3075

Glu Phe Lys Cys Asp Asn Gly Arg Cys Ile Glu Met Met Lys Leu
    3080                3085                3090

Cys Asn His Leu Asp Asp Cys Leu Asp Asn Ser Asp Glu Lys Gly
    3095                3100                3105

Cys Gly Ile Asn Glu Cys His Asp Pro Ser Ile Ser Gly Cys Asp
    3110                3115                3120

His Asn Cys Thr Asp Thr Leu Thr Ser Phe Tyr Cys Ser Cys Arg
    3125                3130                3135

Pro Gly Tyr Lys Leu Met Ser Asp Lys Arg Thr Cys Val Asp Ile
    3140                3145                3150

Asp Glu Cys Thr Glu Met Pro Phe Val Cys Ser Gln Lys Cys Glu
    3155                3160                3165

Asn Val Ile Gly Ser Tyr Ile Cys Lys Cys Ala Pro Gly Tyr Leu
    3170                3175                3180

Arg Glu Pro Asp Gly Lys Thr Cys Arg Gln Asn Ser Asn Ile Glu
    3185                3190                3195

Pro Tyr Leu Ile Phe Ser Asn Arg Tyr Tyr Leu Arg Asn Leu Thr
    3200                3205                3210

Ile Asp Gly Tyr Phe Tyr Ser Leu Ile Leu Glu Gly Leu Asp Asn
    3215                3220                3225

Val Val Ala Leu Asp Phe Asp Arg Val Glu Lys Arg Leu Tyr Trp
    3230                3235                3240

Ile Asp Thr Gln Arg Gln Val Ile Glu Arg Met Phe Leu Asn Lys
    3245                3250                3255

Thr Asn Lys Glu Thr Ile Ile Asn His Arg Leu Pro Ala Ala Glu
    3260                3265                3270

Ser Leu Ala Val Asp Trp Val Ser Arg Lys Leu Tyr Trp Leu Asp
    3275                3280                3285

Ala Arg Leu Asp Gly Leu Phe Val Ser Asp Leu Asn Gly Gly His
    3290                3295                3300

Arg Arg Met Leu Ala Gln His Cys Val Asp Ala Asn Asn Thr Phe
    3305                3310                3315

Cys Phe Asp Asn Pro Arg Gly Leu Ala Leu His Pro Gln Tyr Gly
    3320                3325                3330

Tyr Leu Tyr Trp Ala Asp Trp Gly His Arg Ala Tyr Ile Gly Arg
    3335                3340                3345

Val Gly Met Asp Gly Thr Asn Lys Ser Val Ile Ile Ser Thr Lys
    3350                3355                3360

Leu Glu Trp Pro Asn Gly Ile Thr Ile Asp Tyr Thr Asn Asp Leu
    3365                3370                3375

Leu Tyr Trp Ala Asp Ala His Leu Gly Tyr Ile Glu Tyr Ser Asp
    3380                3385                3390

Leu Glu Gly His His Arg His Thr Val Tyr Asp Gly Ala Leu Pro
    3395                3400                3405

His Pro Phe Ala Ile Thr Ile Phe Glu Asp Thr Ile Tyr Trp Thr
    3410                3415                3420

Asp Trp Asn Thr Arg Thr Val Glu Lys Gly Asn Lys Tyr Asp Gly
    3425                3430                3435

Ser Asn Arg Gln Thr Leu Val Asn Thr Thr His Arg Pro Phe Asp
    3440                3445                3450

Ile His Val Tyr His Pro Tyr Arg Gln Pro Ile Val Ser Asn Pro
```

```
                3455              3460              3465

Cys Gly Thr Asn Gly Gly Cys Ser His Leu Cys Leu Ile Lys
    3470              3475              3480

Pro Gly Gly Lys Gly Phe Thr Cys Glu Cys Pro Asp Asp Phe Arg
    3485              3490              3495

Thr Leu Gln Leu Ser Gly Ser Thr Tyr Cys Met Pro Met Cys Ser
    3500              3505              3510

Ser Thr Gln Phe Leu Cys Ala Asn Asn Glu Lys Cys Ile Pro Ile
    3515              3520              3525

Trp Trp Lys Cys Asp Gly Gln Lys Asp Cys Ser Asp Gly Ser Asp
    3530              3535              3540

Glu Leu Ala Leu Cys Pro Gln Arg Phe Cys Arg Leu Gly Gln Phe
    3545              3550              3555

Gln Cys Ser Asp Gly Asn Cys Thr Ser Pro Gln Thr Leu Cys Asn
    3560              3565              3570

Ala His Gln Asn Cys Pro Asp Gly Ser Asp Glu Asp Arg Leu Leu
    3575              3580              3585

Cys Glu Asn His His Cys Asp Ser Asn Glu Trp Gln Cys Ala Asn
    3590              3595              3600

Lys Arg Cys Ile Pro Glu Ser Trp Gln Cys Asp Thr Phe Asn Asp
    3605              3610              3615

Cys Glu Asp Asn Ser Asp Glu Asp Ser Ser His Cys Ala Ser Arg
    3620              3625              3630

Thr Cys Arg Pro Gly Gln Phe Arg Cys Ala Asn Gly Arg Cys Ile
    3635              3640              3645

Pro Gln Ala Trp Lys Cys Asp Val Asp Asn Asp Cys Gly Asp His
    3650              3655              3660

Ser Asp Glu Pro Ile Glu Glu Cys Met Ser Ser Ala His Leu Cys
    3665              3670              3675

Asp Asn Phe Thr Glu Phe Ser Cys Lys Thr Asn Tyr Arg Cys Ile
    3680              3685              3690

Pro Lys Trp Ala Val Cys Asn Gly Val Asp Asp Cys Arg Asp Asn
    3695              3700              3705

Ser Asp Glu Gln Gly Cys Glu Glu Arg Thr Cys His Pro Val Gly
    3710              3715              3720

Asp Phe Arg Cys Lys Asn His His Cys Ile Pro Leu Arg Trp Gln
    3725              3730              3735

Cys Asp Gly Gln Asn Asp Cys Gly Asp Asn Ser Asp Glu Glu Asn
    3740              3745              3750

Cys Ala Pro Arg Glu Cys Thr Glu Ser Glu Phe Arg Cys Val Asn
    3755              3760              3765

Gln Gln Cys Ile Pro Ser Arg Trp Ile Cys Asp His Tyr Asn Asp
    3770              3775              3780

Cys Gly Asp Asn Ser Asp Glu Arg Asp Cys Glu Met Arg Thr Cys
    3785              3790              3795

His Pro Glu Tyr Phe Gln Cys Thr Ser Gly His Cys Val His Ser
    3800              3805              3810

Glu Leu Lys Cys Asp Gly Ser Ala Asp Cys Leu Asp Ala Ser Asp
    3815              3820              3825

Glu Ala Asp Cys Pro Thr Arg Phe Pro Asp Gly Ala Tyr Cys Gln
    3830              3835              3840

Ala Thr Met Phe Glu Cys Lys Asn His Val Cys Ile Pro Pro Tyr
    3845              3850              3855
```

```
Trp Lys Cys Asp Gly Asp Asp Cys Gly Asp Gly Ser Asp Glu
3860             3865             3870

Glu Leu His Leu Cys Leu Asp Val Pro Cys Asn Ser Pro Asn Arg
3875             3880             3885

Phe Arg Cys Asp Asn Asn Arg Cys Ile Tyr Ser His Glu Val Cys
3890             3895             3900

Asn Gly Val Asp Asp Cys Gly Asp Gly Thr Asp Glu Thr Glu Glu
3905             3910             3915

His Cys Arg Lys Pro Thr Pro Lys Pro Cys Thr Glu Tyr Glu Tyr
3920             3925             3930

Lys Cys Gly Asn Gly His Cys Ile Pro His Asp Asn Val Cys Asp
3935             3940             3945

Asp Ala Asp Asp Cys Gly Asp Trp Ser Asp Glu Leu Gly Cys Asn
3950             3955             3960

Lys Gly Lys Glu Arg Thr Cys Ala Glu Asn Ile Cys Glu Gln Asn
3965             3970             3975

Cys Thr Gln Leu Asn Glu Gly Gly Phe Ile Cys Ser Cys Thr Ala
3980             3985             3990

Gly Phe Glu Thr Asn Val Phe Asp Arg Thr Ser Cys Leu Asp Ile
3995             4000             4005

Asn Glu Cys Glu Gln Phe Gly Thr Cys Pro Gln His Cys Arg Asn
4010             4015             4020

Thr Lys Gly Ser Tyr Glu Cys Val Cys Ala Asp Gly Phe Thr Ser
4025             4030             4035

Met Ser Asp Arg Pro Gly Lys Arg Cys Ala Ala Glu Gly Ser Ser
4040             4045             4050

Pro Leu Leu Leu Leu Pro Asp Asn Val Arg Ile Arg Lys Tyr Asn
4055             4060             4065

Leu Ser Ser Glu Arg Phe Ser Glu Tyr Leu Gln Asp Glu Glu Tyr
4070             4075             4080

Ile Gln Ala Val Asp Tyr Asp Trp Asp Pro Lys Asp Ile Gly Leu
4085             4090             4095

Ser Val Val Tyr Tyr Thr Val Arg Gly Glu Gly Ser Arg Phe Gly
4100             4105             4110

Ala Ile Lys Arg Ala Tyr Ile Pro Asn Phe Glu Ser Gly Arg Asn
4115             4120             4125

Asn Leu Val Gln Glu Val Asp Leu Lys Leu Lys Tyr Val Met Gln
4130             4135             4140

Pro Asp Gly Ile Ala Val Asp Trp Val Gly Arg His Ile Tyr Trp
4145             4150             4155

Ser Asp Val Lys Asn Lys Arg Ile Glu Val Ala Lys Leu Asp Gly
4160             4165             4170

Arg Tyr Arg Lys Trp Leu Ile Ser Thr Asp Leu Asp Gln Pro Ala
4175             4180             4185

Ala Ile Ala Val Asn Pro Lys Leu Gly Leu Met Phe Trp Thr Asp
4190             4195             4200

Trp Gly Lys Glu Pro Lys Ile Glu Ser Ala Trp Met Asn Gly Glu
4205             4210             4215

Asp Arg Asn Ile Leu Val Phe Glu Asp Leu Gly Trp Pro Thr Gly
4220             4225             4230

Leu Ser Ile Asp Tyr Leu Asn Asn Asp Arg Ile Tyr Trp Ser Asp
4235             4240             4245

Phe Lys Glu Asp Val Ile Glu Thr Ile Lys Tyr Asp Gly Thr Asp
4250             4255             4260
```

```
Arg Arg Val Ile Ala Lys Glu Ala Met Asn Pro Tyr Ser Leu Asp
    4265                4270                4275

Ile Phe Glu Asp Gln Leu Tyr Trp Ile Ser Lys Glu Lys Gly Glu
    4280                4285                4290

Val Trp Lys Gln Asn Lys Phe Gly Gln Gly Lys Lys Glu Lys Thr
    4295                4300                4305

Leu Val Val Asn Pro Trp Leu Thr Gln Val Arg Ile Phe His Gln
    4310                4315                4320

Leu Arg Tyr Asn Lys Ser Val Pro Asn Leu Cys Lys Gln Ile Cys
    4325                4330                4335

Ser His Leu Cys Leu Leu Arg Pro Gly Gly Tyr Ser Cys Ala Cys
    4340                4345                4350

Pro Gln Gly Ser Ser Phe Ile Glu Gly Ser Thr Thr Glu Cys Asp
    4355                4360                4365

Ala Ala Ile Glu Leu Pro Ile Asn Leu Pro Pro Cys Arg Cys
    4370                4375                4380

Met His Gly Gly Asn Cys Tyr Phe Asp Glu Thr Asp Leu Pro Lys
    4385                4390                4395

Cys Lys Cys Pro Ser Gly Tyr Thr Gly Lys Tyr Cys Glu Met Ala
    4400                4405                4410

Phe Ser Lys Gly Ile Ser Pro Gly Thr Thr Ala Val Ala Val Leu
    4415                4420                4425

Leu Thr Ile Leu Leu Ile Val Val Ile Gly Ala Leu Ala Ile Ala
    4430                4435                4440

Gly Phe Phe His Tyr Arg Arg Thr Gly Ser Leu Leu Pro Ala Leu
    4445                4450                4455

Pro Lys Leu Pro Ser Leu Ser Ser Leu Val Lys Pro Ser Glu Asn
    4460                4465                4470

Gly Asn Gly Val Thr Phe Arg Ser Gly Ala Asp Leu Asn Met Asp
    4475                4480                4485

Ile Gly Val Ser Gly Phe Gly Pro Glu Thr Ala Ile Asp Arg Ser
    4490                4495                4500

Met Ala Met Ser Glu Asp Phe Val Met Glu Met Gly Lys Gln Pro
    4505                4510                4515

Ile Ile Phe Glu Asn Pro Met Tyr Ser Ala Arg Asp Ser Ala Val
    4520                4525                4530

Lys Val Val Gln Pro Ile Gln Val Thr Val Ser Glu Asn Val Asp
    4535                4540                4545

Asn Lys Asn Tyr Gly Ser Pro Ile Asn Pro Ser Glu Ile Val Pro
    4550                4555                4560

Glu Thr Asn Pro Thr Ser Pro Ala Ala Asp Gly Thr Gln Val Thr
    4565                4570                4575

Lys Trp Asn Leu Phe Lys Arg Lys Ser Lys Gln Thr Thr Asn Phe
    4580                4585                4590

Glu Asn Pro Ile Tyr Ala Gln Met Glu Asn Glu Gln Lys Glu Ser
    4595                4600                4605

Val Ala Ala Thr Pro Pro Pro Ser Pro Ser Leu Pro Ala Lys Pro
    4610                4615                4620

Lys Pro Pro Ser Arg Arg Asp Pro Thr Pro Thr Tyr Ser Ala Thr
    4625                4630                4635

Glu Asp Thr Phe Lys Asp Thr Ala Asn Leu Val Lys Glu Asp Ser
    4640                4645                4650

Glu Val
```

<210> SEQ ID NO 18
<211> LENGTH: 134
<212> TYPE: PRT
<213> ORGANISM: Mus musculus

<400> SEQUENCE: 18

Met Asp Thr Ser His Thr Thr Lys Ser Cys Leu Leu Ile Leu Leu Val
1               5                   10                  15

Ala Leu Leu Cys Ala Glu Arg Ala Gln Gly Leu Glu Cys Tyr Gln Cys
            20                  25                  30

Tyr Gly Val Pro Phe Glu Thr Ser Cys Pro Ser Ile Thr Cys Pro Tyr
        35                  40                  45

Pro Asp Gly Val Cys Val Thr Gln Glu Ala Ala Val Ile Val Asp Ser
    50                  55                  60

Gln Thr Arg Lys Val Lys Asn Asn Leu Cys Leu Pro Ile Cys Pro Pro
65                  70                  75                  80

Asn Ile Glu Ser Met Glu Ile Leu Gly Thr Lys Val Asn Val Lys Thr
                85                  90                  95

Ser Cys Cys Gln Glu Asp Leu Cys Asn Val Ala Val Pro Asn Gly Gly
            100                 105                 110

Ser Thr Trp Thr Met Ala Gly Val Leu Leu Phe Ser Leu Ser Ser Val
        115                 120                 125

Leu Leu Gln Thr Leu Leu
    130

<210> SEQ ID NO 19
<211> LENGTH: 339
<212> TYPE: PRT
<213> ORGANISM: Mus musculus

<400> SEQUENCE: 19

Met Ala Gly Cys Cys Ser Val Leu Gly Ser Phe Leu Phe Glu Tyr Asp
1               5                   10                  15

Thr Pro Arg Ile Val Leu Ile Arg Ser Arg Lys Val Gly Leu Met Asn
            20                  25                  30

Arg Val Val Gln Leu Leu Ile Leu Ala Tyr Val Ile Gly Trp Val Phe
        35                  40                  45

Val Trp Glu Lys Gly Tyr Gln Glu Thr Asp Ser Val Val Ser Ser Val
    50                  55                  60

Thr Thr Lys Ala Lys Gly Val Ala Val Thr Asn Thr Ser Gln Leu Gly
65                  70                  75                  80

Phe Arg Ile Trp Asp Val Ala Asp Tyr Val Val Pro Ala Gln Glu Glu
                85                  90                  95

Asn Ser Leu Phe Ile Met Thr Asn Met Ile Val Thr Val Asn Gln Thr
            100                 105                 110

Gln Gly Thr Cys Pro Glu Ile Pro Asp Lys Thr Ser Ile Cys Asp Ser
        115                 120                 125

Asp Ala Asn Cys Thr Leu Gly Ser Ser Asp Thr His Ser Ser Gly Ile
    130                 135                 140

Gly Thr Gly Arg Cys Val Pro Phe Asn Ala Ser Val Lys Thr Cys Glu
145                 150                 155                 160

Val Ala Ala Trp Cys Pro Val Glu Asn Asp Ala Gly Val Pro Thr Arg
                165                 170                 175

Asn Ile Leu Pro Asn Ile Thr Thr Ser Tyr Leu Lys Ser Cys Ile Tyr
            180                 185                 190

Asn Ala Arg Thr Asp Pro Phe Cys Pro Ile Phe Arg Leu Gly Gln Ile
              195                 200                 205

Val Ala Asp Ala Gly His Ser Phe Gln Glu Met Ala Val Glu Gly Gly
    210                 215                 220

Ile Met Gly Ile Gln Ile Lys Trp Asp Cys Asn Leu Asp Arg Ala Ala
225                 230                 235                 240

Ser His Cys Leu Pro Arg Tyr Ser Phe Arg Leu Asp Thr Arg Asp
              245                 250                 255

Leu Glu His Asn Val Ser Pro Gly Tyr Asn Phe Arg Phe Ala Lys Tyr
              260                 265                 270

Tyr Arg Asp Leu Ala Gly Asn Glu Gln Arg Thr Leu Thr Lys Ala Tyr
    275                 280                 285

Gly Ile Arg Phe Asp Ile Ile Val Phe Gly Lys Ala Thr Val Leu Cys
    290                 295                 300

Asp Val Ile Val Leu Tyr Cys Met Lys Lys Arg Tyr Tyr Arg Asp
305                 310                 315                 320

Lys Lys Tyr Lys Tyr Val Glu Asp Tyr Glu Gln Gly Leu Ser Gly Glu
              325                 330                 335

Met Asn Gln

<210> SEQ ID NO 20
<211> LENGTH: 388
<212> TYPE: PRT
<213> ORGANISM: Homo sapiens

<400> SEQUENCE: 20

Met Ala Gly Cys Cys Ser Ala Leu Ala Ala Phe Leu Phe Glu Tyr Asp
1               5                   10                  15

Thr Pro Arg Ile Val Leu Ile Arg Ser Arg Lys Val Gly Leu Met Asn
              20                  25                  30

Arg Ala Val Gln Leu Leu Ile Leu Ala Tyr Val Ile Gly Trp Val Phe
    35                  40                  45

Val Trp Glu Lys Gly Tyr Gln Glu Thr Asp Ser Val Val Ser Ser Val
50                  55                  60

Thr Thr Lys Val Lys Gly Val Ala Val Thr Asn Thr Ser Lys Leu Gly
65                  70                  75                  80

Phe Arg Ile Trp Asp Val Ala Asp Tyr Val Ile Pro Ala Gln Glu Glu
              85                  90                  95

Asn Ser Leu Phe Val Met Thr Asn Val Ile Leu Thr Met Asn Gln Thr
              100                 105                 110

Gln Gly Leu Cys Pro Glu Ile Pro Asp Ala Thr Thr Val Cys Lys Ser
              115                 120                 125

Asp Ala Ser Cys Thr Ala Gly Ser Ala Gly Thr His Ser Asn Gly Val
    130                 135                 140

Ser Thr Gly Arg Cys Val Ala Phe Asn Gly Ser Val Lys Thr Cys Glu
145                 150                 155                 160

Val Ala Ala Trp Cys Pro Val Glu Asp Asp Thr His Val Pro Gln Pro
              165                 170                 175

Ala Phe Leu Lys Ala Ala Glu Asn Phe Thr Leu Leu Val Lys Asn Asn
    180                 185                 190

Ile Trp Tyr Pro Lys Phe Asn Phe Ser Lys Arg Asn Ile Leu Pro Asn
    195                 200                 205

Ile Thr Thr Thr Tyr Leu Lys Ser Cys Ile Tyr Asp Ala Lys Thr Asp
210                 215                 220

```
Pro Phe Cys Pro Ile Phe Arg Leu Gly Lys Ile Val Glu Asn Ala Gly
225                 230                 235                 240

His Ser Phe Gln Asp Met Ala Val Glu Gly Gly Ile Met Gly Ile Gln
                245                 250                 255

Val Asn Trp Asp Cys Asn Leu Asp Arg Ala Ala Ser Leu Cys Leu Pro
                260                 265                 270

Arg Tyr Ser Phe Arg Arg Leu Asp Thr Arg Asp Val Glu His Asn Val
            275                 280                 285

Ser Pro Gly Tyr Asn Phe Arg Phe Ala Lys Tyr Tyr Arg Asp Leu Ala
        290                 295                 300

Gly Asn Glu Gln Arg Thr Leu Ile Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Ile Gly Ser Gly Leu Ala Leu Leu Gly Met Ala Thr Val Leu
                340                 345                 350

Cys Asp Ile Ile Val Leu Tyr Cys Met Lys Lys Arg Leu Tyr Tyr Arg
            355                 360                 365

Glu Lys Lys Tyr Lys Tyr Val Glu Asp Tyr Gln Gly Leu Ala Ser
            370                 375                 380

Glu Leu Asp Gln
385

<210> SEQ ID NO 21
<211> LENGTH: 828
<212> TYPE: PRT
<213> ORGANISM: Mus musculus

<400> SEQUENCE: 21

Met Ser Asn Thr Val Lys Ile Pro Pro Lys Arg Glu Ser Glu Phe Ser
1               5                   10                  15

Val Ser Lys His Leu Glu Thr Ala Thr Gly Leu Asp Ala Ser Met His
                20                  25                  30

Phe Leu Ile Met Glu Lys Leu Gly Arg Ile His Leu Asn Arg Gln Val
            35                  40                  45

Met Ala Phe Ile Phe Met Met Val Leu Val Gln Val Cys Ser Glu Pro
50                  55                  60

Thr Ile Arg Tyr Ser Ile Leu Glu Glu Thr Glu Ser Gly Ser Phe Val
65                  70                  75                  80

Ala His Leu Ala Lys Asp Leu Gly Leu Gly Ala Arg Glu Leu Ala Ala
                85                  90                  95

Arg Ser Ala Arg Val Leu Ser Asp Asp Tyr Lys Gln Arg Leu Leu Leu
            100                 105                 110

Asp Pro Glu Thr Gly Asp Leu Leu Leu Arg Glu Lys Val Asp Arg Glu
        115                 120                 125

Glu Val Cys Ser Thr Val Asp Pro Cys Val Leu His Phe Gln Val Thr
130                 135                 140

Leu Glu Lys Pro Val Gln Tyr Phe Gln Arg Glu Leu Leu Ile Gln Asp
145                 150                 155                 160

Ile Asn Asp His Ala Pro Glu Phe Pro Asp Arg Glu Leu Leu Leu Arg
                165                 170                 175

Ile Pro Glu Asn Ser Gln Gly Thr Gln Phe Ser Leu Asn Leu Ala
            180                 185                 190

Gln Asp Leu Asp Val Gly Ser Asn Gly Leu Gln Gln Tyr Thr Val Ser
        195                 200                 205
```

-continued

Pro Asn Pro Tyr Phe His Val Leu Thr Gln Asn Asn Ser Lys Gly Lys
210                 215                 220

Lys Tyr Pro Glu Leu Val Gln Asp Arg Gly Leu Asp Arg Glu Glu Gln
225                 230                 235                 240

Ala Glu Leu Ser Leu Thr Leu Thr Ala Leu Asp Gly Gly Ser Pro Pro
            245                 250                 255

Arg Ser Gly Thr Ala Leu Val Arg Ile Leu Ile Met Asp Ile Asn Asp
            260                 265                 270

Asn Ala Pro Glu Phe Val Asn Ser Pro Tyr Glu Val Gln Val Leu Glu
        275                 280                 285

Ser Ser Pro Pro Asp Ser Pro Val Leu Thr Val Leu Ala Arg Asp Ala
290                 295                 300

Asp Ala Gly Asn Phe Gly Arg Val Ser Tyr Gly Phe Phe Gln Ala Ser
305                 310                 315                 320

Asp Glu Ile Gln Gln Thr Phe Ser Ile Asn Ala Thr Ser Gly Asp Met
            325                 330                 335

Arg Leu Lys Lys Lys Leu Asp Phe Glu Lys Ile Lys Ser Tyr His Val
            340                 345                 350

Glu Ile Glu Ala Ile Asp Gly Gly Leu Ser Gly Lys Gly Ser Val
            355                 360                 365

Thr Ile Glu Val Val Asp Val Asn Asp Asn Ala Pro Glu Leu Thr Ile
370                 375                 380

Ser Ser Leu Thr Ser Ser Val Pro Glu Asn Ala Pro Glu Thr Ile Ile
385                 390                 395                 400

Ser Ile Phe Arg Val Gly Asp Arg Asp Ser Gly Glu Asn Gly Lys Met
            405                 410                 415

Val Cys Ser Ile Pro Glu Asn Leu Pro Phe Ile Leu Lys Ser Thr Phe
            420                 425                 430

Lys Asn Phe Tyr Thr Leu Val Thr Glu Ser Pro Leu Asp Arg Glu Ser
            435                 440                 445

Arg Ala Glu Tyr Asn Ile Thr Ile Met Val Ser Asp Met Gly Thr Pro
450                 455                 460

Arg Leu Thr Thr Trp His Thr Ile Lys Val Gln Val Ser Asp Ile Asn
465                 470                 475                 480

Asp Asn Thr Pro Ala Phe Thr Gln Thr Ser Tyr Thr Met Phe Val Arg
            485                 490                 495

Glu Asn Asn Ser Pro Ala Leu His Ile Gly Thr Ile Ser Ala Thr Asp
            500                 505                 510

Ser Asp Ser Gly Ser Asn Ala His Ile Thr Tyr Ser Leu Leu Pro Pro
            515                 520                 525

His Asp Pro Glu Leu Ala Leu Ser Ser Leu Ile Ser Ile Asn Ala Asp
530                 535                 540

Asn Gly Gln Leu Phe Ala Leu Arg Ala Leu Asp Tyr Glu Ala Leu Gln
545                 550                 555                 560

Val Phe Glu Phe His Val Gly Ala Thr Asp Gly Gly Ser Pro Pro Leu
            565                 570                 575

Ser Ser Gln Ala Leu Val Arg Val Val Leu Asp Asp Asn Asp Asn
            580                 585                 590

Ala Pro Phe Val Leu Tyr Pro Met Gln Asn Ala Ser Ala Pro Phe Thr
            595                 600                 605

Glu Leu Leu Pro Arg Ala Ala Glu Pro Gly Tyr Leu Val Thr Lys Val
            610                 615                 620

Val Ala Val Asp Arg Asp Ser Gly Gln Asn Ala Trp Leu Ser Phe Gln
625                 630                 635                 640

```
Leu Leu Lys Ala Thr Glu Pro Gly Leu Phe Ser Val Trp Ala His Asn
                645                 650                 655
Gly Glu Val Arg Thr Thr Arg Leu Leu Ser Glu Arg Asp Val Pro Lys
            660                 665                 670
His Arg Leu Leu Val Val Lys Asp Asn Gly Glu Pro Gln Arg Ser
        675                 680                 685
Ala Ser Val Thr Leu Gln Val Leu Leu Val Asp Gly Phe Ser Gln Ser
    690                 695                 700
Tyr Leu Pro Leu Pro Glu Val Ala Arg Asp Pro Ala His Glu Asp Glu
705                 710                 715                 720
Asp Val Leu Thr Leu Tyr Leu Val Ile Ala Leu Ala Ser Val Ser Ser
                725                 730                 735
Leu Phe Leu Leu Ser Val Leu Leu Phe Val Gly Val Arg Leu Cys Arg
                740                 745                 750
Arg Ala Arg Glu Val Ser Leu Gly Gly Cys Ser Met Pro Gly Glu His
            755                 760                 765
Phe Pro Gly His Leu Val Asp Val Ser Gly Ala Gly Thr Leu Ser Gln
        770                 775                 780
Ser Tyr Gln Tyr Glu Val Cys Leu Arg Gly Asp Ser Gly Thr Gly Glu
785                 790                 795                 800
Phe Lys Phe Leu Lys Pro Met Ile Pro Asn Ala Gly Ile Glu Ile Met
                805                 810                 815
Glu Ser Pro His Cys Arg Asp Ser Phe Val Phe Asn
                820                 825

<210> SEQ ID NO 22
<211> LENGTH: 796
<212> TYPE: PRT
<213> ORGANISM: Homo sapiens

<400> SEQUENCE: 22

Lys Thr Arg Gly Phe Ser Phe Pro Arg Gln Arg Gln Val Leu Phe Leu
1               5                   10                  15
Phe Leu Phe Trp Gly Val Ser Leu Ala Gly Ser Gly Phe Gly Arg Tyr
                20                  25                  30
Ser Val Thr Glu Glu Thr Glu Lys Gly Ser Phe Val Val Asn Leu Ala
            35                  40                  45
Lys Asp Leu Gly Leu Ala Glu Gly Glu Leu Ala Ala Arg Gly Thr Arg
        50                  55                  60
Val Val Ser Asp Asp Asn Lys Gln Tyr Leu Leu Asp Ser His Thr
65                  70                  75                  80
Gly Asn Leu Leu Thr Asn Glu Lys Leu Asp Arg Glu Lys Leu Cys Gly
                85                  90                  95
Pro Lys Glu Pro Cys Met Leu Tyr Phe Gln Ile Leu Met Asp Asp Pro
            100                 105                 110
Phe Gln Ile Tyr Arg Ala Glu Leu Arg Val Arg Asp Ile Asn Asp His
        115                 120                 125
Ser Pro Val Phe Arg His Lys Glu Met Val Leu Lys Ile Ser Glu Asn
    130                 135                 140
Thr Ala Glu Gly Thr Ala Phe Arg Leu Glu Arg Ala Gln Asp Pro Asp
145                 150                 155                 160
Glu Gly His Asn Ser Ile Gln Asn Tyr Thr Ile Ser Ser Asn Ser Phe
                165                 170                 175
Phe His Ile Lys Ile Ser Gly Ser Asp Glu Gly Met Ile Tyr Pro Glu
                180                 185                 190
```

-continued

```
Leu Val Leu Asp Lys Ala Leu Asp Arg Glu Glu Gln Glu Glu Leu Ser
            195                 200                 205
Leu Thr Leu Thr Ala Leu Asp Gly Gly Ser Pro Ser Arg Ser Gly Thr
            210                 215                 220
Ser Thr Ile Arg Ile Val Val Leu Asp Val Asn Asp Asn Ala Pro Gln
225                 230                 235                 240
Phe Ala Gln Ala Leu Tyr Glu Thr Gln Ala Pro Glu Asn Ser Pro Val
            245                 250                 255
Gly Ser Leu Ile Val Lys Val Ser Ala Gly Asp Ala Asp Ser Gly Val
            260                 265                 270
Asn Ala Glu Val Ser Tyr Ser Phe Phe Asp Ala Ser Glu Asp Ile Leu
            275                 280                 285
Thr Thr Phe Gln Ile Asn Pro Phe Ser Gly Glu Ile Phe Leu Arg Glu
            290                 295                 300
Leu Leu Asp Tyr Glu Leu Val Asn Ser Tyr Lys Ile Asn Ile Gln Ala
305                 310                 315                 320
Met Asp Gly Gly Gly Leu Ser Ala Arg Cys Thr Val Leu Ile Lys Val
            325                 330                 335
Leu Asp Ser Asn Asp Asn Pro Pro Glu Leu Ile Ile Ser Ser Leu Ser
            340                 345                 350
Asn Ser Val Ala Glu Asn Ser Pro Gly Ile Val Leu Ala Val Phe Lys
            355                 360                 365
Ile Lys Asp Arg Asp Ser Gly Glu Asn Gly Lys Thr Ile Cys Tyr Val
            370                 375                 380
Gln Asp Asn Leu Pro Phe Phe Leu Lys Pro Ser Val Asp Asn Phe Tyr
385                 390                 395                 400
Ile Leu Met Thr Glu Gly Ala Leu Asp Arg Glu Ser Lys Ala Glu Tyr
            405                 410                 415
Asn Ile Thr Ile Thr Val Thr Asp Leu Gly Thr Pro Arg Leu Lys Thr
            420                 425                 430
Glu His Ser Ile Thr Leu Gln Val Ser Asp Val Asn Asp Asn Ala Pro
            435                 440                 445
Ala Phe Thr Gln Thr Ser Tyr Thr Leu Phe Val Arg Glu Asn Asn Ser
            450                 455                 460
Pro Ala Leu His Ile Gly Ser Val Ser Ala Thr Asp Arg Asp Ser Gly
465                 470                 475                 480
Thr Asn Ala Gln Val Thr Tyr Ser Leu Leu Pro Pro Gln Asp Pro His
            485                 490                 495
Leu Pro Leu Ala Ser Leu Val Ser Ile Asn Ala Asp Asn Gly His Leu
            500                 505                 510
Phe Ala Leu Arg Ser Leu Asp Tyr Glu Ala Leu Gln Ala Phe Asp Phe
            515                 520                 525
Arg Val Gly Ala Ser Asp Arg Gly Ser Pro Ala Leu Ser Ser Glu Ala
            530                 535                 540
Leu Val Arg Val Leu Val Leu Asp Ala Asn Asp Asn Ser Pro Phe Val
545                 550                 555                 560
Leu Tyr Pro Leu Gln Asn Gly Ser Ala Pro Cys Thr Glu Leu Val Pro
            565                 570                 575
Arg Ala Ala Glu Pro Gly Tyr Leu Val Thr Lys Val Val Ala Val Asp
            580                 585                 590
Gly Asp Ser Gly Gln Asn Ala Trp Leu Ser Tyr Gln Leu Leu Lys Ala
            595                 600                 605
Thr Glu Pro Gly Leu Phe Gly Val Trp Ala His Asn Gly Glu Val Arg
```

```
                610                 615                 620
Thr Ala Arg Leu Leu Ser Glu Arg Asp Ala Ala Lys His Arg Leu Val
625                 630                 635                 640

Val Leu Val Lys Asp Asn Gly Glu Pro Pro Arg Ser Ala Thr Ala Thr
                645                 650                 655

Leu His Val Leu Leu Val Asp Gly Phe Ser Gln Pro Tyr Leu Pro Leu
            660                 665                 670

Pro Glu Ala Ala Pro Ala Gln Ala Gln Ala Asp Leu Leu Thr Val Tyr
                675                 680                 685

Pro Val Val Ala Leu Ala Ser Val Ser Ser Leu Phe Leu Leu Ser Val
            690                 695                 700

Leu Leu Phe Val Ala Val Arg Leu Cys Arg Arg Ser Arg Ala Ala Ser
705                 710                 715                 720

Val Gly Arg Cys Ser Val Pro Glu Gly Pro Phe Pro Gly His Leu Val
                725                 730                 735

Asp Val Ser Gly Thr Gly Thr Leu Phe Gln Ser Tyr Gln Tyr Glu Val
            740                 745                 750

Cys Leu Thr Gly Gly Ser Glu Thr Gly Glu Phe Lys Phe Leu Lys Pro
                755                 760                 765

Ile Thr Pro His Leu Pro Pro His Arg Gly Gly Lys Glu Ile Glu Glu
            770                 775                 780

Asn Ser Thr Leu Pro Asn Ser Phe Gly Phe Asn Tyr
785                 790                 795

<210> SEQ ID NO 23
<211> LENGTH: 699
<212> TYPE: PRT
<213> ORGANISM: Mus musculus

<400> SEQUENCE: 23

Met Glu Pro Phe Cys Pro Leu Leu Leu Ala Ser Phe Ser Leu Ser Leu
1               5                   10                  15

Ala Arg Ala Gly Gln Gly Asn Asp Thr Thr Pro Thr Glu Ser Asn Trp
            20                  25                  30

Thr Ser Thr Thr Ala Gly Pro Pro Asp Pro Gly Ala Ser Gln Pro Leu
        35                  40                  45

Leu Thr Trp Leu Leu Leu Pro Leu Leu Leu Leu Phe Leu Leu Ala
    50                  55                  60

Ala Tyr Phe Phe Arg Phe Arg Lys Gln Arg Lys Ala Val Val Ser Ser
65                  70                  75                  80

Asn Asp Lys Lys Met Pro Asn Gly Ile Leu Glu Glu Gln Gln Gln
                85                  90                  95

Arg Val Met Leu Leu Ser Arg Ser Pro Ser Gly Pro Lys Lys Phe Phe
            100                 105                 110

Pro Ile Pro Val Glu His Leu Glu Glu Glu Ile Arg Val Arg Ser Ala
        115                 120                 125

Asp Asp Cys Lys Arg Phe Arg Glu Glu Phe Asn Ser Leu Pro Ser Gly
    130                 135                 140

His Ile Gln Gly Thr Phe Glu Leu Ala Asn Lys Glu Glu Asn Arg Glu
145                 150                 155                 160

Lys Asn Arg Tyr Pro Asn Ile Leu Pro Asn Asp His Cys Arg Val Ile
                165                 170                 175

Leu Ser Gln Val Asp Gly Ile Pro Cys Ser Asp Tyr Ile Asn Ala Ser
            180                 185                 190

Tyr Ile Asp Gly Tyr Lys Glu Lys Asn Lys Phe Ile Ala Ala Gln Gly
```

-continued

```
                195                 200                 205
Pro Lys Gln Glu Thr Val Asn Asp Phe Trp Arg Met Val Trp Glu Gln
210                 215                 220

Arg Ser Ala Thr Ile Val Met Leu Thr Asn Leu Lys Glu Arg Lys Glu
225                 230                 235                 240

Glu Lys Cys Tyr Gln Tyr Trp Pro Asp Gln Gly Cys Trp Thr Tyr Gly
                245                 250                 255

Asn Ile Arg Val Cys Val Glu Asp Cys Val Val Leu Val Asp Tyr Thr
                260                 265                 270

Ile Arg Lys Phe Cys Ile His Pro Gln Leu Pro Asp Ser Cys Lys Ala
                275                 280                 285

Pro Arg Leu Val Ser Gln Leu His Phe Thr Ser Trp Pro Asp Phe Gly
290                 295                 300

Val Pro Phe Thr Pro Ile Gly Met Leu Lys Phe Leu Lys Lys Val Lys
305                 310                 315                 320

Thr Leu Asn Pro Ser His Ala Gly Pro Ile Val Val His Cys Ser Ala
                325                 330                 335

Gly Val Gly Arg Thr Gly Thr Phe Ile Val Ile Asp Ala Met Met Asp
                340                 345                 350

Met Ile His Ser Glu Gln Lys Val Asp Val Phe Glu Phe Val Ser Arg
                355                 360                 365

Ile Arg Asn Gln Arg Pro Gln Met Val Gln Thr Asp Val Gln Tyr Thr
370                 375                 380

Phe Ile Tyr Gln Ala Leu Leu Glu Tyr Tyr Leu Tyr Gly Asp Thr Glu
385                 390                 395                 400

Leu Asp Val Ser Ser Leu Glu Arg His Leu Gln Thr Leu His Ser Thr
                405                 410                 415

Ala Thr His Phe Asp Lys Ile Gly Leu Glu Glu Phe Arg Lys Leu
                420                 425                 430

Thr Asn Val Arg Ile Met Lys Glu Asn Met Arg Thr Gly Asn Leu Pro
                435                 440                 445

Ala Asn Met Lys Lys Ala Arg Val Ile Gln Ile Ile Pro Tyr Asp Phe
450                 455                 460

Asn Arg Val Ile Leu Ser Met Lys Arg Gly Gln Glu Phe Thr Asp Tyr
465                 470                 475                 480

Ile Asn Ala Ser Phe Ile Asp Gly Tyr Arg Gln Lys Asp Tyr Phe Met
                485                 490                 495

Ala Thr Gln Gly Pro Leu Ala His Thr Gly Glu Asp Phe Trp Arg Met
                500                 505                 510

Val Trp Glu Trp Lys Ser His Thr Ile Val Met Leu Thr Glu Val Gln
                515                 520                 525

Glu Arg Glu Gln Asp Lys Cys Tyr Gln Tyr Trp Pro Thr Glu Gly Ser
530                 535                 540

Val Thr His Gly Asp Ile Thr Ile Glu Ile Lys Ser Asp Thr Leu Ser
545                 550                 555                 560

Glu Ala Ile Ser Val Arg Asp Phe Leu Val Thr Phe Lys Gln Pro Leu
                565                 570                 575

Ala Arg Gln Glu Glu Gln Val Arg Met Val Arg Gln Phe His Phe His
                580                 585                 590

Gly Trp Pro Glu Val Gly Ile Pro Ala Glu Gly Lys Gly Ile Ile Asp
                595                 600                 605

Leu Ile Ala Ala Val Gln Lys Gln Gln Gln Gln Thr Gly Asn His Pro
610                 615                 620
```

-continued

```
Ile Thr Val His Cys Ser Ala Gly Ala Gly Arg Thr Gly Thr Phe Ile
625                 630                 635                 640

Ala Leu Ser Asn Ile Leu Glu Arg Val Lys Ala Glu Gly Leu Leu Asp
            645                 650                 655

Val Phe Gln Ala Val Lys Ser Leu Arg Leu Gln Arg Pro His Met Val
        660                 665                 670

Gln Thr Leu Glu Gln Tyr Glu Phe Cys Tyr Lys Val Val Gln Asp Phe
    675                 680                 685

Ile Asp Ile Phe Ser Asp Tyr Ala Asn Phe Lys
690                 695

<210> SEQ ID NO 24
<211> LENGTH: 642
<212> TYPE: PRT
<213> ORGANISM: Homo sapiens

<400> SEQUENCE: 24

Met Ser Asn Arg Ser Ser Phe Ser Arg Leu Thr Trp Phe Arg Lys Gln
1               5                   10                  15

Arg Lys Ala Val Val Ser Thr Ser Asp Lys Lys Met Pro Asn Gly Ile
            20                  25                  30

Leu Glu Glu Gln Glu Gln Arg Val Met Leu Leu Ser Arg Ser Pro
        35                  40                  45

Ser Gly Pro Lys Lys Tyr Phe Pro Ile Pro Val Glu His Leu Glu Glu
50                  55                  60

Glu Ile Arg Ile Arg Ser Ala Asp Asp Cys Lys Gln Phe Arg Glu Glu
65                  70                  75                  80

Phe Asn Ser Leu Pro Ser Gly His Ile Gln Gly Thr Phe Glu Leu Ala
                85                  90                  95

Asn Lys Glu Glu Asn Arg Glu Lys Asn Arg Tyr Pro Asn Ile Leu Pro
            100                 105                 110

Asn Asp His Ser Arg Val Ile Leu Ser Gln Leu Asp Gly Ile Pro Cys
        115                 120                 125

Ser Asp Tyr Ile Asn Ala Ser Tyr Ile Asp Gly Tyr Lys Glu Lys Asn
130                 135                 140

Lys Phe Ile Ala Ala Gln Gly Pro Lys Gln Glu Thr Val Asn Asp Phe
145                 150                 155                 160

Trp Arg Met Val Trp Glu Gln Lys Ser Ala Thr Ile Val Met Leu Thr
                165                 170                 175

Asn Leu Lys Glu Arg Lys Glu Glu Lys Cys His Gln Tyr Trp Pro Asp
            180                 185                 190

Gln Gly Cys Trp Thr Tyr Gly Asn Ile Arg Val Cys Val Glu Asp Cys
        195                 200                 205

Val Val Leu Val Asp Tyr Thr Ile Arg Lys Phe Cys Ile Gln Pro Gln
210                 215                 220

Leu Pro Asp Gly Cys Lys Ala Pro Arg Leu Val Ser Gln Leu His Phe
225                 230                 235                 240

Thr Ser Trp Pro Asp Phe Gly Val Pro Phe Thr Pro Ile Gly Met Leu
                245                 250                 255

Lys Phe Leu Lys Lys Val Lys Thr Leu Asn Pro Val His Ala Gly Pro
            260                 265                 270

Ile Val Val His Cys Ser Ala Gly Val Gly Arg Thr Gly Thr Phe Ile
        275                 280                 285

Val Ile Asp Ala Met Met Ala Met Met His Ala Glu Gln Lys Val Asp
290                 295                 300
```

```
Val Phe Glu Phe Val Ser Arg Ile Arg Asn Gln Arg Pro Gln Met Val
305                 310                 315                 320

Gln Thr Asp Met Gln Tyr Thr Phe Ile Tyr Gln Ala Leu Leu Glu Tyr
            325                 330                 335

Tyr Leu Tyr Gly Asp Thr Glu Leu Asp Val Ser Ser Leu Glu Lys His
        340                 345                 350

Leu Gln Thr Met His Gly Thr Thr His Phe Asp Lys Ile Gly Leu
    355                 360                 365

Glu Glu Glu Phe Arg Lys Leu Thr Asn Val Arg Ile Met Lys Glu Asn
370                 375                 380

Met Arg Thr Gly Asn Leu Pro Ala Asn Met Lys Lys Ala Arg Val Ile
385                 390                 395                 400

Gln Ile Ile Pro Tyr Asp Phe Asn Arg Val Ile Leu Ser Met Lys Arg
                405                 410                 415

Gly Gln Glu Tyr Thr Asp Tyr Ile Asn Ala Ser Phe Ile Asp Gly Tyr
            420                 425                 430

Arg Gln Lys Asp Tyr Phe Ile Ala Thr Gln Gly Pro Leu Ala His Thr
        435                 440                 445

Val Glu Asp Phe Trp Arg Met Ile Trp Glu Trp Lys Ser His Thr Ile
450                 455                 460

Val Met Leu Thr Glu Val Gln Glu Arg Glu Gln Asp Lys Cys Tyr Gln
465                 470                 475                 480

Tyr Trp Pro Thr Glu Gly Ser Val Thr His Gly Ile Thr Ile Glu
                485                 490                 495

Ile Lys Asn Asp Thr Leu Ser Glu Ala Ile Ser Ile Arg Asp Phe Leu
            500                 505                 510

Val Thr Leu Asn Gln Pro Gln Ala Arg Gln Glu Glu Val Arg Val
        515                 520                 525

Val Arg Gln Phe His Phe His Gly Trp Pro Glu Ile Gly Ile Pro Ala
530                 535                 540

Glu Gly Lys Gly Met Ile Asp Leu Ile Ala Ala Val Gln Lys Gln Gln
545                 550                 555                 560

Gln Gln Thr Gly Asn His Pro Ile Thr Val His Cys Ser Ala Gly Ala
                565                 570                 575

Gly Arg Thr Gly Thr Phe Ile Ala Leu Ser Asn Ile Leu Glu Arg Val
            580                 585                 590

Lys Ala Glu Gly Leu Leu Asp Val Phe Gln Ala Val Lys Ser Leu Arg
        595                 600                 605

Leu Gln Arg Pro His Met Val Gln Thr Leu Glu Gln Tyr Glu Phe Cys
610                 615                 620

Tyr Lys Val Val Gln Asp Phe Ile Asp Ile Phe Ser Asp Tyr Ala Asn
625                 630                 635                 640

Phe Lys

<210> SEQ ID NO 25
<211> LENGTH: 1227
<212> TYPE: PRT
<213> ORGANISM: Mus musculus

<400> SEQUENCE: 25

Met Ala Asn Gly Val Ile Pro Pro Gly Gly Ala Ser Pro Leu Pro
1               5                   10                  15

Gln Val Arg Val Pro Leu Glu Glu Pro Leu Gly Pro Asp Val Glu
            20                  25                  30

Glu Glu Asp Asp Asp Leu Gly Lys Thr Leu Ala Val Ser Arg Phe Gly
```

```
                35                  40                  45
Asp Leu Ile Ser Lys Thr Pro Ala Trp Asp Pro Glu Lys Pro Ser Arg
 50                  55                  60
Ser Tyr Ser Glu Arg Asp Phe Glu Phe His Arg His Thr Ser His His
 65                  70                  75                  80
Thr His His Pro Leu Ser Ala Arg Leu Pro Pro His Lys Leu Arg
                 85                  90                  95
Arg Pro Pro Pro Thr Ser Ala Arg His Thr Arg Lys Arg Lys Lys
                100                 105                 110
Glu Lys Thr Ser Ala Pro Pro Ser Glu Gly Thr Pro Ile Gln Glu
                115                 120                 125
Glu Gly Gly Ala Gly Ala Glu Glu Glu Glu Glu Glu Glu Glu Glu
            130                 135                 140
Glu Gly Glu Ser Glu Ala Glu Pro Val Glu Pro Leu Pro Gly Pro
145                 150                 155                 160
Pro Gln Lys Ala Lys Phe Ser Ile Gly Ser Asp Glu Asp Ser Pro
                165                 170                 175
Gly Leu Pro Val Lys Ala Pro Cys Ala Lys Ala Leu Pro Ser Val Gly
                180                 185                 190
Leu Gln Ser Asp Gln Ser Pro Gln Arg Ser Gly Ser Ser Pro Ser Pro
                195                 200                 205
Arg Ala Arg Ala Ser Arg Ile Ser Thr Glu Lys Ser Arg Pro Trp Ser
210                 215                 220
Pro Ser Ala Ser Tyr Asp Leu Arg Glu Arg Leu Cys Pro Gly Ser Ala
225                 230                 235                 240
Leu Gly Asn Pro Gly Pro Glu Gln Arg Val Pro Thr Asp Glu Ala Glu
                245                 250                 255
Ala Gln Met Leu Gly Ser Ala Asp Leu Asp Asp Met Lys Ser His Arg
            260                 265                 270
Leu Glu Asp Asn Pro Gly Val Arg Arg His Leu Val Lys Lys Pro Ser
            275                 280                 285
Arg Ile Gln Gly Gly Arg Gly Ser Pro Ser Gly Leu Ala Pro Ile Leu
    290                 295                 300
Arg Arg Lys Lys Lys Lys Lys Leu Asp Arg Arg Pro His Glu Val
305                 310                 315                 320
Phe Val Glu Leu Asn Glu Leu Met Leu Asp Arg Ser Gln Glu Pro His
                325                 330                 335
Trp Arg Glu Thr Ala Arg Trp Ile Lys Phe Glu Glu Asp Val Glu Glu
                340                 345                 350
Glu Thr Glu Arg Trp Gly Lys Pro His Val Ala Ser Leu Ser Phe Arg
            355                 360                 365
Ser Leu Leu Glu Leu Arg Arg Thr Ile Ala Gln Gly Ala Ala Leu Leu
    370                 375                 380
Asp Leu Glu Gln Thr Thr Leu Pro Gly Ile Ala His Leu Val Val Glu
385                 390                 395                 400
Thr Met Ile Val Ser Asp Gln Ile Arg Pro Glu Asp Arg Ala Ser Val
                405                 410                 415
Leu Arg Thr Leu Leu Leu Lys His Ser His Pro Asn Asp Asp Lys Asp
                420                 425                 430
Ser Gly Phe Phe Pro Arg Asn Pro Ser Ser Ser Val Asn Ser Val
            435                 440                 445
Leu Gly Asn His His Pro Thr Pro Ser His Gly Pro Asp Gly Ala Val
    450                 455                 460
```

```
Pro Thr Met Ala Asp Asp Gln Gly Glu Pro Ala Pro Leu Trp Pro His
465                 470                 475                 480

Asp Pro Asp Ala Lys Glu Lys Pro Leu His Met Pro Gly Gly Asp Gly
            485                 490                 495

His Arg Gly Lys Ser Leu Lys Leu Leu Glu Lys Ile Pro Glu Asp Ala
        500                 505                 510

Glu Ala Thr Val Val Leu Val Gly Cys Val Pro Phe Leu Glu Gln Pro
            515                 520                 525

Ala Gly Ala Phe Val Arg Leu Ser Glu Ala Val Leu Leu Glu Ser Val
        530                 535                 540

Leu Glu Val Pro Val Pro Val Arg Phe Leu Phe Val Met Leu Gly Pro
545                 550                 555                 560

Ser His Thr Ser Thr Asp Tyr His Glu Leu Gly Arg Ser Ile Ala Thr
                565                 570                 575

Leu Met Ser Asp Lys Leu Phe His Glu Ala Ala Tyr Gln Ala Asp Asp
            580                 585                 590

Arg Gln Asp Leu Leu Gly Ala Ile Ser Glu Phe Leu Asp Gly Ser Ile
        595                 600                 605

Val Ile Pro Pro Ser Glu Val Glu Gly Arg Asp Leu Leu Arg Ser Val
610                 615                 620

Ala Ala Phe Gln Arg Glu Leu Leu Arg Lys Arg Glu Arg Glu Gln
625                 630                 635                 640

Thr Lys Val Glu Met Thr Thr Arg Gly Tyr Ala Ala Pro Gly Lys
                645                 650                 655

Glu Leu Ser Leu Glu Met Gly Gly Ser Glu Ala Thr Ser Glu Asp Asp
            660                 665                 670

Pro Leu Gln Arg Thr Gly Ser Val Phe Gly Gly Leu Val Arg Asp Val
        675                 680                 685

Lys Arg Arg Tyr Pro His Tyr Pro Ser Asp Leu Arg Asp Ala Leu His
690                 695                 700

Ser Gln Cys Val Ala Ala Val Leu Phe Ile Tyr Phe Ala Ala Leu Ser
705                 710                 715                 720

Pro Ala Ile Thr Phe Gly Gly Leu Leu Gly Glu Lys Thr Glu Gly Leu
                725                 730                 735

Met Gly Val Ser Glu Leu Ile Val Ser Thr Ala Val Leu Gly Val Leu
            740                 745                 750

Phe Ser Leu Leu Gly Ala Gln Pro Leu Leu Val Val Gly Phe Ser Gly
        755                 760                 765

Pro Leu Leu Val Phe Glu Glu Ala Phe Phe Lys Phe Cys Arg Ala Gln
770                 775                 780

Asp Leu Glu Tyr Leu Thr Gly Arg Val Trp Val Gly Leu Trp Leu Val
785                 790                 795                 800

Val Phe Val Leu Ala Leu Val Ala Ala Glu Gly Thr Phe Leu Val Arg
                805                 810                 815

Tyr Ile Ser Pro Phe Thr Gln Glu Ile Phe Ala Phe Leu Ile Ser Leu
            820                 825                 830

Ile Phe Ile Tyr Glu Thr Phe His Lys Leu Tyr Lys Val Phe Thr Glu
        835                 840                 845

His Pro Leu Leu Pro Phe Tyr Pro Pro Asp Glu Ala Leu Glu Thr Gly
850                 855                 860

Leu Glu Leu Asn Ser Ser Ala Leu Pro Pro Thr Glu Gly Pro Pro Gly
865                 870                 875                 880

Pro Arg Asn Gln Pro Asn Thr Ala Leu Leu Ser Leu Ile Leu Met Leu
                885                 890                 895
```

```
Gly Thr Phe Leu Ile Ala Phe Leu Arg Lys Phe Arg Asn Ser Arg
            900                 905                 910

Phe Leu Gly Gly Lys Ala Arg Arg Ile Ile Gly Asp Phe Gly Ile Pro
        915                 920                 925

Ile Ser Ile Leu Val Met Val Leu Val Asp Tyr Ser Ile Thr Asp Thr
    930                 935                 940

Tyr Thr Gln Lys Leu Thr Val Pro Thr Gly Leu Ser Val Thr Ser Pro
945                 950                 955                 960

His Lys Arg Thr Trp Phe Ile Pro Pro Leu Gly Ser Ala Arg Pro Phe
                965                 970                 975

Pro Pro Trp Met Met Val Ala Ala Val Pro Ala Leu Leu Val Leu
            980                 985                 990

Ile Leu Ile Phe Met Glu Thr Gln Ile Thr Ala Leu Ile Val Ser Gln
        995                 1000                1005

Lys Ala Arg Arg Leu Leu Lys Gly Ser Gly Phe His Leu Asp Leu
    1010                1015                1020

Leu Leu Ile Gly Ser Leu Gly Gly Leu Cys Gly Leu Phe Gly Leu
    1025                1030                1035

Pro Trp Leu Thr Ala Ala Thr Val Arg Ser Val Thr His Val Asn
    1040                1045                1050

Ala Leu Thr Val Met Arg Thr Ala Ile Ala Pro Gly Asp Lys Pro
    1055                1060                1065

Gln Ile Gln Glu Val Arg Glu Gln Arg Val Thr Gly Val Leu Ile
    1070                1075                1080

Ala Ser Leu Val Gly Leu Ser Ile Val Met Gly Ala Val Leu Arg
    1085                1090                1095

Arg Ile Pro Leu Ala Val Leu Phe Gly Ile Phe Leu Tyr Met Gly
    1100                1105                1110

Val Thr Ser Leu Ser Gly Ile Gln Leu Ser Gln Arg Leu Leu Leu
    1115                1120                1125

Ile Phe Met Pro Ala Lys His His Pro Glu Gln Pro Tyr Val Thr
    1130                1135                1140

Lys Val Lys Thr Trp Arg Ile Asp Leu Phe Thr Cys Ile Gln Leu
    1145                1150                1155

Gly Cys Ile Ala Leu Leu Trp Val Val Lys Ser Thr Ala Ala Ser
    1160                1165                1170

Leu Ala Phe Pro Phe Leu Leu Leu Thr Val Pro Leu Ser Gly
    1175                1180                1185

Cys Leu Leu Pro Arg Leu Phe Gln Asp Arg Glu Leu Gln Ala Leu
    1190                1195                1200

Asp Ser Glu Asp Ala Glu Pro Asn Phe Asp Glu Asp Gly Gln Asp
    1205                1210                1215

Glu Tyr Asn Glu Leu His Met Pro Val
    1220                1225

<210> SEQ ID NO 26
<211> LENGTH: 1232
<212> TYPE: PRT
<213> ORGANISM: Homo sapiens

<400> SEQUENCE: 26

Met Ala Asn Gly Val Ile Pro Pro Gly Gly Ala Ser Pro Leu Pro
1               5                   10                  15

Gln Val Arg Val Pro Leu Glu Glu Pro Leu Ser Pro Asp Val Glu
                20                  25                  30
```

Glu Glu Asp Asp Asp Leu Gly Lys Thr Leu Ala Val Ser Arg Phe Gly
           35                  40                  45

Asp Leu Ile Ser Lys Pro Pro Ala Trp Asp Pro Glu Lys Pro Ser Arg
 50                  55                  60

Ser Tyr Ser Glu Arg Asp Phe Glu Phe His Arg His Thr Ser His His
65                   70                  75                  80

Thr His His Pro Leu Ser Ala Arg Leu Pro Pro His Lys Leu Arg
                 85                  90                  95

Arg Leu Pro Pro Thr Ser Ala Arg His Thr Arg Arg Lys Arg Lys Lys
                100                 105                 110

Glu Lys Thr Ser Ala Pro Pro Ser Glu Gly Thr Pro Pro Ile Gln Glu
           115                 120                 125

Glu Gly Gly Ala Gly Val Asp Glu Glu Glu Glu Glu Glu Glu Glu Glu
           130                 135                 140

Glu Gly Glu Ser Glu Ala Glu Pro Val Glu Pro Pro Ser Gly Thr
145                 150                 155                 160

Pro Gln Lys Ala Lys Phe Ser Ile Gly Ser Asp Glu Asp Ser Pro
                165                 170                 175

Gly Leu Pro Gly Arg Ala Ala Val Thr Lys Pro Leu Pro Ser Val Gly
                180                 185                 190

Pro His Thr Asp Lys Ser Pro Gln His Ser Ser Ser Ser Pro Ser Pro
           195                 200                 205

Arg Ala Arg Ala Ser Arg Leu Ala Gly Glu Lys Ser Arg Pro Trp Ser
           210                 215                 220

Pro Ser Ala Ser Tyr Asp Leu Arg Glu Arg Leu Cys Pro Gly Ser Ala
225                 230                 235                 240

Leu Gly Asn Pro Gly Gly Pro Gln Gln Val Pro Thr Asp Glu Ala
                245                 250                 255

Glu Ala Gln Met Leu Gly Ser Ala Asp Leu Asp Asp Met Lys Ser His
           260                 265                 270

Arg Leu Glu Asp Asn Pro Gly Val Arg Arg His Leu Val Lys Lys Pro
           275                 280                 285

Ser Arg Thr Gln Gly Gly Arg Gly Ser Pro Ser Gly Leu Ala Pro Ile
           290                 295                 300

Leu Arg Arg Lys Lys Lys Lys Lys Leu Asp Arg Arg Pro His Glu
305                 310                 315                 320

Val Phe Val Glu Leu Asn Glu Leu Met Leu Asp Arg Ser Gln Glu Pro
               325                 330                 335

His Trp Arg Glu Thr Ala Arg Trp Ile Lys Phe Glu Glu Asp Val Glu
           340                 345                 350

Glu Glu Thr Glu Arg Trp Gly Lys Pro His Val Ala Ser Leu Ser Phe
           355                 360                 365

Arg Ser Leu Leu Glu Leu Arg Arg Thr Ile Ala His Gly Ala Ala Leu
370                 375                 380

Leu Asp Leu Glu Gln Thr Thr Leu Pro Gly Ile Ala His Leu Val Val
385                 390                 395                 400

Glu Thr Met Ile Val Ser Asp Gln Ile Arg Pro Glu Asp Arg Ala Ser
               405                 410                 415

Val Leu Arg Thr Leu Leu Leu Lys His Ser His Pro Asn Asp Asp Lys
           420                 425                 430

Asp Ser Gly Phe Phe Pro Arg Asn Pro Ser Ser Ser Met Asn Ser
           435                 440                 445

Val Leu Gly Asn His His Pro Thr Pro Ser His Gly Pro Asp Gly Ala

```
                450                 455                 460
Val Pro Thr Met Ala Asp Asp Leu Gly Glu Pro Ala Pro Leu Trp Pro
465                 470                 475                 480

His Asp Pro Asp Ala Lys Glu Lys Pro Leu His Met Pro Gly Gly Asp
                485                 490                 495

Gly His Arg Gly Lys Ser Leu Lys Leu Leu Glu Lys Ile Pro Glu Asp
                500                 505                 510

Ala Glu Ala Thr Val Val Leu Val Gly Cys Val Pro Phe Leu Glu Gln
                515                 520                 525

Pro Ala Ala Ala Phe Val Arg Leu Asn Glu Ala Val Leu Leu Glu Ser
530                 535                 540

Val Leu Glu Val Pro Val Pro Val Arg Phe Leu Phe Val Met Leu Gly
545                 550                 555                 560

Pro Ser His Thr Ser Thr Asp Tyr His Glu Leu Gly Arg Ser Ile Ala
                565                 570                 575

Thr Leu Met Ser Asp Lys Leu Phe His Glu Ala Ala Tyr Gln Ala Asp
                580                 585                 590

Asp Arg Gln Asp Leu Leu Ser Ala Ile Ser Glu Phe Leu Asp Gly Ser
                595                 600                 605

Ile Val Ile Pro Pro Ser Glu Val Glu Gly Arg Asp Leu Leu Arg Ser
610                 615                 620

Val Ala Ala Phe Gln Arg Glu Leu Leu Arg Lys Arg Glu Arg Glu
625                 630                 635                 640

Gln Thr Lys Val Glu Met Thr Thr Arg Gly Gly Tyr Thr Ala Pro Gly
                645                 650                 655

Lys Glu Leu Ser Leu Glu Leu Gly Gly Ser Glu Ala Thr Pro Glu Asp
                660                 665                 670

Asp Pro Leu Leu Arg Thr Gly Ser Val Phe Gly Gly Leu Val Arg Asp
                675                 680                 685

Val Arg Arg Arg Tyr Pro His Tyr Pro Ser Asp Leu Arg Asp Ala Leu
690                 695                 700

His Ser Gln Cys Val Ala Ala Val Leu Phe Ile Tyr Phe Ala Ala Leu
705                 710                 715                 720

Ser Pro Ala Ile Thr Phe Gly Gly Leu Leu Gly Glu Lys Thr Glu Gly
                725                 730                 735

Leu Met Gly Val Ser Glu Leu Ile Val Ser Thr Ala Val Leu Gly Val
                740                 745                 750

Leu Phe Ser Leu Leu Gly Ala Gln Pro Leu Leu Val Val Gly Phe Ser
                755                 760                 765

Gly Pro Leu Leu Val Phe Glu Glu Ala Phe Phe Lys Phe Cys Arg Ala
                770                 775                 780

Gln Asp Leu Glu Tyr Leu Thr Gly Arg Val Trp Val Gly Leu Trp Leu
785                 790                 795                 800

Val Val Phe Val Leu Ala Leu Val Ala Ala Glu Gly Ser Phe Leu Val
                805                 810                 815

Arg Tyr Ile Ser Pro Phe Thr Gln Glu Ile Phe Ala Phe Leu Ile Ser
                820                 825                 830

Leu Ile Phe Ile Tyr Glu Thr Phe Tyr Lys Leu Tyr Lys Val Phe Thr
                835                 840                 845

Glu His Pro Leu Leu Pro Phe Tyr Pro Pro Glu Gly Ala Leu Glu Gly
                850                 855                 860

Ser Leu Ala Ala Gly Leu Glu Pro Asn Gly Ser Ala Leu Pro Pro Thr
865                 870                 875                 880
```

-continued

```
Glu Gly Pro Pro Ser Pro Arg Asn Gln Pro Asn Thr Ala Leu Leu Ser
            885                 890                 895
Leu Ile Leu Met Leu Gly Thr Phe Phe Ile Ala Phe Phe Leu Arg Lys
        900                 905                 910
Phe Arg Asn Ser Arg Phe Leu Gly Gly Lys Ala Arg Arg Ile Ile Gly
        915                 920                 925
Asp Phe Gly Ile Pro Ile Ser Ile Leu Val Met Val Leu Val Asp Tyr
    930                 935                 940
Ser Ile Thr Asp Thr Tyr Thr Gln Lys Leu Thr Val Pro Thr Gly Leu
945                 950                 955                 960
Ser Val Thr Ser Pro Asp Lys Arg Ser Trp Phe Ile Pro Leu Gly
                965                 970                 975
Ser Ala Arg Pro Phe Pro Pro Trp Met Met Val Ala Ala Val Pro
        980                 985                 990
Ala Leu Leu Val Leu Ile Leu Ile Phe Met Glu Thr Gln Ile Thr Ala
        995                 1000                1005
Leu Ile Val Ser Gln Lys Ala Arg Arg Leu Leu Lys Gly Ser Gly
    1010                1015                1020
Phe His Leu Asp Leu Leu Ile Gly Ser Leu Gly Gly Leu Cys
    1025                1030                1035
Gly Leu Phe Gly Leu Pro Trp Leu Thr Ala Ala Thr Val Arg Ser
    1040                1045                1050
Val Thr His Val Asn Ala Leu Thr Val Met Arg Thr Ala Ile Ala
    1055                1060                1065
Pro Gly Asp Lys Pro Gln Ile Gln Glu Val Arg Glu Gln Arg Val
    1070                1075                1080
Thr Gly Val Leu Ile Ala Ser Leu Val Gly Leu Ser Ile Val Met
    1085                1090                1095
Gly Ala Val Leu Arg Arg Ile Pro Leu Ala Val Leu Phe Gly Ile
    1100                1105                1110
Phe Leu Tyr Met Gly Val Thr Ser Leu Ser Gly Ile Gln Leu Ser
    1115                1120                1125
Gln Arg Leu Leu Leu Ile Leu Met Pro Ala Lys His His Pro Glu
    1130                1135                1140
Gln Pro Tyr Val Thr Lys Val Lys Thr Trp Arg Met His Leu Phe
    1145                1150                1155
Thr Cys Ile Gln Leu Gly Cys Ile Ala Leu Leu Trp Val Val Lys
    1160                1165                1170
Ser Thr Ala Ala Ser Leu Ala Phe Pro Phe Leu Leu Leu Leu Thr
    1175                1180                1185
Val Pro Leu Arg His Cys Leu Leu Pro Arg Leu Phe Gln Asp Arg
    1190                1195                1200
Glu Leu Gln Ala Leu Asp Ser Glu Asp Ala Glu Pro Asn Phe Asp
    1205                1210                1215
Glu Asp Gly Gln Asp Glu Tyr Asn Glu Leu His Met Pro Val
    1220                1225                1230

<210> SEQ ID NO 27
<211> LENGTH: 810
<212> TYPE: PRT
<213> ORGANISM: Mus musculus

<400> SEQUENCE: 27

Met Ala Gln Ser Leu Ala Leu Ala Leu Asp Val Pro Glu Thr Thr Gly
1               5                   10                  15
```

```
Asp Glu Gly Leu Glu Pro Ser Pro Tyr Glu Ser Glu Val His Asp
         20                  25                  30

Ser Phe His Gln Leu Ile Gln Glu Gln Ser Leu Arg Val Ala Glu Glu
         35                  40                  45

Gly Leu Glu Leu Pro Leu Gly Leu Gly Arg Gly Asp Gln Thr Leu
 50                  55                  60

Pro Gly Leu Glu Gly Ala Pro Ala Leu Ser Ser Ala Thr Leu Arg Ile
 65                  70                  75                  80

Leu Ala Ser Met Pro Ser Arg Thr Ile Gly Arg Ser Arg Gly Ala Ile
                 85                  90                  95

Ile Ser Gln Tyr Tyr Asn Arg Thr Val Arg Leu Arg Arg Ser Ser
         100                 105                 110

Arg Pro Leu Leu Gly Asn Val Val Pro Ser Ala Arg Pro Ser Leu Arg
         115                 120                 125

Leu Tyr Asp Leu Glu Leu Asp Ser Thr Ile Leu Glu Glu Asp Glu Lys
         130                 135                 140

Arg Ser Leu Leu Val Lys Glu Leu Gln Gly Leu Ser Ala Ala Gln Arg
145                 150                 155                 160

Asp His Met Val Arg Asn Met Pro Leu Ser Leu Gly Glu Lys Arg Cys
                 165                 170                 175

Leu Arg Glu Lys Ser Trp Ser Pro Lys Gly Lys Arg His Leu Gln
         180                 185                 190

Gly Arg Ser Gly Ala Phe Ser Cys Cys Ser Arg Leu Arg Tyr Thr Cys
         195                 200                 205

Met Leu Ala Leu His Ser Leu Gly Leu Ala Leu Ser Gly Leu Tyr
 210                 215                 220

Ala Ala Arg Pro Trp Arg Tyr Ala Leu Lys Gln Ile Gly Gly Gln Phe
225                 230                 235                 240

Gly Ser Ser Val Leu Ser Tyr Phe Leu Phe Leu Lys Thr Leu Leu Ala
                 245                 250                 255

Phe Asn Ala Leu Met Leu Leu Pro Leu Leu Ala Phe Leu Val Gly Val
         260                 265                 270

Gln Ala Ala Phe Pro Pro Asp Pro Ala Gly Pro Val Pro Thr Phe Ser
         275                 280                 285

Gly Leu Glu Leu Leu Thr Gly Gly Arg Phe Thr His Thr Val Met
 290                 295                 300

Tyr Tyr Gly Tyr Tyr Ser Asn Ser Thr Leu Ser Pro Ser Cys Asp Ala
305                 310                 315                 320

Pro Arg Glu Gly Gly Gln Cys Ser Pro Arg Leu Gly Ser Leu Pro Tyr
                 325                 330                 335

Asn Met Pro Leu Ala Tyr Leu Phe Thr Met Gly Ala Thr Phe Phe Leu
         340                 345                 350

Thr Cys Ile Ile Leu Val Tyr Ser Met Ser His Ser Phe Gly Glu Ser
         355                 360                 365

Tyr Arg Val Gly Ser Thr Lys Gly Ile His Ala Leu Thr Val Phe Cys
         370                 375                 380

Ser Trp Asp Tyr Lys Val Thr Gln Lys Arg Ala Ser Arg Val Gln Gln
385                 390                 395                 400

Asp Ser Ile Cys Thr Gln Leu Lys Glu Leu Leu Ala Glu Trp His Leu
                 405                 410                 415

Arg Lys Arg Pro Arg Ser Val Cys Gly Gln Leu Arg Gln Val Val Val
         420                 425                 430

Leu Gly Leu Gly Trp Leu Leu Cys Leu Gly Ser Thr Met Gly Cys Thr
         435                 440                 445
```

Val Ala Val Leu Thr Phe Ser Glu Val Met Ile Gln Arg Pro Ala Ser
            450                 455                 460

Gly Gly Gln Gly Val Glu Ala Leu Ala Leu Pro Leu Val Val Ser Val
465                 470                 475                 480

Leu Asn Leu Gly Ala Ser Tyr Leu Phe Arg Gly Leu Ala Thr Leu Glu
                485                 490                 495

Arg His Asp Ser Pro Val Leu Glu Val Tyr Met Ala Ile Cys Arg Asn
            500                 505                 510

Leu Ile Leu Lys Met Ala Val Leu Gly Val Leu Cys Tyr His Trp Leu
        515                 520                 525

Gly Arg Arg Val Ala Thr Leu Gln Gly Gln Cys Trp Glu Asp Phe Val
530                 535                 540

Gly Gln Glu Leu Tyr Arg Phe Met Val Val Asp Phe Ile Phe Met Leu
545                 550                 555                 560

Leu Asp Ser Leu Phe Gly Glu Leu Val Trp Arg Leu Ile Ser Glu Lys
                565                 570                 575

Lys Leu Lys Arg Gly Gln Lys Pro Glu Phe Asp Ile Ala Arg Asn Val
            580                 585                 590

Leu Asp Leu Ile Tyr Gly Gln Thr Leu Thr Trp Leu Gly Val Leu Phe
        595                 600                 605

Ser Pro Leu Leu Pro Ala Val Gln Ile Leu Arg Leu Phe Leu Phe
610                 615                 620

His Ile Lys Lys Ala Ser Leu Met Ala Asn Cys Gln Ala Pro Arg Arg
625                 630                 635                 640

Pro Trp Leu Ala Ser His Met Ser Thr Val Phe Leu Thr Leu Leu Cys
                645                 650                 655

Phe Pro Ser Phe Leu Gly Ala Ala Val Phe Leu Cys Tyr Ala Val Trp
            660                 665                 670

Gln Val Arg Pro Ser Ser Thr Cys Gly Pro Phe Arg Thr Leu Asn Thr
        675                 680                 685

Met Tyr Glu Ala Gly Thr Val Trp Val Arg Arg Leu Glu His Ala Gly
690                 695                 700

Ser Gly Ala Ser Trp Leu Pro Trp Leu His His Phe Leu Val Glu Asn
705                 710                 715                 720

Thr Phe Phe Leu Phe Leu Ala Ser Ala Leu Leu Leu Ala Val Ile Tyr
                725                 730                 735

Phe Asn Ile Gln Val Val Lys Gly Gln Arg Lys Val Ile Cys Leu Leu
            740                 745                 750

Lys Glu Gln Ile Arg Asn Glu Gly Glu Asp Lys Ile Phe Leu Ile Asn
        755                 760                 765

Lys Leu His Ser Val Tyr Glu Glu Glu Gly Arg Ser Arg Pro Gly Arg
770                 775                 780

Thr Gln Asp Ala Thr Glu Pro Ala Trp His Glu Asp Gly Gly Asp
785                 790                 795                 800

Gln Lys Glu Pro Cys Asn Pro Arg Ser Pro
                805                 810

<210> SEQ ID NO 28
<211> LENGTH: 444
<212> TYPE: PRT
<213> ORGANISM: Homo sapiens

<400> SEQUENCE: 28

Met Ala His Ser Phe Gly Glu Ser Tyr Arg Val Gly Ser Thr Ser Gly
1               5                   10                  15

```
Ile His Ala Ile Thr Val Phe Cys Ser Trp Asp Tyr Lys Val Thr Gln
             20                  25                  30

Lys Arg Ala Ser Arg Leu Gln Gln Asp Asn Ile Arg Thr Arg Leu Lys
             35                  40                  45

Glu Leu Leu Ala Glu Trp Gln Leu Arg His Ser Pro Arg Ser Val Cys
 50                  55                  60

Gly Arg Leu Arg Gln Ala Ala Val Leu Gly Leu Val Trp Leu Leu Cys
 65                  70                  75                  80

Leu Gly Thr Ala Leu Gly Cys Ala Val Ala Val His Val Phe Ser Glu
             85                  90                  95

Phe Met Ile Gln Ser Pro Glu Ala Ala Gly Gln Glu Ala Val Leu Leu
            100                 105                 110

Val Leu Pro Leu Val Val Gly Leu Leu Asn Leu Gly Ala Pro Tyr Leu
            115                 120                 125

Cys Arg Val Leu Ala Ala Leu Glu Pro His Asp Ser Pro Val Leu Glu
            130                 135                 140

Val Tyr Val Ala Ile Cys Arg Asn Leu Ile Leu Lys Leu Ala Ile Leu
145                 150                 155                 160

Gly Thr Leu Cys Tyr His Trp Leu Gly Arg Arg Val Gly Val Leu Gln
            165                 170                 175

Gly Gln Cys Trp Glu Asp Phe Val Gly Gln Glu Leu Tyr Arg Phe Leu
            180                 185                 190

Val Met Asp Phe Val Leu Met Leu Leu Asp Thr Leu Phe Gly Glu Leu
            195                 200                 205

Val Trp Arg Ile Ile Ser Glu Lys Lys Leu Lys Arg Arg Lys Pro
            210                 215                 220

Glu Phe Asp Ile Ala Arg Asn Val Leu Glu Leu Ile Tyr Gly Gln Thr
225                 230                 235                 240

Leu Thr Trp Leu Gly Val Leu Phe Ser Pro Leu Leu Pro Ala Val Gln
            245                 250                 255

Ile Ile Lys Leu Leu Leu Val Phe Tyr Val Lys Lys Thr Ser Leu Leu
            260                 265                 270

Ala Asn Cys Gln Ala Pro Arg Arg Pro Trp Leu Ala Ser His Met Ser
            275                 280                 285

Thr Val Phe Leu Thr Leu Leu Cys Phe Pro Ala Phe Leu Gly Ala Ala
            290                 295                 300

Val Phe Leu Cys Tyr Ala Val Trp Gln Val Lys Pro Ser Ser Thr Cys
305                 310                 315                 320

Gly Pro Phe Arg Thr Leu Asp Thr Met Tyr Glu Ala Gly Arg Val Trp
            325                 330                 335

Val Arg His Leu Glu Ala Ala Gly Pro Arg Val Ser Trp Leu Pro Trp
            340                 345                 350

Val His Arg Tyr Leu Met Glu Asn Thr Phe Phe Val Phe Leu Val Ser
            355                 360                 365

Ala Leu Leu Leu Ala Val Ile Tyr Leu Asn Ile Gln Val Val Arg Gly
            370                 375                 380

Gln Arg Lys Val Ile Cys Leu Leu Lys Glu Gln Ile Ser Asn Glu Gly
385                 390                 395                 400

Glu Asp Lys Ile Phe Leu Ile Asn Lys Leu His Ser Ile Tyr Glu Arg
            405                 410                 415

Lys Glu Arg Glu Glu Arg Ser Arg Val Gly Thr Thr Glu Glu Ala Ala
            420                 425                 430

Ala Pro Pro Ala Leu Leu Thr Asp Glu Gln Asp Ala
```

<210> SEQ ID NO 29
<211> LENGTH: 296
<212> TYPE: PRT
<213> ORGANISM: Mus musculus

<400> SEQUENCE: 29

```
Met Val Cys Lys Val Leu Ile Ala Leu Cys Ile Phe Thr Ala Gly Leu
1               5                   10                  15

Arg Val Gln Gly Ser Pro Thr Val Pro Leu Pro Val Ser Leu Met Thr
            20                  25                  30

Lys Ser Ser Ala Pro Val Ala Thr Trp Thr Ser Ala Pro His Thr
        35                  40                  45

Ala Arg Ala Thr Thr Pro Val Ala Ser Ala Thr His Asn Ala Ser Val
    50                  55                  60

Leu Arg Thr Thr Ala Ala Ser Leu Thr Ser Gln Leu Pro Thr Asp His
65                  70                  75                  80

Arg Glu Glu Ala Val Thr Ser Pro Pro Leu Lys Arg Asp Val Asn Ser
                85                  90                  95

Thr Asp Ser Ser Pro Ala Gly Phe Pro Ser Thr Ser Ser Asp Gly His
            100                 105                 110

Leu Ala Pro Thr Pro Glu Glu His Ser Leu Gly Ser Pro Glu Ala Thr
        115                 120                 125

Val Pro Ala Thr Gly Ser Gln Ser Pro Met Leu Leu Ser Ser Gln Ala
    130                 135                 140

Pro Thr Ser Ala Thr Thr Ser Pro Ala Thr Ser Leu Ser Glu Ser Leu
145                 150                 155                 160

Ser Ala Ser Val Thr Ser Ser His Asn Ser Thr Val Ala Asn Ile Gln
                165                 170                 175

Pro Thr Glu Ala Pro Met Ala Pro Ala Ser Pro Thr Glu Glu His Ser
            180                 185                 190

Ser Ser His Thr Pro Thr Ser His Val Thr Ala Glu Pro Val Pro Lys
        195                 200                 205

Glu Lys Ser Pro Gln Asp Thr Glu Pro Gly Lys Val Ile Cys Glu Ser
    210                 215                 220

Glu Thr Thr Thr Pro Phe Leu Ile Met Gln Glu Val Glu Asn Ala Leu
225                 230                 235                 240

Ser Ser Gly Ser Ile Ala Ala Ile Thr Val Thr Val Ile Ala Val Val
                245                 250                 255

Leu Leu Val Phe Gly Gly Ala Ala Tyr Leu Lys Ile Arg His Ser Ser
            260                 265                 270

Tyr Gly Arg Leu Leu Asp Asp His Asp Tyr Gly Ser Trp Gly Asn Tyr
        275                 280                 285

Asn Asn Pro Leu Tyr Asp Asp Ser
    290                 295
```

<210> SEQ ID NO 30
<211> LENGTH: 1663
<212> TYPE: PRT
<213> ORGANISM: Mus musculus

<400> SEQUENCE: 30

```
Met Gly Pro Ala Ser Gly Ser Gln Leu Leu Val Leu Leu Leu Leu Leu
1               5                   10                  15

Ala Ser Ser Pro Leu Ala Leu Gly Ile Pro Met Tyr Ser Ile Ile Thr
            20                  25                  30
```

```
Pro Asn Val Leu Arg Leu Glu Ser Glu Glu Thr Ile Val Leu Glu Ala
         35                  40                  45

His Asp Ala Gln Gly Asp Ile Pro Val Thr Val Thr Val Gln Asp Phe
 50                  55                  60

Leu Lys Arg Gln Val Leu Thr Ser Glu Lys Thr Val Leu Thr Gly Ala
 65                  70                  75                  80

Ser Gly His Leu Arg Ser Val Ser Ile Lys Ile Pro Ala Ser Lys Glu
                 85                  90                  95

Phe Asn Ser Asp Lys Glu Gly His Lys Tyr Val Thr Val Val Ala Asn
            100                 105                 110

Phe Gly Glu Thr Val Val Glu Lys Ala Val Met Val Ser Phe Gln Ser
            115                 120                 125

Gly Tyr Leu Phe Ile Gln Thr Asp Lys Thr Ile Tyr Thr Pro Gly Ser
        130                 135                 140

Thr Val Leu Tyr Arg Ile Phe Thr Val Asp Asn Asn Leu Leu Pro Val
145                 150                 155                 160

Gly Lys Thr Val Val Ile Leu Ile Glu Thr Pro Asp Gly Ile Pro Val
                165                 170                 175

Lys Arg Asp Ile Leu Ser Ser Asn Asn Gln His Gly Ile Leu Pro Leu
            180                 185                 190

Ser Trp Asn Ile Pro Glu Leu Val Asn Met Gly Gln Trp Lys Ile Arg
            195                 200                 205

Ala Phe Tyr Glu His Ala Pro Lys Gln Ile Phe Ser Ala Glu Phe Glu
        210                 215                 220

Val Lys Glu Tyr Val Leu Pro Ser Phe Glu Val Arg Val Glu Pro Thr
225                 230                 235                 240

Glu Thr Phe Tyr Tyr Ile Asp Asp Pro Asn Gly Leu Glu Val Ser Ile
                245                 250                 255

Ile Ala Lys Phe Leu Tyr Gly Lys Asn Val Asp Gly Thr Ala Phe Val
            260                 265                 270

Ile Phe Gly Val Gln Asp Gly Asp Lys Lys Ile Ser Leu Ala His Ser
        275                 280                 285

Leu Thr Arg Val Val Ile Glu Asp Gly Val Gly Asp Ala Val Leu Thr
290                 295                 300

Arg Lys Val Leu Met Glu Gly Val Arg Pro Ser Asn Ala Asp Ala Leu
305                 310                 315                 320

Val Gly Lys Ser Leu Tyr Val Ser Val Thr Val Ile Leu His Ser Gly
                325                 330                 335

Ser Asp Met Val Glu Ala Glu Arg Ser Gly Ile Pro Ile Val Thr Ser
            340                 345                 350

Pro Tyr Gln Ile His Phe Thr Lys Thr Pro Lys Phe Phe Lys Pro Ala
        355                 360                 365

Met Pro Phe Asp Leu Met Val Phe Val Thr Asn Pro Asp Gly Ser Pro
370                 375                 380

Ala Ser Lys Val Leu Val Val Thr Gln Gly Ser Asn Ala Lys Ala Leu
385                 390                 395                 400

Thr Gln Asp Asp Gly Val Ala Lys Leu Ser Ile Asn Thr Pro Asn Ser
                405                 410                 415

Arg Gln Pro Leu Thr Ile Thr Val Arg Thr Lys Lys Asp Thr Leu Pro
            420                 425                 430

Glu Ser Arg Gln Ala Thr Lys Thr Met Glu Ala His Pro Tyr Ser Thr
        435                 440                 445

Met His Asn Ser Asn Asn Tyr Leu His Leu Ser Val Ser Arg Met Glu
```

-continued

```
            450                 455                 460
Leu Lys Pro Gly Asp Asn Leu Asn Val Asn Phe His Leu Arg Thr Asp
465                 470                 475                 480

Pro Gly His Glu Ala Lys Ile Arg Tyr Tyr Thr Tyr Leu Val Met Asn
                    485                 490                 495

Lys Gly Lys Leu Leu Lys Ala Gly Arg Gln Val Arg Glu Pro Gly Gln
                500                 505                 510

Asp Leu Val Val Leu Ser Leu Pro Ile Thr Pro Glu Phe Ile Pro Ser
            515                 520                 525

Phe Arg Leu Val Ala Tyr Tyr Thr Leu Ile Gly Ala Ser Gly Gln Arg
530                 535                 540

Glu Val Val Ala Asp Ser Val Trp Val Asp Val Lys Asp Ser Cys Ile
545                 550                 555                 560

Gly Thr Leu Val Val Lys Gly Asp Pro Arg Asp Asn His Leu Ala Pro
                565                 570                 575

Gly Gln Gln Thr Thr Leu Arg Ile Glu Gly Asn Gln Gly Ala Arg Val
                580                 585                 590

Gly Leu Val Ala Val Asp Lys Gly Val Phe Val Leu Asn Lys Lys Asn
                595                 600                 605

Lys Leu Thr Gln Ser Lys Ile Trp Asp Val Val Glu Lys Ala Asp Ile
610                 615                 620

Gly Cys Thr Pro Gly Ser Gly Lys Asn Tyr Ala Gly Val Phe Met Asp
625                 630                 635                 640

Ala Gly Leu Ala Phe Lys Thr Ser Gln Gly Leu Gln Thr Glu Gln Arg
                645                 650                 655

Ala Asp Leu Glu Cys Thr Lys Pro Ala Ala Arg Arg Arg Arg Ser Val
                660                 665                 670

Gln Leu Met Glu Arg Arg Met Asp Lys Ala Gly Gln Tyr Thr Asp Lys
                675                 680                 685

Gly Leu Arg Lys Cys Cys Glu Asp Gly Met Arg Asp Ile Pro Met Arg
                690                 695                 700

Tyr Ser Cys Gln Arg Arg Ala Arg Leu Ile Thr Gln Gly Glu Asn Cys
705                 710                 715                 720

Ile Lys Ala Phe Ile Asp Cys Cys Asn His Ile Thr Lys Leu Arg Glu
                725                 730                 735

Gln His Arg Arg Asp His Val Leu Gly Leu Ala Arg Ser Glu Leu Glu
                740                 745                 750

Glu Asp Ile Ile Pro Glu Glu Asp Ile Ile Ser Arg Ser His Phe Pro
                755                 760                 765

Gln Ser Trp Leu Trp Thr Ile Glu Glu Leu Lys Glu Pro Glu Lys Asn
770                 775                 780

Gly Ile Ser Thr Lys Val Met Asn Ile Phe Leu Lys Asp Ser Ile Thr
785                 790                 795                 800

Thr Trp Glu Ile Leu Ala Val Ser Leu Ser Asp Lys Lys Gly Ile Cys
                805                 810                 815

Val Ala Asp Pro Tyr Glu Ile Arg Val Met Gln Asp Phe Phe Ile Asp
                820                 825                 830

Leu Arg Leu Pro Tyr Ser Val Val Arg Asn Glu Gln Val Glu Ile Arg
                835                 840                 845

Ala Val Leu Phe Asn Tyr Arg Glu Gln Gln Glu Leu Lys Val Arg Val
                850                 855                 860

Glu Leu Leu His Asn Pro Ala Phe Cys Ser Met Ala Thr Ala Lys Asn
865                 870                 875                 880
```

```
Arg Tyr Phe Gln Thr Ile Lys Ile Pro Pro Lys Ser Val Ala Val
            885                 890                 895

Pro Tyr Val Ile Val Pro Leu Lys Ile Gly Gln Gln Glu Val Glu Val
            900                 905                 910

Lys Ala Ala Val Phe Asn His Phe Ile Ser Asp Gly Val Lys Lys Thr
            915                 920                 925

Leu Lys Val Val Pro Glu Gly Met Arg Ile Asn Lys Thr Val Ala Ile
            930                 935                 940

His Thr Leu Asp Pro Glu Lys Leu Gly Gln Gly Gly Val Gln Lys Val
945                 950                 955                 960

Asp Val Pro Ala Ala Asp Leu Ser Asp Gln Val Pro Asp Thr Asp Ser
            965                 970                 975

Glu Thr Arg Ile Ile Leu Gln Gly Ser Pro Val Val Gln Met Ala Glu
            980                 985                 990

Asp Ala Val Asp Gly Glu Arg Leu Lys His Leu Ile Val Thr Pro Ala
            995                 1000                1005

Gly Cys Gly Glu Gln Asn Met Ile Gly Met Thr Pro Thr Val Ile
        1010                1015                1020

Ala Val His Tyr Leu Asp Gln Thr Glu Gln Trp Glu Lys Phe Gly
        1025                1030                1035

Ile Glu Lys Arg Gln Glu Ala Leu Glu Leu Ile Lys Lys Gly Tyr
        1040                1045                1050

Thr Gln Gln Leu Ala Phe Lys Gln Pro Ser Ser Ala Tyr Ala Ala
        1055                1060                1065

Phe Asn Asn Arg Pro Pro Ser Thr Trp Leu Thr Ala Tyr Val Val
        1070                1075                1080

Lys Val Phe Ser Leu Ala Ala Asn Leu Ile Ala Ile Asp Ser His
        1085                1090                1095

Val Leu Cys Gly Ala Val Lys Trp Leu Ile Leu Glu Lys Gln Lys
        1100                1105                1110

Pro Asp Gly Val Phe Gln Glu Asp Gly Pro Val Ile His Gln Glu
        1115                1120                1125

Met Ile Gly Gly Phe Arg Asn Ala Lys Glu Ala Asp Val Ser Leu
        1130                1135                1140

Thr Ala Phe Val Leu Ile Ala Leu Gln Glu Ala Arg Asp Ile Cys
        1145                1150                1155

Glu Gly Gln Val Asn Ser Leu Pro Gly Ser Ile Asn Lys Ala Gly
        1160                1165                1170

Glu Tyr Ile Glu Ala Ser Tyr Met Asn Leu Gln Arg Pro Tyr Thr
        1175                1180                1185

Val Ala Ile Ala Gly Tyr Ala Leu Ala Leu Met Asn Lys Leu Glu
        1190                1195                1200

Glu Pro Tyr Leu Gly Lys Phe Leu Asn Thr Ala Lys Asp Arg Asn
        1205                1210                1215

Arg Trp Glu Glu Pro Asp Gln Gln Leu Tyr Asn Val Glu Ala Thr
        1220                1225                1230

Ser Tyr Ala Leu Leu Ala Leu Leu Leu Lys Asp Phe Asp Ser
        1235                1240                1245

Val Pro Pro Val Val Arg Trp Leu Asn Glu Gln Arg Tyr Tyr Gly
        1250                1255                1260

Gly Gly Tyr Gly Ser Thr Gln Ala Thr Phe Met Val Phe Gln Ala
        1265                1270                1275

Leu Ala Gln Tyr Gln Thr Asp Val Pro Asp His Lys Asp Leu Asn
        1280                1285                1290
```

```
Met Asp Val Ser Phe His Leu Pro Ser Arg Ser Ala Thr Thr
    1295            1300            1305

Phe Arg Leu Leu Trp Glu Asn Gly Asn Leu Leu Arg Ser Glu Glu
    1310            1315            1320

Thr Lys Gln Asn Glu Ala Phe Ser Leu Thr Ala Lys Gly Lys Gly
    1325            1330            1335

Arg Gly Thr Leu Ser Val Val Ala Val Tyr His Ala Lys Leu Lys
    1340            1345            1350

Ser Lys Val Thr Cys Lys Lys Phe Asp Leu Arg Val Ser Ile Arg
    1355            1360            1365

Pro Ala Pro Glu Thr Ala Lys Lys Pro Glu Glu Ala Lys Asn Thr
    1370            1375            1380

Met Phe Leu Glu Ile Cys Thr Lys Tyr Leu Gly Asp Val Asp Ala
    1385            1390            1395

Thr Met Ser Ile Leu Asp Ile Ser Met Met Thr Gly Phe Ala Pro
    1400            1405            1410

Asp Thr Lys Asp Leu Glu Leu Leu Ala Ser Gly Val Asp Arg Tyr
    1415            1420            1425

Ile Ser Lys Tyr Glu Met Asn Lys Ala Phe Ser Asn Lys Asn Thr
    1430            1435            1440

Leu Ile Ile Tyr Leu Glu Lys Ile Ser His Thr Glu Glu Asp Cys
    1445            1450            1455

Leu Thr Phe Lys Val His Gln Tyr Phe Asn Val Gly Leu Ile Gln
    1460            1465            1470

Pro Gly Ser Val Lys Val Tyr Ser Tyr Asn Leu Glu Glu Ser
    1475            1480            1485

Cys Thr Arg Phe Tyr His Pro Glu Lys Asp Asp Gly Met Leu Ser
    1490            1495            1500

Lys Leu Cys His Ser Glu Met Cys Arg Cys Ala Glu Glu Asn Cys
    1505            1510            1515

Phe Met Gln Gln Ser Gln Glu Lys Ile Asn Leu Asn Val Arg Leu
    1520            1525            1530

Asp Lys Ala Cys Glu Pro Gly Val Asp Tyr Val Tyr Lys Thr Glu
    1535            1540            1545

Leu Thr Asn Ile Lys Leu Leu Asp Asp Phe Asp Glu Tyr Thr Met
    1550            1555            1560

Thr Ile Gln Gln Val Ile Lys Ser Gly Ser Asp Glu Val Gln Ala
    1565            1570            1575

Gly Gln Gln Arg Lys Phe Ile Ser His Ile Lys Cys Arg Asn Ala
    1580            1585            1590

Leu Lys Leu Gln Lys Gly Lys Lys Tyr Leu Met Trp Gly Leu Ser
    1595            1600            1605

Ser Asp Leu Trp Gly Glu Lys Pro Asn Thr Ser Tyr Ile Ile Gly
    1610            1615            1620

Lys Asp Thr Trp Val Glu His Trp Pro Glu Ala Glu Glu Cys Gln
    1625            1630            1635

Asp Gln Lys Tyr Gln Lys Gln Cys Glu Glu Leu Gly Ala Phe Thr
    1640            1645            1650

Glu Ser Met Val Val Tyr Gly Cys Pro Asn
    1655            1660
```

<210> SEQ ID NO 31
<211> LENGTH: 1663
<212> TYPE: PRT

<213> ORGANISM: Homo sapiens

<400> SEQUENCE: 31

```
Met Gly Pro Thr Ser Gly Pro Ser Leu Leu Leu Leu Leu Thr His
  1               5                  10                  15

Leu Pro Leu Ala Leu Gly Ser Pro Met Tyr Ser Ile Ile Thr Pro Asn
             20                  25                  30

Ile Leu Arg Leu Glu Ser Glu Glu Thr Met Val Leu Glu Ala His Asp
         35                  40                  45

Ala Gln Gly Asp Val Pro Val Thr Val Thr Val His Asp Phe Pro Gly
     50                  55                  60

Lys Lys Leu Val Leu Ser Ser Glu Lys Thr Val Leu Thr Pro Ala Thr
 65                  70                  75                  80

Asn His Met Gly Asn Val Thr Phe Thr Ile Pro Ala Asn Arg Glu Phe
                 85                  90                  95

Lys Ser Glu Lys Gly Arg Asn Lys Phe Val Thr Val Gln Ala Thr Phe
            100                 105                 110

Gly Thr Gln Val Val Glu Lys Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
    355                 360                 365

Pro Phe Asp Leu Met Val Phe Val Thr Asn Pro Asp Gly Ser Pro Ala
        370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
```

-continued

```
                405                 410                 415
Gln Lys Pro Leu Ser Ile Thr Val Arg Thr Lys Lys Gln Glu Leu Ser
                420                 425                 430

Glu Ala Glu Gln Ala Thr Arg Thr Met Gln Ala Leu Pro Tyr Ser Thr
            435                 440                 445

Val Gly Asn Ser Asn Asn Tyr Leu His Leu Ser Val Leu Arg Thr Glu
        450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
            500                 505                 510

Asp Leu Val Val Leu Pro Leu Ser Ile Thr Thr Asp Phe Ile Pro Ser
        515                 520                 525

Phe Arg Leu Val Ala Tyr Tyr Thr Leu Ile Gly Ala Ser Gly Gln Arg
    530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
            660                 665                 670

Val Gln Leu Thr Glu Lys Arg Met Asp Lys Val Gly Lys Tyr Pro Lys
        675                 680                 685

Glu Leu Arg Lys Cys Cys Glu Asp Gly Met Arg Glu Asn Pro Met Arg
    690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
        755                 760                 765

Glu Ser Trp Leu Trp Asn Val Glu Asp Leu Lys Glu Pro Pro Lys Asn
    770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
            820                 825                 830
```

-continued

Leu Arg Leu Pro Tyr Ser Val Val Arg Asn Glu Gln Val Glu Ile Arg
    835                 840                 845

Ala Val Leu Tyr Asn Tyr Arg Gln Asn Gln Glu Leu Lys Val Arg Val
850                 855                 860

Glu Leu His Asn Pro Ala Phe Cys Ser Leu Ala Thr Thr Lys Arg
865                 870             875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
            900                 905                 910

Lys Ala Ala Val Tyr His His Phe Ile Ser Asp Gly Val Arg Lys Ser
            915                 920                 925

Leu Lys Val Val Pro Glu Gly Ile Arg Met Asn Lys Thr Val Ala Val
    930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu Lys His Leu Ile Val Thr Pro Ser
        995                 1000                1005

Gly Cys Gly Glu Gln Asn Met Ile Gly Met Thr Pro Thr Val Ile
    1010                1015                1020

Ala Val His Tyr Leu Asp Glu Thr Glu Gln Trp Glu Lys Phe Gly
    1025                1030                1035

Leu Glu Lys Arg Gln Gly Ala Leu Glu Leu Ile Lys Lys Gly Tyr
    1040                1045                1050

Thr Gln Gln Leu Ala Phe Arg Gln Pro Ser Ser Ala Phe Ala Ala
    1055                1060                1065

Phe Val Lys Arg Ala Pro Ser Thr Trp Leu Thr Ala Tyr Val Val
    1070                1075                1080

Lys Val Phe Ser Leu Ala Val Asn Leu Ile Ala Ile Asp Ser Gln
    1085                1090                1095

Val Leu Cys Gly Ala Val Lys Trp Leu Ile Leu Glu Lys Gln Lys
    1100                1105                1110

Pro Asp Gly Val Phe Gln Glu Asp Ala Pro Val Ile His Gln Glu
    1115                1120                1125

Met Ile Gly Gly Leu Arg Asn Asn Asn Glu Lys Asp Met Ala Leu
    1130                1135                1140

Thr Ala Phe Val Leu Ile Ser Leu Gln Glu Ala Lys Asp Ile Cys
    1145                1150                1155

Glu Glu Gln Val Asn Ser Leu Pro Gly Ser Ile Thr Lys Ala Gly
    1160                1165                1170

Asp Phe Leu Glu Ala Asn Tyr Met Asn Leu Gln Arg Ser Tyr Thr
    1175                1180                1185

Val Ala Ile Ala Gly Tyr Ala Leu Ala Gln Met Gly Arg Leu Lys
    1190                1195                1200

Gly Pro Leu Leu Asn Lys Phe Leu Thr Thr Ala Lys Asp Lys Asn
    1205                1210                1215

Arg Trp Glu Asp Pro Gly Lys Gln Leu Tyr Asn Val Glu Ala Thr
    1220                1225                1230

Ser Tyr Ala Leu Leu Ala Leu Leu Gln Leu Lys Asp Phe Asp Phe
    1235                1240                1245

```
Val Pro Pro Val Val Arg Trp Leu Asn Glu Gln Arg Tyr Tyr Gly
    1250            1255                1260

Gly Gly Tyr Gly Ser Thr Gln Ala Thr Phe Met Val Phe Gln Ala
    1265            1270                1275

Leu Ala Gln Tyr Gln Lys Asp Ala Pro Asp His Gln Glu Leu Asn
    1280            1285                1290

Leu Asp Val Ser Leu Gln Leu Pro Ser Arg Ser Ser Lys Ile Thr
    1295            1300                1305

His Arg Ile His Trp Glu Ser Ala Ser Leu Leu Arg Ser Glu Glu
    1310            1315                1320

Thr Lys Glu Asn Glu Gly Phe Thr Val Thr Ala Glu Gly Lys Gly
    1325            1330                1335

Gln Gly Thr Leu Ser Val Val Thr Met Tyr His Ala Lys Ala Lys
    1340            1345                1350

Asp Gln Leu Thr Cys Asn Lys Phe Asp Leu Lys Val Thr Ile Lys
    1355            1360                1365

Pro Ala Pro Glu Thr Glu Lys Arg Pro Gln Asp Ala Lys Asn Thr
    1370            1375                1380

Met Ile Leu Glu Ile Cys Thr Arg Tyr Arg Gly Asp Gln Asp Ala
    1385            1390                1395

Thr Met Ser Ile Leu Asp Ile Ser Met Met Thr Gly Phe Ala Pro
    1400            1405                1410

Asp Thr Asp Asp Leu Lys Gln Leu Ala Asn Gly Val Asp Arg Tyr
    1415            1420                1425

Ile Ser Lys Tyr Glu Leu Asp Lys Ala Phe Ser Asp Arg Asn Thr
    1430            1435                1440

Leu Ile Ile Tyr Leu Asp Lys Val Ser His Ser Glu Asp Asp Cys
    1445            1450                1455

Leu Ala Phe Lys Val His Gln Tyr Phe Asn Val Glu Leu Ile Gln
    1460            1465                1470

Pro Gly Ala Val Lys Val Tyr Ala Tyr Tyr Asn Leu Glu Glu Ser
    1475            1480                1485

Cys Thr Arg Phe Tyr His Pro Glu Lys Glu Asp Gly Lys Leu Asn
    1490            1495                1500

Lys Leu Cys Arg Asp Glu Leu Cys Arg Cys Ala Glu Glu Asn Cys
    1505            1510                1515

Phe Ile Gln Lys Ser Asp Asp Lys Val Thr Leu Glu Glu Arg Leu
    1520            1525                1530

Asp Lys Ala Cys Glu Pro Gly Val Asp Tyr Val Tyr Lys Thr Arg
    1535            1540                1545

Leu Val Lys Val Gln Leu Ser Asn Asp Phe Asp Glu Tyr Ile Met
    1550            1555                1560

Ala Ile Glu Gln Thr Ile Lys Ser Gly Ser Asp Glu Val Gln Val
    1565            1570                1575

Gly Gln Gln Arg Thr Phe Ile Ser Pro Ile Lys Cys Arg Glu Ala
    1580            1585                1590

Leu Lys Leu Glu Glu Lys Lys His Tyr Leu Met Trp Gly Leu Ser
    1595            1600                1605

Ser Asp Phe Trp Gly Glu Lys Pro Asn Leu Ser Tyr Ile Ile Gly
    1610            1615                1620

Lys Asp Thr Trp Val Glu His Trp Pro Glu Glu Asp Glu Cys Gln
    1625            1630                1635

Asp Glu Glu Asn Gln Lys Gln Cys Gln Asp Leu Gly Ala Phe Thr
```

```
                    1640                 1645                  1650
Glu Ser  Met Val Val Phe Gly  Cys Pro Asn
        1655              1660

<210> SEQ ID NO 32
<211> LENGTH: 705
<212> TYPE: PRT
<213> ORGANISM: Mus musculus

<400> SEQUENCE: 32

Thr Ala Thr Ala Gly Asn Ala Ala Thr Thr Ala Ala Thr Thr Gly Gly
1               5                   10                  15

Gly Thr Gly Cys Ala Thr Thr Ala Gly Thr Cys Ala Thr Ala Thr Ala
            20                  25                  30

Ala Thr Ala Thr Ala Thr Gly Ala Thr Ala Gly Thr Thr Thr Gly Gly
        35                  40                  45

Thr Thr Gly Thr Thr Ala Cys Ala Thr Gly Cys Thr Thr Thr Gly Gly
    50                  55                  60

Gly Ala Ala Ala Thr Cys Ala Thr Ala Thr Ala Ala Gly Gly Gly Gly
65                  70                  75                  80

Gly Ala Ala Gly Ala Ala Thr Cys Ala Gly Thr Cys Ala Ala Thr Ala
                85                  90                  95

Thr Ala Thr Cys Cys Thr Thr Thr Ala Thr Cys Cys Ala Cys Thr Gly
            100                 105                 110

Thr Ala Ala Ala Thr Cys Ala Gly Gly Ala Cys Cys Thr Thr Ala Cys
        115                 120                 125

Ala Thr Cys Ala Ala Ala Ala Gly Gly Thr Ala Thr Cys Cys Ala Gly
    130                 135                 140

Gly Ala Ala Ala Ala Thr Cys Thr Gly Ala Gly Ala Ala Ala Gly Thr
145                 150                 155                 160

Thr Cys Thr Gly Ala Ala Thr Ala Gly Ala Ala Ala Cys Ala Gly Ala
                165                 170                 175

Thr Gly Thr Thr Gly Ala Ala Gly Ala Ala Cys Thr Thr Ala Cys Ala
            180                 185                 190

Thr Cys Thr Ala Cys Thr Thr Thr Cys Thr Thr Gly Ala Thr Thr Gly
        195                 200                 205

Ala Ala Ala Thr Ala Gly Thr Thr Thr Gly Thr Cys Cys Thr Thr Gly
    210                 215                 220

Gly Ala Cys Ala Thr Ala Thr Cys Ala Thr Ala Thr Thr Thr Thr Ala
225                 230                 235                 240

Gly Ala Thr Thr Ala Gly Gly Ala Gly Thr Thr Thr Gly Ala Ala Ala
                245                 250                 255

Thr Thr Ala Cys Thr Gly Cys Thr Thr Thr Thr Gly Cys Ala Thr Thr
            260                 265                 270

Thr Thr Gly Gly Cys Ala Ala Thr Ala Gly Thr Thr Thr Thr Thr Ala
        275                 280                 285

Ala Ala Gly Thr Thr Ala Cys Ala Ala Ala Thr Thr Ala Ala Thr Cys
    290                 295                 300

Ala Cys Cys Ala Thr Ala Thr Ala Ala Cys Ala Ala Ala Ala Ala Thr
305                 310                 315                 320

Gly Thr Thr Thr Ala Thr Ala Thr Thr Ala Thr Gly Ala Gly Ala Gly
                325                 330                 335

Ala Gly Ala Cys Ala Thr Gly Ala Gly Thr Thr Ala Ala Ala Cys Ala
            340                 345                 350

Ala Thr Ala Cys Thr Thr Cys Ala Ala Thr Gly Cys Ala Ala Ala Thr
```

```
              355                 360                 365
Thr Gly Ala Ala Ala Gly Thr Ala Thr Ala Thr Ala Gly Thr Cys
    370                 375                 380
Ala Cys Ala Thr Gly Cys Ala Thr Gly Thr Gly Cys Cys Thr Thr Thr
385                 390                 395                 400
Cys Thr Ala Ala Ala Cys Ala Ala Thr Ala Ala Ala Thr Cys Ala
                405                 410                 415
Ala Cys Thr Ala Ala Thr Ala Ala Thr Gly Thr Ala Thr Thr Ala
                420                 425                 430
Thr Gly Ala Thr Thr Thr Thr Ala Thr Ala Cys Ala Cys Ala Ala Gly
            435                 440                 445
Thr Gly Gly Gly Ala Thr Ala Ala Thr Gly Ala Thr Gly Gly Thr
    450                 455                 460
Gly Cys Cys Ala Thr Thr Ala Ala Thr Gly Cys Ala Cys Thr Thr Thr
465                 470                 475                 480
Gly Thr Ala Cys Gly Ala Ala Ala Thr Gly Gly Cys Gly Gly Thr Gly
                485                 490                 495
Ala Ala Thr Cys Thr Cys Thr Thr Gly Cys Thr Thr Ala Thr Ala
                500                 505                 510
Ala Thr Ala Thr Cys Cys Ala Thr Ala Thr Thr Ala Cys Ala Thr
                515                 520                 525
Cys Cys Ala Ala Ala Thr Thr Cys Ala Ala Thr Ala Thr Cys Cys Thr
530                 535                 540
Cys Cys Cys Cys Thr Gly Ala Ala Thr Gly Gly Gly Ala Ala Thr Ala
545                 550                 555                 560
Ala Ala Thr Cys Thr Thr Thr Thr Cys Ala Gly Thr Gly Thr Gly Thr
                565                 570                 575
Cys Thr Cys Cys Ala Thr Thr Thr Gly Ala Gly Ala Ala Thr Ala
                580                 585                 590
Thr Ala Thr Thr Gly Thr Gly Thr Gly Ala Thr Cys Cys Cys Ala Thr
            595                 600                 605
Ala Ala Thr Gly Thr Thr Thr Thr Cys Thr Gly Gly Thr Ala Thr Thr
            610                 615                 620
Ala Cys Ala Cys Ala Thr Gly Cys Ala Thr Gly Thr Ala Ala Gly Cys
625                 630                 635                 640
Ala Thr Gly Thr Thr Gly Thr Gly Gly Cys Thr Ala Gly Ala Cys
                645                 650                 655
Cys Ala Cys Thr Thr Cys Cys Ala Thr Thr Thr Cys Thr Ala Cys Ala
                660                 665                 670
Thr Gly Thr Ala Thr Gly Thr Cys Thr Cys Thr Cys Cys Cys Thr
                675                 680                 685
Thr Ala Ala Gly Ala Gly Ala Thr Ala Thr Ala Cys Thr Thr Cys Thr
    690                 695                 700
Gly
705

<210> SEQ ID NO 33
<211> LENGTH: 449
<212> TYPE: PRT
<213> ORGANISM: Homo sapiens

<400> SEQUENCE: 33

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
```

```
            20                  25                  30
Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
 50                  55                  60

Val Cys Arg Lys Gly Glu Trp Val Ala Leu Asn Pro Leu Arg Lys Cys
 65                  70                  75                  80

Gln Lys Arg Pro Cys Gly His Pro Gly Asp Thr Pro Phe Gly Thr Phe
                 85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
            115                 120                 125

Cys Asp Thr Asp Gly Trp Thr Asn Asp Ile Pro Ile Cys Glu Val Val
        130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
            195                 200                 205

Ser Cys Lys Ser Pro Asp Val Ile Asn Gly Ser Pro Ile Ser Gln Lys
        210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
            275                 280                 285

Glu Ile Thr Tyr Gln Cys Arg Asn Gly Phe Tyr Pro Ala Thr Arg Gly
        290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
            355                 360                 365

Trp Asp His Ile His Cys Thr Gln Asp Gly Trp Ser Pro Ala Val Pro
        370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Ser Phe Thr
            435                 440                 445
```

Leu

<210> SEQ ID NO 34
<211> LENGTH: 694
<212> TYPE: PRT
<213> ORGANISM: Mus musculus

<400> SEQUENCE: 34

```
Met Gly Lys Ser Pro Gly Met Trp Cys Leu Val Leu Phe Ser Leu Leu
1               5                   10                  15

Ala Ser Phe Ser Ala Glu Pro Thr Met His Gly Glu Ile Leu Ser Pro
            20                  25                  30

Asn Tyr Pro Gln Ala Tyr Pro Asn Asp Val Val Lys Ser Trp Asp Ile
        35                  40                  45

Glu Val Pro Glu Gly Phe Gly Ile His Leu Tyr Phe Thr His Val Asp
    50                  55                  60

Ile Glu Pro Ser Glu Ser Cys Ala Tyr Asp Ser Val Gln Ile Ile Ser
65                  70                  75                  80

Gly Gly Ile Glu Glu Gly Arg Leu Cys Gly Gln Lys Thr Ser Lys Ser
                85                  90                  95

Pro Asn Ser Pro Ile Ile Glu Glu Phe Gln Phe Pro Tyr Asn Lys Leu
            100                 105                 110

Gln Val Val Phe Thr Ser Asp Phe Ser Asn Glu Glu Arg Phe Thr Gly
        115                 120                 125

Phe Ala Ala Tyr Tyr Thr Ala Ile Asp Ile Asn Glu Cys Thr Asp Phe
    130                 135                 140

Thr Asp Val Pro Cys Ser His Phe Cys Asn Asn Phe Ile Gly Gly Tyr
145                 150                 155                 160

Phe Cys Ser Cys Pro Pro Glu Tyr Phe Leu His Asp Asp Met Arg Asn
                165                 170                 175

Cys Gly Val Asn Cys Ser Gly Asp Val Phe Thr Ala Leu Ile Gly Glu
            180                 185                 190

Ile Ser Ser Pro Asn Tyr Pro Asn Pro Tyr Pro Glu Asn Ser Arg Cys
        195                 200                 205

Glu Tyr Gln Ile Gln Leu Glu Gly Phe Gln Val Val Thr Met
    210                 215                 220

Gln Arg Glu Asp Phe Asp Val Glu Pro Ala Asp Ser Glu Gly Asn Cys
225                 230                 235                 240

Pro Asp Ser Leu Thr Phe Ala Ser Lys Asn Gln Gln Phe Gly Pro Tyr
                245                 250                 255

Cys Gly Asn Gly Phe Pro Gly Pro Leu Thr Ile Arg Thr Gln Ser Asn
            260                 265                 270

Thr Leu Gly Ile Val Phe Gln Thr Asp Leu Met Gly Gln Lys Lys Gly
        275                 280                 285

Trp Lys Leu Arg Tyr His Gly Asp Pro Ile Ser Cys Ala Lys Lys Ile
    290                 295                 300

Thr Ala Asn Ser Thr Trp Glu Pro Asp Lys Ala Lys Tyr Val Phe Lys
305                 310                 315                 320

Asp Val Val Lys Ile Thr Cys Val Asp Gly Phe Glu Val Val Glu Gly
                325                 330                 335

His Val Ser Ser Thr Ser Tyr Tyr Ser Thr Cys Gln Ser Asp Gly Gln
            340                 345                 350

Trp Ser Asn Ser Gly Leu Lys Cys Gln Pro Val Tyr Cys Gly Ile Pro
        355                 360                 365

Asp Pro Ile Ala Asn Gly Lys Val Glu Glu Pro Glu Asn Ser Val Phe
```

```
                370             375             380
Gly Thr Val Val His Tyr Thr Cys Glu Glu Pro Tyr Tyr Met Glu
385             390             395             400

His Glu Glu Gly Gly Glu Tyr Arg Cys Ala Ala Asn Gly Arg Trp Val
                405             410             415

Asn Asp Gln Leu Gly Ile Glu Leu Pro Arg Cys Ile Pro Ala Cys Gly
            420             425             430

Val Pro Thr Glu Pro Phe Gln Val His Gln Arg Ile Phe Gly Gly Gln
            435             440             445

Pro Ala Lys Ile Glu Asn Phe Pro Trp Gln Val Phe Phe Asn His Pro
450             455             460

Arg Ala Ser Gly Ala Leu Ile Asn Glu Tyr Trp Val Leu Thr Ala Ala
465             470             475             480

His Val Leu Glu Lys Ile Ser Asp Pro Leu Met Tyr Val Gly Thr Met
                485             490             495

Ser Val Arg Thr Thr Leu Leu Glu Asn Ala Gln Arg Leu Tyr Ser Lys
            500             505             510

Arg Val Phe Ile His Pro Ser Trp Lys Lys Glu Asp Asp Pro Asn Thr
            515             520             525

Arg Thr Asn Phe Asp Asn Asp Ile Ala Leu Val Gln Leu Lys Asp Pro
530             535             540

Val Lys Met Gly Pro Lys Val Ser Pro Ile Cys Leu Pro Gly Thr Ser
545             550             555             560

Ser Glu Tyr Asn Val Ser Pro Gly Asp Met Gly Leu Ile Ser Gly Trp
                565             570             575

Gly Ser Thr Glu Lys Lys Val Phe Val Ile Asn Leu Arg Gly Ala Lys
            580             585             590

Val Pro Val Thr Ser Leu Glu Thr Cys Lys Gln Val Lys Glu Glu Asn
            595             600             605

Pro Thr Val Arg Pro Glu Asp Tyr Val Phe Thr Asp Asn Met Ile Cys
            610             615             620

Ala Gly Glu Lys Gly Val Asp Ser Cys His Gly Asp Ser Gly Gly Ala
625             630             635             640

Phe Ala Phe Gln Val Pro Asn Val Thr Val Pro Lys Phe Tyr Val Ala
                645             650             655

Gly Leu Val Ser Trp Gly Lys Arg Cys Gly Thr Tyr Gly Val Tyr Thr
            660             665             670

Lys Val Lys Asn Tyr Val Asp Trp Ile Leu Lys Thr Met Gln Glu Asn
            675             680             685

Ser Gly Pro Arg Lys Asp
    690

<210> SEQ ID NO 35
<211> LENGTH: 688
<212> TYPE: PRT
<213> ORGANISM: Homo sapiens

<400> SEQUENCE: 35

Met Trp Cys Ile Val Leu Phe Ser Leu Leu Ala Trp Val Tyr Ala Glu
1               5               10              15

Pro Thr Met Tyr Gly Glu Ile Leu Ser Pro Asn Tyr Pro Gln Ala Tyr
                20              25              30

Pro Ser Glu Val Glu Lys Ser Trp Asp Ile Glu Val Pro Glu Gly Tyr
            35              40              45

Gly Ile His Leu Tyr Phe Thr His Leu Asp Ile Glu Leu Ser Glu Asn
```

```
            50                  55                  60
Cys Ala Tyr Asp Ser Val Gln Ile Ile Ser Gly Asp Thr Glu Gly
 65                  70                  75                  80

Arg Leu Cys Gly Gln Arg Ser Ser Asn Asn Pro His Ser Pro Ile Val
                 85                  90                  95

Glu Glu Phe Gln Val Pro Tyr Asn Lys Leu Gln Val Ile Phe Lys Ser
                100                 105                 110

Asp Phe Ser Asn Glu Glu Arg Phe Thr Gly Phe Ala Ala Tyr Tyr Val
                115                 120                 125

Ala Thr Asp Ile Asn Glu Cys Thr Asp Phe Val Asp Val Pro Cys Ser
130                 135                 140

His Phe Cys Asn Asn Phe Ile Gly Gly Tyr Phe Cys Ser Cys Pro Pro
145                 150                 155                 160

Glu Tyr Phe Leu His Asp Asp Met Lys Asn Cys Gly Val Asn Cys Ser
                165                 170                 175

Gly Asp Val Phe Thr Ala Leu Ile Gly Glu Ile Ala Ser Pro Asn Tyr
                180                 185                 190

Pro Lys Pro Tyr Pro Glu Asn Ser Arg Cys Glu Tyr Gln Ile Arg Leu
                195                 200                 205

Glu Lys Gly Phe Gln Val Val Val Thr Leu Arg Arg Glu Asp Phe Asp
210                 215                 220

Val Glu Ala Ala Asp Ser Ala Gly Asn Cys Leu Asp Ser Leu Val Phe
225                 230                 235                 240

Val Ala Gly Asp Arg Gln Phe Gly Pro Tyr Cys Gly His Gly Phe Pro
                245                 250                 255

Gly Pro Leu Asn Ile Glu Thr Lys Ser Asn Ala Leu Asp Ile Ile Phe
                260                 265                 270

Gln Thr Asp Leu Thr Gly Gln Lys Lys Gly Trp Lys Leu Arg Tyr His
                275                 280                 285

Gly Asp Pro Met Pro Cys Pro Lys Glu Asp Thr Pro Asn Ser Val Trp
                290                 295                 300

Glu Pro Ala Lys Ala Lys Tyr Val Phe Arg Asp Val Val Gln Ile Thr
305                 310                 315                 320

Cys Leu Asp Gly Phe Glu Val Val Glu Gly Arg Val Gly Ala Thr Ser
                325                 330                 335

Phe Tyr Ser Thr Cys Gln Ser Asn Gly Lys Trp Ser Asn Ser Lys Leu
                340                 345                 350

Lys Cys Gln Pro Val Asp Cys Gly Ile Pro Glu Ser Ile Glu Asn Gly
                355                 360                 365

Lys Val Glu Asp Pro Glu Ser Thr Leu Phe Gly Ser Val Ile Arg Tyr
370                 375                 380

Thr Cys Glu Glu Pro Tyr Tyr Met Glu Asn Gly Gly Gly Gly Glu
385                 390                 395                 400

Tyr His Cys Ala Gly Asn Gly Ser Trp Val Asn Glu Val Leu Gly Pro
                405                 410                 415

Glu Leu Pro Lys Cys Val Pro Val Cys Gly Val Pro Arg Glu Pro Phe
                420                 425                 430

Glu Glu Lys Gln Arg Ile Ile Gly Gly Ser Asp Ala Asp Ile Lys Asn
                435                 440                 445

Phe Pro Trp Gln Val Phe Phe Asp Asn Pro Trp Ala Gly Gly Ala Leu
                450                 455                 460

Ile Asn Glu Tyr Trp Val Leu Thr Ala Ala His Val Val Glu Gly Asn
465                 470                 475                 480
```

```
Arg Glu Pro Thr Met Tyr Val Gly Ser Thr Ser Val Gln Thr Ser Arg
                485                 490                 495

Leu Ala Lys Ser Lys Met Leu Thr Pro Glu His Val Phe Ile His Pro
            500                 505                 510

Gly Trp Lys Leu Leu Glu Val Pro Glu Gly Arg Thr Asn Phe Asp Asn
            515                 520                 525

Asp Ile Ala Leu Val Arg Leu Lys Asp Pro Val Lys Met Gly Pro Thr
            530                 535                 540

Val Ser Pro Ile Cys Leu Pro Gly Thr Ser Ser Asp Tyr Asn Leu Met
545                 550                 555                 560

Asp Gly Asp Leu Gly Leu Ile Ser Gly Trp Gly Arg Thr Glu Lys Arg
                565                 570                 575

Asp Arg Ala Val Arg Leu Lys Ala Ala Arg Leu Pro Val Ala Pro Leu
            580                 585                 590

Arg Lys Cys Lys Glu Val Lys Val Glu Lys Pro Thr Ala Asp Ala Glu
            595                 600                 605

Ala Tyr Val Phe Thr Pro Asn Met Ile Cys Ala Gly Gly Glu Lys Gly
            610                 615                 620

Met Asp Ser Cys Lys Gly Asp Ser Gly Gly Ala Phe Ala Val Gln Asp
625                 630                 635                 640

Pro Asn Asp Lys Thr Lys Phe Tyr Ala Ala Gly Leu Val Ser Trp Gly
                645                 650                 655

Pro Gln Cys Gly Thr Tyr Gly Leu Tyr Thr Arg Val Lys Asn Tyr Val
                660                 665                 670

Asp Trp Ile Met Lys Thr Met Gln Glu Asn Ser Thr Pro Arg Glu Asp
                675                 680                 685

<210> SEQ ID NO 36
<211> LENGTH: 573
<212> TYPE: DNA
<213> ORGANISM: Mus musculus

<400> SEQUENCE: 36
aagggttaga agatcacttt attggtagtc tatcataggc tttatataaa tgttatgtaa     60
acaagtctct tgagtgtttt tatctcatgg aattgtacaa aactcttaga taacaccatc    120
cctcccagat gctgggttta aagtctccat ccctaaggcc tgtgtctgag gtattgggct    180
gccataaatc ttggagatgg acagtgaca gtgctgccaa tagatgttct tggggccaag     240
cagcaggcca tgaaggacca actgtagcca gccactgtcc atttctgtcc atagccacac    300
cgctcatccc tgctgcctgc tggagtgctc tcgtatttca gtaggaaata tggagccatt    360
tcctactgaa gtccttgttt tatgagctcc gaggacccga cttttcccca cctcccccta    420
acacagctcc ttggcaggct gaagtgtcgc agatccctgg ggtaccctga gcaccagcag    480
ctccaggaag gccaggatca ccgggaaggc caggctcacc atgagcacca tctcgaccat    540
ctttgctgat gccaggtaca ccttgaggcc ctt                                 573

<210> SEQ ID NO 37
<211> LENGTH: 684
<212> TYPE: PRT
<213> ORGANISM: Homo sapiens

<400> SEQUENCE: 37

Met Ala Gly Pro Arg Ala Cys Ala Pro Leu Leu Leu Leu Leu Leu Leu
1               5                   10                  15

Gly Glu Leu Leu Ala Ala Ala Gly Ala Gln Arg Val Gly Leu Pro Gly
            20                  25                  30
```

Pro Pro Gly Pro Pro Gly Pro Pro Gly Lys Pro Gly Gln Asp Gly Ile
            35                  40                  45

Asp Gly Glu Ala Gly Pro Pro Gly Leu Pro Gly Pro Pro Gly Pro Lys
 50                  55                  60

Gly Ala Pro Gly Lys Pro Gly Lys Pro Gly Glu Ala Gly Leu Pro Gly
 65                  70                  75                  80

Leu Pro Gly Val Asp Gly Leu Thr Gly Arg Asp Gly Pro Pro Gly Pro
                 85                  90                  95

Lys Gly Ala Pro Gly Glu Arg Gly Ser Leu Gly Pro Pro Gly Pro Pro
            100                 105                 110

Gly Leu Gly Gly Lys Gly Leu Pro Gly Pro Pro Gly Glu Ala Gly Val
            115                 120                 125

Ser Gly Pro Pro Gly Gly Ile Gly Leu Arg Gly Pro Pro Gly Pro Ser
            130                 135                 140

Gly Leu Pro Gly Leu Pro Gly Pro Pro Gly Pro Pro Gly Pro Pro Gly
145                 150                 155                 160

His Pro Gly Val Leu Pro Glu Gly Ala Thr Asp Leu Gln Cys Pro Ser
                165                 170                 175

Ile Cys Pro Pro Gly Pro Pro Gly Pro Pro Gly Met Pro Gly Phe Lys
            180                 185                 190

Gly Pro Thr Gly Tyr Lys Gly Glu Gln Gly Glu Val Gly Lys Asp Gly
            195                 200                 205

Glu Lys Gly Asp Pro Gly Pro Pro Gly Pro Ala Gly Leu Pro Gly Ser
            210                 215                 220

Val Gly Leu Gln Gly Pro Arg Gly Leu Arg Gly Leu Pro Gly Pro Leu
225                 230                 235                 240

Gly Pro Pro Gly Asp Arg Gly Pro Ile Gly Phe Arg Gly Pro Pro Gly
                245                 250                 255

Ile Pro Gly Ala Pro Gly Lys Ala Gly Asp Arg Gly Glu Arg Gly Pro
            260                 265                 270

Glu Gly Phe Arg Gly Pro Lys Gly Asp Leu Gly Arg Pro Gly Pro Lys
            275                 280                 285

Gly Thr Pro Gly Val Ala Gly Pro Ser Gly Glu Pro Gly Met Pro Gly
            290                 295                 300

Lys Asp Gly Gln Asn Gly Val Pro Gly Leu Asp Gly Gln Lys Gly Glu
305                 310                 315                 320

Ala Gly Arg Asn Gly Ala Pro Gly Glu Lys Gly Pro Asn Gly Leu Pro
            325                 330                 335

Gly Leu Pro Gly Arg Ala Gly Ser Lys Gly Glu Lys Gly Glu Arg Gly
            340                 345                 350

Arg Ala Gly Glu Leu Gly Glu Ala Gly Pro Ser Gly Glu Pro Gly Val
            355                 360                 365

Pro Gly Asp Ala Gly Met Pro Gly Glu Arg Gly Glu Ala Gly His Arg
            370                 375                 380

Gly Ser Ala Gly Ala Leu Gly Pro Gln Gly Pro Pro Gly Ala Pro Gly
385                 390                 395                 400

Val Arg Gly Phe Gln Gly Gln Lys Gly Ser Met Gly Asp Pro Gly Leu
                405                 410                 415

Pro Gly Pro Gln Gly Leu Arg Gly Asp Val Gly Asp Arg Gly Pro Gly
            420                 425                 430

Gly Ala Ala Gly Pro Lys Gly Asp Gln Gly Ile Ala Gly Ser Asp Gly
            435                 440                 445

Leu Pro Gly Asp Lys Gly Glu Leu Gly Pro Ser Gly Leu Val Gly Pro

```
                450             455             460
Lys Gly Glu Ser Gly Ser Arg Gly Glu Leu Gly Pro Lys Gly Thr Gln
465                     470                 475                 480

Gly Pro Asn Gly Thr Ser Gly Val Gln Gly Val Pro Gly Pro Pro Gly
                485                 490                 495

Pro Leu Gly Leu Gln Gly Val Pro Gly Val Pro Gly Ile Thr Gly Lys
                500                 505                 510

Pro Gly Val Pro Gly Lys Glu Ala Ser Glu Gln Arg Ile Arg Glu Leu
                515                 520                 525

Cys Gly Gly Met Ile Ser Glu Gln Ile Ala Gln Leu Ala Ala His Leu
                530                 535                 540

Arg Lys Pro Leu Ala Pro Gly Ser Ile Gly Arg Pro Gly Pro Ala Gly
545                 550                 555                 560

Pro Pro Gly Pro Pro Gly Pro Pro Gly Ser Ile Gly His Pro Gly Ala
                565                 570                 575

Arg Gly Pro Pro Gly Tyr Arg Gly Pro Thr Gly Glu Leu Gly Asp Pro
                580                 585                 590

Gly Pro Arg Gly Asn Gln Gly Asp Arg Gly Asp Lys Gly Ala Ala Gly
                595                 600                 605

Ala Gly Leu Asp Gly Pro Glu Gly Asp Gln Gly Pro Gln Gly Pro Gln
                610                 615                 620

Gly Val Pro Gly Thr Ser Lys Asp Gly Gln Asp Gly Ala Pro Gly Glu
625                 630                 635                 640

Pro Gly Pro Pro Gly Asp Pro Gly Leu Pro Gly Ala Ile Gly Ala Gln
                645                 650                 655

Gly Thr Pro Gly Ile Cys Asp Thr Ser Ala Cys Gln Gly Ala Val Leu
                660                 665                 670

Gly Gly Val Gly Glu Lys Ser Gly Ser Arg Ser Ser
                675                 680

<210> SEQ ID NO 38
<211> LENGTH: 184
<212> TYPE: PRT
<213> ORGANISM: Mus musculus

<400> SEQUENCE: 38

Met Asn Arg Thr Ala Tyr Thr Val Gly Ala Leu Leu Leu Leu Leu Gly
1               5                   10                  15

Thr Leu Leu Pro Thr Ala Glu Gly Lys Lys Gly Ser Gln Gly Ala
                20                  25                  30

Ile Pro Pro Pro Asp Lys Ala Gln His Asn Asp Ser Glu Gln Thr Gln
                35                  40                  45

Ser Pro Pro Gln Pro Gly Ser Arg Thr Arg Gly Arg Gly Gln Gly Arg
                50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Gly Cys Asn Ser Arg Thr
                100                 105                 110

Ile Ile Asn Arg Phe Cys Tyr Gly Gln Cys Asn Ser Phe Tyr Ile Pro
                115                 120                 125

Arg His Ile Arg Lys Glu Glu Gly Ser Phe Gln Ser Cys Ser Phe Cys
                130                 135                 140

Lys Pro Lys Lys Phe Thr Thr Met Met Val Thr Leu Asn Cys Pro Glu
```

```
                145                 150                 155                 160
Leu Gln Pro Pro Thr Lys Lys Arg Val Thr Arg Val Lys Gln Cys
                    165                 170                 175

Arg Cys Ile Ser Ile Asp Leu Asp
            180

<210> SEQ ID NO 39
<211> LENGTH: 184
<212> TYPE: PRT
<213> ORGANISM: Homo sapiens

<400> SEQUENCE: 39

Met Ser Arg Thr Ala Tyr Thr Val Gly Ala Leu Leu Leu Leu Gly
1               5                   10                  15

Thr Leu Pro Ala Ala Glu Gly Lys Lys Gly Ser Gln Gly Ala
                20                  25                  30

Ile Pro Pro Pro Asp Lys Ala Gln His Asn Asp Ser Glu Gln Thr Gln
                35                  40                  45

Ser Pro Gln Gln Pro Gly Ser Arg Asn Arg Gly Arg Gly Gln Gly Arg
            50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
                100                 105                 110

Ile Ile Asn Arg Phe Cys Tyr Gly Gln Cys Asn Ser Phe Tyr Ile Pro
            115                 120                 125

Arg His Ile Arg Lys Glu Glu Gly Ser Phe Gln Ser Cys Ser Phe Cys
        130                 135                 140

Lys Pro Lys Lys Phe Thr Thr Met Met Val Thr Leu Asn Cys Pro Glu
145                 150                 155                 160

Leu Gln Pro Pro Thr Lys Lys Arg Val Thr Arg Val Lys Gln Cys
                    165                 170                 175

Arg Cys Ile Ser Ile Asp Leu Asp
            180

<210> SEQ ID NO 40
<211> LENGTH: 754
<212> TYPE: PRT
<213> ORGANISM: Mus musculus

<400> SEQUENCE: 40

Met Arg Ala Val Ser Val Trp Tyr Cys Cys Pro Trp Gly Leu Leu Leu
1               5                   10                  15

Leu His Cys Leu Cys Ser Phe Ser Val Gly Ser Pro Ser Pro Ser Ile
                20                  25                  30

Ser Pro Glu Lys Lys Val Gly Ser Gln Gly Leu Arg Phe Arg Leu Ala
            35                  40                  45

Gly Phe Pro Arg Lys Pro Tyr Glu Gly Arg Val Glu Ile Gln Arg Ala
        50                  55                  60

Gly Glu Trp Gly Thr Ile Cys Asp Asp Asp Phe Thr Leu Gln Ala Ala
65                  70                  75                  80

His Val Leu Cys Arg Glu Leu Gly Phe Thr Glu Ala Thr Gly Trp Thr
                85                  90                  95

His Ser Ala Lys Tyr Gly Pro Gly Thr Gly Arg Ile Trp Leu Asp Asn
                100                 105                 110
```

```
Leu Ser Cys Arg Gly Thr Glu Gly Ser Val Thr Glu Cys Ala Ser Arg
        115                 120                 125

Gly Trp Gly Asn Ser Asp Cys Thr His Asp Glu Asp Ala Gly Val Ile
        130                 135                 140

Cys Lys Asp Gln Arg Leu Pro Gly Phe Ser Asp Ser Asn Val Ile Glu
145                 150                 155                 160

Val Glu His Gln Leu Gln Val Glu Glu Val Arg Leu Arg Pro Ala Val
                165                 170                 175

Glu Trp Gly Arg Arg Pro Leu Pro Val Thr Glu Gly Leu Val Glu Val
                180                 185                 190

Arg Leu Pro Glu Gly Trp Ser Gln Val Cys Asp Lys Gly Trp Ser Ala
        195                 200                 205

His Asn Ser His Val Val Cys Gly Met Leu Gly Phe Pro Gly Glu Lys
        210                 215                 220

Arg Val Asn Met Ala Phe Tyr Arg Met Leu Ala Gln Lys Lys Gln His
225                 230                 235                 240

Ser Phe Gly Leu His Ser Val Ala Cys Val Gly Thr Glu Ala His Leu
                245                 250                 255

Ser Leu Cys Ser Leu Glu Phe Tyr Arg Ala Asn Asp Thr Thr Arg Cys
                260                 265                 270

Ser Gly Gly Asn Pro Ala Val Val Ser Cys Val Leu Gly Pro Leu Tyr
        275                 280                 285

Ala Thr Phe Thr Gly Gln Lys Lys Gln Gln His Ser Lys Pro Gln Gly
        290                 295                 300

Glu Ala Arg Val Arg Leu Lys Gly Gly Ala His Gln Gly Glu Gly Arg
305                 310                 315                 320

Val Glu Val Leu Lys Ala Gly Thr Trp Gly Thr Val Cys Asp Arg Lys
                325                 330                 335

Trp Asp Leu Gln Ala Ala Ser Val Val Cys Arg Glu Leu Gly Phe Gly
                340                 345                 350

Thr Ala Arg Glu Ala Leu Ser Gly Ala Arg Met Gly Gln Gly Met Gly
        355                 360                 365

Ala Ile His Leu Ser Glu Val Arg Cys Ser Gly Gln Glu Pro Ser Leu
        370                 375                 380

Trp Arg Cys Pro Ser Lys Asn Ile Thr Ala Glu Asp Cys Ser His Ser
385                 390                 395                 400

Gln Asp Ala Gly Val Arg Cys Asn Leu Pro Tyr Thr Gly Val Glu Thr
                405                 410                 415

Lys Ile Arg Leu Ser Gly Gly Arg Ser Arg Tyr Glu Gly Arg Val Glu
                420                 425                 430

Val Gln Ile Gly Ile Pro Gly His Leu Arg Trp Gly Leu Ile Cys Gly
        435                 440                 445

Asp Asp Trp Gly Thr Leu Glu Ala Met Val Ala Cys Arg Gln Leu Gly
        450                 455                 460

Leu Gly Tyr Ala Asn His Gly Leu Gln Glu Thr Trp Tyr Trp Asp Ser
465                 470                 475                 480

Gly Asn Val Thr Glu Val Val Met Ser Gly Val Arg Cys Thr Gly Ser
                485                 490                 495

Glu Leu Ser Leu Asn Gln Cys Ala His His Ser Ser His Ile Thr Cys
                500                 505                 510

Lys Lys Thr Gly Thr Arg Phe Thr Ala Gly Val Ile Cys Ser Glu Thr
        515                 520                 525

Ala Ser Asp Leu Leu Leu His Ser Ala Leu Val Gln Glu Thr Ala Tyr
```

```
                    530                 535                 540
Ile Glu Asp Arg Pro Leu His Met Leu Tyr Cys Ala Ala Glu Glu Asn
545                 550                 555                 560

Cys Leu Ala Ser Ser Ala Arg Ser Ala Asn Trp Pro Tyr Gly His Arg
                565                 570                 575

Arg Leu Leu Arg Phe Ser Ser Gln Ile His Asn Leu Gly Arg Ala Asp
                580                 585                 590

Phe Arg Pro Lys Ala Gly Arg His Ser Trp Val Trp His Glu Cys His
                595                 600                 605

Gly His Tyr His Ser Met Asp Ile Phe Thr His Tyr Asp Ile Leu Thr
                610                 615                 620

Pro Asn Gly Thr Lys Val Ala Glu Gly His Lys Ala Ser Phe Cys Leu
625                 630                 635                 640

Glu Asp Thr Glu Cys Gln Glu Asp Val Ser Lys Arg Tyr Glu Cys Ala
                645                 650                 655

Asn Phe Gly Glu Gln Gly Ile Thr Val Gly Cys Trp Asp Leu Tyr Arg
                660                 665                 670

His Asp Ile Asp Cys Gln Trp Ile Asp Ile Thr Asp Val Lys Pro Gly
                675                 680                 685

Asn Tyr Ile Leu Gln Val Val Ile Asn Pro Asn Phe Glu Val Ala Glu
                690                 695                 700

Ser Asp Phe Thr Asn Asn Ala Met Lys Cys Asn Cys Lys Tyr Asp Gly
705                 710                 715                 720

His Arg Ile Trp Val His Asn Cys His Ile Gly Asp Ala Phe Ser Glu
                725                 730                 735

Glu Ala Asn Arg Arg Phe Glu Arg Tyr Pro Gly Gln Thr Ser Asn Gln
                740                 745                 750

Ile Val

<210> SEQ ID NO 41
<211> LENGTH: 608
<212> TYPE: PRT
<213> ORGANISM: Homo sapiens

<400> SEQUENCE: 41

Met Arg Pro Val Ser Val Trp Gln Trp Ser Pro Trp Gly Leu Leu Leu
1               5                   10                  15

Cys Leu Leu Cys Ser Ser Cys Leu Gly Ser Pro Ser Pro Ser Thr Gly
                20                  25                  30

Pro Glu Lys Lys Ala Gly Ser Gln Gly Leu Arg Phe Arg Leu Ala Gly
                35                  40                  45

Phe Pro Arg Lys Pro Tyr Glu Gly Arg Val Glu Ile Gln Arg Ala Gly
                50                  55                  60

Glu Trp Gly Thr Ile Cys Asp Asp Phe Thr Leu Gln Ala Ala His
65              70                  75                  80

Ile Leu Cys Arg Glu Leu Gly Phe Thr Glu Ala Thr Gly Trp Thr His
                85                  90                  95

Ser Ala Lys Tyr Gly Pro Gly Thr Gly Arg Ile Trp Leu Asp Asn Leu
                100                 105                 110

Ser Cys Ser Gly Thr Glu Gln Ser Val Thr Glu Cys Ala Ser Arg Gly
                115                 120                 125

Trp Gly Asn Ser Asp Cys Thr His Asp Glu Asp Ala Gly Val Ile Cys
                130                 135                 140

Lys Asp Gln Arg Leu Pro Gly Phe Ser Asp Ser Asn Val Ile Glu Ala
145                 150                 155                 160
```

```
Arg Val Arg Leu Lys Gly Gly Ala His Pro Gly Glu Gly Arg Val Glu
                165                 170                 175
Val Leu Lys Ala Ser Thr Trp Gly Thr Val Cys Asp Arg Lys Trp Asp
                180                 185                 190
Leu His Ala Ala Ser Val Val Cys Arg Glu Leu Gly Phe Gly Ser Ala
                195                 200                 205
Arg Glu Ala Leu Ser Gly Ala Arg Met Gly Gln Gly Met Gly Ala Ile
                210                 215                 220
His Leu Ser Glu Val Arg Cys Ser Gly Gln Glu Leu Ser Leu Trp Lys
225                 230                 235                 240
Cys Pro His Lys Asn Ile Thr Ala Glu Asp Cys Ser His Ser Gln Asp
                245                 250                 255
Ala Gly Val Arg Cys Asn Leu Pro Tyr Thr Gly Ala Glu Thr Arg Ile
                260                 265                 270
Arg Leu Ser Gly Gly Arg Ser Gln His Glu Gly Arg Val Glu Val Gln
                275                 280                 285
Ile Gly Gly Pro Gly Pro Leu Arg Trp Gly Leu Ile Cys Gly Asp Asp
                290                 295                 300
Trp Gly Thr Leu Glu Ala Met Val Ala Cys Arg Gln Leu Gly Leu Gly
305                 310                 315                 320
Tyr Ala Asn His Gly Leu Gln Glu Thr Trp Tyr Trp Asp Ser Gly Asn
                325                 330                 335
Ile Thr Glu Val Val Met Ser Gly Val Arg Cys Thr Gly Thr Glu Leu
                340                 345                 350
Ser Leu Asp Gln Cys Ala His His Gly Thr His Ile Thr Cys Lys Arg
                355                 360                 365
Thr Gly Thr Arg Phe Thr Ala Gly Val Ile Cys Ser Gly Thr Ala Ser
                370                 375                 380
Asp Leu Leu Leu His Ser Ala Leu Val Gln Glu Thr Ala Tyr Ile Glu
385                 390                 395                 400
Asp Arg Pro Leu His Met Leu Tyr Cys Ala Ala Glu Glu Asn Cys Leu
                405                 410                 415
Ala Ser Ser Ala Arg Ser Ala Asn Trp Pro Tyr Gly His Arg Arg Leu
                420                 425                 430
Leu Arg Phe Ser Ser Gln Ile His Asn Leu Gly Arg Ala Asp Phe Arg
                435                 440                 445
Pro Lys Ala Gly Arg His Ser Trp Val Trp His Glu Cys His Gly His
                450                 455                 460
Tyr His Ser Met Asp Ile Phe Thr His Tyr Asp Ile Leu Thr Pro Asn
465                 470                 475                 480
Gly Thr Lys Val Ala Glu Gly His Lys Ala Ser Phe Cys Leu Glu Asp
                485                 490                 495
Thr Glu Cys Gln Glu Asp Val Ser Lys Arg Tyr Glu Cys Ala Asn Phe
                500                 505                 510
Gly Glu Gln Gly Ile Thr Val Gly Cys Trp Asp Leu Tyr Arg His Asp
                515                 520                 525
Ile Asp Cys Gln Trp Ile Asp Ile Thr Asp Val Lys Pro Gly Asn Tyr
                530                 535                 540
Ile Leu Gln Val Val Ile Asn Pro Asn Phe Glu Val Ala Glu Ser Asp
545                 550                 555                 560
Phe Thr Asn Asn Ala Met Lys Cys Asn Cys Lys Tyr Asp Gly His Arg
                565                 570                 575
Ile Trp Val His Asn Cys His Ile Gly Asp Ala Phe Ser Glu Glu Ala
```

```
                    580                 585                 590
Asn Arg Arg Phe Glu Arg Tyr Pro Gly Gln Thr Ser Asn Gln Ile Ile
                595                 600                 605

<210> SEQ ID NO 42
<211> LENGTH: 164
<212> TYPE: PRT
<213> ORGANISM: Mus musculus

<400> SEQUENCE: 42

Met Leu Phe Leu Gly Gln Lys Ala Leu Leu Val Leu Ala Ile Ser
1               5                   10                  15

Ile Pro Ser Asp Trp Leu Pro Leu Gly Val Ser Gly Gln Arg Gly Asp
                20                  25                  30

Asp Val Pro Glu Thr Phe Thr Asp Pro Asn Leu Val Asn Asp Pro
            35                  40                  45

Ser Thr Asp Asp Thr Ala Leu Ala Asp Ile Thr Pro Ser Thr Asp Asp
        50                  55                  60

Leu Ala Gly Asp Lys Asn Ala Thr Ala Glu Cys Arg Asp Glu Lys Phe
65                  70                  75                  80

Ala Cys Thr Arg Leu Tyr Ser Val His Arg Pro Val Arg Gln Cys Val
                85                  90                  95

His Gln Ser Cys Phe Thr Ser Leu Arg Arg Met Tyr Ile Ile Asn Asn
            100                 105                 110

Glu Ile Cys Ser Arg Leu Val Cys Lys Glu His Glu Ala Met Lys Asp
        115                 120                 125

Glu Leu Cys Arg Gln Met Ala Gly Leu Pro Pro Arg Arg Leu Arg Arg
130                 135                 140

Ser Asn Tyr Phe Arg Leu Pro Pro Cys Glu Asn Met Asn Leu Gln Arg
145                 150                 155                 160

Pro Asp Gly Leu

<210> SEQ ID NO 43
<211> LENGTH: 173
<212> TYPE: PRT
<213> ORGANISM: Homo sapiens

<400> SEQUENCE: 43

Met Ser Leu Leu Gly Pro Lys Val Leu Leu Phe Leu Ala Ala Phe Ile
1               5                   10                  15

Ile Thr Ser Asp Trp Ile Pro Leu Gly Val Asn Ser Gln Arg Gly Asp
                20                  25                  30

Asp Val Thr Gln Ala Thr Pro Glu Thr Phe Thr Glu Asp Pro Asn Leu
            35                  40                  45

Val Asn Asp Pro Ala Thr Asp Glu Thr Val Leu Ala Val Leu Ala Asp
        50                  55                  60

Ile Ala Pro Ser Thr Asp Asp Leu Ala Ser Leu Ser Glu Lys Asn Thr
65                  70                  75                  80

Thr Ala Glu Cys Trp Asp Glu Lys Phe Thr Cys Thr Arg Leu Tyr Ser
                85                  90                  95

Val His Arg Pro Val Lys Gln Cys Ile His Gln Leu Cys Phe Thr Ser
            100                 105                 110

Leu Arg Arg Met Tyr Ile Val Asn Lys Glu Ile Cys Ser Arg Leu Val
        115                 120                 125

Cys Lys Glu His Glu Ala Met Lys Asp Glu Leu Cys Arg Gln Met Ala
130                 135                 140
```

-continued

Gly Leu Pro Pro Arg Arg Leu Arg Arg Ser Asn Tyr Phe Arg Leu Pro
145                 150                 155                 160

Pro Cys Glu Asn Val Asp Leu Gln Arg Pro Asn Gly Leu
            165                 170

<210> SEQ ID NO 44
<211> LENGTH: 104
<212> TYPE: PRT
<213> ORGANISM: Mus musculus

<400> SEQUENCE: 44

Met Lys Ser Leu Leu Pro Leu Ala Ile Leu Ala Ala Leu Ala Val Ala
1               5                   10                  15

Thr Leu Cys Tyr Glu Ser His Glu Ser Met Glu Ser Tyr Glu Ile Ser
                20                  25                  30

Pro Phe Ile Asn Arg Arg Asn Ala Asn Thr Phe Met Ser Pro Gln Gln
            35                  40                  45

Arg Trp Arg Ala Lys Ala Gln Lys Arg Val Glu Arg Asn Lys Pro
    50                  55                  60

Ala Tyr Glu Ile Asn Arg Glu Ala Cys Asp Asp Tyr Lys Leu Cys Glu
65                  70                  75                  80

Arg Tyr Ala Met Val Tyr Gly Tyr Asn Ala Ala Tyr Asn Arg Tyr Phe
                85                  90                  95

Arg Gln Arg Arg Gly Ala Lys Tyr
            100

<210> SEQ ID NO 45
<211> LENGTH: 103
<212> TYPE: PRT
<213> ORGANISM: Homo sapiens

<400> SEQUENCE: 45

Met Lys Ser Leu Ile Leu Leu Ala Ile Leu Ala Ala Leu Ala Val Val
1               5                   10                  15

Thr Leu Cys Tyr Glu Ser His Glu Ser Met Glu Ser Tyr Glu Leu Asn
                20                  25                  30

Pro Phe Ile Asn Arg Arg Asn Ala Asn Thr Phe Ile Ser Pro Gln Gln
            35                  40                  45

Arg Trp Arg Ala Lys Val Gln Glu Arg Ile Arg Glu Arg Ser Lys Pro
    50                  55                  60

Val His Glu Leu Asn Arg Glu Ala Cys Asp Asp Tyr Arg Leu Cys Glu
65                  70                  75                  80

Arg Tyr Ala Met Val Tyr Gly Tyr Asn Ala Ala Tyr Asn Arg Tyr Phe
                85                  90                  95

Arg Lys Arg Arg Gly Ala Lys
            100

<210> SEQ ID NO 46
<211> LENGTH: 415
<212> TYPE: PRT
<213> ORGANISM: Mus musculus

<400> SEQUENCE: 46

Met Leu Gln Lys Thr Val Leu Leu Ala Leu Val Ala Gln Val Leu
1               5                   10                  15

Met Leu Glu Asn Gly Leu Leu Arg Thr Pro Pro Met Gly Trp Leu Ala
                20                  25                  30

Trp Glu Arg Phe Arg Cys Asn Ile Asp Cys Val Glu Asp Pro Lys Asn
            35                  40                  45

```
Cys Ile Ser Glu Arg Leu Phe Met Glu Met Ala Asp Arg Leu Ala Gln
     50                  55                  60

Asp Gly Trp Arg Asp Leu Gly Tyr Val Tyr Leu Asn Ile Asp Asp Cys
65                  70                  75                  80

Trp Ile Gly Gly Arg Asp Ala Ser Gly Arg Leu Ile Pro Asp Pro Lys
                85                  90                  95

Arg Phe Pro His Gly Ile Ala Phe Leu Ala Asp Tyr Ala His Ser Leu
                100                 105                 110

Gly Leu Lys Leu Gly Ile Tyr Glu Asp Met Gly Lys Met Thr Cys Met
            115                 120                 125

Gly Tyr Pro Gly Thr Thr Leu Asp Lys Val Glu Leu Asp Ala Glu Thr
            130                 135                 140

Phe Ala Glu Trp Lys Val Asp Met Leu Lys Leu Asp Gly Cys Phe Ser
145                 150                 155                 160

Ser Ser Arg Glu Arg Ala Glu Gly Tyr Pro Lys Met Ala Ala Ala Leu
                165                 170                 175

Asn Ala Thr Gly Arg Pro Ile Ala Phe Ser Cys Ser Trp Pro Ala Tyr
            180                 185                 190

Glu Gly Gly Leu Pro Pro Lys Val Asn Tyr Thr Glu Val Ser Arg Val
            195                 200                 205

Cys Asn Leu Trp Arg Asn Tyr Lys Asp Ile Gln Asp Ser Trp Lys Ser
210                 215                 220

Val Leu Ser Ile Leu Asp Trp Phe Val Arg His Gln Asp Val Pro Gln
225                 230                 235                 240

Pro Val Ala Gly Pro Gly His Trp Asn Asp Pro Asp Met Leu Leu Ile
                245                 250                 255

Gly Asn Phe Gly Leu Ser Phe Asp Glu Ser Arg Ala Gln Met Ala Leu
            260                 265                 270

Trp Thr Val Leu Ala Ala Pro Leu Leu Met Ser Thr Asp Leu Arg Thr
            275                 280                 285

Ile Ser Pro Gln Asn Met Asp Ile Leu Gln Asn Pro Leu Met Ile Lys
            290                 295                 300

Ile Asn Gln Asp Pro Leu Gly Ile Gln Gly Arg Arg Ile Leu Lys Ser
305                 310                 315                 320

Lys Ser His Ile Glu Val Phe Lys Arg Tyr Leu Ser Asn Gln Ala Ser
                325                 330                 335

Ala Leu Val Phe Phe Ser Arg Arg Thr Asp Met Pro Phe Arg Phe His
            340                 345                 350

Cys Ser Leu Leu Glu Leu Asn Tyr Pro Lys Gly Arg Val Tyr Glu Gly
            355                 360                 365

Gln Asn Val Phe Thr Gly Asp Ile Phe Ser Gly Leu Gln Thr Glu Val
            370                 375                 380

Asn Phe Thr Val Ile Ile Asn Pro Ser Gly Val Val Met Trp Tyr Leu
385                 390                 395                 400

Tyr Pro Ile Lys Asp Leu Gly Ile Ser Thr Met Met Ser His Trp
                405                 410                 415

<210> SEQ ID NO 47
<211> LENGTH: 411
<212> TYPE: PRT
<213> ORGANISM: Homo sapiens

<400> SEQUENCE: 47

Met Leu Leu Lys Thr Val Leu Leu Leu Gly His Val Ala Gln Val Leu
1               5                   10                  15
```

Met Leu Asp Asn Gly Leu Leu Gln Thr Pro Pro Met Gly Trp Leu Ala
                 20                  25                  30

Trp Glu Arg Phe Arg Cys Asn Ile Asn Cys Asp Glu Asp Pro Lys Asn
             35                  40                  45

Cys Ile Ser Glu Gln Leu Phe Met Glu Met Ala Asp Arg Met Ala Gln
         50                  55                  60

Asp Gly Trp Arg Asp Met Gly Tyr Thr Tyr Leu Asn Ile Asp Asp Cys
 65                  70                  75                  80

Trp Ile Gly Gly Arg Asp Ala Ser Gly Arg Leu Met Pro Asp Pro Lys
                 85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
            115                 120                 125

Gly Tyr Pro Gly Thr Thr Leu Asp Lys Val Val Gln Asp Ala Gln Thr
            130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Ser Trp Pro Ala Tyr
            180                 185                 190

Glu Gly Gly Leu Pro Pro Arg Val Asn Tyr Ser Leu Leu Ala Asp Ile
            195                 200                 205

Cys Asn Leu Trp Arg Asn Tyr Asp Asp Ile Gln Asp Ser Trp Trp Ser
210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
            245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
            275                 280                 285

Ile Ser Ala Gln Asn Met Asp Ile Leu Gln Asn Pro Leu Met Ile Lys
            290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
            355                 360                 365

Gln Asp Val Tyr Ser Gly Asp Ile Ile Ser Gly Leu Arg Asp Glu Thr
            370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
            405                 410

<210> SEQ ID NO 48
<211> LENGTH: 178
<212> TYPE: PRT

<213> ORGANISM: Mus musculus

<400> SEQUENCE: 48

Met Leu Trp Val Leu Val Gly Ala Val Leu Pro Val Met Leu Leu Ala
1               5                   10                  15

Ala Pro Pro Ile Asn Lys Leu Ala Leu Phe Pro Asp Lys Ser Ala
            20                  25                  30

Trp Cys Glu Ala Lys Asn Ile Thr Gln Ile Val Gly His Ser Gly Cys
        35                  40                  45

Glu Ala Lys Ser Ile Gln Asn Arg Ala Cys Leu Gly Gln Cys Phe Ser
50                  55                  60

Tyr Ser Val Pro Asn Thr Phe Pro Gln Ser Thr Glu Ser Leu Val His
65                  70                  75                  80

Cys Asp Ser Cys Met Pro Ala Gln Ser Met Trp Glu Ile Val Thr Leu
                85                  90                  95

Glu Cys Pro Asp His Glu Glu Val Pro Arg Val Asp Lys Leu Val Glu
            100                 105                 110

Lys Ile Val His Cys Ser Cys Gln Ala Cys Gly Lys Glu Pro Ser His
        115                 120                 125

Glu Gly Leu Asn Val Tyr Val Gln Gly Glu Asp Ser Pro Gly Ser Gln
130                 135                 140

Pro Gly Pro His Ser His Ala His Pro His Pro Gly Gly Gln Thr Pro
145                 150                 155                 160

Glu Pro Glu Glu Pro Pro Gly Ala Pro Gln Val Glu Glu Gly Ala
            165                 170                 175

Glu Asp

<210> SEQ ID NO 49
<211> LENGTH: 181
<212> TYPE: PRT
<213> ORGANISM: Homo sapiens

<400> SEQUENCE: 49

Met Met Leu Arg Val Leu Val Gly Ala Val Leu Pro Ala Met Leu Leu
1               5                   10                  15

Ala Ala Pro Pro Pro Ile Asn Lys Leu Ala Leu Phe Pro Asp Lys Ser
            20                  25                  30

Ala Trp Cys Glu Ala Lys Asn Ile Thr Gln Ile Val Gly His Ser Gly
        35                  40                  45

Cys Glu Ala Lys Ser Ile Gln Asn Arg Ala Cys Leu Gly Gln Cys Phe
50                  55                  60

Ser Tyr Ser Val Pro Asn Thr Phe Pro Gln Ser Thr Glu Ser Leu Val
65                  70                  75                  80

His Cys Asp Ser Cys Met Pro Ala Gln Ser Met Trp Glu Ile Val Thr
                85                  90                  95

Leu Glu Cys Pro Gly His Glu Glu Val Pro Arg Val Asp Lys Leu Val
            100                 105                 110

Glu Lys Ile Leu His Cys Ser Cys Gln Ala Cys Gly Lys Glu Pro Ser
        115                 120                 125

His Glu Gly Leu Ser Val Tyr Val Gln Gly Glu Asp Gly Pro Gly Ser
130                 135                 140

Gln Pro Gly Thr His Pro His Pro His Pro His Pro His Pro Gly Gly
145                 150                 155                 160

Gln Thr Pro Glu Pro Glu Asp Pro Pro Gly Ala Pro His Thr Glu Glu
            165                 170                 175

Glu Gly Ala Glu Asp
        180

<210> SEQ ID NO 50
<211> LENGTH: 307
<212> TYPE: PRT
<213> ORGANISM: Mus musculus

<400> SEQUENCE: 50

Met Leu Cys Leu Lys Pro Val Lys Leu Gly Ser Leu Glu Val Gly His
1               5                   10                  15

Gly Gln His Gly Gly Val Leu Ala Cys Gly Arg Ala Val Gln Gly Ala
            20                  25                  30

Gly Trp His Ala Gly Pro Lys Leu Thr Ser Val Ser Gly Pro Asn Lys
        35                  40                  45

Gly Phe Ala Lys Asp Ala Ala Phe Tyr Thr Gly Arg Ser Glu Val His
    50                  55                  60

Ser Val Met Ser Met Leu Phe Tyr Thr Leu Ile Thr Ala Phe Leu Ile
65                  70                  75                  80

Gly Val Gln Ala Glu Pro Tyr Thr Asp Ser Asn Val Pro Glu Gly Asp
                85                  90                  95

Ser Val Pro Glu Ala His Trp Thr Lys Leu Gln His Ser Leu Asp Thr
            100                 105                 110

Ala Leu Arg Arg Ala Arg Ser Ala Pro Thr Ala Pro Ile Ala Ala Arg
        115                 120                 125

Val Thr Gly Gln Thr Arg Asn Ile Thr Val Asp Pro Arg Leu Phe Lys
    130                 135                 140

Lys Arg Arg Leu His Ser Pro Arg Val Leu Phe Ser Thr Gln Pro Pro
145                 150                 155                 160

Pro Thr Ser Ser Asp Thr Leu Asp Leu Asp Phe Gln Ala His Gly Thr
                165                 170                 175

Ile Pro Phe Asn Arg Thr His Arg Ser Lys Arg Ser Ser Thr His Pro
            180                 185                 190

Val Phe His Met Gly Glu Phe Ser Val Cys Asp Ser Val Ser Val Trp
        195                 200                 205

Val Gly Asp Lys Thr Thr Ala Thr Asp Ile Lys Gly Lys Glu Val Thr
    210                 215                 220

Val Leu Ala Glu Val Asn Ile Asn Asn Ser Val Phe Arg Gln Tyr Phe
225                 230                 235                 240

Phe Glu Thr Lys Cys Arg Ala Ser Asn Pro Val Glu Ser Gly Cys Arg
                245                 250                 255

Gly Ile Asp Ser Lys His Trp Asn Ser Tyr Cys Thr Thr Thr His Thr
            260                 265                 270

Phe Val Lys Ala Leu Thr Thr Asp Glu Lys Gln Ala Ala Trp Arg Phe
        275                 280                 285

Ile Arg Ile Asp Thr Ala Cys Val Cys Val Leu Ser Arg Lys Ala Thr
    290                 295                 300

Arg Arg Gly
305

<210> SEQ ID NO 51
<211> LENGTH: 299
<212> TYPE: PRT
<213> ORGANISM: Homo sapiens

<400> SEQUENCE: 51

Gly Arg Val Gly Ala Gly Ser Arg Arg Gly Ala Gln Arg Val Leu Ala

```
            1               5                  10                 15
Ser Gly Arg Ala Val Gln Gly Ala Gly Trp His Ala Gly Pro Lys Leu
                20                 25                 30

Ser Ser Ala Ser Gly Pro Asn Asn Ser Phe Thr Lys Gly Ala Ala Phe
                35                 40                 45

Tyr Pro Gly His Thr Glu Val His Ser Val Met Ser Met Leu Phe Tyr
                50                 55                 60

Thr Leu Ile Thr Ala Phe Leu Ile Gly Ile Gln Ala Glu Pro His Ser
 65                 70                 75                 80

Glu Ser Asn Val Pro Ala Gly His Thr Ile Pro Gln Val His Trp Thr
                85                 90                 95

Lys Leu Gln His Ser Leu Asp Thr Ala Leu Arg Arg Ala Arg Ser Ala
                100                105                110

Pro Ala Ala Ala Ile Ala Ala Arg Val Ala Gly Gln Thr Arg Asn Ile
                115                120                125

Thr Val Asp Pro Arg Leu Phe Lys Lys Arg Arg Leu Arg Ser Pro Arg
                130                135                140

Val Leu Phe Ser Thr Gln Pro Pro Arg Glu Ala Ala Asp Thr Gln Asp
145                 150                155                160

Leu Asp Phe Glu Val Gly Gly Ala Ala Pro Phe Asn Arg Thr His Arg
                165                170                175

Ser Lys Arg Ser Ser Ser His Pro Ile Phe His Arg Gly Glu Phe Ser
                180                185                190

Val Cys Asp Ser Val Ser Val Trp Val Gly Asp Lys Thr Thr Ala Thr
                195                200                205

Asp Ile Lys Gly Lys Glu Val Met Val Leu Gly Glu Val Asn Ile Asn
                210                215                220

Asn Ser Val Phe Lys Gln Tyr Phe Phe Glu Thr Lys Cys Arg Asp Pro
225                 230                235                240

Asn Pro Val Asp Ser Gly Cys Arg Gly Ile Asp Ser Lys His Trp Asn
                245                250                255

Ser Tyr Cys Thr Thr Thr His Thr Phe Val Lys Ala Leu Thr Met Asp
                260                265                270

Gly Lys Gln Ala Ala Trp Arg Phe Ile Arg Ile Asp Thr Ala Cys Val
                275                280                285

Cys Val Leu Ser Arg Lys Ala Val Arg Arg Ala
                290                295

<210> SEQ ID NO 52
<211> LENGTH: 592
<212> TYPE: PRT
<213> ORGANISM: Mus musculus

<400> SEQUENCE: 52

Met Ala Val Leu Leu Ala Ala Val Leu Ala Ser Ser Leu Tyr Leu Gln
 1               5                  10                 15

Val Ala Ala Asp Phe Asp Gly Arg Trp Pro Arg Gln Ile Val Ser Ser
                20                 25                 30

Ile Gly Leu Cys Arg Tyr Gly Arg Ile Asp Cys Cys Trp Gly Trp
                35                 40                 45

Ala Arg Gln Ser Trp Gly Gln Cys Gln Pro Val Cys Gln Pro Gln Cys
                50                 55                 60

Lys His Gly Glu Cys Val Gly Pro Asn Lys Cys Lys Cys His Pro Gly
 65                 70                 75                 80

Phe Ala Gly Lys Thr Cys Asn Gln Asp Glu Ser Phe His Pro Thr Pro
```

-continued

```
                    85                  90                  95
Leu Asp Gln Gly Ser Glu Gln Pro Leu Phe Gln Pro Asp His Gln
                100                 105                 110

Ala Thr Asn Val Pro Ser Arg Asp Leu Asn Glu Cys Gly Leu Lys Pro
                115                 120                 125

Arg Pro Cys Lys His Arg Cys Met Asn Thr Phe Gly Ser Tyr Lys Cys
                130                 135                 140

Tyr Cys Leu Asn Gly Tyr Met Leu Leu Pro Asp Gly Ser Cys Ser Ser
145                 150                 155                 160

Ala Leu Ser Cys Ser Met Ala Asn Cys Gln Tyr Gly Cys Asp Val Val
                165                 170                 175

Lys Gly Gln Val Arg Cys Gln Cys Pro Ser Pro Gly Leu Gln Leu Ala
                180                 185                 190

Pro Asp Gly Arg Thr Cys Val Asp Ile Asp Glu Cys Ala Thr Gly Arg
                195                 200                 205

Val Ser Cys Pro Arg Phe Arg Gln Cys Val Asn Thr Phe Gly Ser Tyr
                210                 215                 220

Ile Cys Lys Cys His Thr Gly Phe Asp Leu Met Tyr Ile Gly Gly Lys
225                 230                 235                 240

Tyr Gln Cys His Asp Ile Asp Glu Cys Ser Leu Gly Gln His Gln Cys
                245                 250                 255

Ser Ser Tyr Ala Arg Cys Tyr Asn Ile His Gly Ser Tyr Lys Cys Gln
                260                 265                 270

Cys Arg Asp Gly Tyr Glu Gly Asp Gly Leu Asn Cys Val Tyr Ile Pro
                275                 280                 285

Lys Val Met Ile Glu Pro Ser Gly Pro Ile His Met Pro Glu Arg Asn
                290                 295                 300

Gly Thr Ile Ser Lys Gly Asp Gly Gly His Ala Asn Arg Ile Pro Asp
305                 310                 315                 320

Ala Gly Ser Thr Arg Trp Pro Leu Lys Thr Pro Tyr Ile Pro Pro Val
                325                 330                 335

Ile Thr Asn Arg Pro Thr Ser Lys Pro Thr Thr Arg Pro Thr Pro Asn
                340                 345                 350

Pro Thr Pro Gln Pro Thr Pro Pro Pro Pro Pro Leu Pro Thr Glu
                355                 360                 365

Pro Arg Thr Thr Pro Leu Pro Pro Thr Pro Glu Arg Pro Ser Thr Arg
                370                 375                 380

Pro Thr Thr Ile Ala Pro Ala Thr Ser Thr Thr Thr Arg Val Ile Thr
385                 390                 395                 400

Val Asp Asn Arg Ile Gln Thr Asp Pro Gln Lys Pro Arg Gly Asp Val
                405                 410                 415

Phe Ile Pro Arg Gln Pro Thr Asn Asp Leu Phe Glu Ile Phe Glu Ile
                420                 425                 430

Glu Arg Gly Val Ser Ala Asp Glu Glu Val Lys Asp Asp Pro Gly Ile
                435                 440                 445

Leu Ile His Ser Cys Asn Phe Asp His Gly Leu Cys Gly Trp Ile Arg
450                 455                 460

Glu Lys Asp Ser Asp Leu His Trp Glu Thr Ala Arg Asp Pro Ala Gly
465                 470                 475                 480

Gly Gln Tyr Leu Thr Val Ser Ala Ala Lys Ala Pro Gly Gly Lys Ala
                485                 490                 495

Ala Arg Leu Val Leu Arg Leu Gly His Leu Met His Ser Gly Asp Leu
                500                 505                 510
```

-continued

```
Cys Leu Ser Phe Arg His Lys Val Thr Gly Leu His Ser Gly Thr Leu
        515                 520                 525

Gln Val Phe Val Arg Lys His Gly Thr His Gly Ala Ala Leu Trp Gly
    530                 535                 540

Arg Asn Gly Gly His Gly Trp Arg Gln Thr Gln Ile Thr Leu Arg Gly
545                 550                 555                 560

Ala Asp Val Lys Ser Val Ile Phe Lys Gly Glu Lys Arg Arg Gly His
                565                 570                 575

Thr Gly Glu Ile Gly Leu Asp Asp Val Ser Leu Lys Arg Gly Arg Cys
            580                 585                 590

<210> SEQ ID NO 53
<211> LENGTH: 565
<212> TYPE: PRT
<213> ORGANISM: Homo sapiens

<400> SEQUENCE: 53

Met Asp Phe Leu Leu Ala Leu Val Leu Val Ser Ser Leu Tyr Leu Gln
1               5                   10                  15

Ala Ala Ala Glu Phe Asp Gly Arg Trp Pro Arg Gln Ile Val Ser Ser
            20                  25                  30

Ile Gly Leu Cys Arg Tyr Gly Gly Arg Ile Asp Cys Cys Trp Gly Trp
        35                  40                  45

Ala Arg Gln Ser Trp Gly Gln Cys Gln Pro Val Cys Gln Pro Arg Cys
    50                  55                  60

Lys His Gly Glu Cys Ile Gly Pro Asn Lys Cys Lys Cys His Pro Gly
65                  70                  75                  80

Tyr Ala Gly Lys Thr Cys Asn Gln Asp Leu Asn Glu Cys Gly Leu Lys
                85                  90                  95

Pro Arg Pro Cys Lys His Arg Cys Met Asn Thr Tyr Gly Ser Tyr Lys
            100                 105                 110

Cys Tyr Cys Leu Asn Gly Tyr Met Leu Met Pro Asp Gly Ser Cys Ser
        115                 120                 125

Ser Ala Leu Thr Cys Ser Met Ala Asn Cys Gln Tyr Gly Cys Asp Val
    130                 135                 140

Val Lys Gly Gln Ile Arg Cys Gln Cys Pro Ser Pro Gly Leu Gln Leu
145                 150                 155                 160

Ala Pro Asp Gly Arg Thr Cys Val Asp Val Asp Glu Cys Ala Thr Gly
                165                 170                 175

Arg Ala Ser Cys Pro Arg Phe Arg Gln Cys Val Asn Thr Phe Gly Ser
            180                 185                 190

Tyr Ile Cys Lys Cys His Lys Gly Phe Asp Leu Met Tyr Ile Gly Gly
        195                 200                 205

Lys Tyr Gln Cys His Asp Ile Asp Glu Cys Ser Leu Gly Gln Tyr Gln
    210                 215                 220

Cys Ser Ser Phe Ala Arg Cys Tyr Asn Ile Arg Gly Ser Tyr Lys Cys
225                 230                 235                 240

Lys Cys Lys Glu Gly Tyr Gln Gly Asp Gly Leu Thr Cys Val Tyr Ile
                245                 250                 255

Pro Lys Val Met Ile Glu Pro Ser Gly Pro Ile His Val Pro Lys Gly
            260                 265                 270

Asn Gly Thr Ile Leu Lys Gly Asp Thr Gly Asn Asn Asn Trp Ile Pro
        275                 280                 285

Asp Val Gly Ser Thr Trp Trp Pro Pro Lys Thr Pro Tyr Ile Pro Pro
    290                 295                 300
```

Ile Ile Thr Asn Arg Pro Thr Ser Lys Pro Thr Arg Pro Thr Pro
305                 310                 315                 320

Lys Pro Thr Pro Ile Pro Thr Pro Pro Pro Pro Pro Leu Pro Thr
            325                 330                 335

Glu Leu Arg Thr Pro Leu Pro Pro Thr Thr Pro Glu Arg Pro Thr Thr
            340                 345                 350

Gly Leu Thr Thr Ile Ala Pro Ala Ser Thr Pro Gly Gly Ile
            355                 360                 365

Thr Val Asp Asn Arg Val Gln Thr Asp Pro Gln Lys Pro Arg Gly Asp
            370                 375                 380

Val Phe Ile Pro Arg Gln Pro Ser Asn Asp Leu Phe Glu Ile Phe Glu
385                 390                 395                 400

Ile Glu Arg Gly Val Ser Ala Asp Asp Glu Ala Lys Asp Asp Pro Gly
                405                 410                 415

Val Leu Val His Ser Cys Asn Phe Asp His Gly Leu Cys Gly Trp Ile
            420                 425                 430

Arg Glu Lys Asp Asn Asp Leu His Trp Glu Pro Ile Arg Asp Pro Ala
            435                 440                 445

Gly Gly Gln Tyr Leu Thr Val Ser Ala Ala Lys Ala Pro Gly Gly Lys
450                 455                 460

Ala Ala Arg Leu Val Leu Pro Leu Gly Arg Leu Met His Ser Gly Asp
465                 470                 475                 480

Leu Cys Leu Ser Phe Arg His Lys Val Thr Gly Leu His Ser Gly Thr
                485                 490                 495

Leu Gln Val Phe Val Arg Lys His Gly Ala His Gly Ala Ala Leu Trp
                500                 505                 510

Gly Arg Asn Gly Gly His Gly Trp Arg Gln Thr Gln Ile Thr Leu Arg
            515                 520                 525

Gly Ala Asp Ile Lys Ser Val Val Phe Lys Gly Glu Lys Arg Arg Gly
            530                 535                 540

His Thr Gly Glu Ile Gly Leu Asp Asp Val Ser Leu Lys Lys Gly His
545                 550                 555                 560

Cys Ser Glu Glu Arg
                565

<210> SEQ ID NO 54
<211> LENGTH: 457
<212> TYPE: PRT
<213> ORGANISM: Mus musculus

<400> SEQUENCE: 54

Met Gln Pro Ala Arg Lys Leu Leu Ser Leu Leu Val Leu Leu Val Met
1               5                   10                  15

Gly Thr Glu Leu Thr Gln Val Leu Pro Thr Asn Pro Glu Glu Ser Trp
            20                  25                  30

Gln Val Tyr Ser Ser Ala Gln Asp Ser Glu Gly Arg Cys Ile Cys Thr
        35                  40                  45

Val Val Ala Pro Gln Gln Thr Met Cys Ser Arg Asp Ala Arg Thr Lys
    50                  55                  60

Gln Leu Arg Gln Leu Leu Glu Lys Val Gln Asn Met Ser Gln Ser Ile
65                  70                  75                  80

Glu Val Leu Asp Arg Arg Thr Gln Arg Asp Leu Gln Tyr Val Glu Lys
                85                  90                  95

Met Glu Asn Gln Met Lys Gly Leu Glu Thr Lys Phe Lys Gln Val Glu
            100                 105                 110

Glu Ser His Lys Gln His Leu Ala Arg Gln Phe Lys Ala Ile Lys Ala
        115                 120                 125

Lys Met Asp Glu Leu Arg Pro Leu Ile Pro Val Leu Glu Glu Tyr Lys
    130                 135                 140

Ala Asp Ala Lys Leu Val Leu Gln Phe Lys Glu Val Gln Asn Leu
145                 150                 155                 160

Thr Ser Val Leu Asn Glu Leu Gln Glu Glu Ile Gly Ala Tyr Asp Tyr
                165                 170                 175

Asp Glu Leu Gln Ser Arg Val Ser Asn Leu Glu Glu Arg Leu Arg Ala
            180                 185                 190

Cys Met Gln Lys Leu Ala Cys Gly Lys Leu Thr Gly Ile Ser Asp Pro
        195                 200                 205

Val Thr Val Lys Thr Ser Gly Ser Arg Phe Gly Ser Trp Met Thr Asp
    210                 215                 220

Pro Leu Ala Pro Glu Gly Asp Asn Arg Val Trp Tyr Met Asp Gly Tyr
225                 230                 235                 240

His Asn Asn Arg Phe Val Arg Glu Tyr Lys Ser Met Val Asp Phe Met
                245                 250                 255

Asn Thr Asp Asn Phe Thr Ser His Arg Leu Pro His Pro Trp Ser Gly
            260                 265                 270

Thr Gly Gln Val Val Tyr Asn Gly Ser Ile Tyr Phe Asn Lys Phe Gln
        275                 280                 285

Ser His Ile Ile Ile Arg Phe Asp Leu Lys Thr Glu Ala Ile Leu Lys
    290                 295                 300

Thr Arg Ser Leu Asp Tyr Ala Gly Tyr Asn Asn Met Tyr His Tyr Ala
305                 310                 315                 320

Trp Gly Gly His Ser Asp Ile Asp Leu Met Val Asp Glu Asn Gly Leu
                325                 330                 335

Trp Ala Val Tyr Ala Thr Asn Gln Asn Ala Gly Asn Ile Val Ile Ser
            340                 345                 350

Lys Leu Asp Pro Val Ser Leu Gln Ile Leu Gln Thr Trp Asn Thr Ser
        355                 360                 365

Tyr Pro Lys Arg Ser Ala Gly Glu Ala Phe Ile Ile Cys Gly Thr Leu
    370                 375                 380

Tyr Val Thr Asn Gly Tyr Ser Gly Gly Thr Lys Val His Tyr Ala Tyr
385                 390                 395                 400

Gln Thr Asn Ala Ser Thr Tyr Glu Tyr Ile Asp Ile Pro Phe Gln Asn
                405                 410                 415

Lys Tyr Ser His Ile Ser Met Leu Asp Tyr Asn Pro Lys Asp Arg Ala
            420                 425                 430

Leu Tyr Ala Trp Asn Asn Gly His Gln Thr Leu Tyr Asn Val Thr Leu
        435                 440                 445

Phe His Val Ile Arg Ser Asp Glu Leu
450                 455

<210> SEQ ID NO 55
<211> LENGTH: 485
<212> TYPE: PRT
<213> ORGANISM: Homo sapiens

<400> SEQUENCE: 55

Met Ser Val Pro Leu Leu Lys Ile Gly Val Val Leu Ser Thr Met Ala
1               5                   10                  15

Met Ile Thr Asn Trp Met Ser Gln Thr Leu Pro Ser Leu Val Gly Leu
            20                  25                  30

```
Asn Thr Thr Arg Leu Ser Ala Ala Ser Gly Gly Thr Leu Asp Arg Ser
         35                  40                  45

Thr Gly Val Leu Pro Thr Asn Pro Glu Glu Ser Trp Gln Val Tyr Ser
 50                  55                  60

Ser Ala Gln Asp Ser Glu Gly Arg Cys Ile Cys Thr Val Val Ala Pro
 65                  70                  75                  80

Gln Gln Thr Met Cys Ser Arg Asp Ala Arg Thr Lys Gln Leu Arg Gln
                 85                  90                  95

Leu Leu Glu Lys Val Gln Asn Met Ser Gln Ser Ile Glu Val Leu Asp
            100                 105                 110

Arg Arg Thr Gln Arg Asp Leu Gln Tyr Val Glu Lys Met Glu Asn Gln
            115                 120                 125

Met Lys Gly Leu Glu Ser Lys Phe Lys Gln Val Glu Glu Ser His Lys
    130                 135                 140

Gln His Leu Ala Arg Gln Phe Lys Ala Ile Lys Ala Lys Met Asp Glu
145                 150                 155                 160

Leu Arg Pro Leu Ile Pro Val Leu Glu Glu Tyr Lys Ala Asp Ala Lys
                165                 170                 175

Leu Val Leu Gln Phe Lys Glu Glu Val Gln Asn Leu Thr Ser Val Leu
            180                 185                 190

Asn Glu Leu Gln Glu Glu Ile Gly Ala Tyr Asp Tyr Asp Glu Leu Gln
            195                 200                 205

Ser Arg Val Ser Asn Leu Glu Glu Arg Leu Arg Ala Cys Met Gln Lys
210                 215                 220

Leu Ala Cys Gly Lys Leu Thr Gly Ile Ser Asp Pro Val Thr Val Lys
225                 230                 235                 240

Thr Ser Gly Ser Arg Phe Gly Ser Trp Met Thr Asp Pro Leu Ala Pro
                245                 250                 255

Glu Gly Asp Asn Arg Val Trp Tyr Met Asp Gly Tyr His Asn Asn Arg
            260                 265                 270

Phe Val Arg Glu Tyr Lys Ser Met Val Asp Phe Met Asn Thr Asp Asn
            275                 280                 285

Phe Thr Ser His Arg Leu Pro His Pro Trp Ser Gly Thr Gly Gln Val
    290                 295                 300

Val Tyr Asn Gly Ser Ile Tyr Phe Asn Lys Phe Gln Ser His Ile Ile
305                 310                 315                 320

Ile Arg Phe Asp Leu Lys Thr Glu Thr Ile Leu Lys Thr Arg Ser Leu
                325                 330                 335

Asp Tyr Ala Gly Tyr Asn Asn Met Tyr His Tyr Ala Trp Gly Gly His
            340                 345                 350

Ser Asp Ile Asp Leu Met Val Asp Glu Ser Gly Leu Trp Ala Val Tyr
            355                 360                 365

Ala Thr Asn Gln Asn Ala Gly Asn Ile Val Val Ser Arg Leu Asp Pro
    370                 375                 380

Val Ser Leu Gln Thr Leu Gln Thr Trp Asn Thr Ser Tyr Pro Lys Arg
385                 390                 395                 400

Ser Ala Gly Glu Ala Phe Ile Ile Cys Gly Thr Leu Tyr Val Thr Asn
                405                 410                 415

Gly Tyr Ser Gly Gly Thr Lys Val His Tyr Ala Tyr Gln Thr Asn Ala
            420                 425                 430

Ser Thr Tyr Glu Tyr Ile Asp Ile Pro Phe Gln Asn Lys Tyr Ser His
            435                 440                 445

Ile Ser Met Leu Asp Tyr Asn Pro Lys Asp Arg Ala Leu Tyr Ala Trp
450                 455                 460
```

```
Asn Asn Gly His Gln Ile Leu Tyr Asn Val Thr Leu Phe His Val Ile
465                 470                 475                 480

Arg Ser Asp Glu Leu
            485

<210> SEQ ID NO 56
<211> LENGTH: 118
<212> TYPE: PRT
<213> ORGANISM: Mus musculus

<400> SEQUENCE: 56

Met Lys Val Val Ile Leu Met Ala Leu Leu Val Leu Thr Ala His Cys
1               5                   10                  15

Val Pro Val Ser Arg Phe Pro Gly Lys Ile Phe Leu Tyr Cys Pro Phe
            20                  25                  30

Phe Asn Arg Lys His Cys Gln Arg Phe Cys Glu Phe Phe Lys Ile Cys
        35                  40                  45

Arg Lys Pro Pro Leu Ser Arg Arg Thr Thr Val Val Pro Ser Phe Pro
    50                  55                  60

Leu Thr Thr Glu Ala Asp Leu Ser Leu Thr Gly Gly Pro Leu Thr Pro
65                  70                  75                  80

Thr Gly Gly Glu Ile Gln Asp Ser Arg Val Pro His Ser Pro Glu Lys
                85                  90                  95

Pro Leu Pro Pro His Ser Ala His Ala Thr Val Gly Ser Cys Phe Gln
            100                 105                 110

Leu Leu Pro Ala Pro Gln
        115

<210> SEQ ID NO 57
<211> LENGTH: 32
<212> TYPE: DNA
<213> ORGANISM: Artificial
<220> FEATURE:
<223> OTHER INFORMATION: primer

<400> SEQUENCE: 57
ggcggcgcgg ccgcatggag aagatgttgg tg                              32

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58
ggcggcccgc ggtctgtatt ttaggcgatt                                 30

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
ggcggcctcg agatggagaa gatgttggtg                                 30

<210> SEQ ID NO 60
<211> LENGTH: 36
<212> TYPE: DNA
<213> ORGANISM: Artificial
```

-continued

```
<220> FEATURE:
<223> OTHER INFORMATION: primer

<400> SEQUENCE: 60
ccggccgaat tctcaatggt gatggtgatg atgacc                                36

<210> SEQ ID NO 61
<211> LENGTH: 30
<212> TYPE: DNA
<213> ORGANISM: Artificial
<220> FEATURE:
<223> OTHER INFORMATION: primer

<400> SEQUENCE: 61
ggcgccggat ccatgaatgt atgtgcgttc                                       30

<210> SEQ ID NO 62
<211> LENGTH: 30
<212> TYPE: DNA
<213> ORGANISM: Artificial
<220> FEATURE:
<223> OTHER INFORMATION: primer

<400> SEQUENCE: 62
ggcgccggat ccatgaatgt atgtgcgttc                                       30

<210> SEQ ID NO 63
<211> LENGTH: 30
<212> TYPE: DNA
<213> ORGANISM: Artificial
<220> FEATURE:
<223> OTHER INFORMATION: primer

<400> SEQUENCE: 63
ggcgccagat ctatgaatgt atgtgcgttc                                       30

<210> SEQ ID NO 64
<211> LENGTH: 36
<212> TYPE: DNA
<213> ORGANISM: Artificial
<220> FEATURE:
<223> OTHER INFORMATION: primer

<400> SEQUENCE: 64
ccggccgaat tctcaatggt gatggtgatg atgacc                                36

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
ggcggcggat ccatggggac cgtatccaga                                       30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
ggcggcccgc ggttcttcct tggacccagg                                       30
```

-continued

```
<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
ggcgccagat ctatgaatgt atgtgcgttc                                  30

<210> SEQ ID NO 68
<211> LENGTH: 33
<212> TYPE: DNA
<213> ORGANISM: Artificial
<220> FEATURE:
<223> OTHER INFORMATION: primer

<400> SEQUENCE: 68
ggccgggtta actcaatggt gatggtgatg atg                              33

<210> SEQ ID NO 69
<211> LENGTH: 30
<212> TYPE: DNA
<213> ORGANISM: Artificial
<220> FEATURE:
<223> OTHER INFORMATION: primer

<400> SEQUENCE: 69
ggcggcaagc ttatgctgcc gccacagctg                                  30

<210> SEQ ID NO 70
<211> LENGTH: 30
<212> TYPE: DNA
<213> ORGANISM: Artificial
<220> FEATURE:
<223> OTHER INFORMATION: primer

<400> SEQUENCE: 70
ggcggcccgc ggtccttgtt tcctgggctg                                  30

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
ggcggcctcg agatgtggcc ccaaccaccc                                  30

<210> SEQ ID NO 72
<211> LENGTH: 36
<212> TYPE: DNA
<213> ORGANISM: Artificial
<220> FEATURE:
<223> OTHER INFORMATION: primer

<400> SEQUENCE: 72
ccggccgaat tctcaatggt gatggtgatg atgacc                           36

<210> SEQ ID NO 73
<211> LENGTH: 30
<212> TYPE: DNA
<213> ORGANISM: Artificial
<220> FEATURE:
<223> OTHER INFORMATION: primer

<400> SEQUENCE: 73
```
ggcggcaagc ttatgctgtt cttggggcag                                30

<210> SEQ ID NO 74
<211> LENGTH: 30
<212> TYPE: DNA
<213> ORGANISM: Artificial
<220> FEATURE:
<223> OTHER INFORMATION: primer

<400> SEQUENCE: 74
ggcggcccgc ggcagaccat cgggtctctg                                30

<210> SEQ ID NO 75
<211> LENGTH: 30
<212> TYPE: DNA
<213> ORGANISM: Artificial
<220> FEATURE:
<223> OTHER INFORMATION: primer

<400> SEQUENCE: 75
ggcggcctcg agatgtggcc ccaaccaccc                                30

<210> SEQ ID NO 76
<211> LENGTH: 36
<212> TYPE: DNA
<213> ORGANISM: Artificial
<220> FEATURE:
<223> OTHER INFORMATION: primer

<400> SEQUENCE: 76
ccggccgaat tctcaatggt gatggtgatg atgacc                         36

<210> SEQ ID NO 77
<211> LENGTH: 30
<212> TYPE: DNA
<213> ORGANISM: Artificial
<220> FEATURE:
<223> OTHER INFORMATION: primer

<400> SEQUENCE: 77
ggcggcaagc ttatggcgtc tcgggagtca                                30

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
ggcggcccgc ggtgaagcct tggctttccg                                30

<210> SEQ ID NO 79
<211> LENGTH: 30
<212> TYPE: DNA
<213> ORGANISM: Artificial
<220> FEATURE:
<223> OTHER INFORMATION: primer

<400> SEQUENCE: 79
ggcggcgaat tcatggcgtc tcgggagtca                                30

<210> SEQ ID NO 80
<211> LENGTH: 36
<212> TYPE: DNA
<213> ORGANISM: Artificial

```
<220> FEATURE:
<223> OTHER INFORMATION: primer

<400> SEQUENCE: 80
ccggccgaat tctcaatggt gatggtgatg atgacc                              36

<210> SEQ ID NO 81
<211> LENGTH: 30
<212> TYPE: DNA
<213> ORGANISM: Artificial
<220> FEATURE:
<223> OTHER INFORMATION: primer

<400> SEQUENCE: 81
ggcggcccgc ggtgaagcct tggctttccg                                     30

<210> SEQ ID NO 82
<211> LENGTH: 30
<212> TYPE: DNA
<213> ORGANISM: Artificial
<220> FEATURE:
<223> OTHER INFORMATION: primer

<400> SEQUENCE: 82
ggcggcccgc ggcaaatcct cacgggaggg                                     30

<210> SEQ ID NO 83
<211> LENGTH: 30
<212> TYPE: DNA
<213> ORGANISM: Artificial
<220> FEATURE:
<223> OTHER INFORMATION: primer

<400> SEQUENCE: 83
ggcggcagat ctatgcacct gctgcttgca                                     30

<210> SEQ ID NO 84
<211> LENGTH: 36
<212> TYPE: DNA
<213> ORGANISM: Artificial
<220> FEATURE:
<223> OTHER INFORMATION: primer

<400> SEQUENCE: 84
ccggccctcg agtcaatggt gatggtgatg atgacc                              36

<210> SEQ ID NO 85
<211> LENGTH: 21
<212> TYPE: DNA
<213> ORGANISM: Artificial
<220> FEATURE:
<223> OTHER INFORMATION: primer

<400> SEQUENCE: 85
aatgtttgat ggacaagccc c                                              21

<210> SEQ ID NO 86
<211> LENGTH: 20
<212> TYPE: DNA
<213> ORGANISM: Artificial
<220> FEATURE:
<223> OTHER INFORMATION: primer

<400> SEQUENCE: 86
tgcttggatt cctctccgaa                                                20
```

```
<210> SEQ ID NO 87
<211> LENGTH: 21
<212> TYPE: DNA
<213> ORGANISM: Artificial
<220> FEATURE:
<223> OTHER INFORMATION: primer

<400> SEQUENCE: 87
accaggaacg cctacctttt c                                    21

<210> SEQ ID NO 88
<211> LENGTH: 21
<212> TYPE: DNA
<213> ORGANISM: Artificial
<220> FEATURE:
<223> OTHER INFORMATION: primer

<400> SEQUENCE: 88
tccagtttcc tacttgccag c                                    21

<210> SEQ ID NO 89
<211> LENGTH: 21
<212> TYPE: DNA
<213> ORGANISM: Artificial
<220> FEATURE:
<223> OTHER INFORMATION: primer

<400> SEQUENCE: 89
ctgccagtgg agttcaaatg c                                    21

<210> SEQ ID NO 90
<211> LENGTH: 21
<212> TYPE: DNA
<213> ORGANISM: Artificial
<220> FEATURE:
<223> OTHER INFORMATION: primer

<400> SEQUENCE: 90
tcattgtccc caggacagtt g                                    21

<210> SEQ ID NO 91
<211> LENGTH: 21
<212> TYPE: DNA
<213> ORGANISM: Artificial
<220> FEATURE:
<223> OTHER INFORMATION: primer

<400> SEQUENCE: 91
ggcattcaaa cctctcgtga a                                    21

<210> SEQ ID NO 92
<211> LENGTH: 21
<212> TYPE: DNA
<213> ORGANISM: Artificial
<220> FEATURE:
<223> OTHER INFORMATION: primer

<400> SEQUENCE: 92
tcatggacac gaagttcctg g                                    21

<210> SEQ ID NO 93
<211> LENGTH: 20
<212> TYPE: DNA
<213> ORGANISM: Artificial
<220> FEATURE:
<223> OTHER INFORMATION: primer

<400> SEQUENCE: 93
```
cggaggaatt cgtggaaaga                                              20

<210> SEQ ID NO 94
<211> LENGTH: 21
<212> TYPE: DNA
<213> ORGANISM: Artificial
<220> FEATURE:
<223> OTHER INFORMATION: primer

<400> SEQUENCE: 94
ccactaaagc cacgttcctc a                                            21

<210> SEQ ID NO 95
<211> LENGTH: 21
<212> TYPE: DNA
<213> ORGANISM: Artificial
<220> FEATURE:
<223> OTHER INFORMATION: primer

<400> SEQUENCE: 95
tccccaaggc taacagaacc a                                            21

<210> SEQ ID NO 96
<211> LENGTH: 21
<212> TYPE: DNA
<213> ORGANISM: Artificial
<220> FEATURE:
<223> OTHER INFORMATION: primer

<400> SEQUENCE: 96
cccctttaag cccatttcct c                                            21

<210> SEQ ID NO 97
<211> LENGTH: 19
<212> TYPE: DNA
<213> ORGANISM: Artificial
<220> FEATURE:
<223> OTHER INFORMATION: primer

<400> SEQUENCE: 97
cagacatcgc atccgcaaa                                               19

<210> SEQ ID NO 98
<211> LENGTH: 21
<212> TYPE: DNA
<213> ORGANISM: Artificial
<220> FEATURE:
<223> OTHER INFORMATION: primer

<400> SEQUENCE: 98
aatgatccag tcgttccagc c                                            21

<210> SEQ ID NO 99
<211> LENGTH: 20
<212> TYPE: DNA
<213> ORGANISM: Artificial
<220> FEATURE:
<223> OTHER INFORMATION: primer

<400> SEQUENCE: 99
aaccccttca aacggaacca                                              20

<210> SEQ ID NO 100
<211> LENGTH: 21
<212> TYPE: DNA
<213> ORGANISM: Artificial

-continued

```
<220> FEATURE:
<223> OTHER INFORMATION: primer

<400> SEQUENCE: 100
tcgacgtgga cagctgaaga a                                             21

<210> SEQ ID NO 101
<211> LENGTH: 21
<212> TYPE: DNA
<213> ORGANISM: Artificial
<220> FEATURE:
<223> OTHER INFORMATION: primer

<400> SEQUENCE: 101
ctcgttcttc gttccaggtt g                                             21

<210> SEQ ID NO 102
<211> LENGTH: 21
<212> TYPE: DNA
<213> ORGANISM: Artificial
<220> FEATURE:
<223> OTHER INFORMATION: primer

<400> SEQUENCE: 102
agcagcagcg gtgacatcta t                                             21

<210> SEQ ID NO 103
<211> LENGTH: 20
<212> TYPE: DNA
<213> ORGANISM: Artificial
<220> FEATURE:
<223> OTHER INFORMATION: primer

<400> SEQUENCE: 103
ggacaactgc aatcgatgca                                               20

<210> SEQ ID NO 104
<211> LENGTH: 21
<212> TYPE: DNA
<213> ORGANISM: Artificial
<220> FEATURE:
<223> OTHER INFORMATION: primer

<400> SEQUENCE: 104
gcctcggttg atggctttaa t                                             21

<210> SEQ ID NO 105
<211> LENGTH: 21
<212> TYPE: DNA
<213> ORGANISM: Artificial
<220> FEATURE:
<223> OTHER INFORMATION: primer

<400> SEQUENCE: 105
aagtgtgaca gaatgcgcct c                                             21

<210> SEQ ID NO 106
<211> LENGTH: 21
<212> TYPE: DNA
<213> ORGANISM: Artificial
<220> FEATURE:
<223> OTHER INFORMATION: primer

<400> SEQUENCE: 106
acttgcaact gatgctccac c                                             21
```

```
<210> SEQ ID NO 107
<211> LENGTH: 21
<212> TYPE: DNA
<213> ORGANISM: Artificial
<220> FEATURE:
<223> OTHER INFORMATION: primer

<400> SEQUENCE: 107
agtgtgccaa tggttcctcc t                                              21

<210> SEQ ID NO 108
<211> LENGTH: 21
<212> TYPE: DNA
<213> ORGANISM: Artificial
<220> FEATURE:
<223> OTHER INFORMATION: primer

<400> SEQUENCE: 108
tgcaggtctg tgacgttctc a                                              21

<210> SEQ ID NO 109
<211> LENGTH: 21
<212> TYPE: DNA
<213> ORGANISM: Artificial
<220> FEATURE:
<223> OTHER INFORMATION: primer

<400> SEQUENCE: 109
cacaggcatc ctgatctttg c                                              21

<210> SEQ ID NO 110
<211> LENGTH: 20
<212> TYPE: DNA
<213> ORGANISM: Artificial
<220> FEATURE:
<223> OTHER INFORMATION: primer

<400> SEQUENCE: 110
tgaaattggc caccaggaag                                                20

<210> SEQ ID NO 111
<211> LENGTH: 21
<212> TYPE: DNA
<213> ORGANISM: Artificial
<220> FEATURE:
<223> OTHER INFORMATION: primer

<400> SEQUENCE: 111
ggtgatggag gacatgcgaa t                                              21

<210> SEQ ID NO 112
<211> LENGTH: 21
<212> TYPE: DNA
<213> ORGANISM: Artificial
<220> FEATURE:
<223> OTHER INFORMATION: primer

<400> SEQUENCE: 112
ttgttggctt ggaagtaggc c                                              21

<210> SEQ ID NO 113
<211> LENGTH: 21
<212> TYPE: DNA
<213> ORGANISM: Artificial
<220> FEATURE:
<223> OTHER INFORMATION: primer

<400> SEQUENCE: 113
```
aatctgatcg atggtgccct t                                          21

<210> SEQ ID NO 114
<211> LENGTH: 21
<212> TYPE: DNA
<213> ORGANISM: Artificial
<220> FEATURE:
<223> OTHER INFORMATION: primer

<400> SEQUENCE: 114
cgaatgtccg tttctttgtg c                                          21

<210> SEQ ID NO 115
<211> LENGTH: 21
<212> TYPE: DNA
<213> ORGANISM: Artificial
<220> FEATURE:
<223> OTHER INFORMATION: primer

<400> SEQUENCE: 115
caccaaatgg aagacccatc a                                          21

<210> SEQ ID NO 116
<211> LENGTH: 21
<212> TYPE: DNA
<213> ORGANISM: Artificial
<220> FEATURE:
<223> OTHER INFORMATION: primer

<400> SEQUENCE: 116
atcatctgct ttccctgctc c                                          21

<210> SEQ ID NO 117
<211> LENGTH: 25
<212> TYPE: DNA
<213> ORGANISM: Artificial
<220> FEATURE:
<223> OTHER INFORMATION: primer

<400> SEQUENCE: 117
gcagaggaac gagacccaca gcatc                                      25

<210> SEQ ID NO 118
<211> LENGTH: 22
<212> TYPE: DNA
<213> ORGANISM: Artificial
<220> FEATURE:
<223> OTHER INFORMATION: primer

<400> SEQUENCE: 118
gtgcccagcc cacttcacac tg                                         22

<210> SEQ ID NO 119
<211> LENGTH: 24
<212> TYPE: DNA
<213> ORGANISM: Artificial
<220> FEATURE:
<223> OTHER INFORMATION: primer

<400> SEQUENCE: 119
gcttgtcttg gcagtcagca tccc                                       24

<210> SEQ ID NO 120
<211> LENGTH: 25
<212> TYPE: DNA
<213> ORGANISM: Artificial

```
<220> FEATURE:
<223> OTHER INFORMATION: primer

<400> SEQUENCE: 120
ggtcgtctgt gaatgtctca ggcac                                             25

<210> SEQ ID NO 121
<211> LENGTH: 36
<212> TYPE: DNA
<213> ORGANISM: Artificial
<220> FEATURE:
<223> OTHER INFORMATION: primer

<400> SEQUENCE: 121
ggcggcctcg aggccaccat ggtgctgctg tcccgc                                 36

<210> SEQ ID NO 122
<211> LENGTH: 36
<212> TYPE: DNA
<213> ORGANISM: Artificial
<220> FEATURE:
<223> OTHER INFORMATION: primer

<400> SEQUENCE: 122
ggcggcgtta actcatgaat tcaagtcctc ttcaga                                 36

<210> SEQ ID NO 123
<211> LENGTH: 773
<212> TYPE: DNA
<213> ORGANISM: Mus musculus

<400> SEQUENCE: 123
acggacacac tcagcagcca gaggccaccg gcagacagat cgcagctctg tagacaatat       60
gctgttcttg gggcagaagg ccttgctgct tgtcttggca gtcagcatcc cctctgactg      120
gctacccta ggggtcagtg gtcaacgtgg agatgatgtg cctgagacat tcacagacga      180
ccctaatctg gtgaacgatc cctctacaga cgatacagct ctggctgata tcacaccttc      240
cacggacgac ctagctgatg acaaaaatgc tactgcagag tgccgggatg agaagtttgc      300
ttgtacaaga ctgtactctg tccatcggcc agtcagacag tgtgtgcacc agtcctgctt      360
caccagttta cggcgcatgt acatcatcaa taatgagatc tgttcccgac tcgtctgtaa      420
agaacatgaa gctatgaaag atgagctttg ccggcagatg gcaggcctgc ctccaaggcg      480
actccggcgc tccaactact tccgacttcc tccctgtgaa aatatgaatt tgcagagacc      540
cgatggtctg tgatcaccaa ggaagaaaga agaaaatgtg gatgaaggaa tcgaaaattc      600
tttctccttc aacccctgcc atctgtcccg tagacatgta ttttttaaact aagcccttg      660
caatgccccg gcttcctacc ctactctaat tttcactggt gctggtaacg tttgtctcat      720
tttgcggtac tgacaataca ttgtctatat tgtgaaaaaa aaaaaaaaaa aaa             773

<210> SEQ ID NO 124
<211> LENGTH: 1240
<212> TYPE: DNA
<213> ORGANISM: Homo sapiens

<400> SEQUENCE: 124
gatcatgcca ctgtactcca gcctgggtga cagagcaaga ccctatctta aaaaaaagaa       60
aaaatcctgg atcagagaaa gtgttatcta cacattatat gatctaagga aaaatattgg      120
tagaaaatga ggcaagcata ataaccttgc ctttcaattt tctttgggca tctgattgca      180
ttttatcctt aagagcccag aaacccagat tcttagttaa gctcaaacaa agccaaaaga      240
```

```
caaagtaagg ctggcacccc tttcacagag cttctctaca tttgaaaatg atttggagag    300
ttctgaaaag ttcctcaact tttataacc ctaaggtagc cagccttcct cttggacaaa    360
actcataagg tatctgtgtt cgcttggttg tgagaataca taggatattc caagggaaa    420 aaaaacaaga agagtctaaa tgtgtaggtc aagaaagagg cagagatgaa aaagaaatac    480
aggaataaaa agaaatttgt tagtgctgaa gagacgaata ttgaaaaaga aagtgagaaa    540
gaaggatgaa ggaatgattc aaatatggaa tataaggagg ctgaggcagg ataattgctt    600
gaactcagga ggcggaggtt gcagtgagcc aagatcacat cattgcactc cagcctgggt    660
gacaggagca aaactctgtc ttaaaaaaaa aaaacaaaaa acaaagaaga agaagatagc    720
cagagagaga gaaacagcat ctataatgtg cattaaaaca caccaaggag gagacggaac    780
ttttcggtaa gaaagaaccc aaggaacaaa ggggagctgg gaccagatcg tgagaggagg    840
gaaaataggc taatggaaga aaggcaatac atgagctggg gccaacactt ccagggagca    900
gcaagagctc tcaccagtgt agtcataaca tttggaatga gggtgtgagc aactgcaaat    960
tcccatctcc cttctcattc cagcctcatt gtaacacaca ttctacgcct agcctggctt   1020
tcttgctctc cctcatctca ttgtttcagc ggaggccaaa tctgaagtcc tttccaggga   1080
gtggctctgt tcatcttatt cgccagccaa agtaggaaca gcgtaagagg agagagacac   1140
attcagcagc caaaggactc ggtggaaaga gcagaacacc atagacagtg agttatttga   1200
ttacctgaaa ccctaaagag acagagggaa tgtgtgtatg                         1240
```